United States Patent [19]

Tai et al.

[11] Patent Number: 5,219,706
[45] Date of Patent: Jun. 15, 1993

[54] NAPHTHALOCYANINE DERIVATIVE AND PRODUCTION PROCESS THEREOF, AS WELL AS OPTICAL INFORMATION RECORDING MEDIA USING THE DERIVATIVES AND PRODUCTION PROCESS THEREOF

[75] Inventors: Seiji Tai; Shigeru Hayashida; Nobuyuki Hayashi; Yasushi Iwakabe; Shunichi Numata; Noriyuki Kinjo; Susumu Era; Setsuo Kobayashi, all of Hitachi; Akio Mukoh, Mito; Yoshio Sato, Hitachi, all of Japan

[73] Assignee: Hitachi, Ltd., Tokyo, Japan

[21] Appl. No.: 825,783

[22] Filed: Jan. 21, 1992

Related U.S. Application Data

[63] Continuation of Ser. No. 569,585, Aug. 20, 1990, abandoned, which is a continuation of Ser. No. 172,301, Mar. 23, 1988, abandoned.

[30] Foreign Application Priority Data

| Mar. 23, 1987 | [JP] | Japan | 62-68315 |
| Apr. 3, 1987 | [JP] | Japan | 62-82429 |
| Apr. 21, 1987 | [JP] | Japan | 62-98024 |
| Apr. 21, 1987 | [JP] | Japan | 62-98025 |
| Jun. 19, 1987 | [JP] | Japan | 62-153959 |
| Aug. 12, 1987 | [JP] | Japan | 62-201401 |
| Oct. 14, 1987 | [JP] | Japan | 62-258588 |

[51] Int. Cl.$^5$ .......................... G03C 1/72; G03C 1/74
[52] U.S. Cl. ...................... 430/270; 430/338; 430/495; 430/964; 346/135.1; 540/128; 540/129; 540/139; 540/140
[58] Field of Search ............... 430/270, 338, 495, 964, 430/945; 540/128, 129, 139, 140; 346/135.1

[56] References Cited

U.S. PATENT DOCUMENTS

| 4,522,755 | 11/1985 | Achar et al. | 528/327 |
| 4,622,179 | 11/1986 | Eda | 540/139 |
| 4,725,525 | 2/1988 | Kenney et al. | 430/270 |
| 4,798,781 | 1/1989 | Hirose et al. | 430/270 |
| 5,059,510 | 10/1991 | Jones et al. | 430/338 |

Primary Examiner—Richard L. Schilling
Attorney, Agent, or Firm—Antonelli, Terry, Stout & Kraus

[57] ABSTRACT

There are disclosed a novel naphthalocyanine derivative represented by the general formula [I] or [II] shown below, a process for preparing said derivative, an optical information recording medium using said derivative, and a process for preparing thereof:

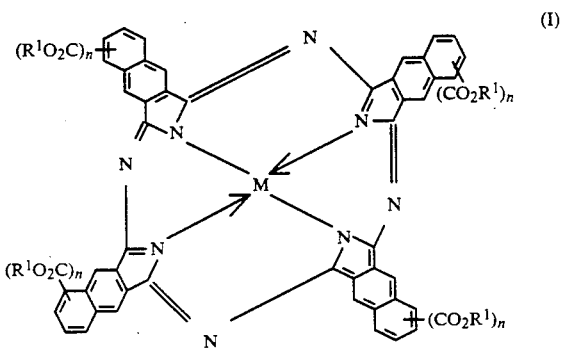

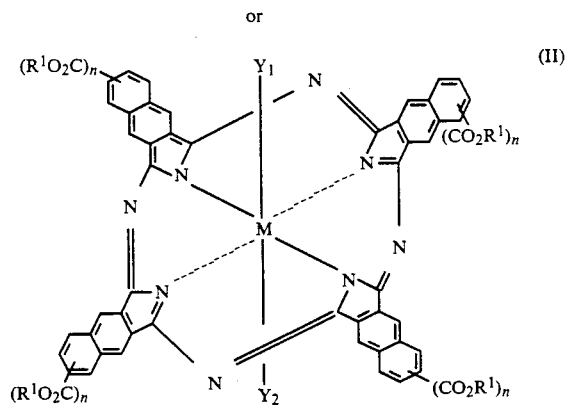

wherein M is a metal, metal oxide, metal hydroxide and the like, $R^1$ is an alkyl group of 1–22 carbon atoms, n is an integer of 1 to 4, and $Y_1$ and $Y_2$ aryloxy group and the like.

17 Claims, 97 Drawing Sheets

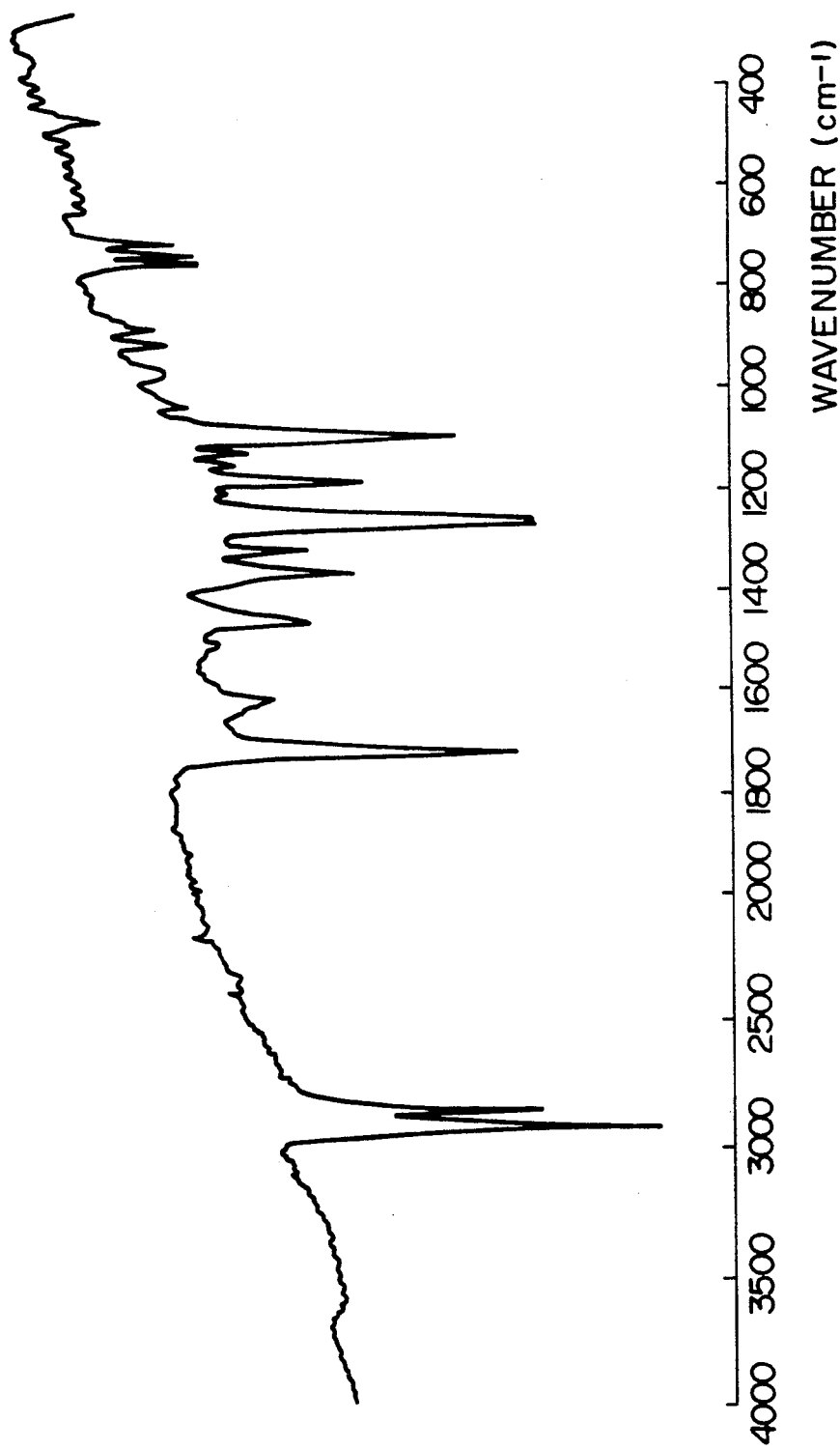
F I G. 32

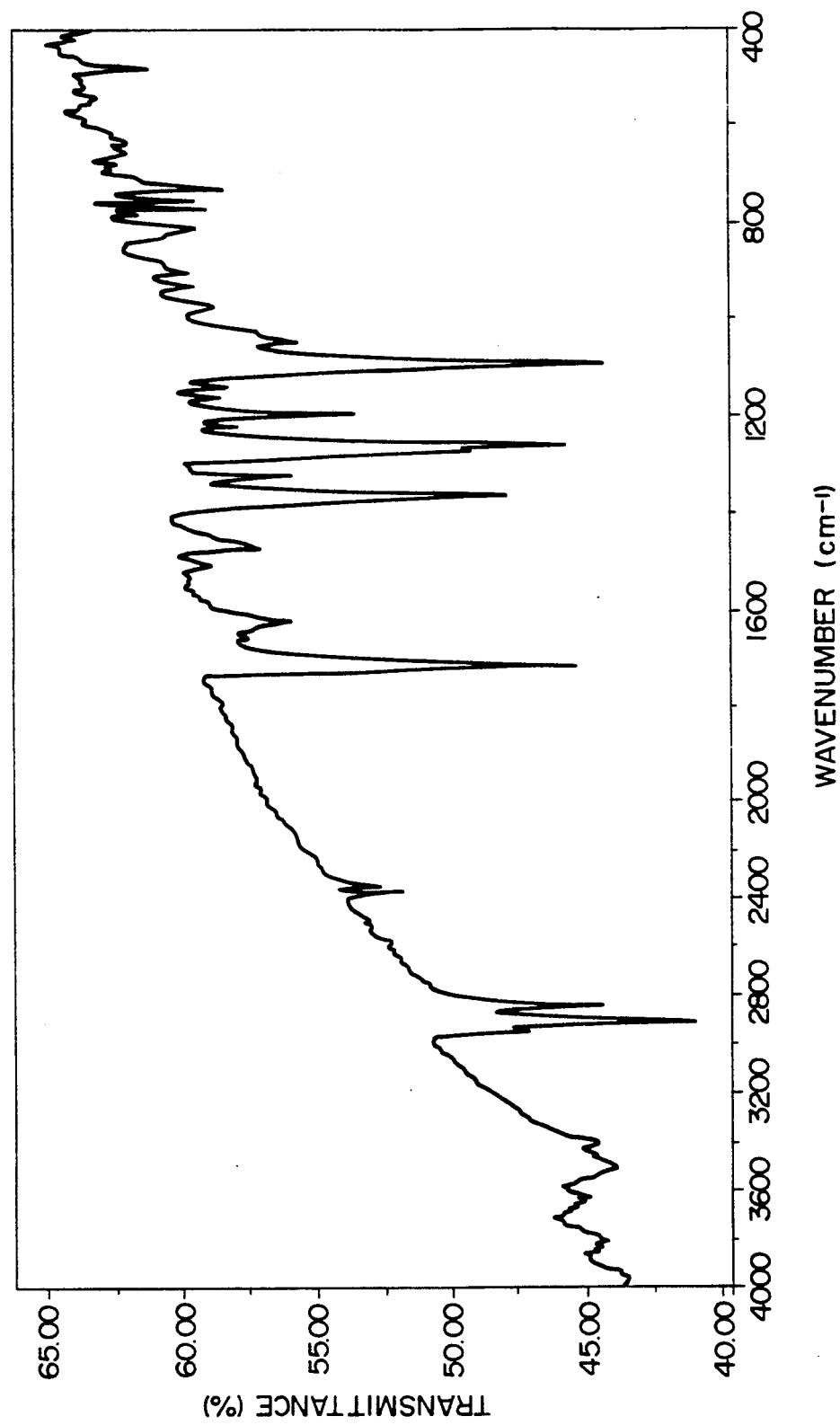
F I G. 84

NAPHTHALOCYANINE DERIVATIVE AND PRODUCTION PROCESS THEREOF, AS WELL AS OPTICAL INFORMATION RECORDING MEDIA USING THE DERIVATIVES AND PRODUCTION PROCESS THEREOF

This application is a continuation application of application Ser. No. 07/569,585, filed Aug. 20, 1990, now abandoned, which is a continuation of application Ser. No. 07/172,301 filed Mar. 23, 1988, now abandoned.

FIELD OF THE INVENTION AND RELATED ART STATEMENT

The present invention relates to novel naphthalocyanine derivatives and processes for producing the derivatives, as well as to optical information recording media using the derivatives and processes for producing the media.

In recent years, it is proposed to use a diode laser beam for the purpose of writing or reading out in apparatuses such as compact disc, video disc, liquid crystal display, optical character reader and the like, or as a light source for electrophotographs. In writing or reading out by diode laser beam, there is required a substance capable of absorbing a diode laser beam, i.e., a near-infrared ray.

Cyanine dyes are conventionally known well as an organic dye absorbing a near-infrared ray, and metal complexes of an oxime or a thiol and aminated quinone derivatives are also known as a dye absorbing a near-infrared ray [Journal of Synthetic Organic Chemistry, Japan, Vol. 43, p. 334 (1985); Journal of the Japan Society of Color Material, Vol. 53, p. 197 (1980); and Journal of the Japan Society of Color Material, Vol. 58, p. 220 (1985)].

However, the cyanine dyes have very poor stability against light; therefore, their use inevitably has various restrictions. The metal complexes of an oxime or a thiol have a drawback in that when they are present in certain types of media, the metals are eliminated from the complexes, whereby the complexes lose an absorbability for near-infrared ray. The aminated quinone derivatives have a very low absorbability for near-infrared ray.

Naphthalocyanine derivatives are recently known as a material which can overcome the above mentioned problems. Conventional unsubstituted metal naphthalocyanines (Zhurnal Obschchei Khimii, Vol. 39, p. 2554, 1969; Mol. Cryst. Liq. Cryst., Vol. 112, p. 345, 1984) are insoluble in organic solvents, thus making their purification very difficult. Synthesis of naphthalocyanine derivatives soluble in organic solvents are recently reported [Japanese Patent Application Kokai (Laid-Open) Nos. 23451/1985, 184565/1985, 215662/1986 and 215663/1986]; however, these naphthalocyanine derivatives have drawbacks in that their absorption for diode laser beam varies greatly depending upon, for example, the type of solvent used, their cocentration and the temperature employed and is very low when they take a form of a high concentration solution or a solid film and further in that they give a very low reflectivity at a diode laser beam region (780–830 nm) (this reflectivity is very important when a reflected light is used for reading out the information recorded in optical discs).

SUMMARY OF THE INVENTION

The first aspect of the present invention relates to a naphthalocyanine derivative represented by the general formula (I)

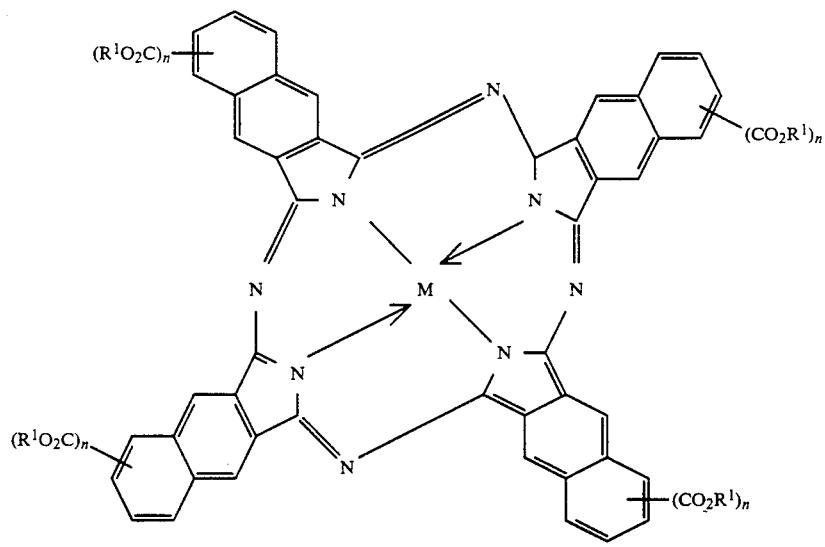

[in the formula (I), each $R^1$ is an alkyl group of 1–22 carbon atoms or $R^1$ is an alkyl group from 13 to 22 carbon atoms and a plurality of $R^1$s may be same or different; each n is an integer of 1–4 and a plurality of ns may be same or different; and M is one member selected from metals of group Ib of periodic table, such as Cu and the like, group IIa metals such as Mg and the like, group IIb metals such as Zn and the like, group IIIa metals and their halides and hydroxides such as Al, ClAl, HOAl, In, ClIn and the like, group IVa metals and their halides and hydroxides such as Si, $Cl_2Si$, $(HO)_2Si$, Ge, $Cl_2Ge$, $(HO)_2Ge$, Sn, $Cl_2Sn$, $(HO)_2Sn$, Pb and the like, group IVb metals and their oxides such as Ti, OTi and the like, oxides of group Vb metals such as OV and the like, group VIb metals such as Cr, Mo and the like, group VIIb metals and their halides such as Mn, ClMn and the like, and group VIII metals and their halides such as Fe, ClFe, Co, Ni, Pt, Pd and the like].

The second aspect of the present invention relates to a naphthalocyanine derivative represented by the general formula (II)

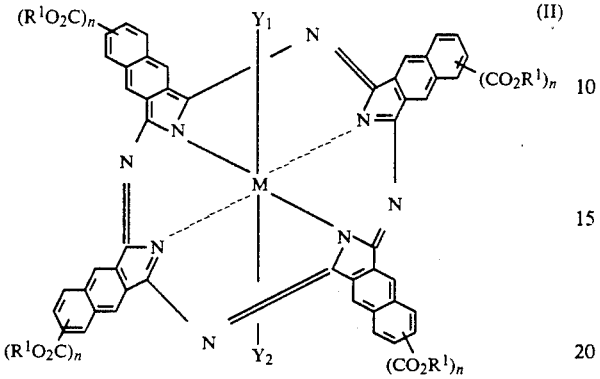

[In the formula (II), each $R^1$ is an alkyl group of 1-22 carbon atoms and a plurality of $R^1$s may be same or different; each n is an integer of 1-4 and a plurality of ns may be same or different; $Y_1$ and $Y_2$ which may be same or different are each an aryloxyl group, an alkoxyl group, a trialkylsiloxyl group, a triarylsiloxyl group, a trialkoxysiloxyl group, a triaryloxysiloxyl group or a trityloxyl group; M is Al, Ti, Si, Ge or Sn; and only $Y_1$ covalently binds with M when M is Al, and $Y_1$ and $Y_2$ covalently bind with M when M is Ti, Si, Ge or Sn].

The third aspect of the present invention relates to a process for producing a naphthalocyanine derivative represented by the generla formula (I)

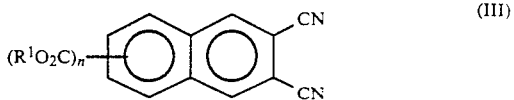

[in the formula (III), $R^1$ is an alkyl group of 1-22 carbon atoms and n is an integer of 1-4] with a metal or metal salt represented by the general formula (IV)

$$MX_p \qquad (IV)$$

[in the formula (IV), X is a halogen atom or an acyloxyl group; p is O or positive integer showing the number of X atoms binding to M; and M is a metal selected from Ib group metals such as Cu and the like, IIa group metals such as Mg and the like, IIb group metals such as Zn and the like, IIIa group metals such as Al, In and the like, IVa group metals such as Si, Ge, Sn, Pb and the like, IVb group metals such as Ti and the like, Vb group metals such as V and the like, VIb group metals such as Cr, Mo and the like, VIIb group metals such as Mn and the like and VIII group metals such as Fe, Co, Ni, Pt, Pd and the like].

The fourth aspect of the present invention relates to a process for producing a naphthalocyanine derivative represented by the general formula (II)

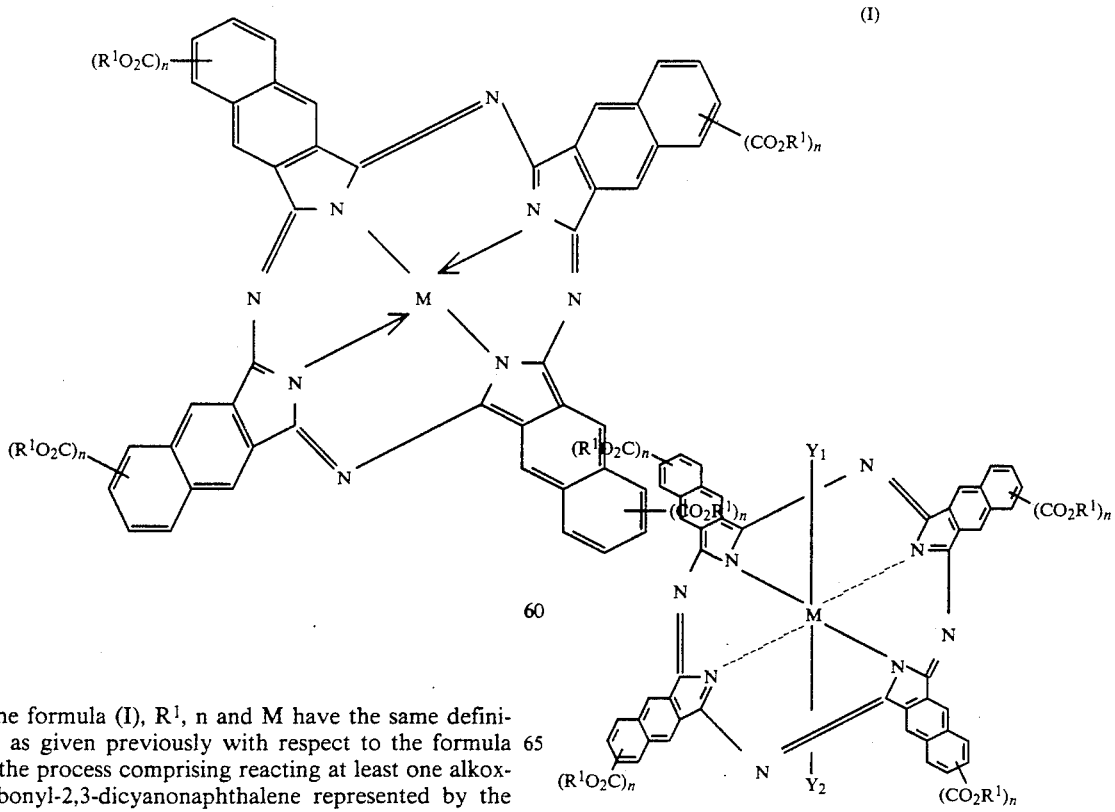

[in the formula (I), $R^1$, n and M have the same definitions as given previously with respect to the formula (I)], the process comprising reacting at least one alkoxycarbonyl-2,3-dicyanonaphthalene represented by the general formula (III)

[In the formula (II), $R^1$, n, $Y_1$, $Y_2$ and M have the same definitions as given previously with respect to the formula (II)], the process comprising reacting an alkoxycarbonyl-2,3-dicyanonaphthalene represented by the general formula (III)

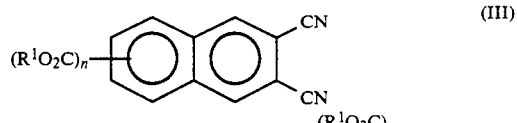

[in the formula (III), $R^1$ is an alkyl group of 1-22 carbon atoms and n is an integer of 1-4] with a metal halide represented by the general formula (IV-1)

$$MX_p \qquad (IV-1)$$

[in the formula (IV-1), M is a metal selected from Al, Ti, Si, Ge or Sn; X is a halogen atom; and p is a positive integer showing the number of X atoms binding to M] to synthesize a naphthalocyanine derivative represented by the general formula (V)

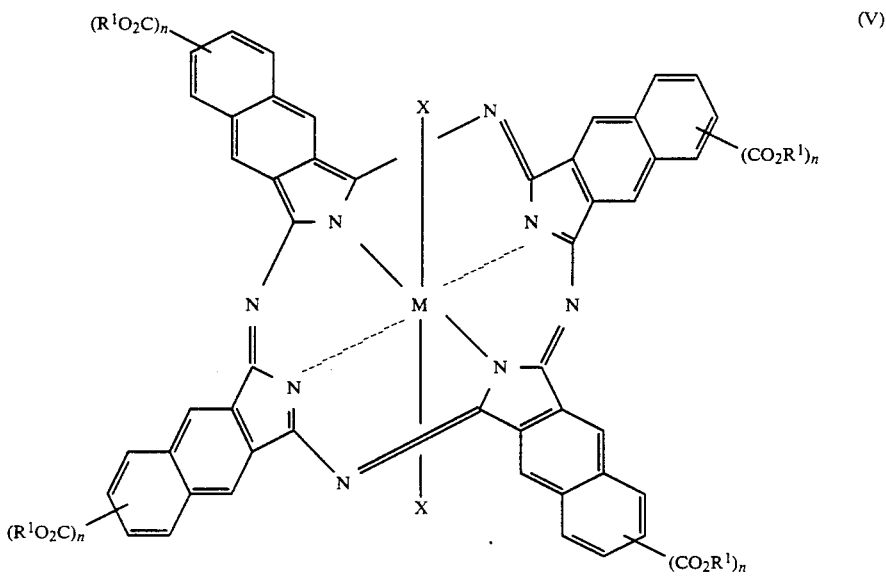

[in the formula (V), each $R^1$ is an alkyl group of 1-22 carbon atoms and a plurality of $R^1$s may be same or different; each n is an integer of 1-4 and a plurality of ns may be same or different; X is a halogen atom], hydrolyzing the compound represented by the formula (V) to obtain a naphthalocyanine derivative represented by the general formula (VI)

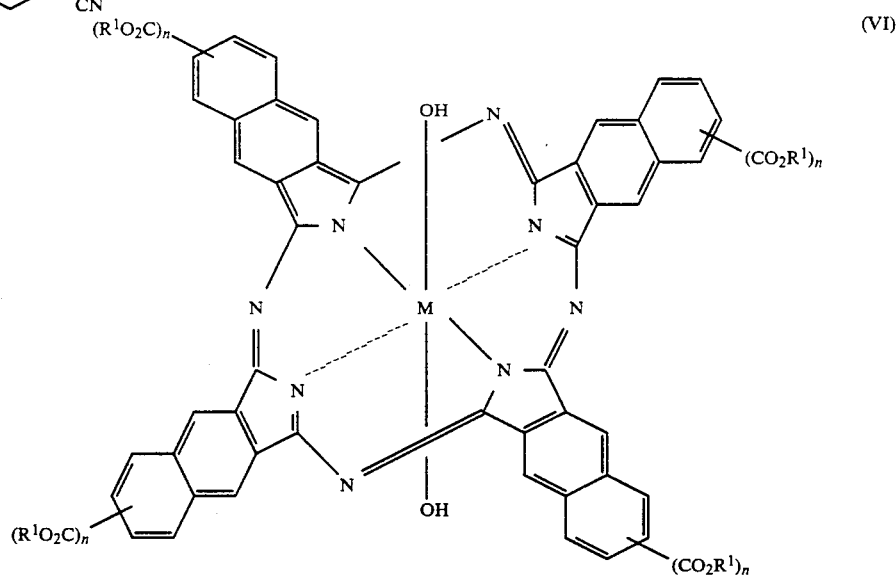

[in the formula (VI), each $R^1$ is an alkyl group of 1-22 carbon atoms and a plurality of $R^1$s may be same or different; each n is an integer of 1-4 and a plurality of ns may be same or different], and then reacting the compound represented by the formula (VI) with a silanol represented by the general formula (VII)

$$(R^2)_3SiOH \qquad (VII)$$

[in the formula (VII), $R^2$ is an alkyl group, an aryl group, an alkoxyl group or an aryloxyl group] or with an alcohol represented by the general formula (VIII)

$$R^3OH \qquad (VIII)$$

[in the formula (VIII), $R^3$ is an alkyl group, an aryl group or a trityl group].

The fifth aspect of the present invention relates to an optical information recording medium comprising (a) a substrate and (b) a recording film layer formed thereon and composed mainly of a naphthalocyanine derivative represented by the general formula (I)

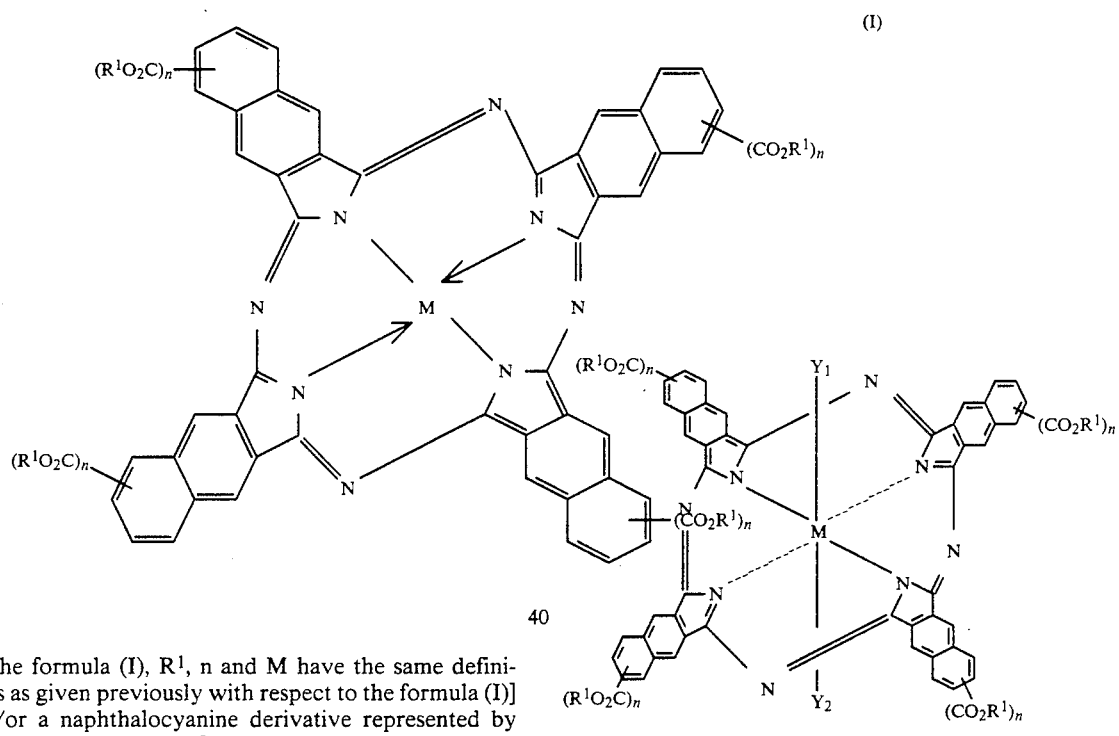

[in the formula (I), $R^1$, n and M have the same definitions as given previously with respect to the formula (I)] and/or a naphthalocyanine derivative represented by the general formula (II)]

[in the formula (II), $R^1$, n, $Y_1$, $Y_2$ and M have the same definitions as given previously with respect to the formula (II)].

The sixth aspect of the present invention relates to a process for producing an optical information recording medium, which comprises forming a recording film on a substrate by coating on the substrate an organic solvent solution containing mainly a naphthalocyanine derivative represented by the general formula (I)

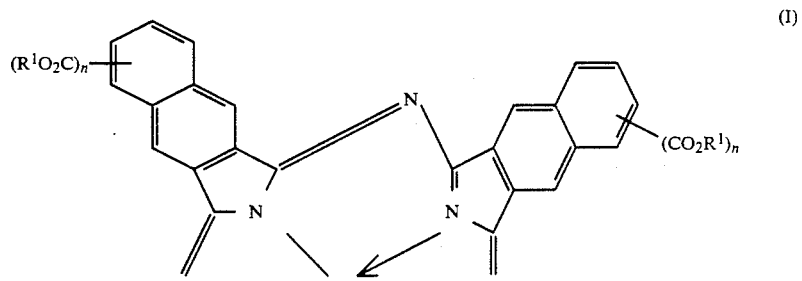

-continued

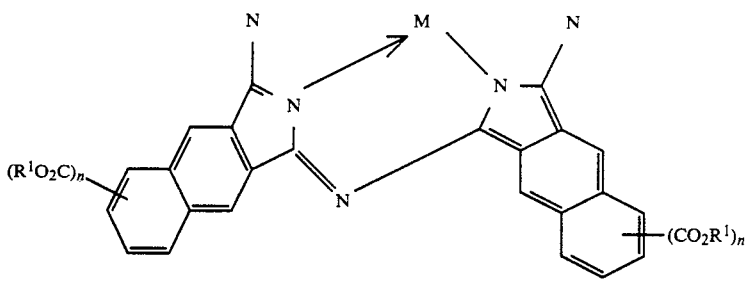

[in the formula (I), $R^1$, n and M have the same definitions as given previously with respect to the formula (I); and/or a naphthalocyanine derivative represented by the general formula (II)

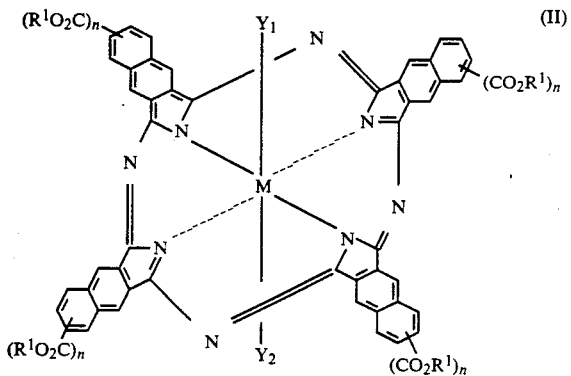

[in the formula (II), $R^1$, n, $Y_1$, $Y_2$ and M have the same definitions as given previously with respect to the formula (II)].

BRIEF DESCRIPTION OF DRAWINGS

FIG. 32 is an IR spectrum of tetrakis(n-octadecyloxycarbonyl) copper naphthalocyanine;

FIG. 84 is an IR spectrum of bis(n-octadecyloxy)germanium-tetrakis(n-octyloxycarbonyl)naphthalocyanine;

DETAILED DESCRIPTION OF PREFERRED EMBODIMENTS

Figure 1:
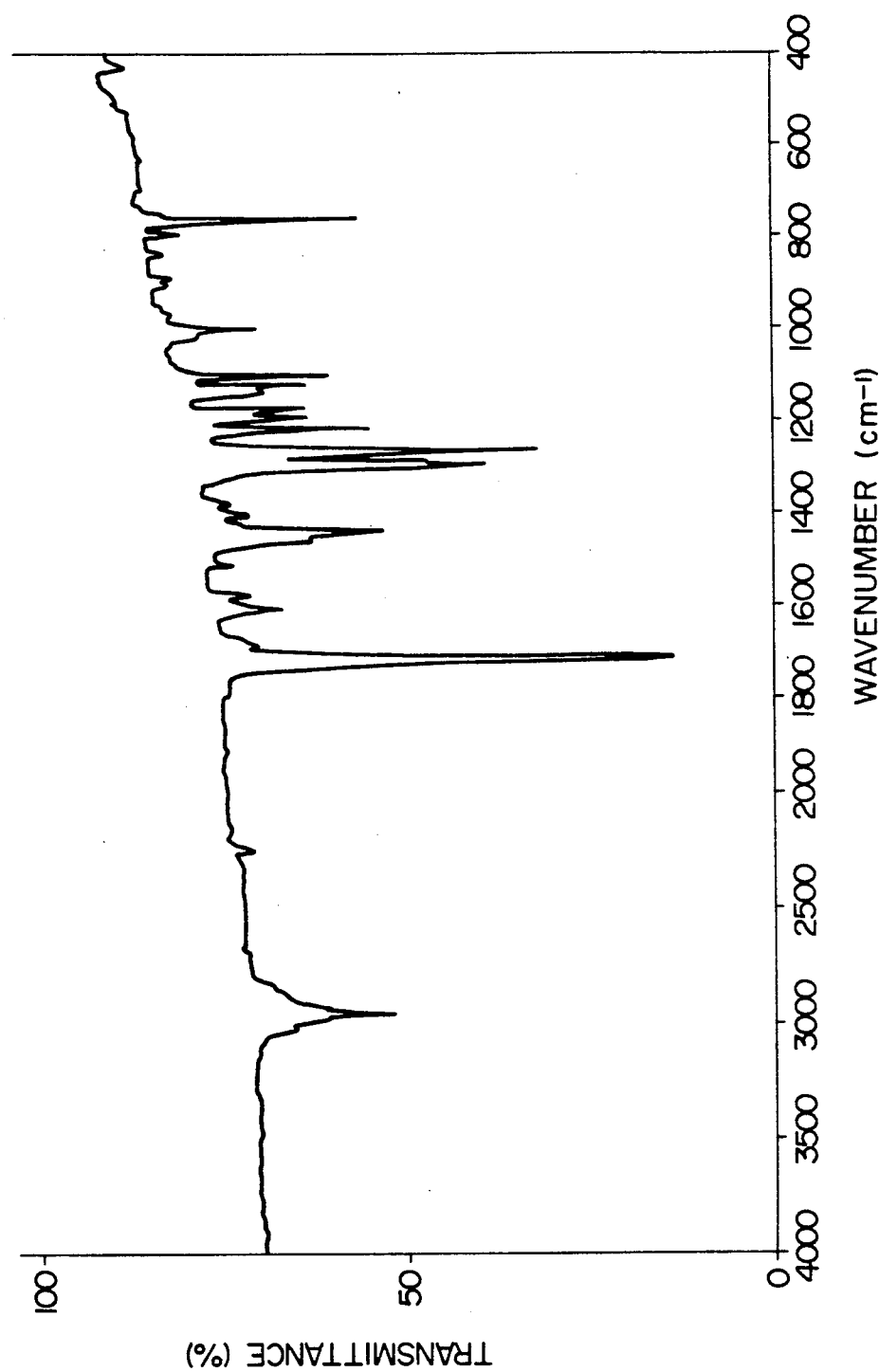
FIG. 1 is an IR spectrum of methyl 3,4-dimethylbenzoate.

The naphthalocyanine derivatives represented by the general formula (I)

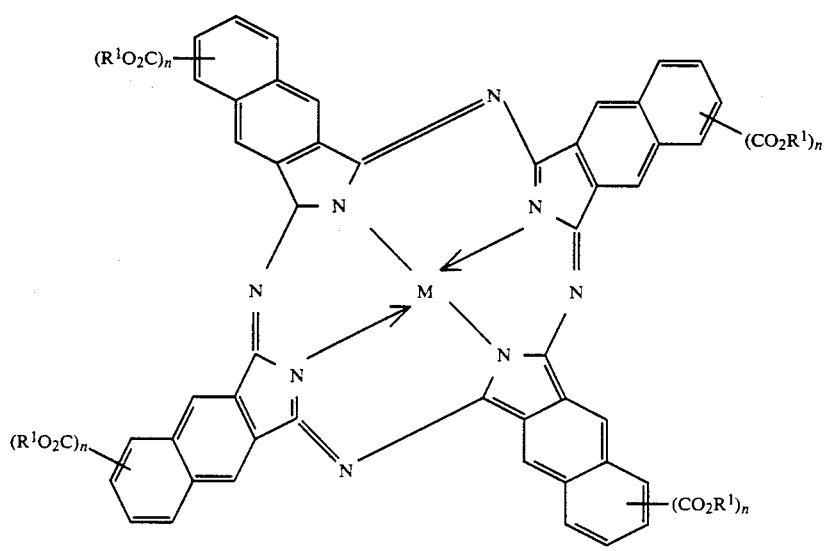

[in the formula (I), $R^1$, n and M have the same definitions as given previously] and the general formula (II)

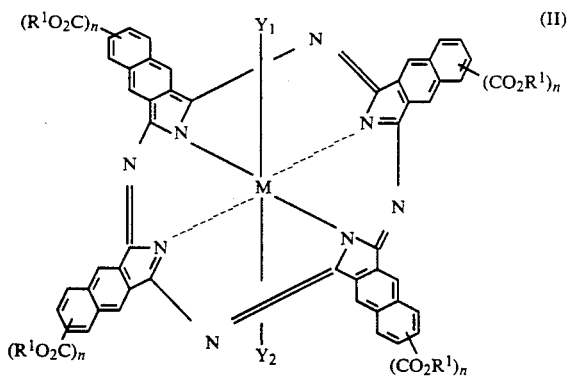

[in the formula (II), $R^1$, n, $Y_1$, $Y_2$ and M have the same definitions as given previously] which are the first and second aspects of the present invention, respectively, are soluble in solvents of aromatic hydrocarbon type, halogenated hydrocarbon type, ester type, ketone type and saturated hydrocarbon type and accordingly can be easily purified to increase the purity. Moreover, they have a very high absorbability for diode laser beam.

In the general formulas (I) and (II), as examples of $R^1$ which is an alkyl group of 1–22 carbon atoms, there can be mentioned groups such as methyl, ethyl, n-propyl, sec-propyl, n-butyl, sec-butyl, t-butyl, n-amyl, t-amyl, 2-amyl, 3-amyl, hexyl, heptyl, octyl, decyl, dodecyl, tetradecyl, hexadecyl, octadecyl, eicosyl, docosyl and the like.

In the general formula (I), as examples of M, there can be mentioned Cu, Mg, Zn, Al, ClAl, HOAl, In, ClIn, Si, $Cl_2Si$, $(HO)_2Si$, Ge, $Cl_2Ge$, $(HO)_2Ge$, Sn, $Cl_2Sn$, $(HO)_2Sn$, Pb, Ti, OTi, OV, Cr, Mo, Mn, ClMn, Fe, ClFe, Co, Ni, Pt, Pd, etc.

In the general formula (II), as examples of M, there can be mentioned Al, Ti, Si, Ge, Sn, etc. Also in the general formula (II), as examples of $Y_1$ and $Y_2$, the aryloxyl group includes phenoxyl, tolyloxyl, anisyloxyl, etc.; the alkoxyl group includes amyloxyl, hexyloxyl, octyloxyl, decyloxyl, dodecyloxyl, tetradecyloxyl, hexadecyloxyl, octadecyloxyl, eicosyloxyl, docosyloxyl, etc.; the trialkylsiloxyl group includes trimethylsiloxyl, triethylsiloxyl, tripropylsiloxyl, tributylsiloxyl, etc.; the triarylsiloxyl group includes triphenylsiloxyl, trianisylsiloxyl, tritolylsiloxyl, etc.; the trialkoxysiloxyl group includes trimethoxysiloxyl, triethoxysiloxyl, tripropoxysiloxyl, tributoxysiloxyl, etc.; and the triaryloxysiloxyl group includes triphenoxysiloxyl, trianisyloxysiloxyl, tritolyloxysiloxyl, etc.

The compounds of the present invention represented by the general formula (I) or (II) are illustrated in the following table, but the scope of the present invention is not restricted to the following illustrative compounds.

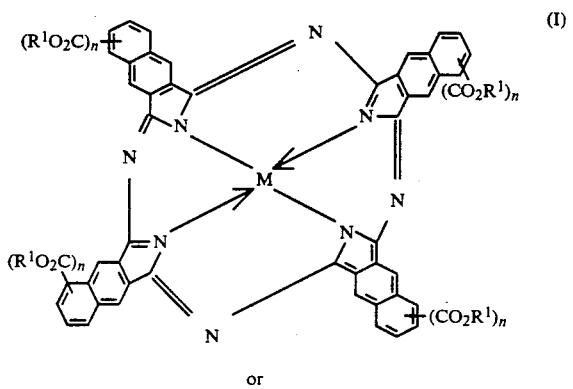

or

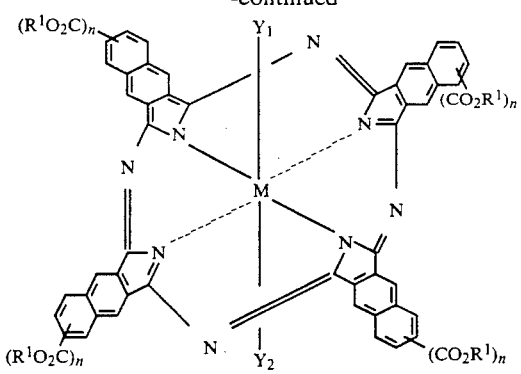

(II)

[in the formulas (I) and (II), $R^1$, n, M, $Y^1$ and $Y_2$ have the same definitions as given previously].

In the following table the substituent $R^1O_2C$ may be positioned at any of 5, 6, 7 and 8 positions.

TABLE

| Compound No. | $R^1$ | n | M | $Y_1$ | $Y_2$ | General formula (I) or (II) |
|---|---|---|---|---|---|---|
| 1 | n-$C_5H_{11}$ | 1 | OV | — | — | (I) |
| 2 | n-$C_8H_{17}$ | 1 | OV | — | — | " |
| 3 | n-$C_{14}H_{29}$ | 1 | OV | — | — | " |
| 4 | n-$C_{16}H_{33}$ | 1 | OV | — | — | " |
| 5 | n-$C_{18}H_{37}$ | 1 | OV | — | — | " |
| 6 | n-$C_{20}H_{41}$ | 1 | OV | — | — | " |
| 7 | n-$C_{22}H_{45}$ | 1 | OV | — | — | " |
| 8 | n-$C_5H_{11}$ | 1 | Cu | — | — | " |
| 9 | n-$C_8H_{17}$ | 1 | Cu | — | — | " |
| 10 | n-$C_{14}H_{29}$ | 1 | Cu | — | — | (I) |
| 11 | n-$C_{20}H_{41}$ | 1 | Cu | — | — | " |
| 12 | n-$C_{18}H_{37}$ | 1 | Cu | — | — | " |
| 13 | n-$C_5H_{11}$ | 1 | Zn | — | — | " |
| 14 | n-$C_8H_{17}$ | 1 | Zn | — | — | " |
| 15 | n-$C_{16}H_{33}$ | 1 | Zn | — | — | " |
| 16 | n-$C_5H_{11}$ | 1 | Ni | — | — | " |
| 17 | n-$C_{14}H_{29}$ | 1 | Ni | — | — | " |
| 18 | n-$C_5H_{11}$ | 1 | Pd | — | — | " |
| 19 | n-$C_{16}H_{33}$ | 1 | Pd | — | — | (I) |
| 20 | n-$C_5H_{11}$ | 1 | Co | — | — | " |
| 21 | n-$C_{20}H_{41}$ | 1 | Co | — | — | " |
| 22 | n-$C_5H_{11}$ | 1 | Mn | — | — | " |
| 23 | n-$C_{22}H_{45}$ | 1 | Mn | — | — | " |
| 24 | n-$C_8H_{17}$ | 1 | AlCl | — | — | " |
| 25 | n-$C_{22}H_{45}$ | 1 | Al | — | — | " |
| 26 | n-$C_{14}H_{29}$ | 1 | Al—OH | — | — | " |
| 27 | n-$C_8H_{17}$ | 1 | In—Cl | — | — | " |
| 28 | n-$C_{16}H_{33}$ | 1 | In—Cl | — | — | (I) |
| 29 | n-$C_5H_{11}$ | 1 | Si | — | — | " |
| 30 | n-$C_{20}H_{41}$ | 1 | Si | — | — | " |
| 31 | n-$C_5H_{11}$ | 1 | Ge | — | — | " |
| 32 | n-$C_{14}H_{29}$ | 1 | Ge | — | — | " |
| 33 | n-$C_5H_{11}$ | 1 | Sn | — | — | " |
| 34 | n-$C_{18}H_{37}$ | 1 | Sn | — | — | " |
| 35 | $CH_3$ | 4 | OV | — | — | " |
| 36 | n-$C_5H_{11}$ | 2 | OV | — | — | " |
| 37 | $CH_3$ | 2 | OV | — | — | (I) |
| 38 | n-$C_5H_{11}$ | 2 | In—Cl | — | — | " |
| 39 | $C_2H_5$ | 4 | In—Cl | — | — | " |
| 40 | n-$C_4H_9$ | 4 | In—Cl | — | — | " |
| 41 | n-$C_5H_{11}$ | 1 | Ge | OSi$(C_2H_5)_3$ | OSi$(C_2H_5)_3$ | (II) |
| 42 | n-$C_{18}H_{37}$ | 1 | Ge | OSi(n-$C_4H_9)_3$ | OSi(n-$C_4H_9)_3$ | " |
| 43 | n-$C_5H_{11}$ | 1 | Ge | OSi(n-$C_4H_9)_3$ | OSi(n-$C_4H_9)_3$ | " |
| 44 | n-$C_8H_{17}$ | 1 | Ge | OSi$(C_2H_5)_3$ | OSi$(C_2H_5)_3$ | " |
| 45 | n-$C_8H_{17}$ | 1 | Ge | OSi(n-$C_4H_9)_3$ | OSi(n-$C_4H_9)_3$ | " |
| 46 | n-$C_{18}H_{37}$ | 1 | Ge | OSi$(C_2H_5)_3$ | OSi$(C_2H_5)_3$ | (II) |
| 47 | n-$C_6H_{13}$ | 1 | Ge | OSi$(C_2H_5)_3$ | OSi$(C_2H_5)_3$ | " |
| 48 | n-$C_4H_9$ | 1 | Ge | OSi(n-$C_4H_9)_3$ | OSi(n-$C_4H_9)_3$ | " |
| 49 | n-$C_{10}H_{21}$ | 1 | Ge | OSi$(C_2H_5)_3$ | OSi$(C_2H_5)_3$ | " |
| 50 | n-$C_7H_{15}$ | 1 | Ge | OSi(n-$C_4H_9)_3$ | OSi(n-$C_4H_9)_3$ | " |
| 51 | $C_2H_5$ | 2 | Ge | OSi(n-$C_4H_9)_3$ | OSi(n-$C_4H_9)_3$ | " |
| 52 | $C_2H_5$ | 4 | Ge | OSi$(C_2H_5)_3$ | OSi$(C_2H_5)_3$ | " |
| 53 | n-$C_5H_{11}$ | 1 | Ge | O(n-$C_{12}H_{25}$) | O(n-$C_{12}H_{25}$) | " |
| 54 | n-$C_5H_{11}$ | 1 | Ge | O(n-$C_{18}H_{37}$) | O(n-$C_{18}H_{37}$) | " |
| 55 | n-$C_8H_{17}$ | 1 | Ge | O(n-$C_{12}H_{25}$) | O(n-$C_{12}H_{25}$) | (II) |
| 56 | n-$C_8H_{17}$ | 1 | Ge | O(n-$C_{18}H_{37}$) | O(n-$C_{18}H_{37}$) | " |
| 57 | n-$C_{18}H_{37}$ | 1 | Ge | O(n-$C_{12}H_{25}$) | O(n-$C_{12}H_{25}$) | " |
| 58 | n-$C_{18}H_{37}$ | 1 | Ge | O(n-$C_{18}H_{37}$) | O(n-$C_{18}H_{37}$) | " |
| 59 | n-$C_{10}H_{21}$ | 1 | Ge | O(t-$C_4H_9$) | O(t-$C_4H_9$) | " |
| 60 | n-$C_{14}H_{29}$ | 1 | Ge | O(t-$C_5H_{11}$) | O(t-$C_5H_{11}$) | " |
| 61 | $C_2H_5$ | 1 | Mn—Cl | — | — | (I) |
| 62 | n-$C_5H_{11}$ | 1 | $GeCl_2$ | — | — | " |
| 63 | n-$C_8H_{17}$ | 1 | $SnCl_2$ | — | — | " |
| 64 | n-$C_5H_{11}$ | 1 | Sn | OSi(n-$C_6H_{13})_3$ | OSi(n-$C_6H_{13})_3$ | (II) |
| 65 | n-$C_8H_{17}$ | 1 | Sn | OSi(n-$C_4H_9)_3$ | OSi(n-$C_4H_9)_3$ | " |
| 66 | n-$C_5H_{11}$ | 1 | Sn | OSi(n-$C_3H_7)_3$ | OSi(n-$C_3H_7)_3$ | " |

TABLE-continued

| Compound No. | R¹ | n | M | Y₁ | Y₂ | General formula (I) or (II) |
|---|---|---|---|---|---|---|
| 67 | n-$C_8H_{17}$ | 1 | Sn | $OSi(C_2H_5)_3$ | $OSi(C_2H_5)_3$ | " |
| 68 | $CH_3$ | 1 | Ti | $OSi(n-C_4H_9)_3$ | $OSi(n-C_4H_9)_3$ | " |
| 69 | n-$C_5H_{11}$ | 1 | Al | $OSi(n-C_6H_{13})_3$ | — | " |
| 70 | n-$C_5H_{11}$ | 1 | Al | $OC_6H_5$ | — | " |
| 71 | $C_2H_5$ | 1 | Sn | $OC_2H_5$ | $OC_2H_5$ | " |
| 72 | $CH_3$ | 1 | Si | $OSi(C_6H_5)_3$ | $OSi(C_6H_5)_3$ | " |
| 73 | n-$C_4H_9$ | 1 | Ge | $OC(C_6H_5)_3$ | $OC(C_6H_5)_3$ | (II) |
| 74 | n-$C_5H_{11}$ | 1 | Sn | $O(n-C_8H_{17})$ | $O(n-C_8H_{17})$ | " |

The third aspect of the present invention relates to a process for producing a naphthalocyanine derivative represented by the general formula (I).

The naphthalocyanine derivative represented by the general formula (I) can be obtained by reacting 1 mole of an alkoxycarbonyl-2,3-dicyanonaphthalene represented by the general formula (III) with 0.1–1 mole of a metal or metal salt represented by the general formula (IV) with heating. The reaction temperature is preferably 150°–300° C. and the reaction time is preferably 30 minutes to 10 hours. To obtain these conditions, it is preferred that the reaction be conducted without using any solvent or using a solvent such as urea, tetralin, quinoline, 1-chloronaphthalene, 1-bromonaphthalene, 1,2,3-trimethylbenzene, dichlorobenzene, trichlorobenzene or the like. The metal or metal salt includes Mg, Zn, $AlCl_3$, $InCl_3$, $SiCl_4$, $GeCl_4$, $SnCl_2$, $PbCl_2$, $TiCl_4$, $VCl_3$, $CrCl_2$, $MoCl_2$, $Mn(OCOCH_3)_2$, $FeCl_3$, $CoCl_2$, $NiCl_2$, $PtCl_2$, $PdCl_2$, etc.

The isolation of the resulting naphthalocyanine derivative from the reaction mixture and the subsequent purification of the derivative can be conducted by, for example, a method of washing the reaction mixture with dilute hydrochloric acid, then thoroughly washing the resulting product with a poor solvent for naphthalocyanines, such as water, alcohol, acetone or the like, extracting the resulting product with a halogenated hydrocarbon solvent or an aromatic hydrocarbon solvent, and concentrating the resulting extract to dryness to collect a solid.

The alkoxycarbonyl-2,3-dicyanonaphthalene represented by the general formula (III) can be produced as follows, for example:

In one method, an alkoxycarbonyl-o-xylene represented by the general formula (IX)

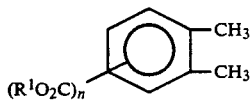

(IX)

[in the formula (IX), R¹ is an alkyl group of 1–22 carbon atoms and n is an integer of 1–4] and N-bromosuccinimide represented by the formula (X)

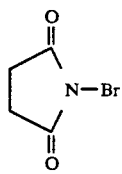

(X)

are reacted with heating under light irradiation to obtain a compound represented by the general formula (XI)

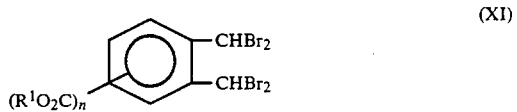

(XI)

[in the formula (XI), R¹ is an alkyl group of 1–22 carbon atoms and n is an integer of 1–4]; and the compound represented by the general formula (XI) is reacted with fumaronitrile represented by the formula (XII)

(XII)

with heating to obtain an alkoxycarbonyl-2,3-dicyanonaphthalene represented by the general formula (III).

In other method, an alkoxycarbonyl-2,3-dicyanonaphthalene of the general formula (III) obtained in the above method

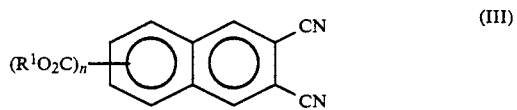

(III)

[in the formula (III), R¹ and n have the same definitions as given previously] is reacted with an alcohol represented by the general formula (XIII)

R⁴OH (XIII)

[in the formula (XIII), R⁴ is an alkyl group of 1–22 carbon atoms different from R¹] with heating to obtain another alkoxycarbonyl-2,3-dicyanonaphthalene represented by the general formula (III')

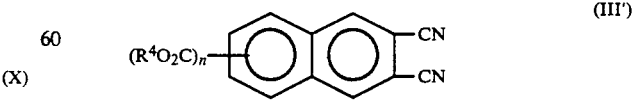

(III')

[in the formula (III'), R⁴ is an alkyl group of 1–22 carbon atoms and n is an integer of 1–4].

In general, the reaction of the alkoxycarbonyloxylene represented by the general formula (IX) with N-bromosuccinimide represented by the formula (X)

can be conducted by refluxing, with heating, 0.2 mole of the alkoxycarbonyl-o-xylene and 0.8 mole of N-bromosuccinimide under the irradiation by a high pressure mercury lamp, in a solvent inactive to the light for 4–12 hours. The reaction requires the addition of a peroxide (a radical generating agent) as a reaction initiator. As the peroxide, there can be mentioned benzoyl peroxide, octanoyl peroxide, cyclohexanone peroxide, isobutyryl peroxide, 2,4-dichlorobenzoyl peroxide, methyl ethyl ketone peroxide, etc. The peroxide is used in an amount of ordinarily 500 mg to 2 g per 500 ml of the solvent. The solvent inactive to the light is appropriately selected from halogenated hydrocarbon solvents such as chloroform, carbon tetrachloride and the like and aromatic hydrocarbon solvents such as benzene, chlorobenzene and the like.

The reaction of the compound of the general formula (XI) with fumaronitrile of the formula (XII) is conducted using 1 mole of the former compound and 1–2 moles of the latter compound. The reaction temperature is preferably 70°–100° C. and the reaction time is preferably 5–10 hours. As the solvent, there are preferably used polar organic solvents such as N,N-dimethylformamide, N,N-dimethylacetamide, dimethyl sulfoxide, N,N-diethylformamide, N,N-diethylacetamide and the like.

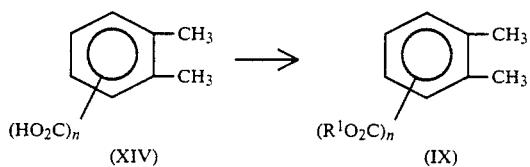

That is, 1 mole of a hydroxycarbonyl-o-xylene represented by the formula (XIV) [in the formula (XIV), n is an integer of 1–4] and at least 1 mole of an alcohol represented by $R^1OH$ ($R^1$ is an alkyl group of 1–22 carbon atoms) are subjected to heating and dehydration in the presence of a solvent or in the absence of any solvent using 25–50 mole %, based on the hydroxycarbonyl-o-xylene, of a Lewis acid as a catalyst to obtain an alkoxycarbonyl-o-xylene represented by the general formula (IX). As the solvent, there are preferably used benzene, toluene, xylene, chlorobenzene, dichlorobenzene, trimethylbenzene, 1-chloronaphthalene, etc. As the catalyst, there are preferably used sulfuric acid, p-toluenesulfonic acid, benzenesulfonic acid, etc. The reaction temperature is preferably 80°–240° C. and the reaction time is preferably 1–10 hours.

1 mole of an alkoxycarbonyl-2,3-dicyanonaphthalene represented by the general formula (III) [in the formula (III), $R^1$ is an alkyl group of 1–22 carbon atoms and n is an integer of 1–4] and at least 1 mole of an alcohol represented by the general formula (XIII) are subjected to heating and refluxing in the presence of a solvent or in the absence of any solvent using, as a catalyst, a Lewis acid of an amount at least equal (in terms of moles) to that of the alkoxycarbonyl-2,3-dicyanonaphthalene, to effect a transesterification reaction, whereby another alkoxycarbonyl-2,3-dicyanonaphthalene can be obtained. As the solvent, there are preferably used benzene, toluene, xylene, chlorobenzene, dichlorobenzene, trimethylbenzene, 1-chloronaphthalene, etc. As the catalyst, there are preferably used sulfuric acid, p-toluenesulfonic acid, benzenesulfonic acid, etc. The reaction temperature is preferably 80°–240° C. and the reaction time is preferably 1–50 hours.

The isolation of the alkoxycarbonyl-2,3-dicyanonaphthalene represented by the general formula (III) [in the formula (III), $R^1$ is an alkyl group of 1–22 carbon atoms] from the reaction mixture and the subsequent purification of the isolation product can be conducted by extracting the reaction mixture with chloroform and then subjecting the extract to recrystallization, column chromatography, etc.

The fourth aspect of the present invention relates to a process for producing a naphthalocyanine derivative represented by the general formula (II)

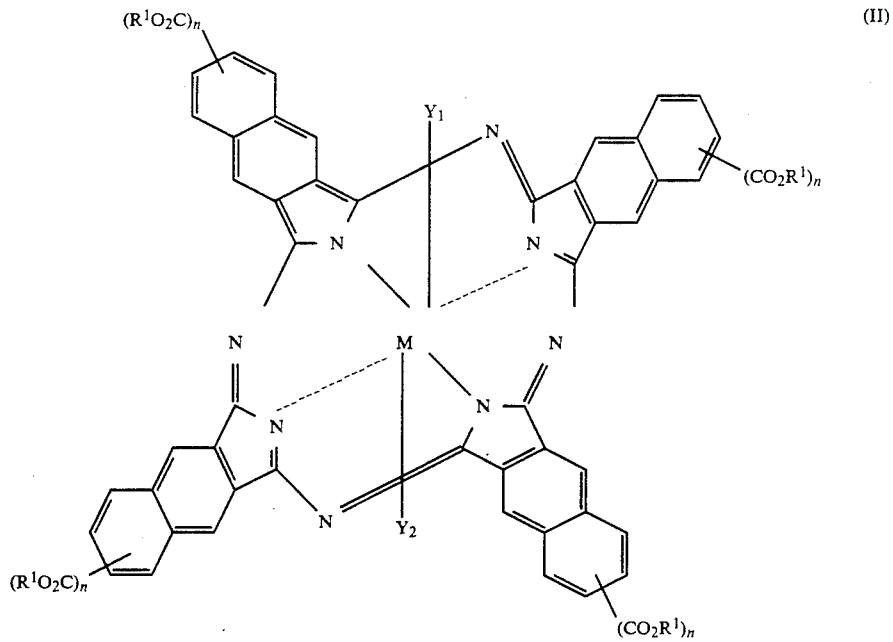

[in the formula (II), $R^1$, n, $Y_1$, $Y_2$ and M have the same definitions as given previously with respect to the formula (II)], the process comprising reacting an alkoxycarbonyl-2,3-dicyanonaphthalene represented by the general formula (III)

(III)

different; each n is an integer of 1-4 and a plurality of ns may be same or different; X is a halogen atom], hydrolyzing the compound represented by the formula (V) to obtain a naphthalocyanine derivative represented by the general formula (VI)

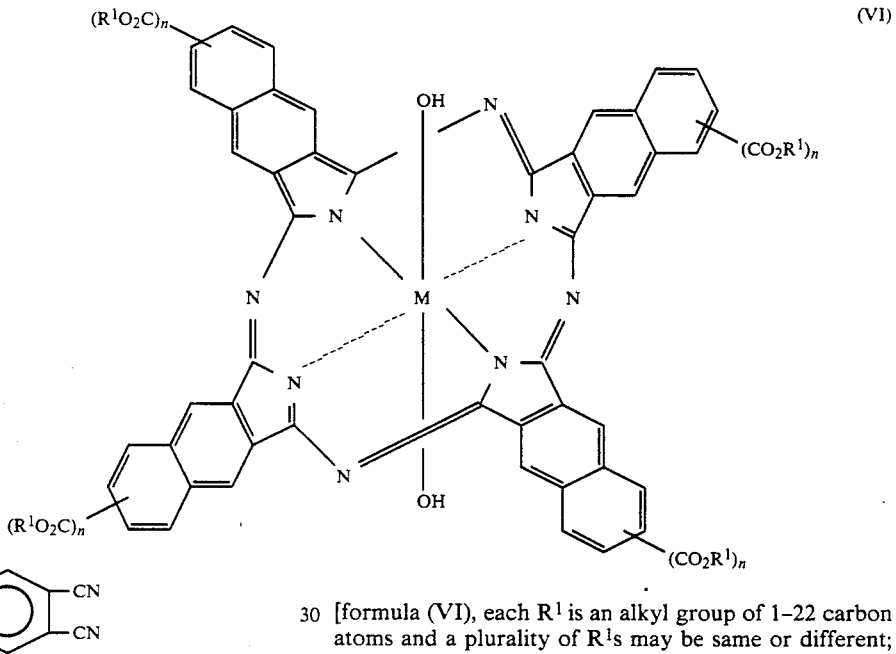

(VI)

[in the formula (III), $R^1$ and n have the same definitions as given previously] with a metal halide represented by the general formula (IV-1)

$$MX_p \quad (IV-1)$$

[in the formula (IV-1), M, X and p have the same definitions as given previously] to synthesize a naphthalocyanine derivative represented by the general formula (V)

[formula (VI), each $R^1$ is an alkyl group of 1-22 carbon atoms and a plurality of $R^1$s may be same or different; each n is an integer of 1-4 and a plurality of ns may be same or different], and then reacting the compound represented by the formula (VI) with a silanol represented by the general formula (VII)

$$(R^2)_3SiOH \quad (VII)$$

[in the formula (VII), $R^2$ is an alkyl group, an aryl group, an alkoxyl group or an aryloxyl group] or with an alcohol represented by the general formula (VIII)

$$R^3OH \quad (VIII)$$

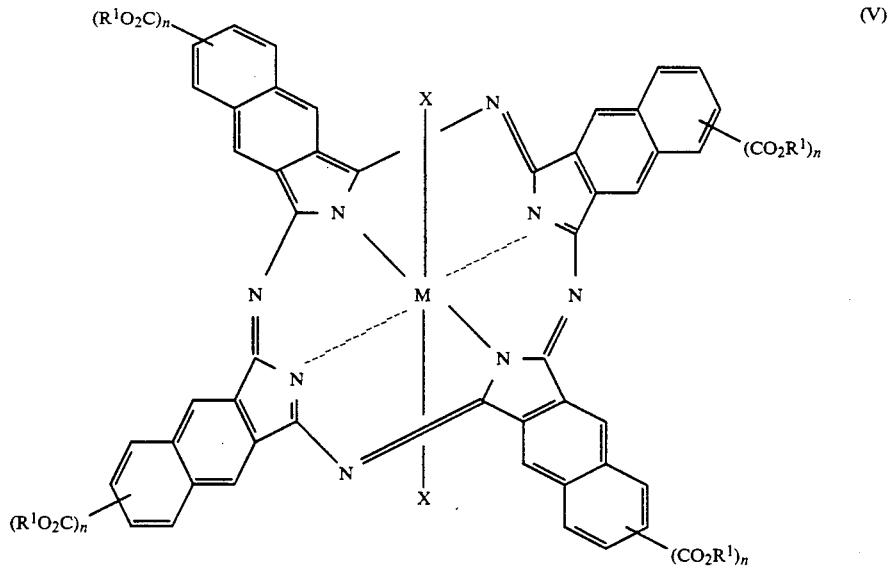

(V)

[in the formula (V), each $R^1$ is an alkyl group of 1-22 carbon atoms and a plurality of $R^1$s may be same or

[in the formula (VIII), $R^3$ is an alkyl group, an aryl group or a trityl group].

The naphthalocyanine derivative represented by the general formula (II) can be obtained by subjecting a compound represented by the general formula (VI) and a large excess of a silanol represented by the general formula (VII) or an alcohol represented by the general formula (VIII) to heating and dehydration. In this case, the reaction temperature is preferably 80°–250° C. and the reaction time is preferably 30 minutes to 10 hours. The reaction is conducted in the presence of a solvent or in the absence of any solvent. As the solvent, there are preferably used benzene, toluene, xylene, trimethylbenzene, chlorobenzene, dichlorobenzene, trichlorobenzene, 1-chloronaphthalene, tetralin, quinoline, etc.

The isolation of the naphthalocyanine derivative represented by the general formula (II) from the reaction mixture and its purification can be conducted by subjecting the reaction mixture to column chromatography or to thin layer chromatography and then purifying the isolation product by recrystallization.

The naphthalocyanine derivative represented by the general formula (VI) can be obtained by hydrolyzing a compound represented by the general formula (V) with heating. The reaction temperature is preferably 50°–150° C. and the reaction time is preferably 30 minutes to 10 hours. To achieve these conditions, it is preferred that the reaction be conducted in a mixed solvent such as pyridine/water, pyridine/aqueous ammonia, methanol/aqueous ammonia, ethanol/aqueous ammonia, propanol/aqueous ammonia and the like.

The naphthalocyanine derivative represented by the general formula (V) can be obtained by reacting 1 mole of an alkoxycarbonyl-2,3-dicyanonaphthalene represented by the general formula (III) with 0.25–1 mole of a metal halide represented by the general formula (IV-1) with heating. The reaction temperature is preferably 150°–300° C. and the reaction time is preferably 30 minutes to 5 hours. To achieve these conditions, it is preferred that the reaction be conducted in the presence of a solvent or in the absence of any solvent. As the solvent, there are preferably used urea, tetralin, quinoline, 1-chloronaphthalene, 1-bromonaphthalene, 1,2,4-trimethylbenzene, 1,2,3-trimethylbenzene, dichlorobenzene, trichlorobenzene, etc. The metal halide includes $AlCl_3$, $TiCl_4$, $SiCl_4$, $GeCl_4$, $SnCl_2$, $SnI_2$, etc.

The alkoxycarbonyl-2,3-dicyanonaphthalene represented by the general formula (III) can be produced according to one of the methods previously described in the third aspect of the present invention.

The optical information recording medium which is the fifth aspect of the present invention comprises (a) a substrate and (b) a recording film layer formed thereon and composed mainly of a naphthalocyanine derivative represented by the general formula (I) and/or (II) which is the first and/or second aspect of the present invention. This medium can further comprises other layers such as an underlying layer (beneath the recording film layer) and a protective layer, as necessary.

The material used for the substrate is already known to those skilled in the art and can be transparent or nontransparent to a laser beam used. However, when writing and reading out are conducted with a laser beam from the substrate side of the recording medium, the substrate material must be transparent to the laser beam. When writing and reading out are conducted from the side of the recording medium opposite to the substrate side, the substrate material need not be transparent to the laser beam used. As the substrate material, there can be mentioned inorganic materials such as glass, quartz, mica, ceramics, metal sheet or foil and the like; paper; and sheets of organic polymers such as polycarbonate, polyester, cellulose acetate, nitrocellulose, polyethylene, polypropylene, polyvinyl chloride, vinylidene chloride copolymer, polyamide, polystyrene, polymethyl methacrylate, methyl methacrylate copolymer and the like. The substrate material is not restricted to these. Desirably, the substrate is composed of an organic polymer of low heat conductivity because such a polymer can minimize heat loss during recording and can increase the sensitivity. The substrate can have guide grooves formed by convexes and concaves, as necessary.

The sixth aspect of the present invention relates to a process for producing an optical information recording medium, which comprises forming a recording film layer on a substrate by coating on the substrate an organic solvent solution containing mainly a naphthalocyanine derivative represented by the general formula (I) and/or (II).

The organic solvent is selected from organic solvents capable of dissolving the naphthalocyanine derivative represented by the general formula (I) or (II), such as the above mentioned aromatic hydrocarbons, halogenated hydrocarbons, ethers, ketones and saturated hydrocarbons. It can be a single solvent or a mixed solvent. The organic solvent must not attack the substrate.

The aromatic hydrocarbon solvents include benzene, toluene, xylene, chlorobenzene, dichlorobenzene, trimethylbenzene, 1-chloronaphthalene, quinoline, etc; the halogenated hydrocarbon solvents include methylene chloride, chloroform, carbon tetrachloride, trichloroethane, etc.; the ether solvents include diethyl ether, dibutyl ether, tetrahydrofuran, ethylene glycol monomethyl ether, ethylene glycol dimethyl ether, diethylene glycol monomethyl ether, diethylene glycol dimethyl ether, etc.; the ketone solvents include acetone, methyl ethyl ketone, methyl propyl ketone, cyclopentanone, cyclohexanone, acetone alcohol, etc.; and the saturated hydrocarbon solvents include pentane, hexane, heptane, octane, nonane, decane, undecane, etc.

The formation of a recording film layer on a substrate by coating on the substrate an organic solvent solution containing a naphthalocyanine derivative represented by the general formula (I) and/or (II) can be conducted according to a coating method, a printing method, a dipping method or the like. Specifically, the naphthalocyanine is dissolved in one of the above mentioned solvents and the resulting solution is applied on the substrate by spraying, roller coating, spin coating, dipping or the like. During formation of a recording medium, it is possible to add, as necessary, a binder (e.g. polymer binder), a stabilizer, etc. to the solution. As the binder, there can be mentioned a polyimide resin, a polyamide resin, a polystyrene resin, an acrylic resin, etc., but the binder is not restricted to these.

The recording layer material can be a single material or a combination of at least two materials. In the latter case, the recording layer can have a laminate structure consisting of a plurality of layers or a single layer structure consisting of a mixed material. The thickness of the recording layer is preferably 50–10,000 Å, particularly 100–5,000 Å.

A reflected light is often used when a recorded image is regenerated optically. In this case, when writing and reading out are conducted from the substrate side, it is possible to provide, on the surface of the recording layer opposite to the substrate, a metal layer of high reflectivity as an effective means of obtaining an increased contrast. When writing and reading out are conducted from the recording layer side, it is possible to provide a metal layer of high reflectivity between the substrate and the recording layer. As the metal of high reflectivity, there can be used, Al, Cr, Au, Pt, Sn, etc. This metal layer can be formed according to a known tecknique for thin film formation, such as vaccum vapor deposition, sputtering, plasma vapor deposition or the like. The thickness of the metal layer is selected between 100 Å and 10,000 Å.

It is not necessary to provide a reflecting metal layer when the recording layer is composed of a naphthalocyanine derivative represented by the general formula (II), because the derivative has a high reflectivity by itself.

When the surface smoothness of the substrate has a problem, it is desirable to form a uniform film of an organic polymer on the substrate. As such a polymer, there can be used a commercially available polymer such as polyester, polyvinyl chloride or the like.

It is also possible to form, as an outermost layer, a protective layer composed mainly of an organic polymer to increase the stability and safety of the recording medium and further to form a layer capable of increasing the reduced sensitivity caused by the reduction of surface reflectivity. As such an organic polymer, there can be used a polyvinylidene chloride, a polyvinyl chloride, a vinylidene chloride-acrylonitrile copolymer, a polyvinyl acetate, a polyimide, a polymethyl methacrylate, a polystyrene, a polyisoprene, a polybutadiene, a polyurethane, a polyvinyl butyral, a fluororubber, a polyester, an epoxy resin, a silicone resin, cellulose acetate, etc. These organic polymers can be used singly or as a mixture of two or more. Allowing the protective layer to contain a silicone oil, an antistatic agent, a crosslinking agent, etc. is desirable to increase the capabilities of the recording layer. The protective layer can be formed in two layers. The protective layer can be formed by dissolving an organic polymer in an appropriate solvent and coating the resulting solution or by preparing a thin film of an organic polymer and laminating the film on the recording layer or on the metal layer. The thickness of the protective layer is 0.1-10 μm, preferably 0.1-2 μm.

The present invention is illustrated by way of the following Examples, but it is in no way restricted to these Examples.

SYNTHESIS EXAMPLE 1

Synthesis of methyl 3,4-dimethylbenzoate 47.6 g (0.317 mol) of 3,4-dimethylbenzoic acid was added to 200 ml of methanol. The resulting mixture was refluxed in the presence of about 6 ml of concentrated sulfuric acid for about 4 hours with continuous extraction of water by using Molecular Sieves 3A (a desiccant manufactured by Wako Pure Chemical Industries, Ltd.). After cooling, about 600 ml of water was added thereto. The whole mixture was extracted with about 200 ml of benzene three times. The benzene solution was washed with a saturated aqueous sodium hydrogencarbonate solution three times and then with water three times. Thereto was added anhydrous sodium sulfate to dry the benzene solution. The dried benzene solution was concentrated and then subjected to distillation under reduced pressure to obtain 49.4 g of a colorless liquid having a boiling point of 133°-134° C. at 30 mmHg. The following analytical results confirmed that the liquid was methyl 3,4-dimethylbenzoate.

| (1) Elemental analysis | | |
|---|---|---|
| | C | H |
| Calculated (%) | 73.15 | 7.37 |
| Found (%) | 73.13 | 7.46 |

(2) NMR spectrum (solvent: CDCl$_3$)
δ7.81 (1H, br-s); 7.76 (1H, dd, J=7.93, 1.53 Hz); 7.18 (1H, d, J=7.93 Hz); 3.89 (3H, s); 2.30 (6H, s);

(3) IR spectrum (neat)
Shown in FIG. 1. There is an absorption attributable to the stretching vibration of C=O of ester, at about 1710 cm$^{-1}$.

SYNTHESIS EXAMPLE 2

Synthesis of 6-methoxycarbonyl-2,3-dicyanonaphthalene 1 g of benzoyl peroxide was added to a solution of 33.8 g (0.2 mol) of methyl 3,4-dimethylbenzoate and 142.4 g (0.88 mol) of N-bromosuccinimide dissolved in 500 ml of carbon tetrachloride. The mixture was refluxed for 8 to 12 hours under light irradiation by a high pressure mercury lamp (100 W). After cooling, the resulting white crystal precipitated was removed by filtration. The filtrate was concentrated under reduced pressure to remove carbon tetrachloride. The resulting solid was recrystallized from hexane/methylene chloride to obtain 79 g of methyl 3,4-bis(dibromomethyl)benzoate as a colorless crystal. This methyl 3,4-bis(dibromomethyl)benzoate has the following properties.

(1) Melting point: 99.5°-100.5° C.

| (2) Elemental analysis | | | |
|---|---|---|---|
| | C | H | Br |
| Calculated (%) | 25.03 | 1.68 | 66.62 |
| Found (%) | 25.07 | 1.54 | 65.72 |

Figure 2:
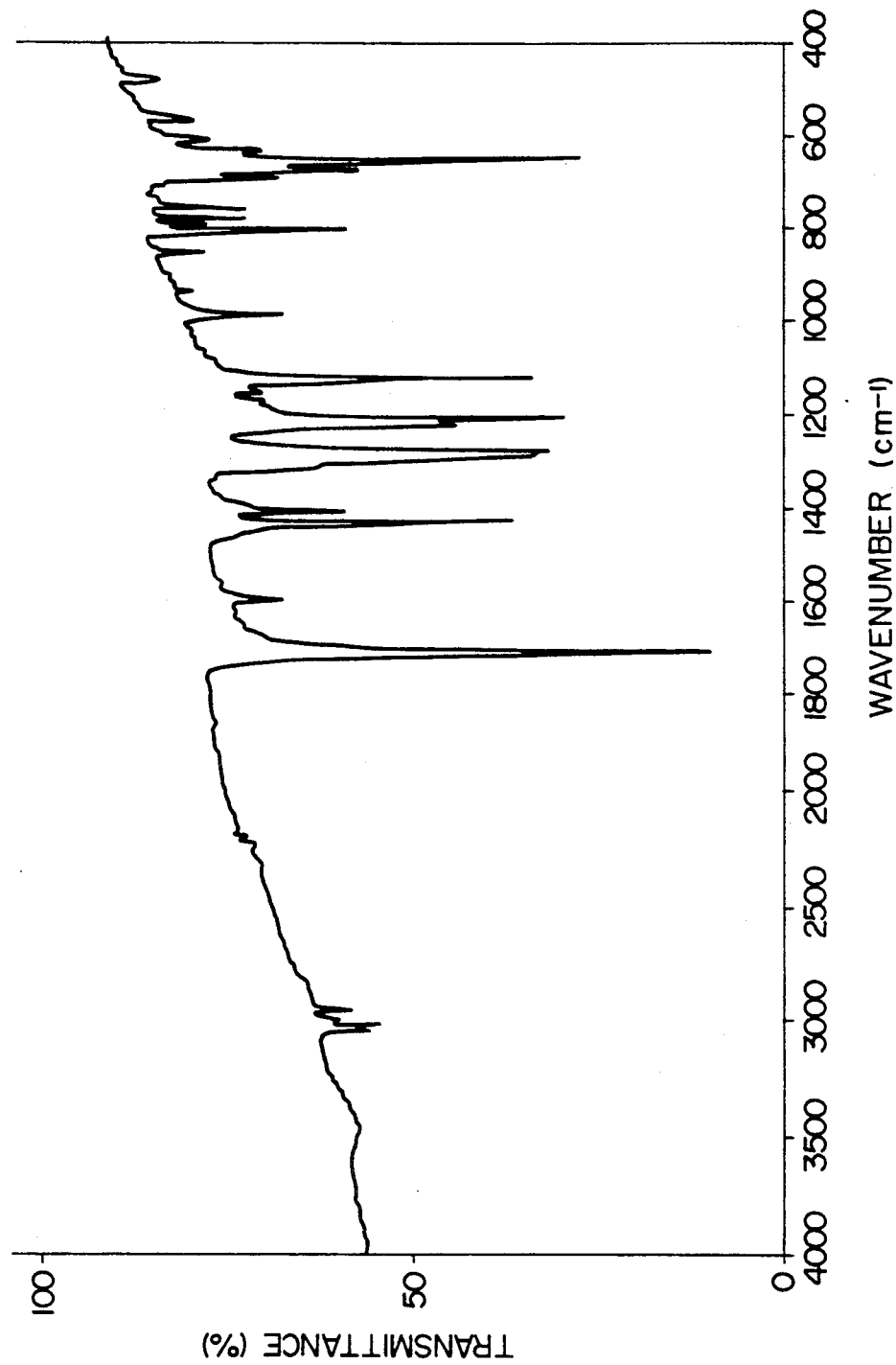
FIG. 2 is an IR spectrum of methyl 3,4-bis(dibromomethyl)benzoate.

(3) NMR spectrum (solvent: CDCl$_3$)
δ 8.29 (1H, br-s); 8.03 (1H, dd, J=8.24, 1.53 Hz); 7.81 (1H, d, J=8.24 Hz); 7.18 (1H, br-s); 7.09 (1H, br-s); 3.96 (3H, s);

(4) IR spectrum (KBr)
Shown in FIG. 2. There is an absorption attributable to the stretching vibration of C=O of ester, at about 1305 cm$^{-1}$.

To a solution of 48 g (0.1 mol) of the above obtained methyl 3,4-bis(dibromomethyl)benzoate and 3.5 g (0.173 mol) of fumaronitrile dissolved in 400 ml of anhydrous N,N-dimethylformamide was added 100 g (0.67 mol) of sodium iodide with thorough stirring. The mixture was stirred at about 75° C. for about 7 hours in a nitrogen atmosphere. After the reaction, the reaction mixture was poured into about 2 kg of ice. Thereto was slowly added sodium hydrogensulfite until the reddish brown solution turned light yellow. Further, a slight excess of sodium hydrogensulfite was added and stirring was conducted for a while. Then, the mixture was allowed to stand overnight at room temperature. The resulting light yellow solid was collected by filtration and thoroughly washed with water and methanol in this order. The light yellow solid was then recrystallized from acetone/methanol to obtain 13.9 g of colorless needles. The following analytical results confirmed that the crystal was 6-methoxycarbonyl-2,3-dicyanonaphthalene.

(1) Melting point: 264°–265° C.

| | (2) Elemental analysis | | |
|---|---|---|---|
| | C | H | N |
| Calculated (%) | 71.18 | 3.41 | 11.86 |
| Found (%) | 71.21 | 3.37 | 11.87 |

(3) NMR spectrum (solvent: $CDCl_3$)

δ 8.72 (1H, br-s); 8.47 (1H, s); 8.41 (1H, s); 8.38 (1H, dd, J=8.55, 1.53 Hz); 8.06 (1H, d, J=8.55 Hz); 4.04 (3H, s);

(4) IR spectrum (KBr)

Figure 3:
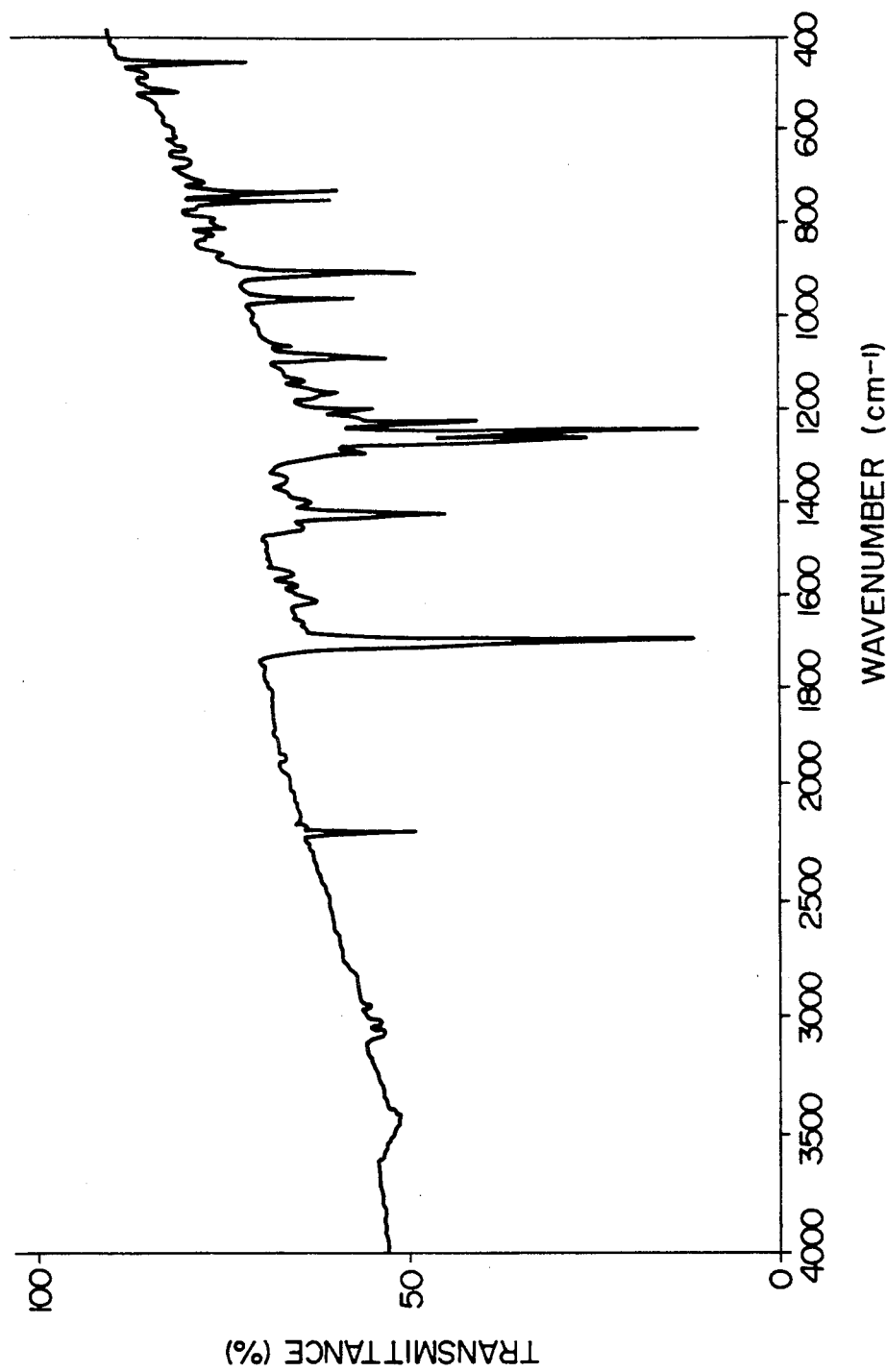
FIG. 3 is an IR spectrum of 6-methoxycarbonyl-2,3-dicyanonaphthalene.

Shown in FIG. 3. There is an absorption attributable to the strentching vibration of C=O of ester, at about 1,700 $cm^{-1}$.

SYNTHESIS EXAMPLE 3

Synthesis of n-amyl 3,4-dimethylbenzoate

To 150 ml of benzene were added 60 g (0.4 mol) of 3,4-dimethylbenzoic acid, 43 ml (0.4 mol) of n-amyl alcohol and 22 g (0.116 mol) of p-toluenesulfonic acid monohydrate. The mixture was refluxed for about 6 hours with continuous extraction of water by using a Dean-Stark trap and then Molecular Sieves 3A. After cooling, the reaction mixture was washed with 100 ml of a saturated aqueous sodium hydrogencarbonate solution three times and then with water three times. The resulting benzene solution was dried with anhydrous magnesium sulfate and concentrated under reduced pressure. The resulting oil was subjected to distillation under reduced pressure to obtain 77 g of a colorless liquid having a boiling point of 145°–148° C. at 8 mmHg. The following analytical results confirmed that the liquid was n-amyl 3,4-dimethylbenzoate.

| | (1) Elemental analysis | |
|---|---|---|
| | C | H |
| Calculated (%) | 76.33 | 9.15 |
| Found (%) | 76.22 | 9.25 |

(2) NMR spectrum (solvent: $CDCl_3$)

δ 7.81 (1H, br-s); 7.77 (1H, dd, J=7.94, 1.98 Hz); 7.18 (1H, d, J=7.94 Hz); 4.29 (2H, t, J=6.72 Hz); 2.30 (6H, s); 1.76 (2H, quintet, J=6.72 Hz); 1.40 (4H, m); 0.93 (3H, t, J=6.72 Hz).

(3) IR spectrum (neat)

Figure 4:
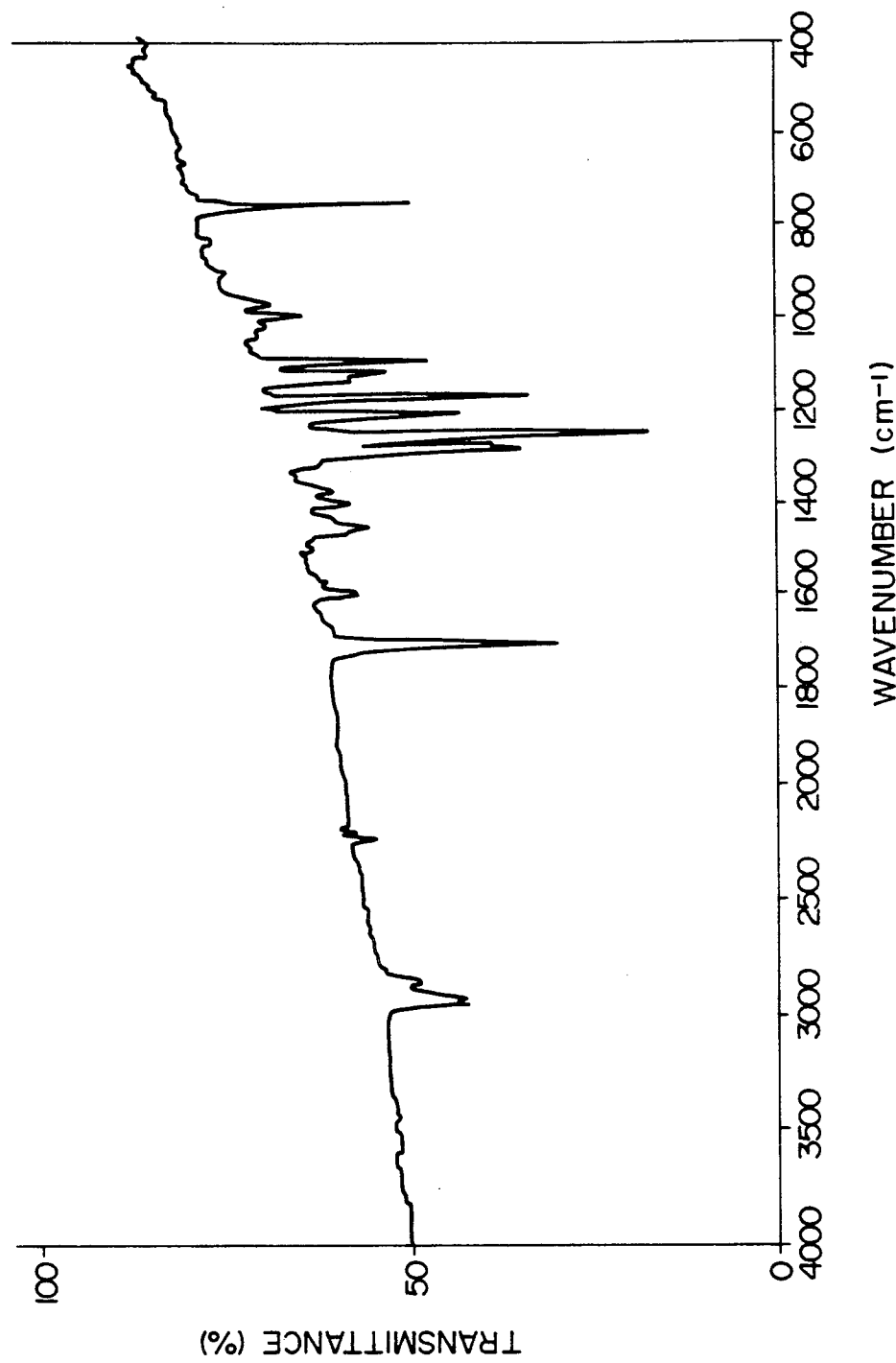
FIG. 4 is an IR spectrum of n-amyl 3,4-dimethylbenzoate.

Shown in FIG. 4. There is an absorption attributable to the stretching vibration of C=O of ester, at about 1,710 $cm^{-1}$.

SYNTHESIS EXAMPLE 4

Synthesis of 6-(n-amyloxycarbonyl)-2,3-dicyanonaphthalene 1 g of benzoyl peroxide was added to a solution of 44.1 g (0.2 mol) of n-amyl 3,4-dimethylbenzoate and 142.4 g (0.8 mol) of N-bromosuccinimide dissolved in 500 ml of carbon tetrachloride. The mixture was refluxed in for 11 hours under light irradiation by a high pressure mercury lamp (100 W). After cooling, the resulting white crystal precipitated was removed by filtration. The filtrate (the carbon tetrachloride solution) was concentrated sufficiently under reduced pressure. The resulting light brown oil was dissolved in 800 ml of N,N-dimethylformamide. To the solution were added 27 g (0.346 mol) of fumaronitrile and then, with thorough stirring, 200 g (1.34 mol) of sodium iodide. The mixture was stirred in a nitrogen atmosphere at 75° C. for about 7 hours. After the reaction, the reaction mixture was poured into about 4 kg of ice. Thereto was added sodium hydrogensulfite until the reddish brown aqueous solution turned light yellow. Further, a slight excess of sodium hydrogensulfite was added and stirring was conducted for a while. The mixture was allowed to stand overnight at room temperature. The resulting light yellow solid was collected by filtration. The solid was washed with water thoroughly and then with methanol several times. The light yellow solid was dissolved in about 500 ml of chloroform. The chloroform layer was separated from the aqueous layer and dried over anhydrous magnesium sulfate. The resulting chloroform solution was concentrated under reduced pressure, and the residue was recrystallized twice from chloroform/ethanol to obtain 20 g of colorless needles. The following analytical results confirmed that the crystal was 6-(n-amyloxycarbonyl)-2,3-dicyanonaphthalene.

(1) Melting point: 150°–152° C.

| | (2) Elemental analysis | | |
|---|---|---|---|
| | C | H | N |
| Calculated (%) | 73.95 | 5.52 | 9.52 |
| Found (%) | 73.82 | 5.38 | 9.51 |

(3) NMR spectrum (solvent: $CDCl_3$)

δ 8.70 (1H, br-s); 8.49 (1H, s); 8.41 (1H, s); 8.38 (1H, dd, J=8.55, 1.53 Hz); 8.06 (1H, d, J=8.55 Hz); 4.43 (2H, t, J=6.72 Hz); 1.84 (2H, quintet, J=6.72 Hz); 1.44 (4H, m); 0.96 (3H, t, J=6.72 Hz).

(4) IR spectrum (KBr)

Figure 5:
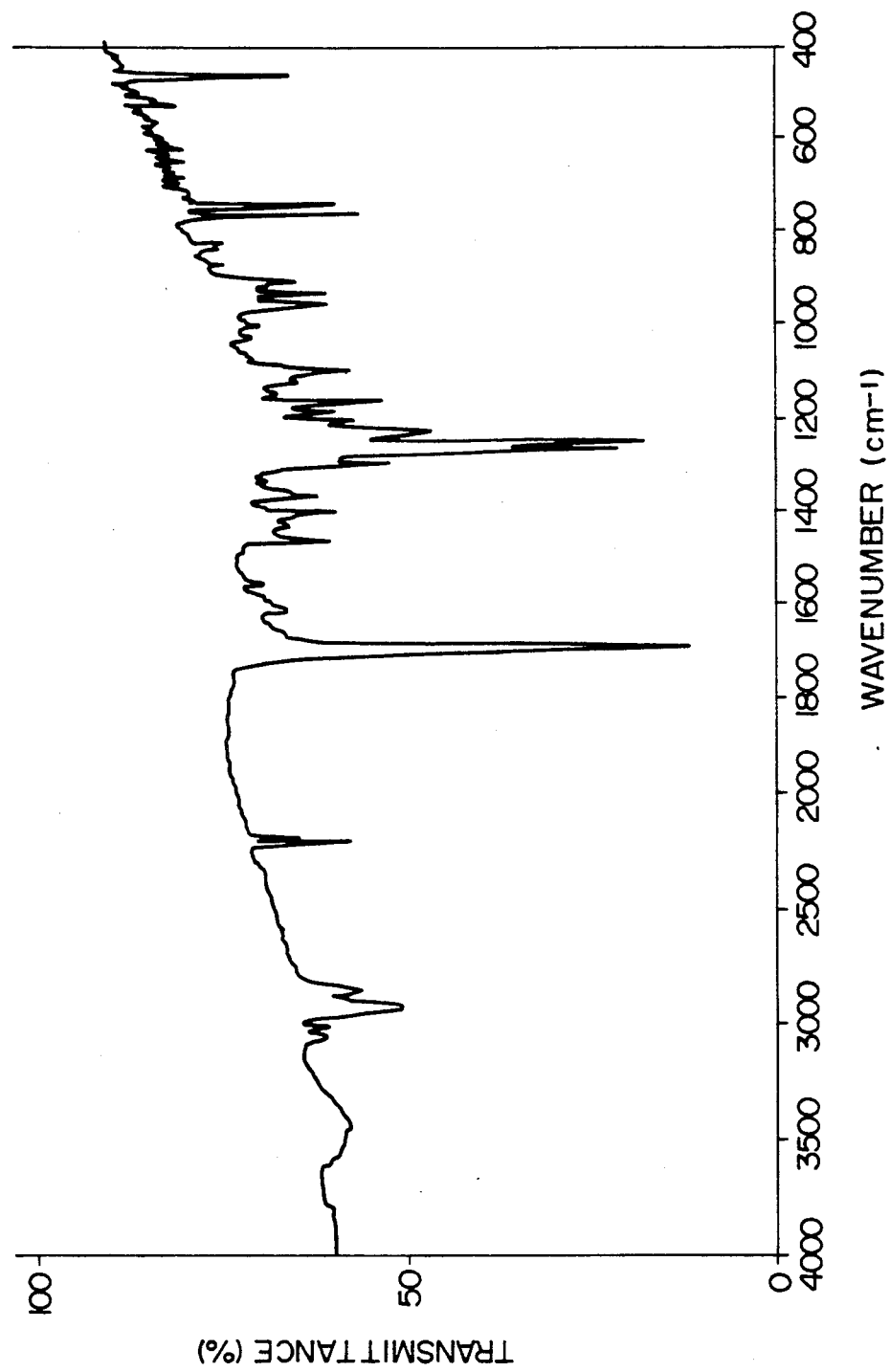
FIG. 5 is an IR spectrum of 6-(n-amyloxycarbonyl)-2,3-dicyanonaphthalene.

Shown in FIG. 5. There is an absorption attributable to the stretching vibration of C=O of ester, at about 1,700 $cm^{-1}$.

SYNTHESIS EXAMPLE 5

Synthesis of n-octyl 3,4-dimethylbenzoate

To 100 ml of benzene were added 40 g (0.27 mol) of 3,4-dimethyl benzoic acid, 100 ml (0.635 mol) of n-octanol and 22 g (0.116 mol) of p-toluenesulfonic acid monohydrate. The mixture was refluxed for about 6 hours with continuous extraction of water by using a Dean-Stark trap and then Molecular Sieves 3A. After cooling, the reaction mixture was treated in the same manner as in Synthesis Example 3 and then subjected to distillation under reduced pressure to obtain 60.5 g of a colorless liquid having a boiling point of 148°–152° C. at 3 mmHg. The following analytical results confirmed that the liquid was n-octyl 3,4-dimethylbebzoate.

| | (1) Elemental analysis | |
|---|---|---|
| | C | H |
| Calculated (%) | 77.82 | 9.99 |
| Found (%) | 77.21 | 10.07 |

(2) NMR spectrum (solvent: $CDCl_3$)

δ 7.81 (1H, br-s); 7.77 (1H, dd, J=7.63, 1.83 Hz); 7.19 (1H, d, J=7.63 Hz); 4.29 (2H, t, J=6.72 Hz); 2.31 (6H, s); 1.76 (2H, quintet, J=6.72 Hz); 1.1-1.5 (10H, m); 0.88 (3H, t, J=6.72 Hz).

(3) IR spectrum (neat)

Figure 6:
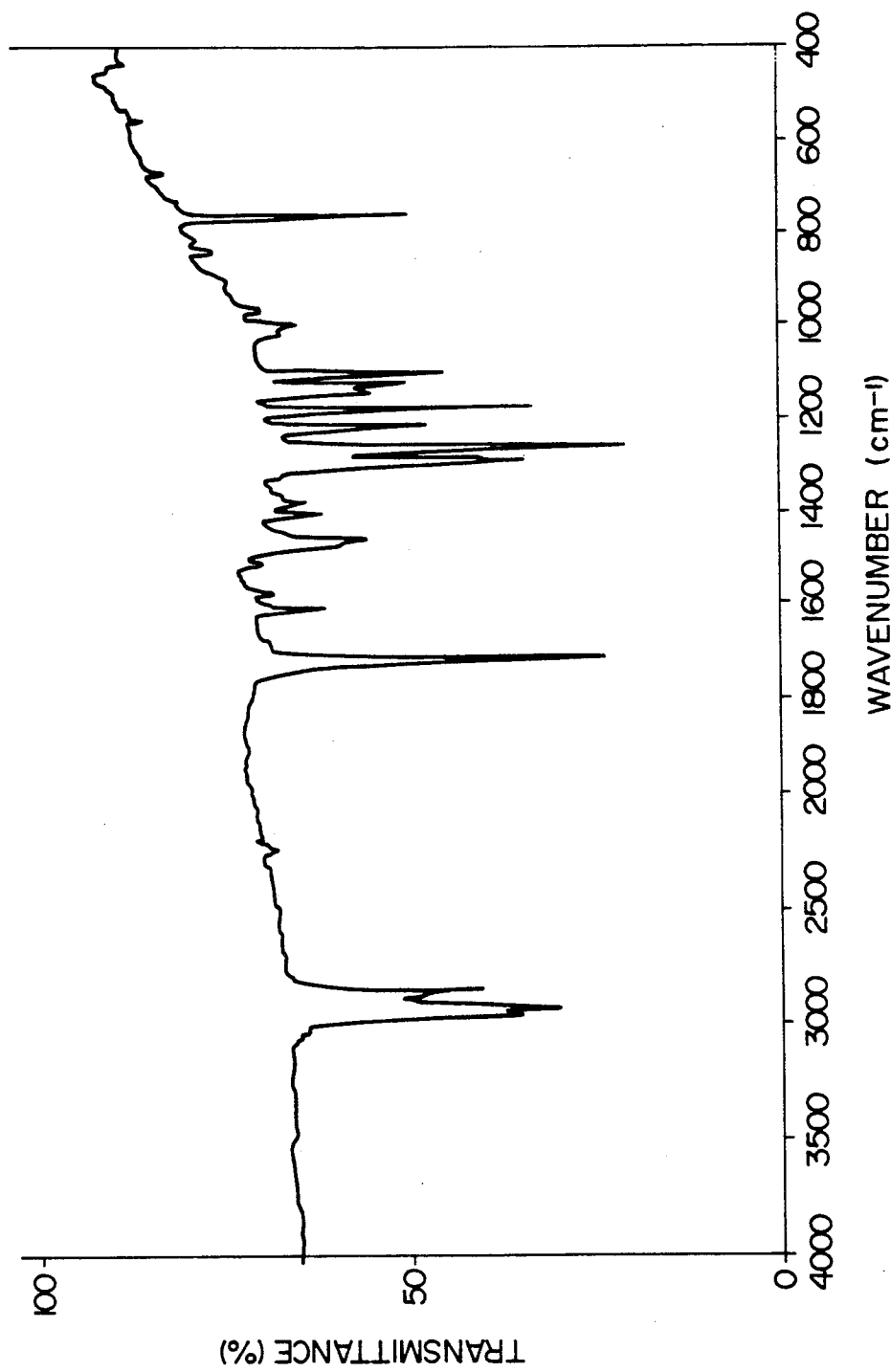
FIG. 6 is an IR spectrum of n-octyl 3,4-dimethylbenzoate.

Shown in FIG. 6. There is an absorption attributable to the stretching vibration of C=O of ester, at about 1,710 cm$^{-1}$.

SYNTHESIS EXAMPLE 6

Synthesis of 6-(n-octyloxycarbonyl)-2,3-dicyanonaphthalene 1 g of benzoyl peroxide was added to a solution of 52.5 g (0.2 mol) of n-octyl 3,4-dimethylbenzoate and 142.4 g (0.8 mol) of N-bromosuccinimide dissolved in 500 ml of carbon tetrachloride. The mixture was refluxed for about 11 hours under light irradiation by a high pressure mercury lamp (100 W). After cooling, the reaction mixture was treated in the same manner as in Example 4. The product obtained was reacted with fumaronitrile and the reaction mixture was treated in the same manner as in Example 4. The resulting residue was recrystallized from chloroform/ethanol several times to obtain about 7 g of colorless needles. The following analytical results confirmed that the crystal was 6-(n-octyloxycarbonyl)-2,3-dicyanonaphthalene.

(1) Melting point: 142°-144° C.

|  | (2) Elemental analysis | | |
|---|---|---|---|
|  | C | H | N |
| Calculated (%) | 75.42 | 6.63 | 8.38 |
| Found (%) | 75.20 | 6.41 | 7.99 |

(3) NMR spectrum (solvent: CDCl$_3$)

δ 8.70 (1H, br-s); 8.49 (1H, s); 8.42 (1H, s); 8.38 (1H, dd, J=8.55, 1.52 Hz); 8.06 (1H, d, J=8.55 Hz); 4.42 (2H, t, J=6.72 Hz); 1.83 (2H, quintet, J=6.72 Hz); 1.2-1.6 (10H, m); 0.89 (3H, t, J=6.72 Hz).

(4) IR spectrum (KBr)

Figure 7:
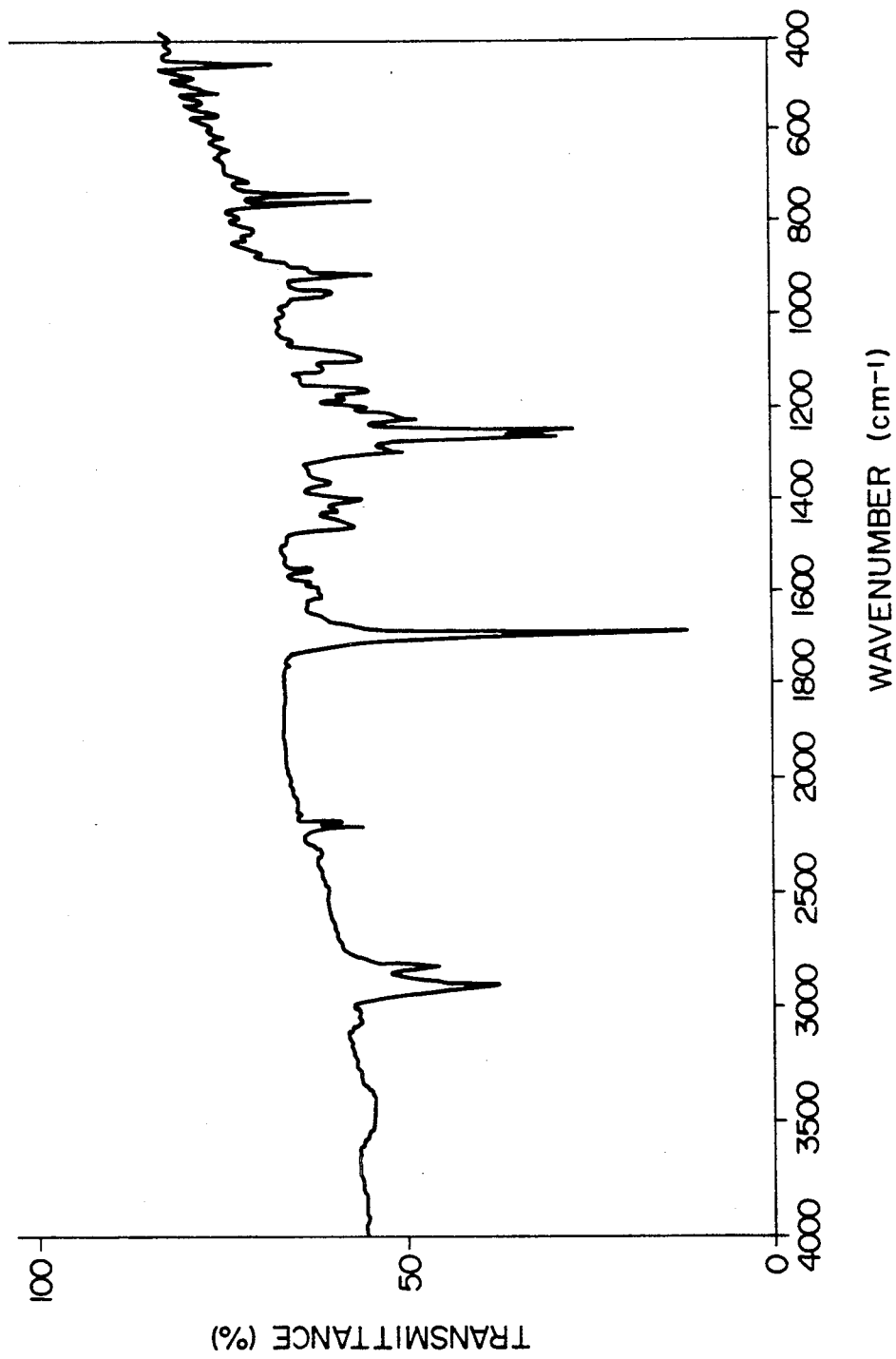
FIG. 7 is an IR spectrum of 6-(n-octyloxycarbonyl)-2,3-dicyanonaphthalene.

Shown in FIG. 7. There is an absorption attributable to the stretching vibration of C=O of ester, at about 1,700 cm$^{-1}$.

SYNTHESIS EXAMPLE 7

Synthesis of 6-(n-octadecyloxycarbonyl)-2,3-dicyanonaphthalene

A solution of 3.14 g (13.3 mol) of 6-methoxycarbonyl-2,3-dicyanonaphthalene and 3.6 g (13.3 mol) of 1-octadecanol dissolved in 40 ml of benzene was refluxed in the presence of 2.2 g (11.6 mol) of p-toluenesulfonic acid monohydrate for about 6 hours with continuous extraction of water and methanol by using Molecular Sieves 3A. After cooling, about 150 ml of chloroform was added thereto. The chloroform solution was washed with a saturated aqueous sodium hydrogencarbonate solution three times and with water three times, and then dried with anhydrous sodium sulfate. The resulting chloroform solution was concentrated. The residue was purified by silica gel column chromatography using benzene as an eluent. The resulting colorless solid was recrystallized from ethanol/chloroform to obtain 0.68 g of colorless needles. The following analytical results confirmed that the crystal was 6-(n-octadecyloxycarbonyl)-2,3-dicyanonaphthalene.

(1) Melting point: 139°-140° C.

|  | (2) Elemental analysis | | |
|---|---|---|---|
|  | C | H | N |
| Calculated (%) | 78.44 | 8.92 | 5.90 |
| Found (%) | 78.52 | 9.05 | 5.87 |

(3) NMR spectrum (solvent: CDCl$_3$)

δ 8.71 (1H, br-s); 8.49 (1H, s); 8.42 (1H, s); 8.38 (1H, dd, J=8.55, 1.53 Hz); 8.06 (1H, d, J=8.55 Hz); 4.42 (2H, t, J=6.72 Hz); 1.83 (2H, quintet, J=6.72 Hz); 1.25 (30H, br-s); 0.88 (3H, t, J=6.72 Hz).

(4) IR spectrum (KBr)

Figure 8:
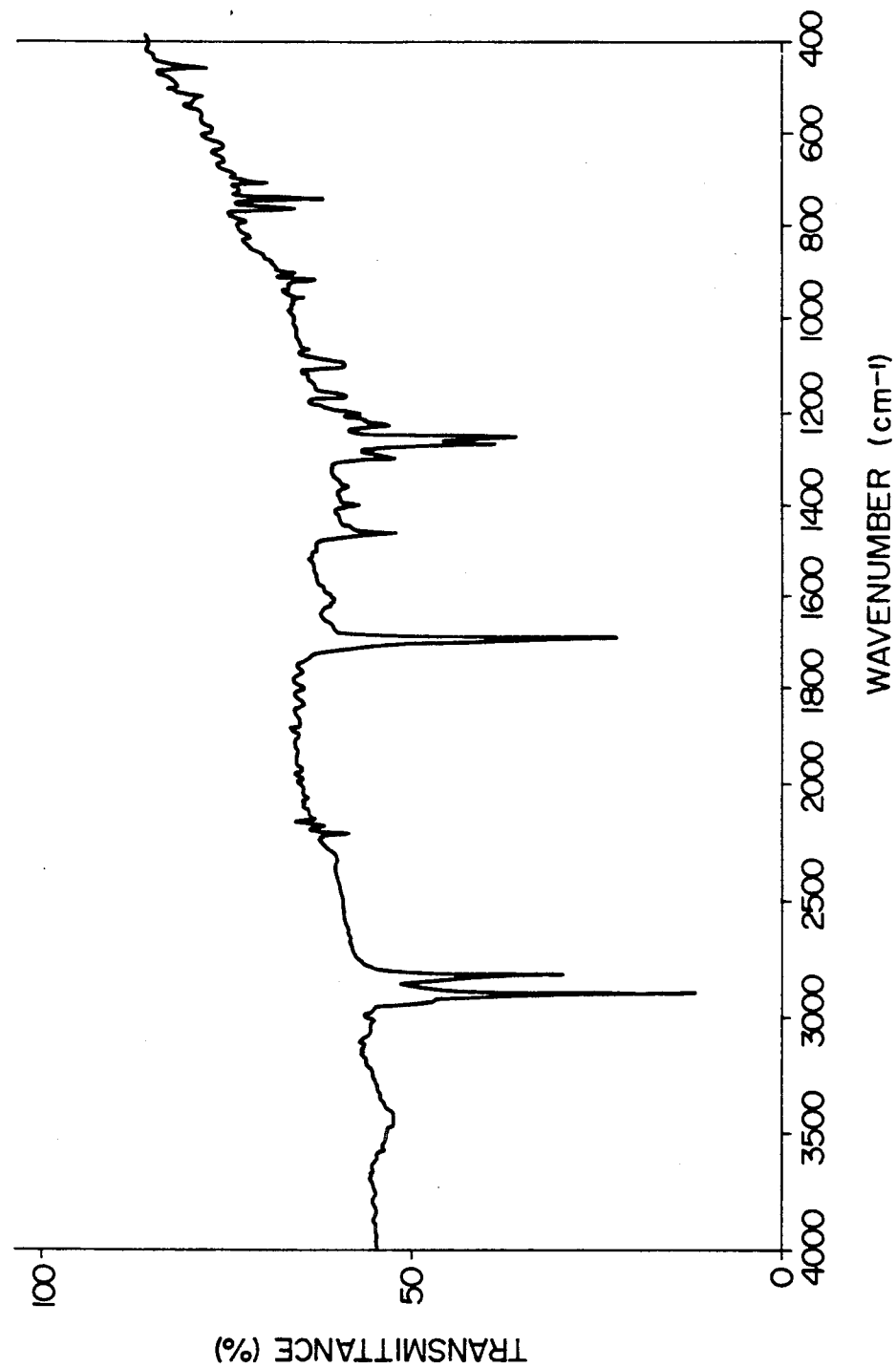
FIG. 8 is an IR spectrum of 6-(n-octadecyloxycarbonyl)-2,3-dicyanonaphthalene.

Shown in FIG. 8. There is an absorption attributable to the stretching vibration of C=O of ester, at about 1,700 cm$^{-1}$.

SYNTHESIS EXAMPLE 8

Synthesis of 6-(n-tetradecyloxycarbonyl)-2,3-dicyanonaphthalene

A solution of 236 mg (1 mmol) of 6-methoxycarbonyl-2,3-dicyanonaphthalene and 10.7 g (50 mmol) of 1-tetradecanol dissolved in 100 ml of benzene was refluxed in the presence of 1.94 g (10.2 mmol) of p-toluenesulfonic acid monohydrate for about 12 hours with continuous extraction of water and methanol by using Molecular Sieves 3A. After cooling, benzene was removed by distillation and the residue was purified according to silica gel column chromatography using toluene/chloroform (1:1 by volume) as an eluent. The product obtained was recrystallized from methanol/chloroform to obtain 103 mg of a white crystal. The following analytical results confirmed that the white crystal was 6-(n-tetradecyloxycarbonyl)-2,3-dicyanonaphthalene.

(1) Melting point: 142°-142.5° C.

|  | (2) Elemental analysis | | |
|---|---|---|---|
|  | C | H | N |
| Calculated (%) | 77.48 | 8.19 | 6.69 |
| Found (%) | 77.53 | 8.11 | 6.76 |

(3) NMR spectrum (solvent: CDCl$_3$)

δ 8.68 (1H, br-s); 8.47 (1H, s); 8.39 (1H, s); 8.36 (1H, dd, J=8.85, 1.52 Hz); 8.04 (1H, d, J=8.85 Hz); 4.40 (2H, t, J=6.71 Hz); 1.81 (2H, quintet, J=6.71 Hz); 1.25 (22H, br-s); 0.87 (3H, t, J=6.71 Hz).

(4) IR spectrum (KBr)

Figure 9:
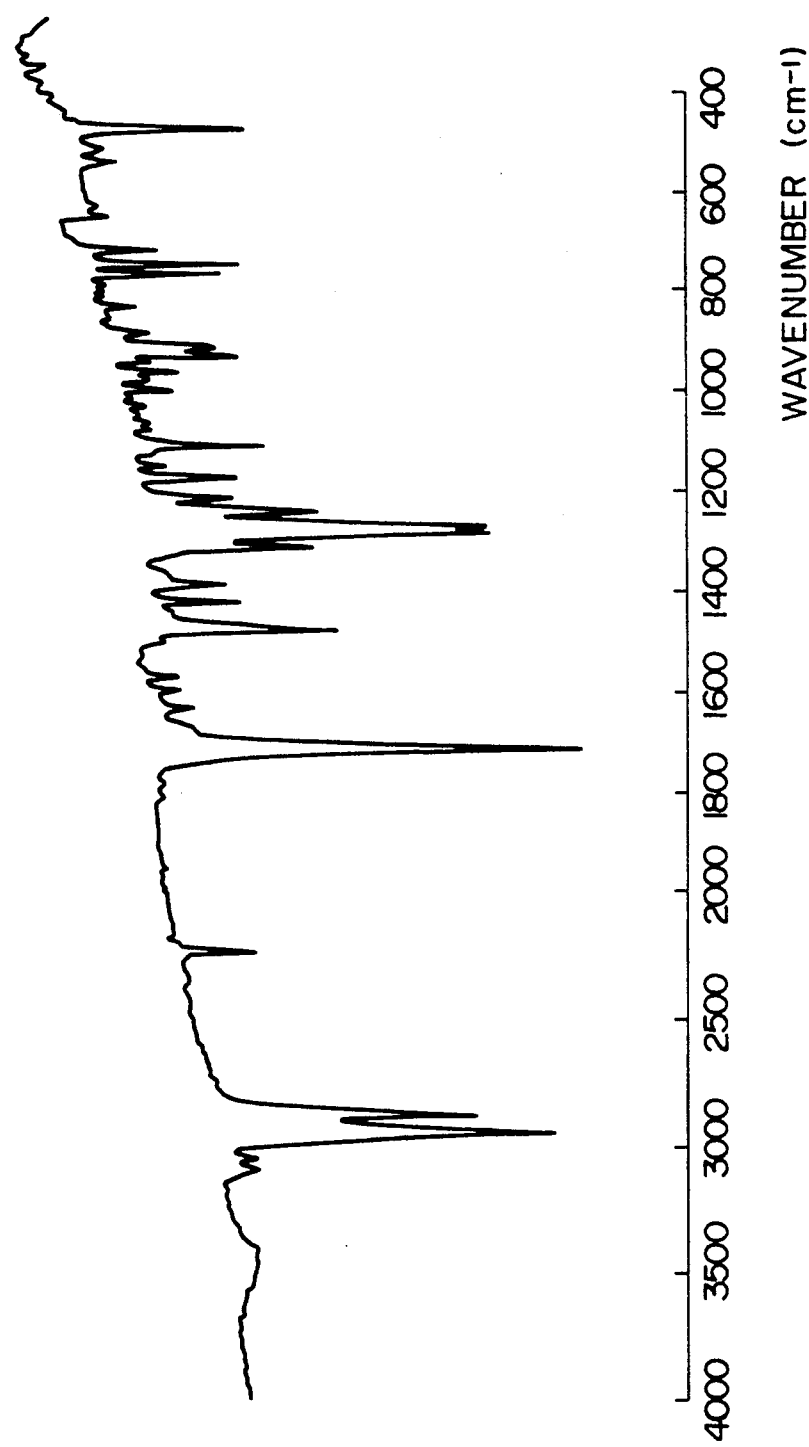
FIG. 9 is an IR spectrum of 6-(n-tetradecyloxycarbonyl)-2,3-dicyanonaphthalene.

Shown in FIG. 9. There is an absorption attributable to the stretching vibration of C=O of ester, at about 1,170 cm$^{-1}$.

SYNTHESIS EXAMPLE 9

Synthesis of 6-(n-hexadecyloxycarbonyl)-2,3-dicyanonaphthalene

A solution of 236 mg (1 mmol) of 6-methoxycarbonyl-2,3-dicyanonaphthalene and 12.1 g (50 mmol) of 1-hexadecanol dissolved in 100 ml of benzene was refluxed in the presence of 1.94 g (10.2 mmol) of p-toluenesulfonic acid monohydrate for about 12 hours with continuous extraction of water and methanol. After cooling, benzene was removed by distillation and the residue was purified according to silica gel column chromatography using toluene/chloroform (1:1 by volume) as an eluent. The product obtained was recrystallized from acetone/methanol to obtain 247 mg of a white crystal. The following analytical results confirmed that the white crystal was 6-(n-hexadecyloxycarbonyl)-2,3-dicyanonaphthalene.

(1) Melting point: 141°–142° C.

|  | (2) Elemental analysis | | |
| --- | --- | --- | --- |
|  | C | H | N |
| Calculated (%) | 77.99 | 8.58 | 6.27 |
| Found (%) | 78.07 | 8.51 | 6.19 |

(3) NMR spectrum (solvent: $CDCl_3$)

δ 8.69 (1H, br-s); 8.47 (1H, s); 8.39 (1H, s); 8.37 (1H, dd, J=8.55, 1.53 Hz); 8.04 (1H, d, J=8.55 Hz); 4.41 (2H, t, J=6.72 Hz); 1.81 (2H, quintet, 6.72 Hz); 1.25 (26H, br-s); 0.87 (3H, t, J=6.72 Hz).

(4) IR spectrum (KBr)

Figure 10:
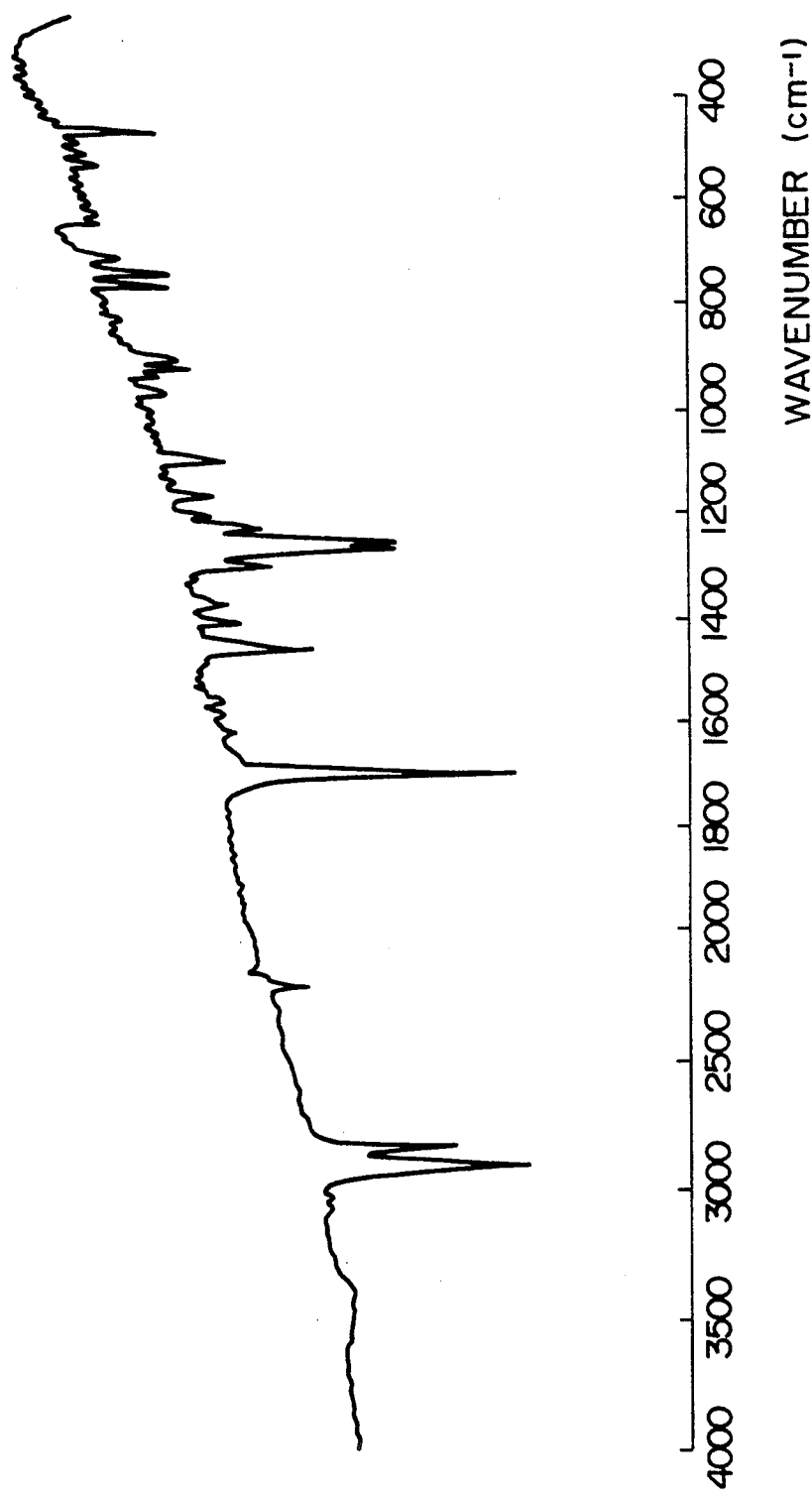
FIG. 10 is an IR spectrum of 6-(n-hexadecyloxycarbonyl)-2,3-dicyanonaphthalene.

Shown in FIG. 10. There is an absorption attributable to the stretching vibration of C=O of ester at about 1.710 $cm^{-1}$.

SYNTHESIS EXAMPLE 10

Synthesis of 6-(n-eicosyloxycarbonyl)-2,3-dicyanonaphthalene

A solution of 236 mg (1 mmol) of 6-methoxycarbonyl-2,3-dicyanonaphthalene and 15.6 g (50 mmol) of 1-eicosanol dissolved in 100 ml of benzene was refluxed in the presence of 1.94 g (10.2 mmol) of p-toluenesulfonic acid monohydrate for about 28 hours with continuous extraction of water and methanol by using Molecular Sieves 3A. After cooling, benzene was removed by distillation and the residue was purified according to silica gel column chromatography using toluene/n-hexane (4:1 by volume) as an eluent. The product obtained was recrystallized from acetone/methanol to obtain 166 mg of a white crystal. The following analytical results confirmed that the white crystal was 6-(n-eicosyloxycarbonyl)-2,3-dicyanonaphthalene.

(1) Melting point: 138°–138.5° C.

|  | (2) Elemental analysis | | |
| --- | --- | --- | --- |
|  | C | H | N |
| Calculated (%) | 78.84 | 9.22 | 5.57 |
| Found (%) | 78.89 | 9.31 | 5.52 |

(3) NMR spectrum (solvent: $CDCl_3$)

δ 8.70 (1H, br-s); 8.48 (1H, s); 8.41 (1H, s); 8.38 (1H, dd, J=8.85, 1.52 Hz); 8.05 (1H, d, J=8.85 Hz); 4.42 (2H, t, J=6.71 Hz); 1.83 (2H, quintet, J=6.71 Hz); 1.25 (34H, br-s); 0.88 (3H, t, J=6.71 Hz).

(4) IR spectrum (KBr)

Figure 11:
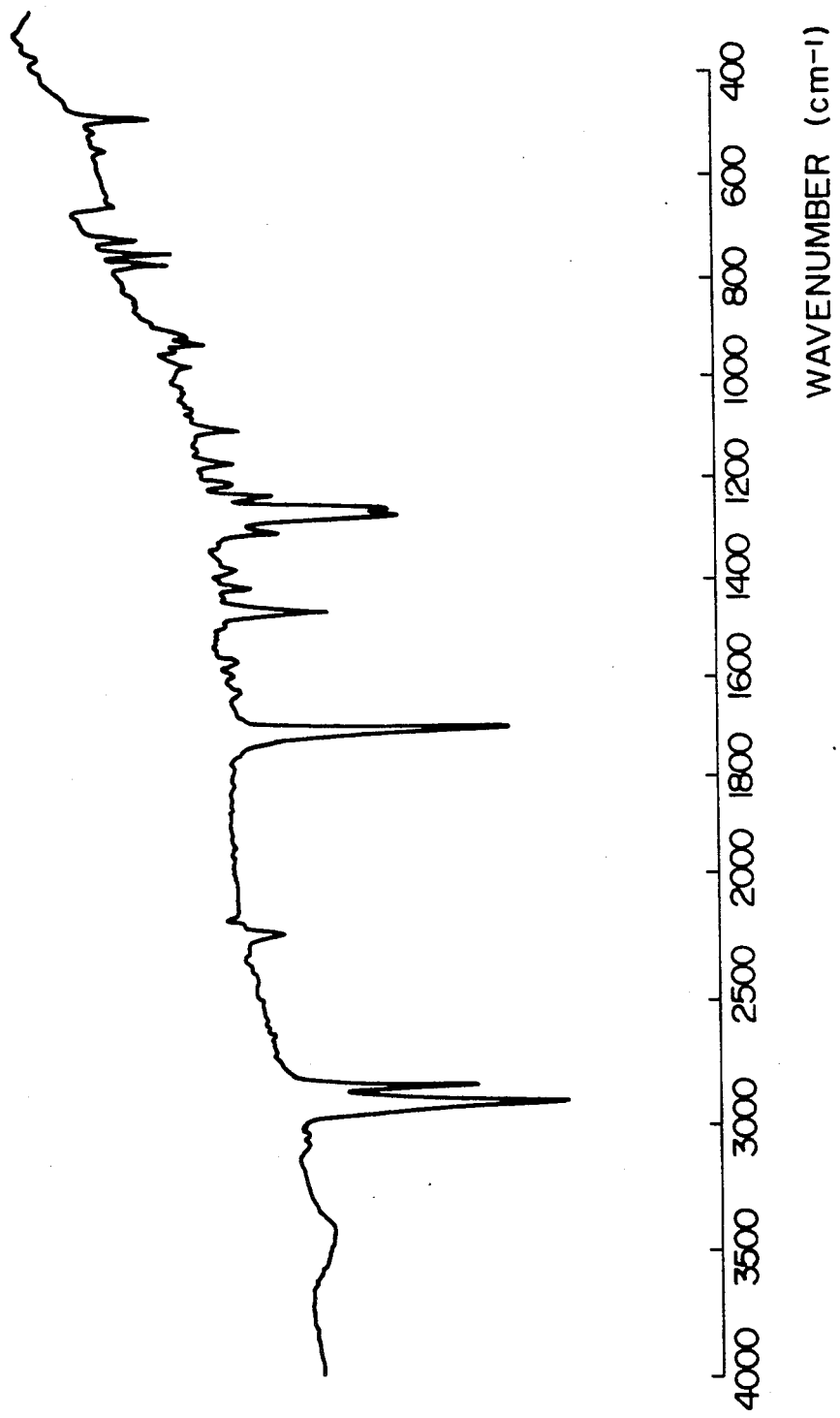
FIG. 11 is an IR spectrum of 6-(n-eicosyloxycarbonyl)-2,3-dicyanonaphthalene.

Shown in FIG. 11. There is an absorption attributable to the stretching vibration of C=O of ester, at about 1,710 $cm^{-1}$.

SYNTHESIS EXAMPLE 11

Synthesis of 6-(n-docosyloxycarbonyl)-2,3-dicyanonaphthalene

A solution of 236 mg (1 mmol) of 6-methoxycarbonyl-2,3-dicyanonaphthalene and 16.3 g (50 mmol) of 1-docosanol dissolved in 100 ml of benzene was refluxed in the presence of 1.94 g (10.2 mmol) of p-toluenesulfonic acid monohydrate for about 28 hours with continuous extraction of water and methanol by using Molecular Sieves 3A. After cooling, benzene was removed by distillation and the residue was purified according to silica gel column chromatography using toluene/n-hexane (4:1 by volume) as an eluent. The product obtained was recrystallized from acetone/methanol to obtain 161 mg of a white crystal. The following analytical results confirmed that the white crystal was 6-(n-docosyloxycarbonyl)-2,3-dicyanonaphthalene.

(1) Melting point: 135°–136.5° C.

|  | (2) Elemental analysis | | |
| --- | --- | --- | --- |
|  | C | H | N |
| Calculated (%) | 79.20 | 9.49 | 5.28 |
| Found (%) | 79.12 | 9.59 | 5.14 |

(3) NMR spectrum (solvent: $CDCl_3$)

δ 8.70 (1H, br-s); 8.48 (1H, s); 8.41 (1H, s); 8.37 (1H, dd, J=8.55, 1.53 Hz); 8.05 (1H, d, J=8.55 Hz); 4.42 (2H, t, J=6.72 Hz); 1.83 (2H, quintet, J=6.72 Hz); 1.25 (38H, br-s); 0.88 (3H, t, J=6.72 Hz).

(4) IR spectrum (KBr)

Figure 12:
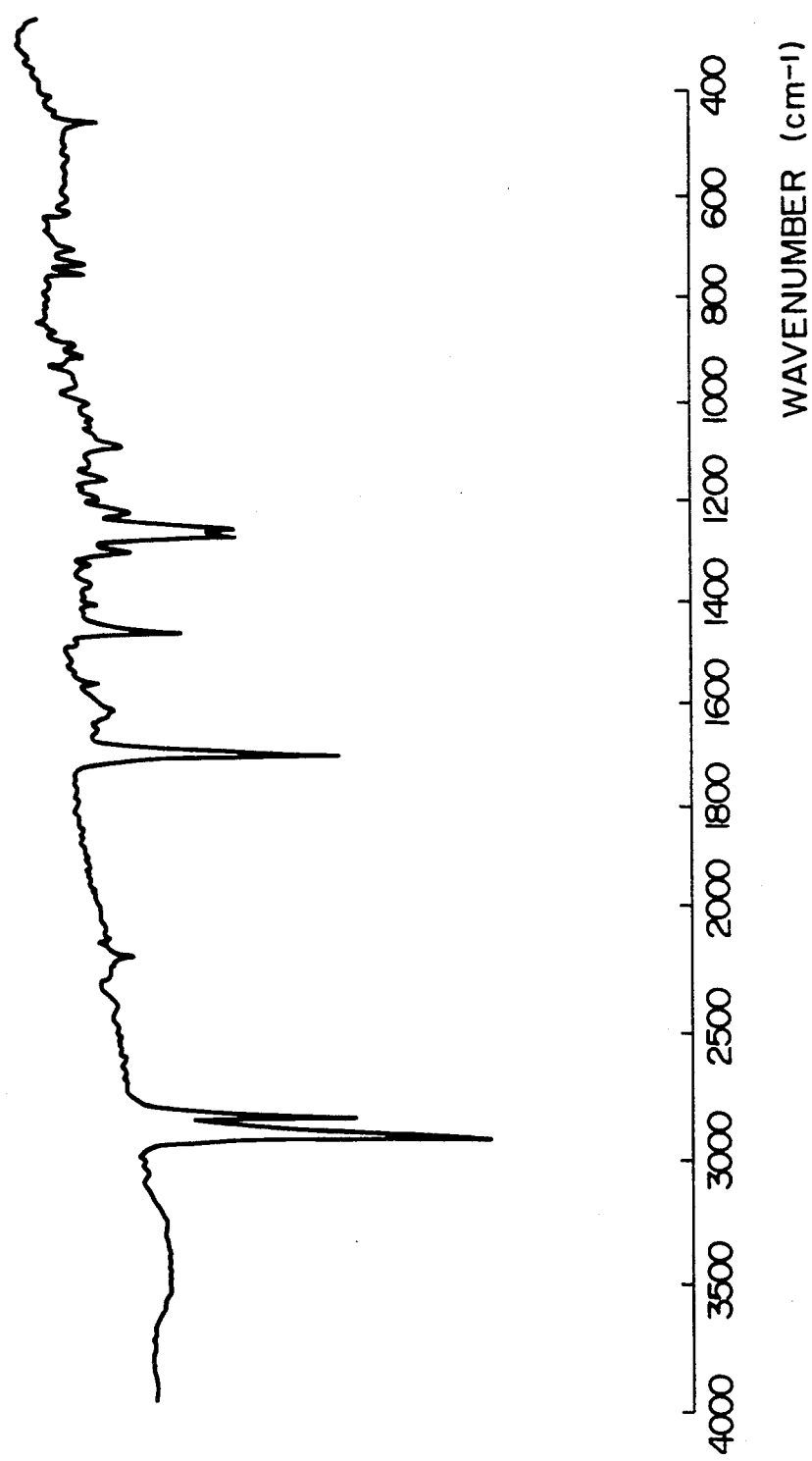
FIG. 12 is an IR spectrum of 6-(n-docosyloxycarbonyl)-2,3-dicyanonaphthalene.

Shown in FIG. 12. There is an absorption attributable to the stretching vibration of C=O of ester, at about 1,710 $cm^{-1}$.

EXAMPLE 1

Synthesis of tetrakis(n-amyloxycarbonyl) vanadyl naphthalocyanine [illustrative compound (1)]

1.46 g (5 mmol) of 6-(n-amyloxycarbonyl)-2,3-dicyanonaphthalene, 0.32 g (2.01 mmol) of vanadium trichloride, 10 mg of ammonium molybdate and 5 g of urea were reacted at about 220° C. for about 2.5 hours with thorough stirring. After cooling, the reaction mixture in solid form was mixed with 40 ml of 5% hydrochloric acid. This mixture was stirred thoroughly at about 50° C. for 30 minutes. Then, the insoluble material were collected by filtration and thoroughly washed with water, methanol and acetone in this order. The resulting solid was extracted with a mixed solvent consisting of methanol/acetone (1:1) in a Soxhlet's extractor for about 50 hours. Then, Soxhlet extraction was conducted with chloroform for 20 hours. The resulting deep green chloroform solution was subjected to filtration when hot and then concentrated to dryness to obtain 861 mg of a black crystal with luster. The following analytical results confirmed that the crystal was tetrakis(n-amyloxycarbonyl) vanadyl naphthalocyanine.

(1) Melting point: above 300° C. (stable at least at 300° C. or below)

|  | (2) Elemental analysis | | |
| --- | --- | --- | --- |
|  | C | H | N |
| Calculated (%) | 69.95 | 5.22 | 9.06 |
| Found (%) | 70.13 | 5.14 | 9.33 |

(3) Electronic spectrum ($CHCl_3$ solution)

Figure 13:
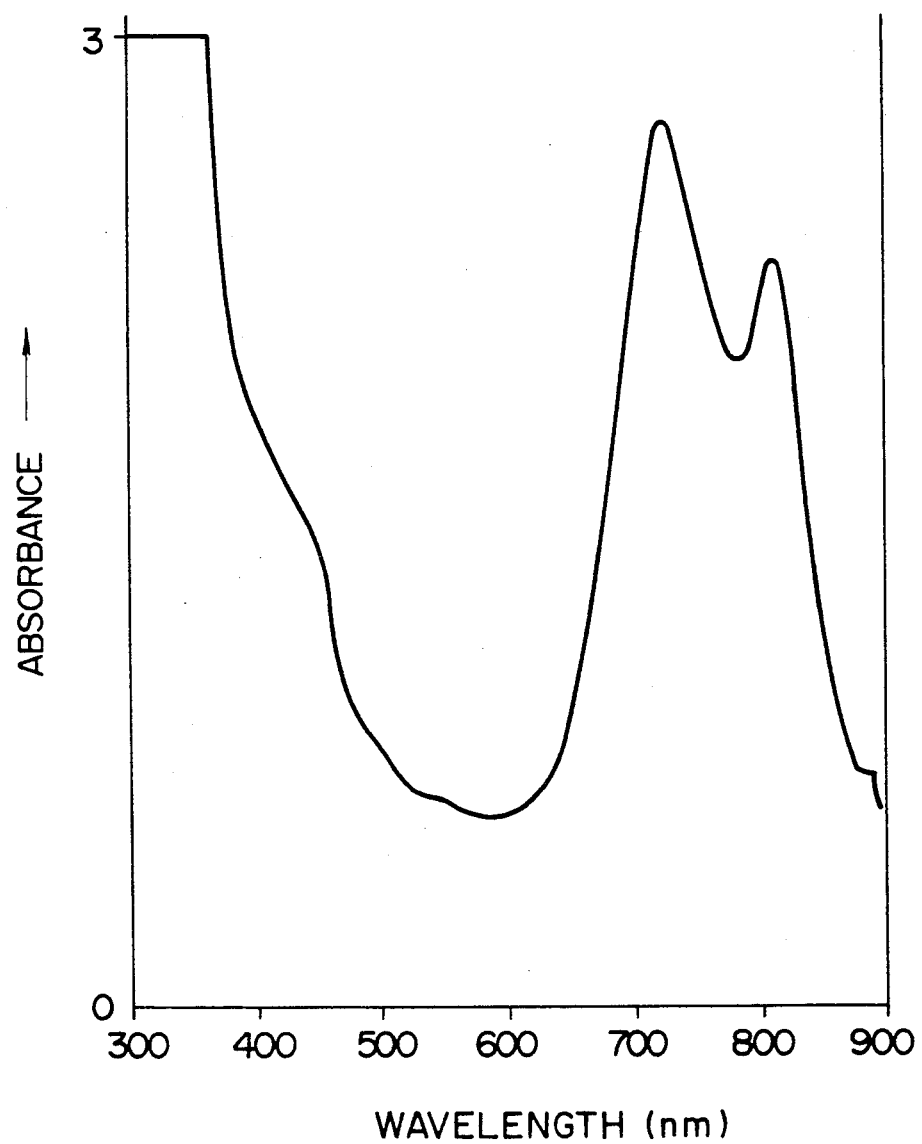
FIG. 13 is an electronic spectrum of tetrakis(n-amyloxycarbonyl) vanadyl naphthalocyanine.

Shown in FIG. 13.

(4) IR spectrum (KBr)

Figure 14:
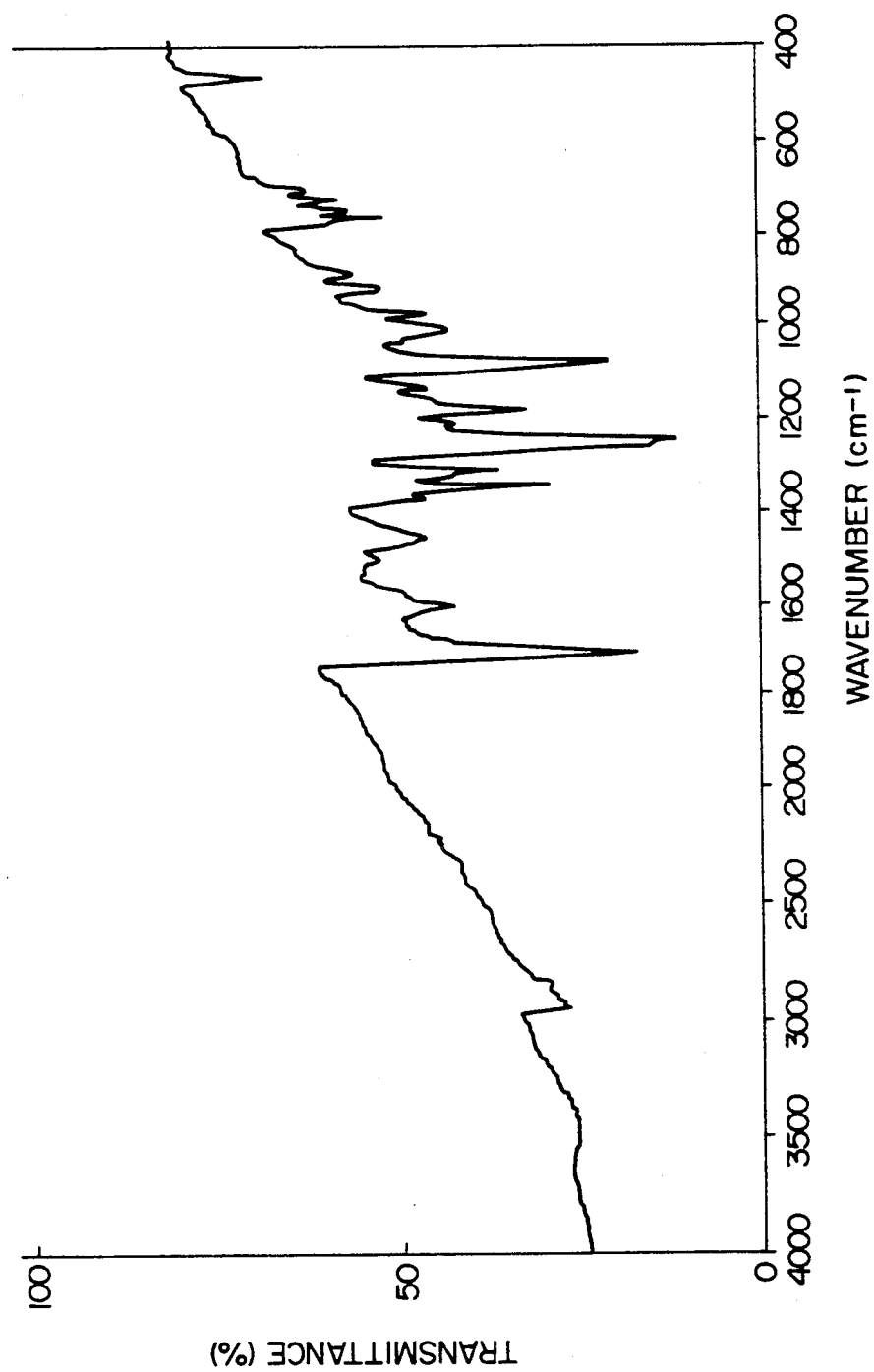
FIG. 14 is an IR spectrum of tetrakis(n-amyloxycarbonyl) vanadyl naphthalocyanine.

Shown in FIG. 14. There is an absorption attributable to the stretching vibration of C=O of ester, at about 1,700 $cm^{-1}$.

EXAMPLE 2

Synthesis of tetrakis(n-amyloxycarbonyl) copper naphthalocyanine [illustrative compound (8)]

1.46 g (5 mmol) of 6-(n-amyloxycarbonyl)-2,3-dicyanonaphthalene, 273 mg (1.6 mmol) of cupric chloride dihydrate, 10 mg of ammonium molybdate and 5 g of urea were reacted at about 220° C. for about 2.5 hours with thorough stirring. After cooling, the reaction mixture was treated in the same manner as in Example 1 to obtain 987 mg of a black crystal with luster. The following analytical results confirmed that the crystal was tetrakis(n-amyloxycarbonyl) copper naphthalocyanine.

(1) Melting point: Above 300° C. (stable at least at 300° C. or below)

|  | (2) Elemental analysis | | |
|---|---|---|---|
|  | C | H | N |
| Calculated (%) | 70.14 | 5.23 | 9.06 |
| Found (%) | 69.45 | 5.20 | 9.17 |

Figure 15:
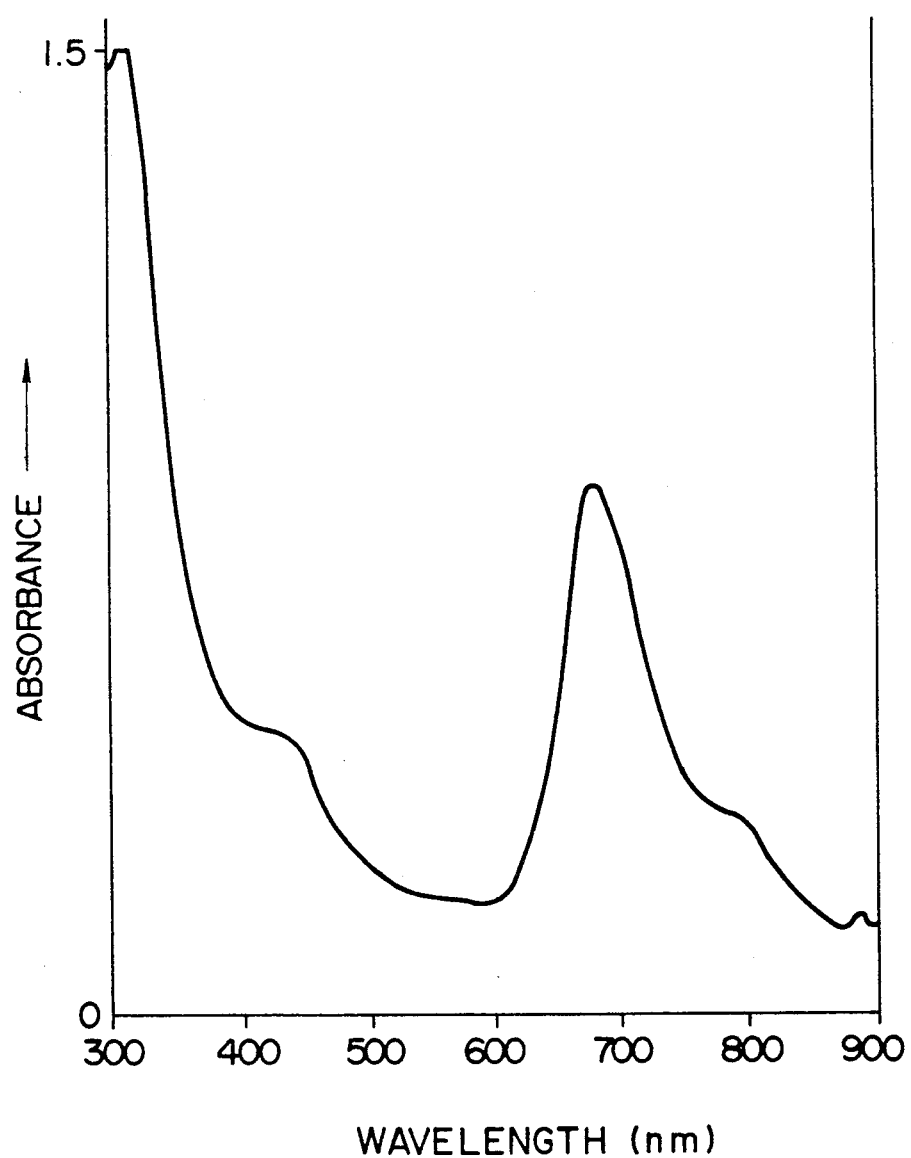
FIG. 15 is an electronic spectrum of tetrakis(n-amyloxycarbonyl) copper naphthalocyanine.
Figure 16:
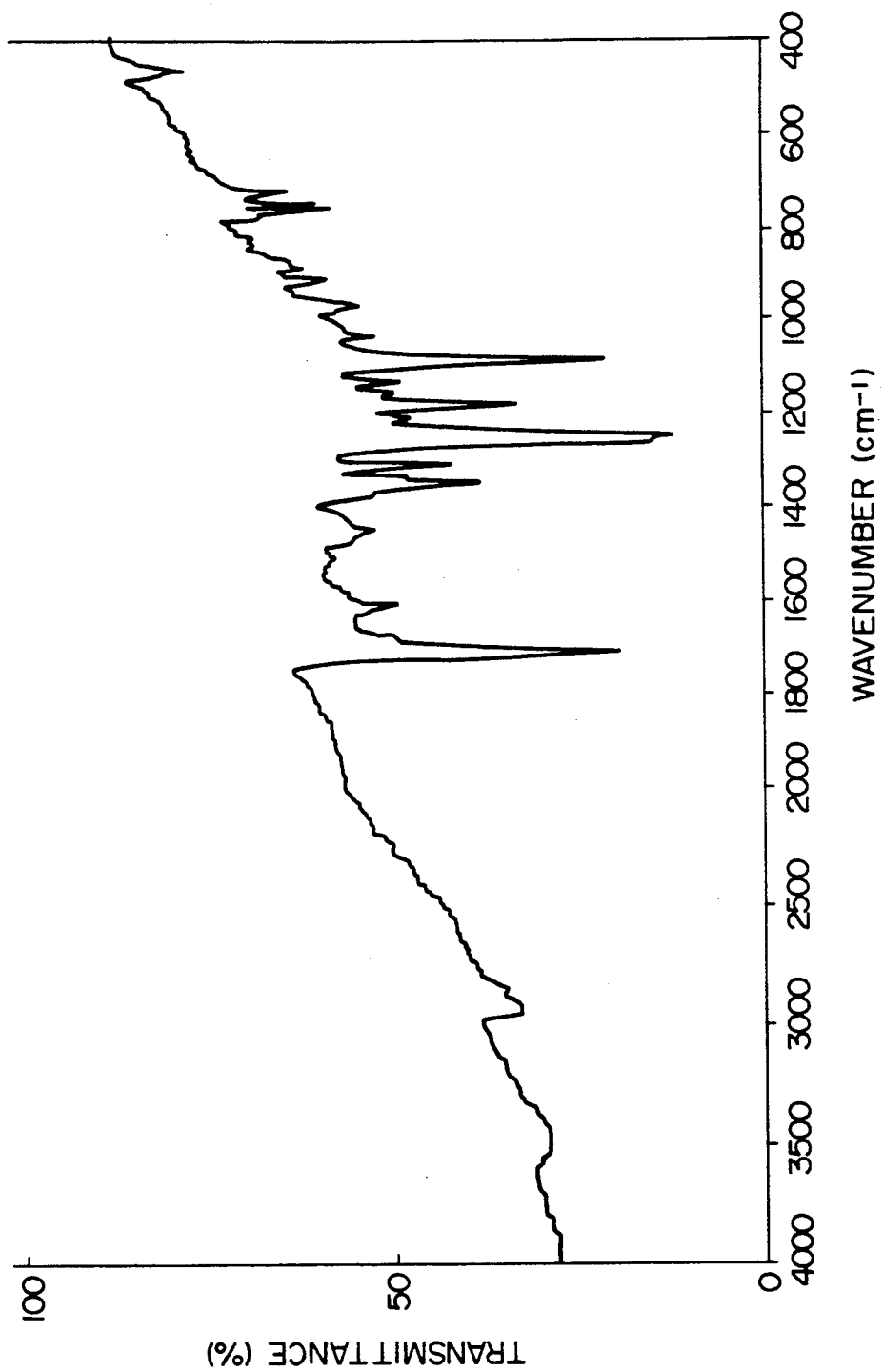
FIG. 16 is an IR spectrum of tetrakis(n-amyloxycarbonyl) copper naphthalocyanine.

(3) Electronic spectrum (CHCl$_3$ solution)
Shown in FIG. 15.
(4) IR spectrum (KBr)
Shown in FIG. 16. There is an absorption attributable to the stretching vibration of C=O of ester, at about 1,700 cm$^{-1}$.

EXAMPLE 3

Synthesis of tetrakis(n-amyloxycarbonyl) zinc naphthalocyanine [illustrative compound (13)]

1.46 g (5 mmol) of 6-(n-amyloxycarbonyl)-2,3-dicyanonaphthalene, 105 mg (1.6 mmol) of powdery zinc, 10 mg of ammonium molybdate and 5 g of urea were reacted at about 220° C. for about 2.5 hours with thorough stirring. After cooling, the reaction mixture was treated in the same manner as in Example 1 to obtain 937 mg of a black crystal with luster. The following analytical results confirmed that the crystal was tetrakis(n-amyloxycarbonyl) zinc naphthalocyanine.

(1) Melting point: Above 300° C. (stable at least at 300° C. or below)

|  | (2) Elemental analysis | | |
|---|---|---|---|
|  | C | H | N |
| Calculated (%) | 70.04 | 5.22 | 9.08 |
| Found (%) | 69.35 | 5.22 | 9.08 |

Figure 17:
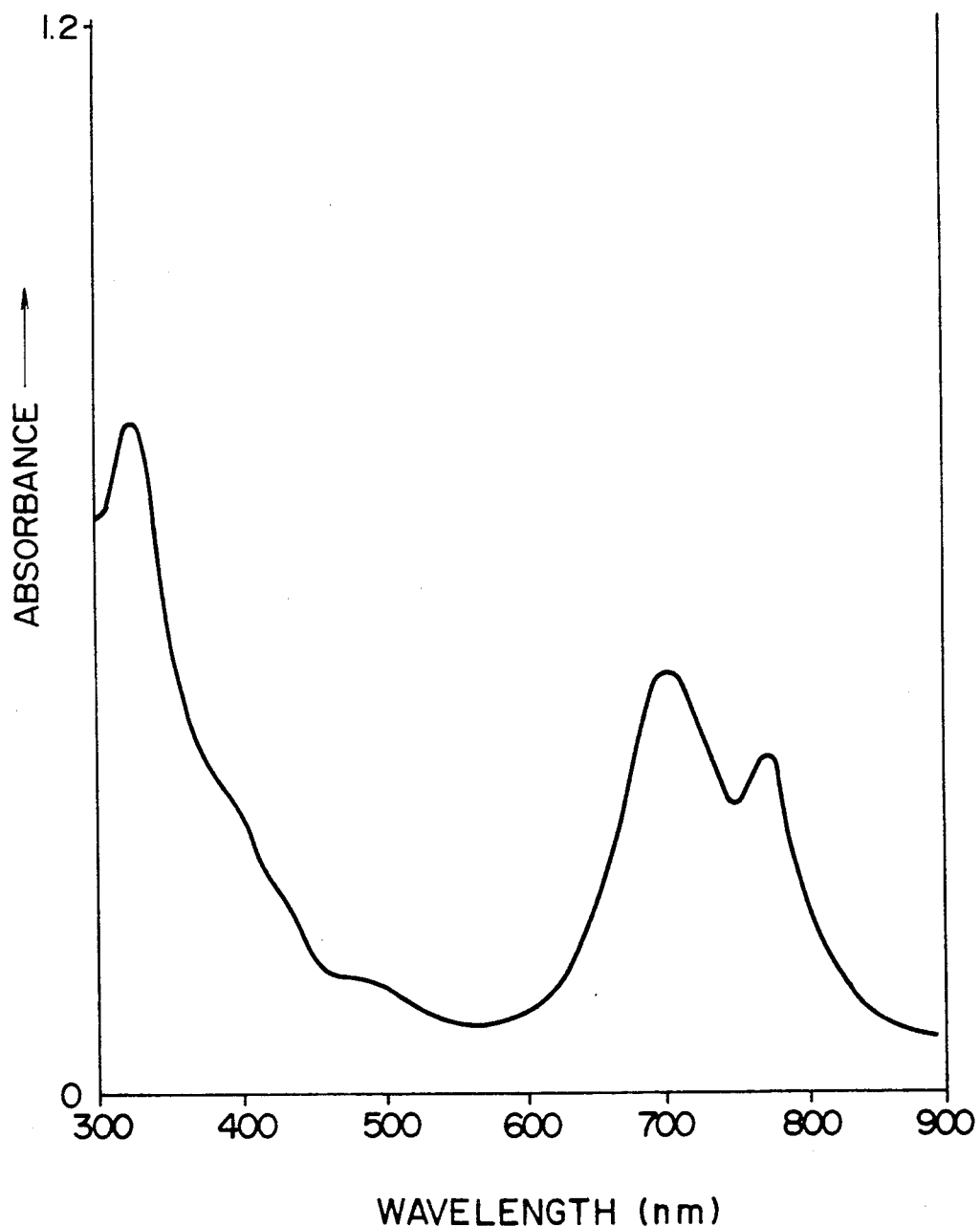
FIG. 17 is an electronic spectrum of tetrakis(n-amyloxycarbonyl) zinc naphthalocyanine.
Figure 18:
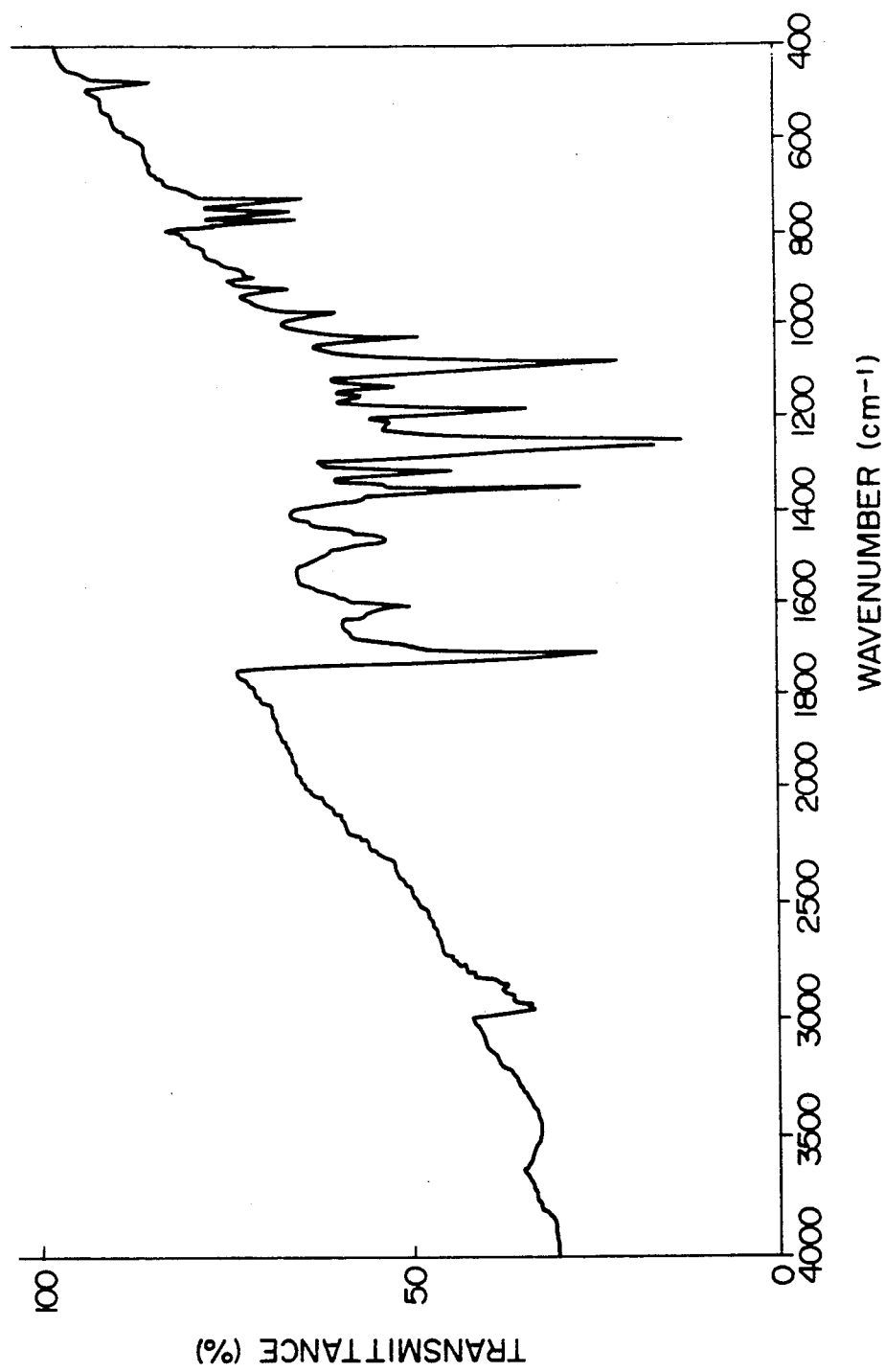
FIG. 18 is an IR spectrum of tetrakis(n-amyloxycarbonyl) zinc naphthalocyanine.

(3) Electronic spectrum (CHCl$_3$ solution)
Shown in FIG. 17.
(4) IR spectrum (KBr)
Shown in FIG. 18. There is an absorption attributable to the stretching vibration of C=O of ester, at about 1,700 cm$^{-1}$.

EXAMPLE 4

Synthesis of tetrakis(n-octyloxycarbonyl)vanadylnaphthalocyanine [illustrative compound (2)]

1.67 g (5 mmol) of 6-(n-octyloxycarbonyl)-2,3-dicyanonaphthalene, 0.32 g (1.6 mmol) of vanadium trichloride, 10 mg of ammonium molybdate and 5 g of urea were reacted at about 220° C. for about 2.5 hours with thorough stirring. After cooling, the reaction mixture was treated in the same manner as in Example 1 to obtain 1.33 g of a black crystal with luster. The following analytical results confirmed that the crystal was tetrakis(n-octyloxycarbonyl) vanadyl naphthalocyanine.

(1) Melting point: Above 300° C. (stable at least at 300° C. or below)

|  | (2) Elemental analysis | | |
|---|---|---|---|
|  | C | H | N |
| Calculated (%) | 71.83 | 6.31 | 7.98 |
| Found (%) | 71.99 | 6.18 | 8.29 |

Figure 19:
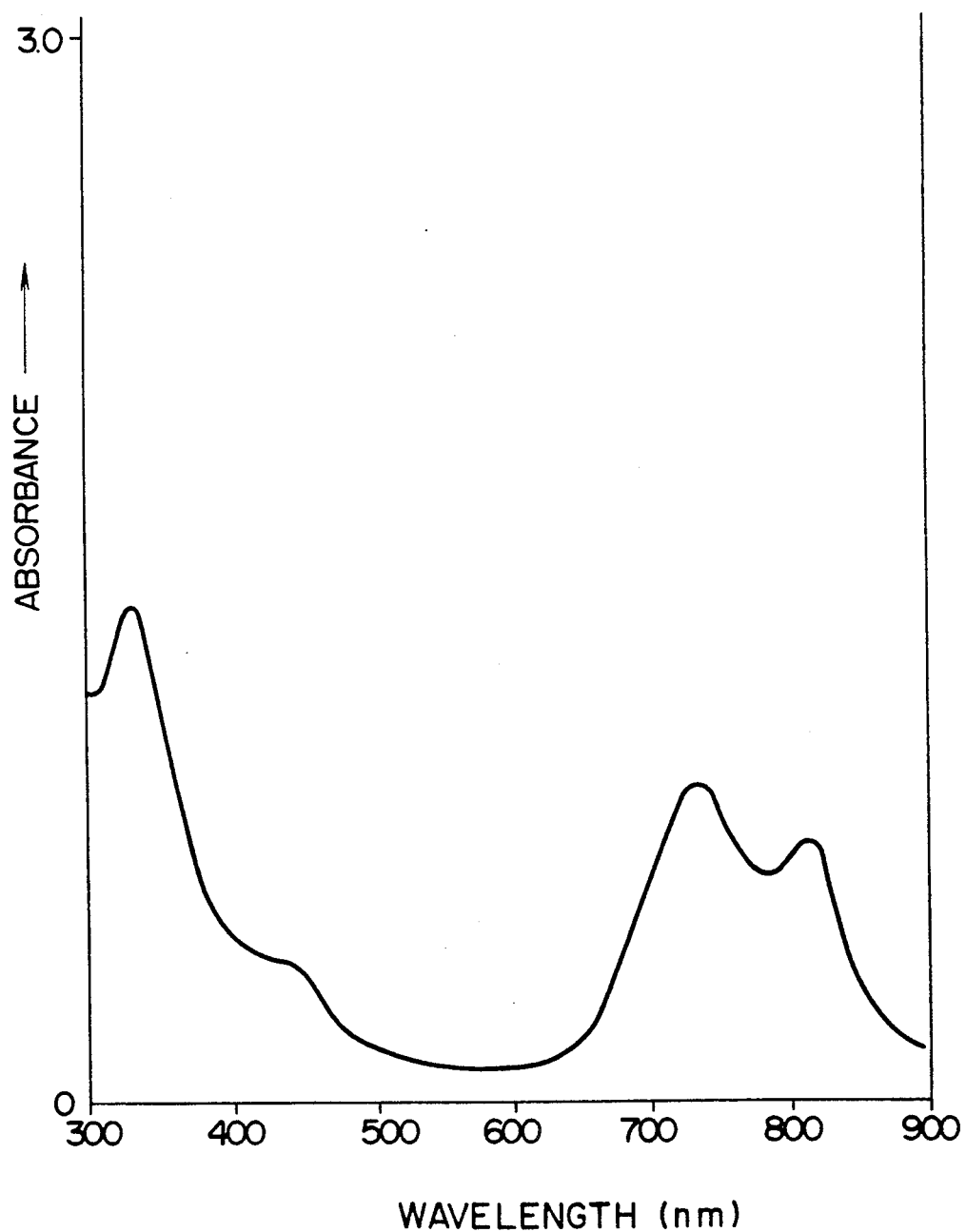
FIG. 19 is an electronic spectrum of tetrakis(n-octyloxycarbonyl) vanadyl naphthalocyanine.
Figure 20:
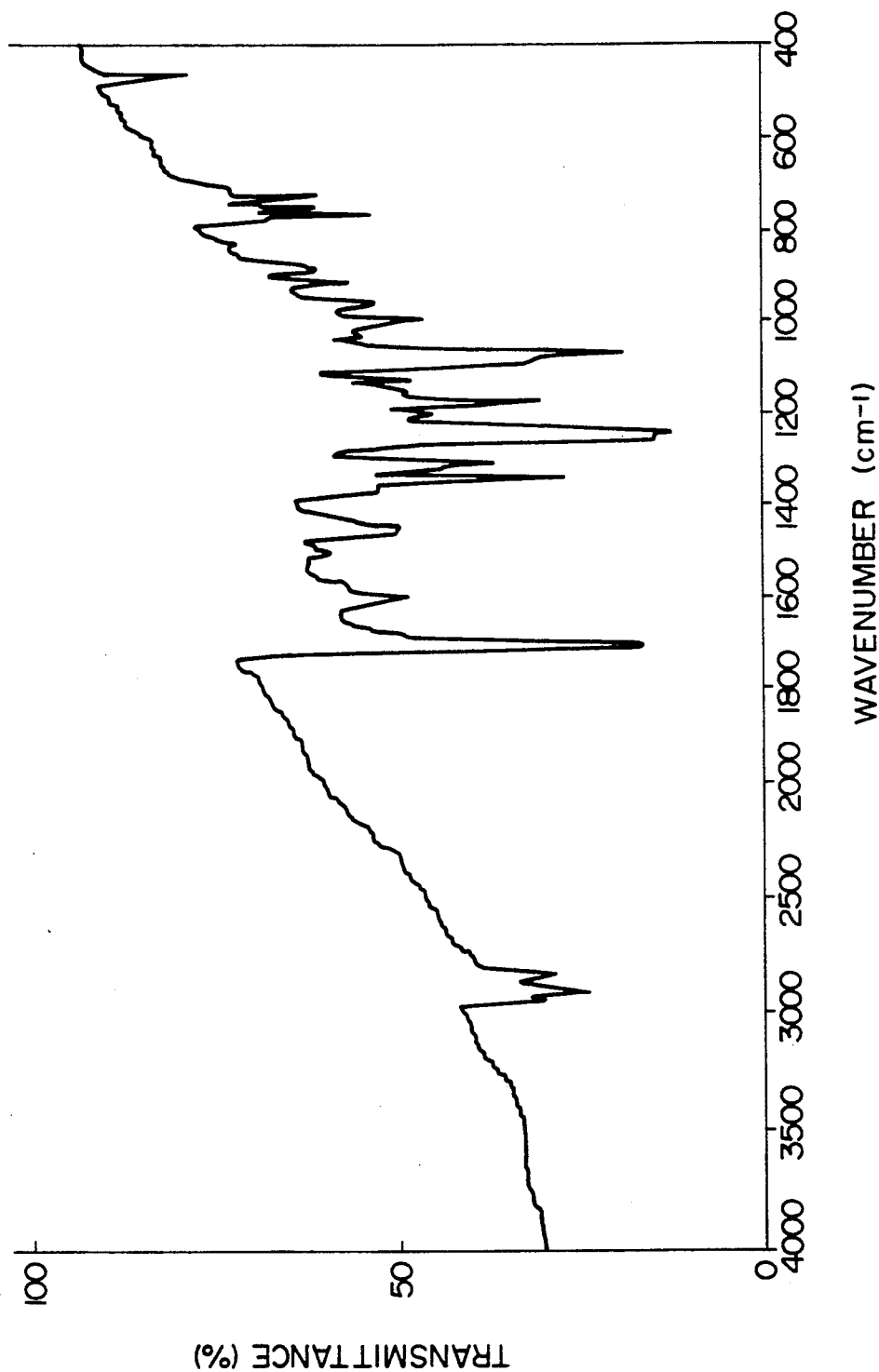
FIG. 20 is an IR spectrum of tetrakis(n-octyloxycarbonyl) vanadyl naphthalocyanine.

(3) Electronic spectrum (CHCl$_3$ solution)
Shown in FIG. 19.
(4) IR spectrum (KBr)
Shown in FIG. 20. There is an absorption attributable to the stretching vibration of C=O of ester, at about 1,700 cm$^{-1}$.

EXAMPLE 5

Synthesis of tetrakis(n-octyloxycarbonyl) copper naphthalocyanine [illustrative compound (9)]

1.67 g (5 mmol) of 6-(n-octyloxycarbonyl)2,3-dicyanonaphthalene, 273 mg (1.6 mmol) of cupric chloride dihydrate, 10 mg of ammonium molybdate and 5 g of urea were reacted at about 220° C. for about 2.5 hours with thorough stirring. After cooling, the reaction mixture was treated in the same manner as in Example 1 to obtain 1.39 g of a black crystal with luster. The following analytical results confirmed that the crystal was tetrakis(n-octyloxycarbonyl) copper naphthalocyanine.

(1) Melting point: Above 300° C. (stable at least at 300° C. or below)

|  | (2) Elemental analysis | | |
|---|---|---|---|
|  | C | H | N |
| Calculated (%) | 72.00 | 6.33 | 8.00 |
| Found (%) | 71.95 | 6.08 | 8.14 |

Figure 21:
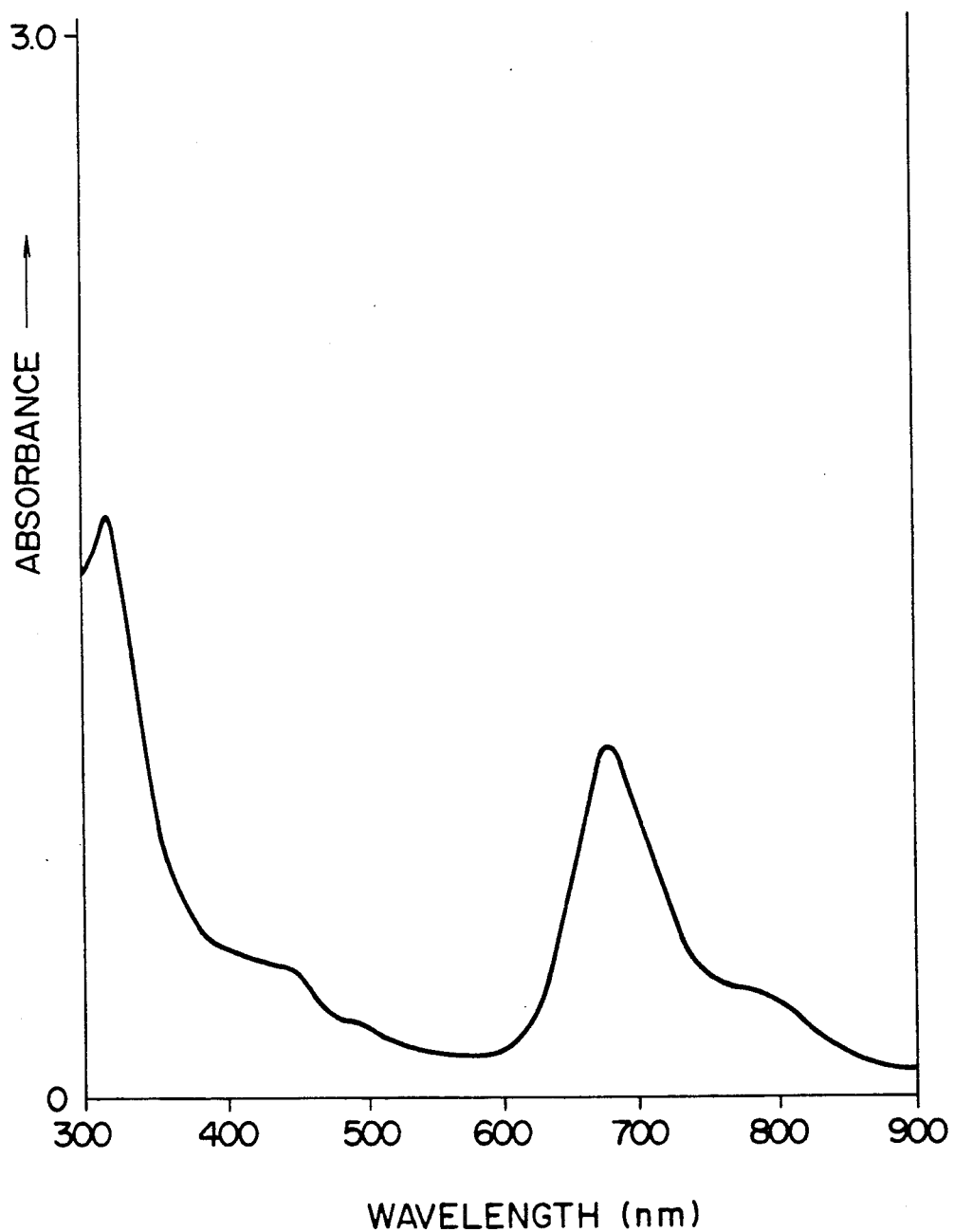
FIG. 21 is an electronic spectrum of tetrakis(n-octyloxycarbonyl) copper naphthalocyanine.
Figure 22:
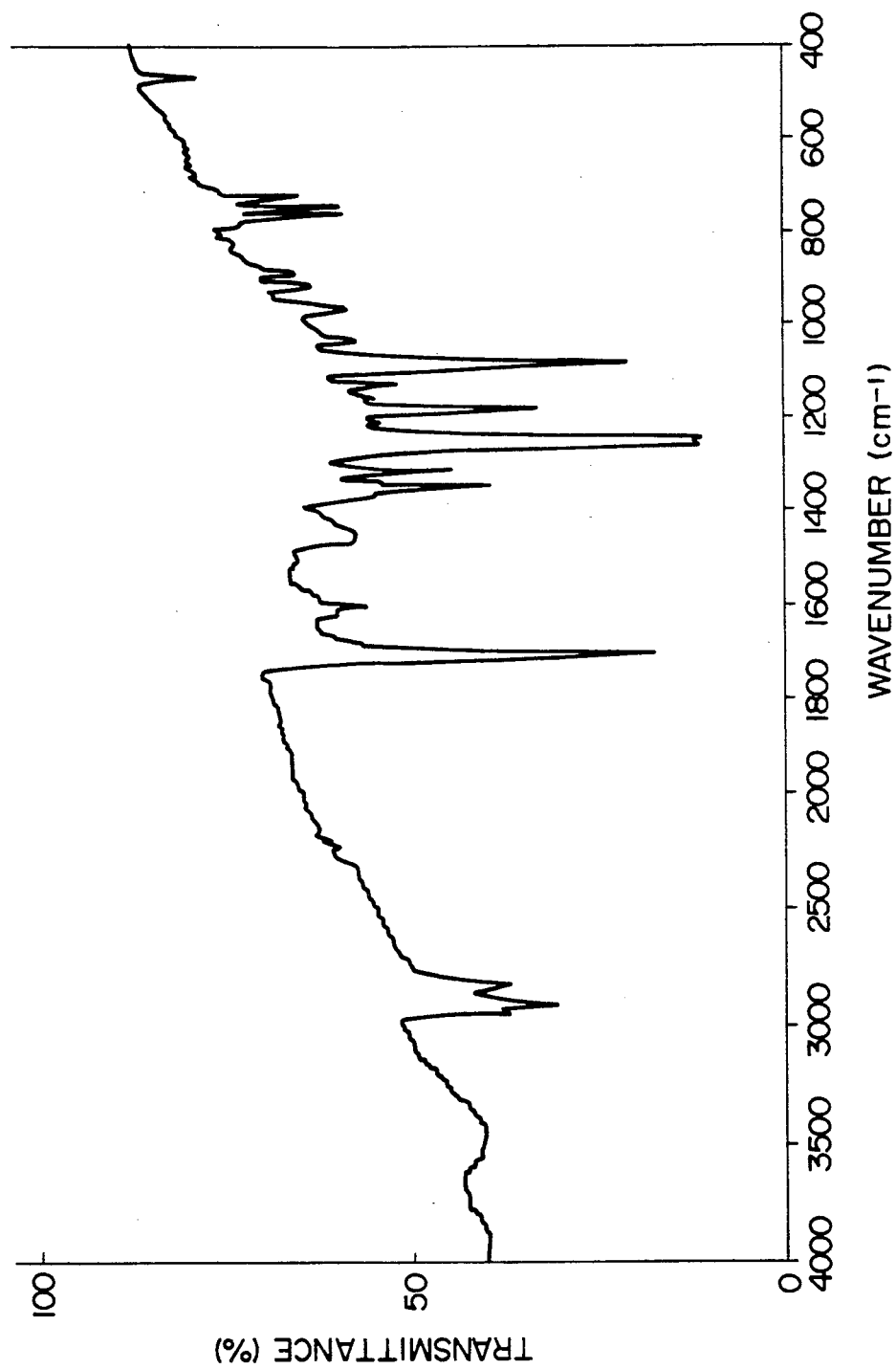
FIG. 22 is an IR spectrum of tetrakis(n-octyloxycarbonyl) copper naphthalocyanine.

(3) Electronic spectrum (CHCl$_3$ solution)
Shown in FIG. 21.
(4) IR spectrum (KBr)
Shown in FIG. 22. There is an absorption attributable to the stretching vibration of C=O of ester, at about 1,700 cm$^{-1}$.

EXAMPLE 6

Synthesis of tetrakis(n-octyloxycarbonyl) zinc naphthalocyanine [illustrative compound (14)]

1.67 g (5 mmol) of 6-(n-octyloxycarbonyl)-2,3-dicyanonaphthalene, 105 mg (1.6 mmol) of powdery zinc, 10 mg of ammonium molybdate and 5 g of urea were reacted at about 220° C. for about 2.5 hours with thorough stirring. After cooling, the reaction mixture was treated in the same manner as in Example 1 to obtain 1.26 g of a black crystal with luster. The following analytical results confirmed that the crystal was tetrakis(n-octyloxycarbonyl) zinc naphthalocyanine.

(1) Melting point: Above 300° C. (stable at least at 300° C. or below)

| (2) Elemental analysis | | | |
| --- | --- | --- | --- |
| | C | H | N |
| Calculated (%) | 71.89 | 6.32 | 7.98 |
| Found (%) | 71.90 | 6.20 | 8.02 |

Figure 23:
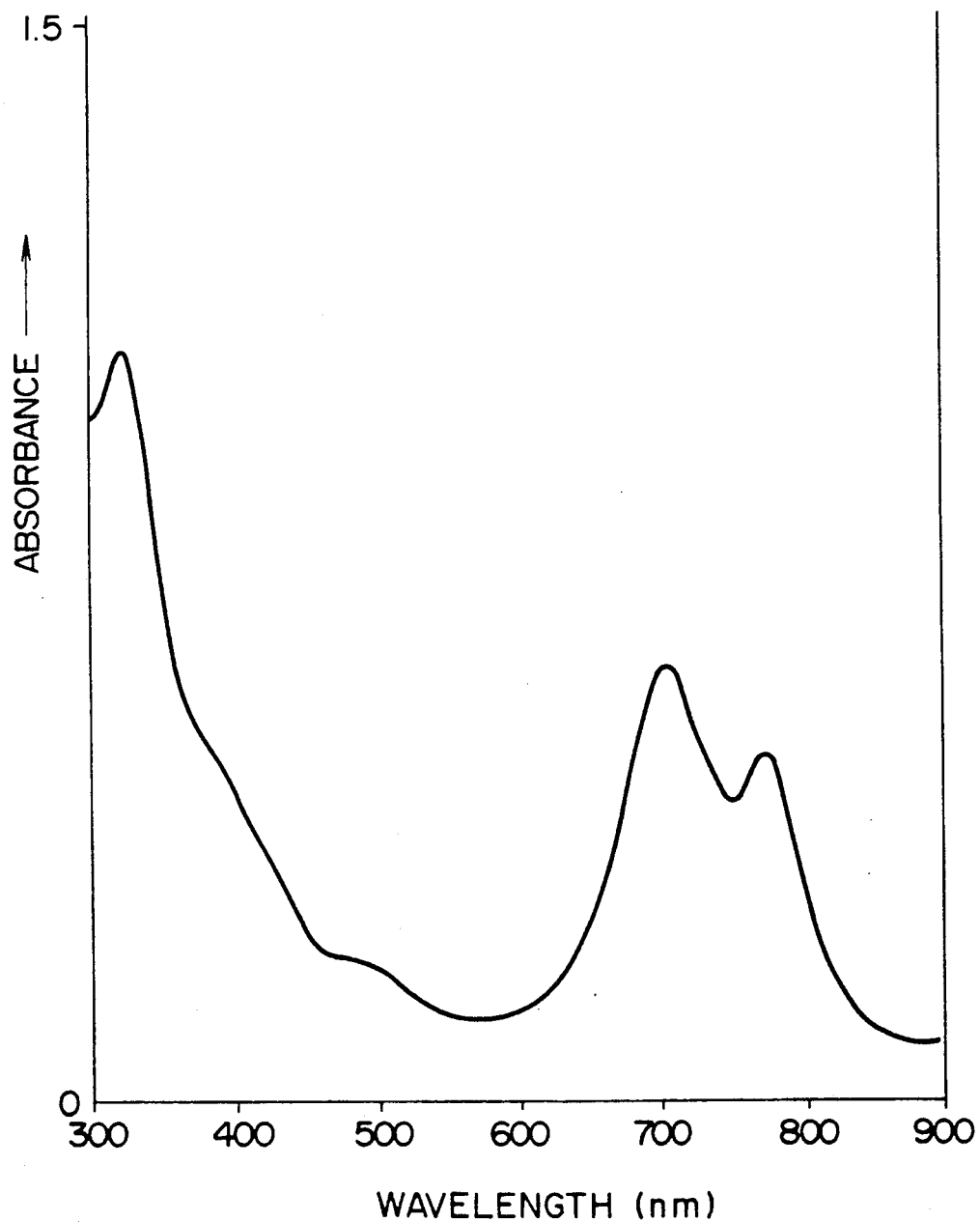
FIG. 23 is an electronic spectrum of tetrakis(n-octyloxycarbonyl) zinc naphthalocyanine.

(3) Electronic spectrum (CHCl$_3$ solution)
Shown in FIG. 23.

Figure 24:
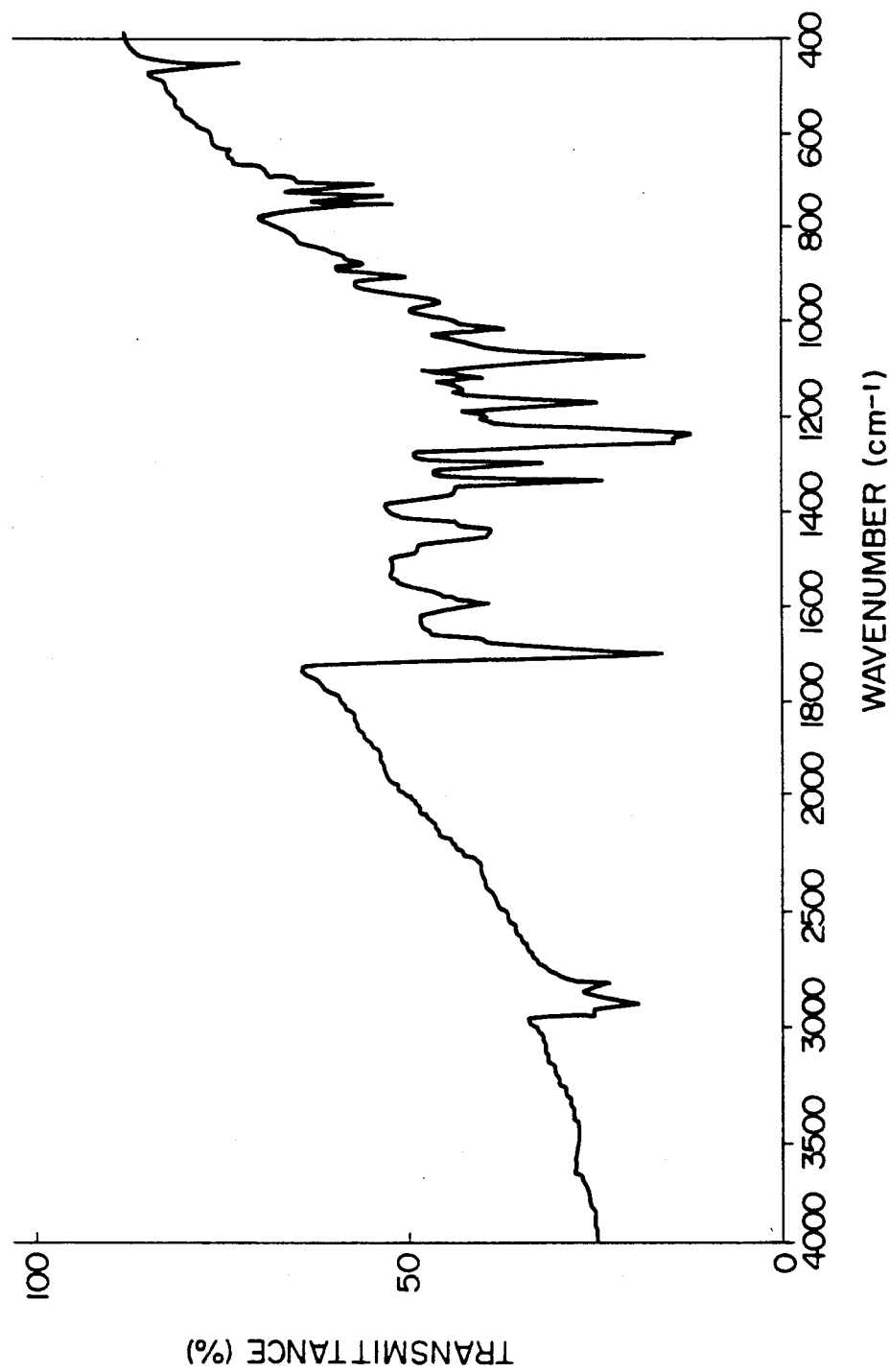
FIG. 24 is an IR spectrum of tetrakis(n-octyloxycarbonyl) zinc naphthalocyanine.

(4) IR spectrum (KBr)
Shown in FIG. 24. There is an absorption attributable to the stretching vibration of C=O of ester, at about 1,700 cm$^{-1}$.

EXAMPLE 7

Synthesis of tetrakis(n-amyloxycarbonyl) nickel naphthalocyanine [illustrative compound (16)]

Figure 25:
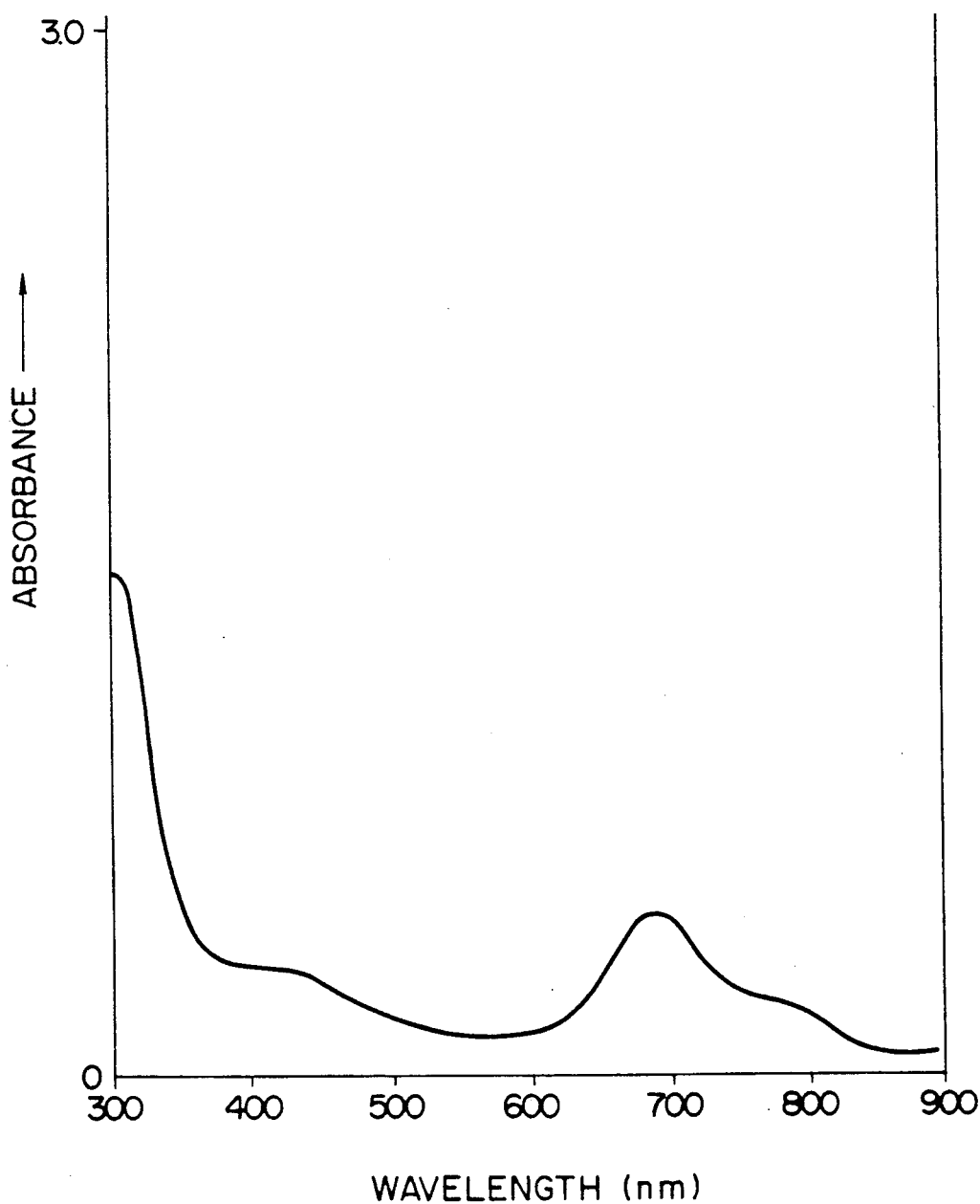
FIG. 25 is an electronic spectrum of tetrakis(-namyloxycarbonyl) nickel naphthalocyanine.

1.46 g (5 mmol) of 6-(n-amyloxycarbonyl)-2,3-dicyanonaphthalene, 380 mg (1.6 mmol) of nickel chloride hexahydrate, 10 mg of ammonium molybdate and 5 g of urea were reacted at about 220° C. for about 2.5 hours with thorough stirring. After cooling, the reaction mixture was treated in the same manner as in Example to obtain 287 mg of tetrakis(n-amyloxycarbonyl) nickel naphthalocyanine as a black crystal with luster. Its electronic spectrum (CHCl$_3$ solution) is shown in FIG. 25. This compound also is stable at least at 300° C. or below.

Figure 26:
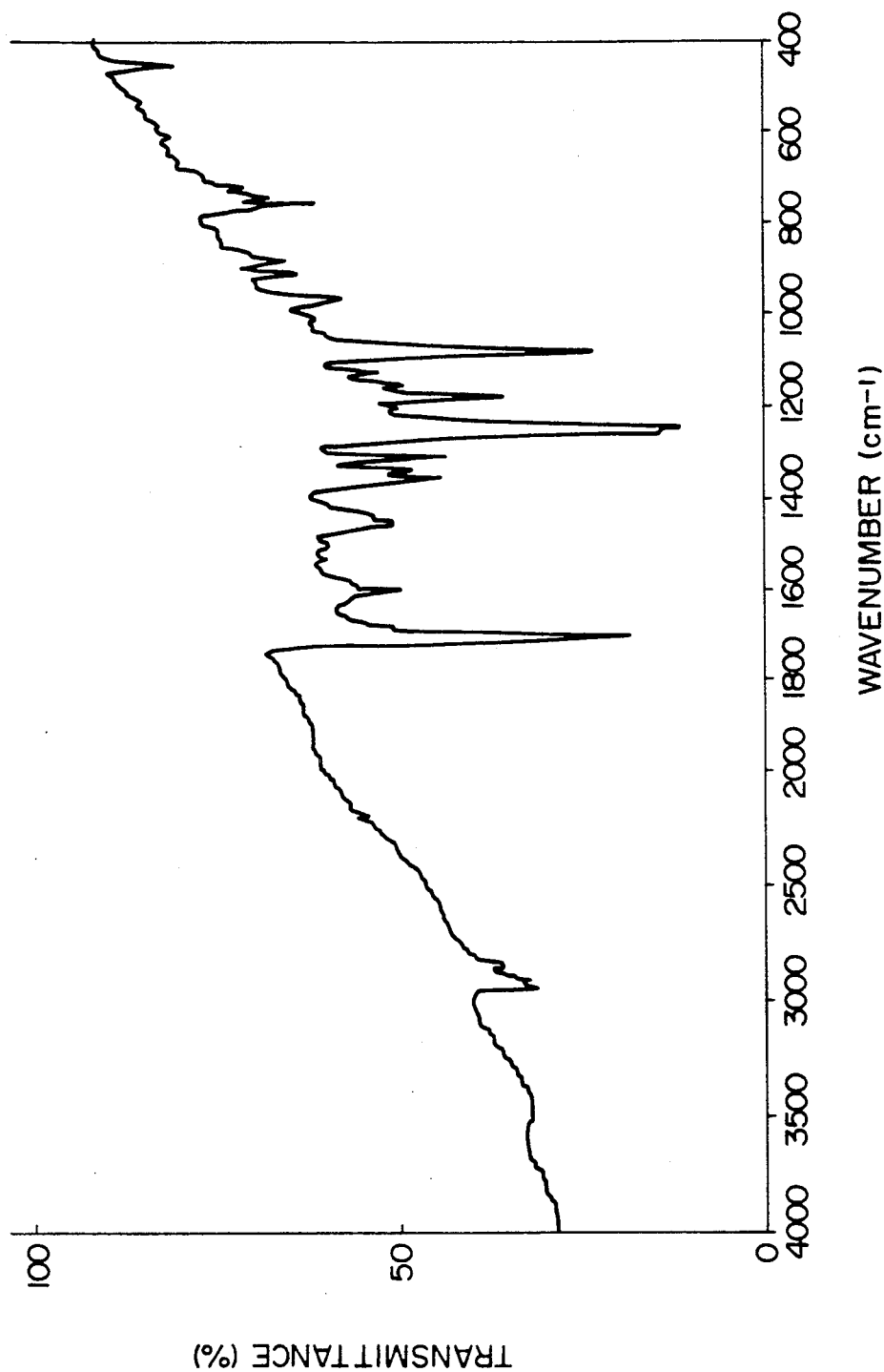
FIG. 26 is an IR spectrum of tetrakis(n-amyloxycarbonyl) nickel naphthalocyanine.

The IR spectrum (KBr) of the compound is shown in FIG. 26. There is an absorption attributable to the stretching vibration of C=O of ester, at about 1,700 cm$^{-1}$.

EXAMPLE 8

Synthesis of tetrakis(n-amyloxycarbonyl) palladium naphthalocyanine [illustrative compound (18)]

Figure 27:
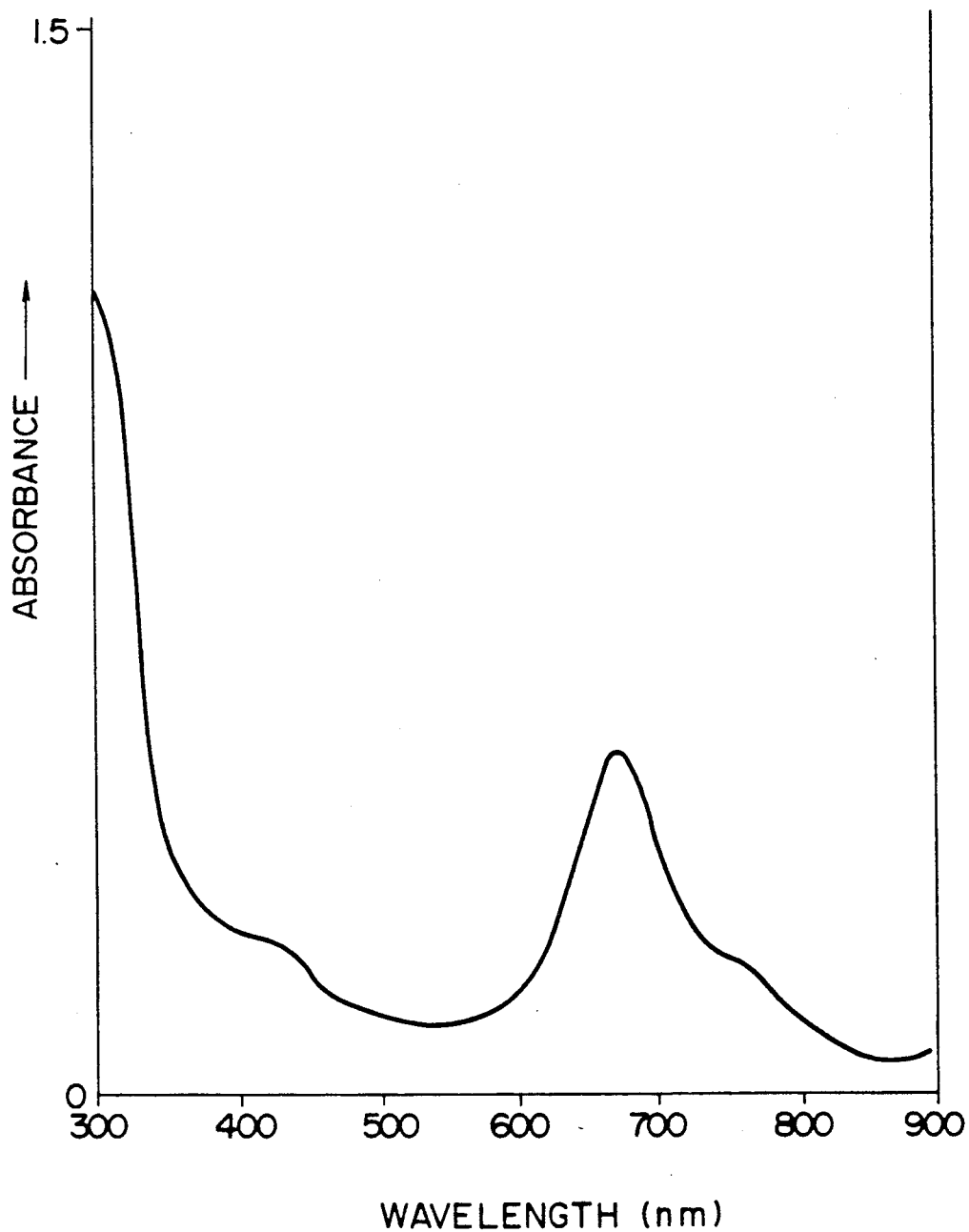
FIG. 27 is an electronic spectrum of tetrakis(n-amyloxycarbonyl) palladium naphthalocyanine.
Figure 28:
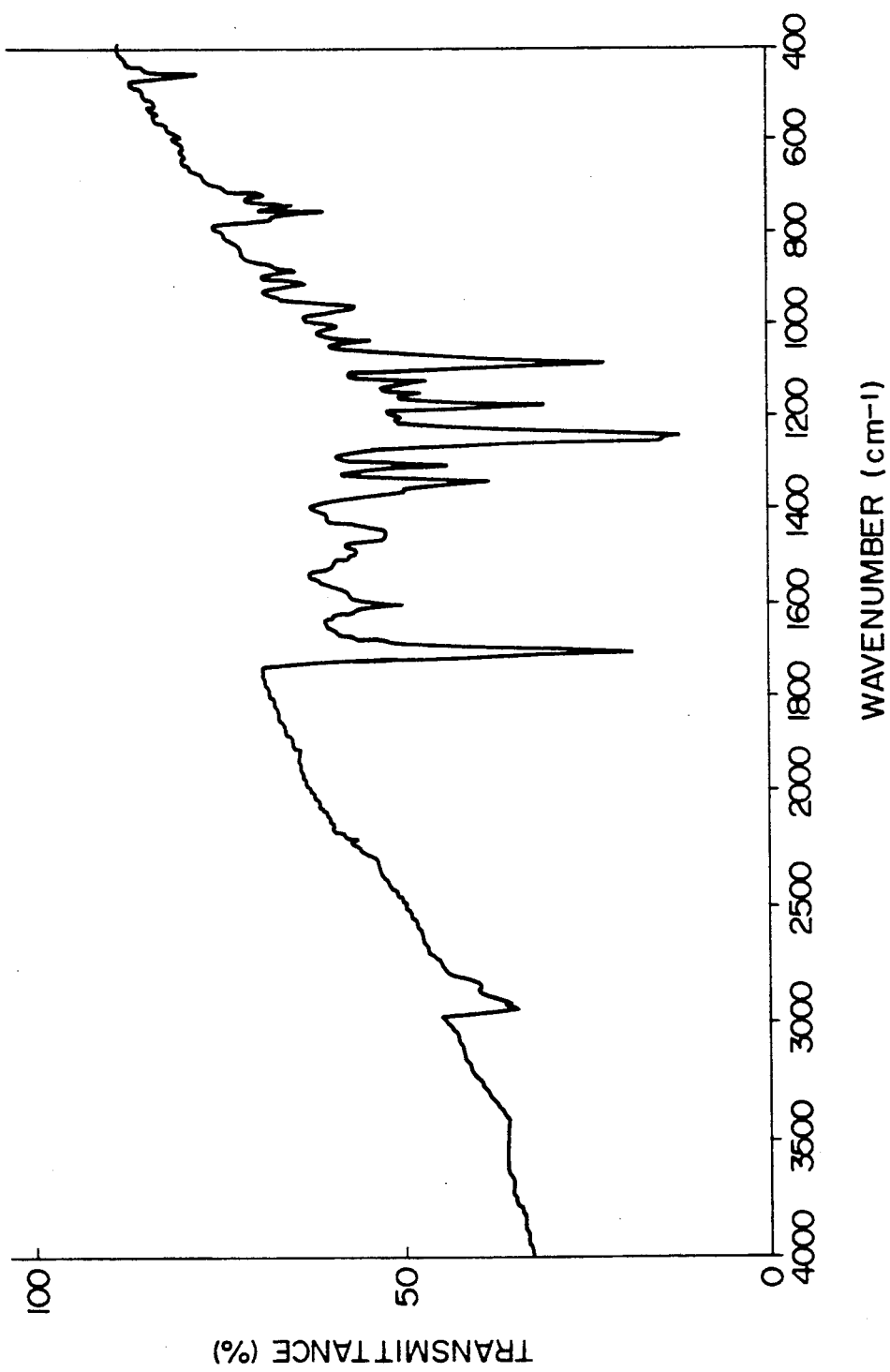
FIG. 28 is an IR spectrum of tetrakis(n-amyloxycarbonyl) palladium naphthalocyanine.

1.46 g (5 mmol) of 6-(n-amyloxycarbonyl)-2,3-dicyanonaphthalene, 284 mg (1.6 mmol) of palladium chloride, 10 mg of ammonium molybdate and 5 g of urea were reacted at about 220° C. for about 2.5 hours with thorough stirring. After cooling, the reaction mixture was treated in the same manner as in Example 1 to obtain 405 mg of tetrakis(n-amyloxycarbonyl) palladium naphthalocyanine as a black crystal with luster. Its electronic spectrum (CHCl$_3$ solution) is shown in FIG. 27. This compound also is stable at least at 300° C. or below. The IR spectrum (KBr) of the compound is shown in FIG. 28. There is an absorption attributable to the stretching vibration of C=O of ester, at about 1,700 cm$^{-1}$

EXAMPLE 9

Synthesis of tetrakis(n-octadecyloxycarbonyl) vanadyl naphthalocyanine [illustrative compound (5)]

650 mg (1.37 mmol) of 6-(n-octadecyloxycarbonyl)-2,3-dicyanonaphthalene, 88 mg (1.6 mmol) of vanadium trichloride, 3 mg of ammonium molybdate and 1.37 g of a urea were reacted at about 220° C. for about 2.5 hours with thorough stirring. After cooling, the reaction mixture was treated in the same manner as in Example 1 to obtain 556 mg of tetrakis(n-octadecyloxycarbonyl) vanadyl naphthalocyanine as a black crystal with luster. The following analytical results confirmed that the crystal was tetrakis(n-octadecyloxycarbonyl) vanadyl naphthalocyanine.

(1) Softening point: 135°–138° C.

| (2) Elemental analysis | | | |
| --- | --- | --- | --- |
| | C | H | N |
| Calculated (%) | 75.77 | 8.61 | 5.70 |
| Found (%) | 75.25 | 8.51 | 6.17 |

Figure 29:
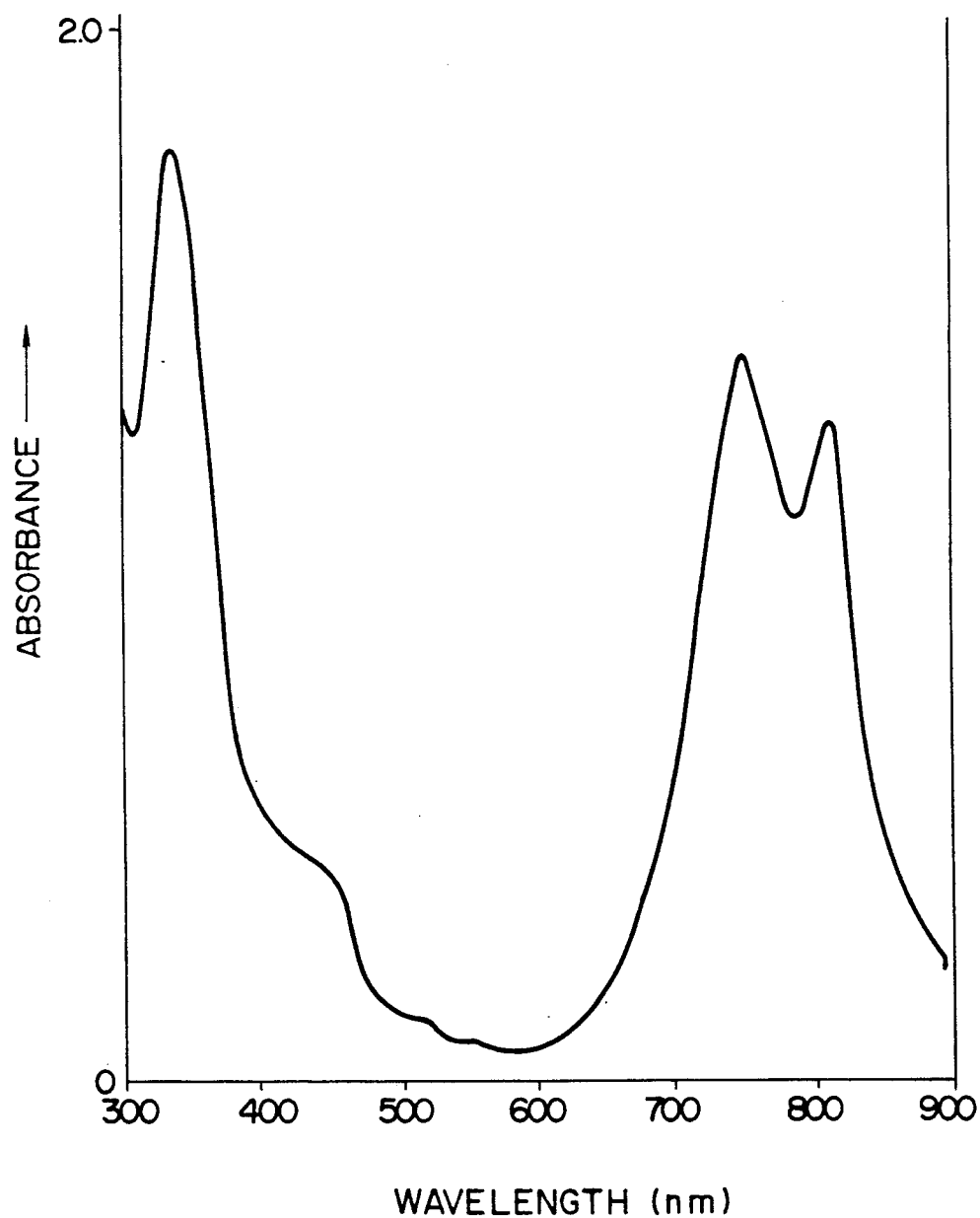
FIG. 29 is an electronic spectrum of tetrakis(n-octadecyloxycarbonyl) vanadyl naphthalocyanine.

(3) Electronic spectrum (CHCl$_3$ solution)
Shown in FIG. 29.

Figure 30:
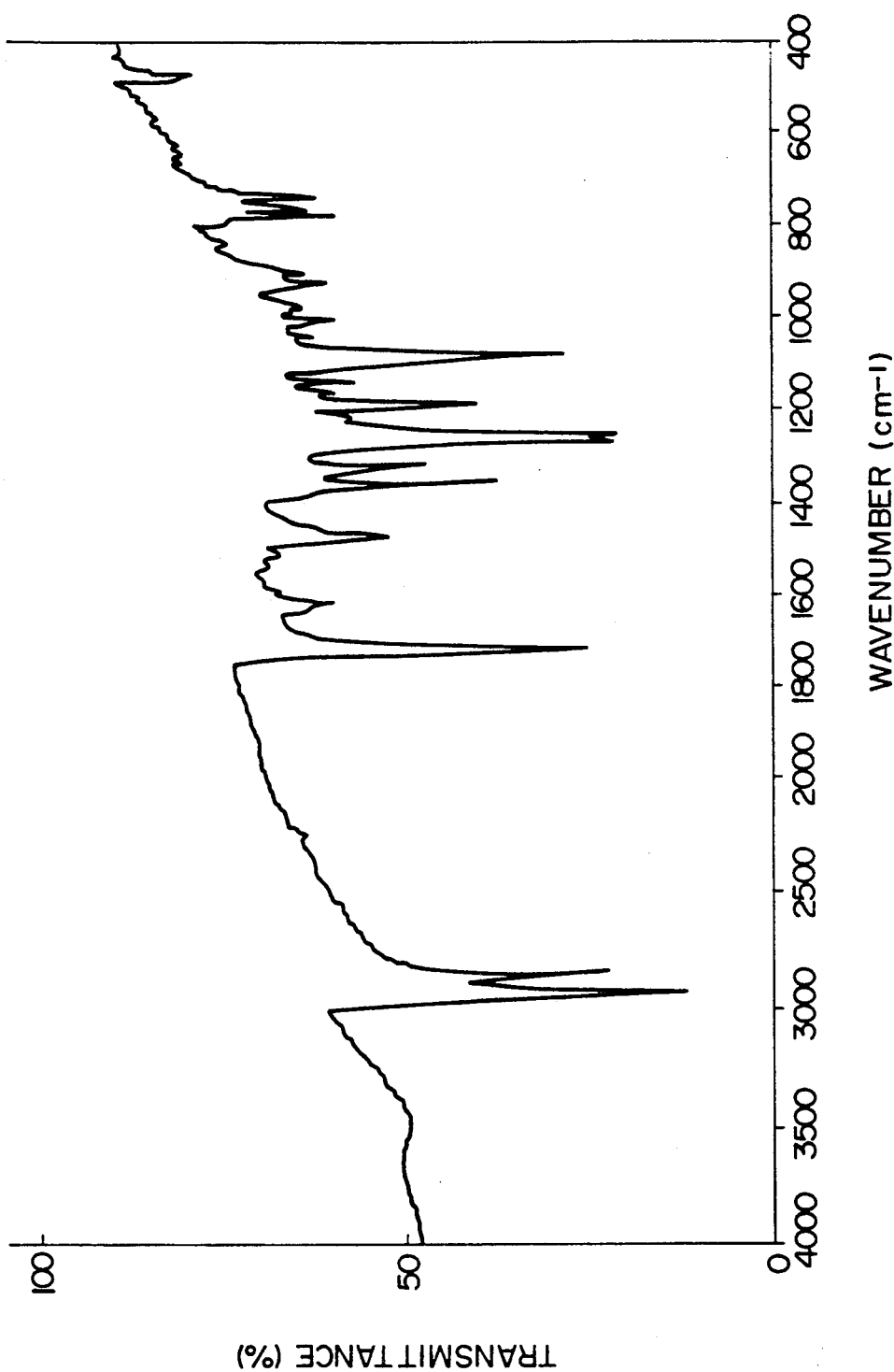
FIG. 30 is an IR spectrum of tetrakis(n-octadecyloxycarbonyl) vanadyl naphthalocyanine.

(4) IR spectrum (KBr)
Shown in FIG. 30. There is an absorption attributable to the stretching vibration of C=O of ester, at about 1,700 cm$^{-1}$.

EXAMPLE 10

Synthesis of tetrakis(n-octadecyloxycarbonyl) copper naphthalocyanine [illustrative compound (12)]

200 mg (0.42 mmol) of 6-(n-octadecyloxycarbonyl)-2,3-dicyanonaphthalene, 23 mg (0.13 mmol) of cupric chloride dihydrate, 1 mg of ammonium molybdate and 0.42 g of urea were reacted at about 220° C. for about 2.5 hours with thorough stirring. After cooling, the reaction mixture was treated in the same manner as in Example 1 to obtain 160 mg of tetrakis(n-octadecyloxycarbonyl) copper naphthalocyanine as a black crystal with luster. The following analytical results confirmed that the crystal was tetrakis(n-octadecyloxycarbonyl) copper naphthalocyanine.

(1) Softening point: 119°–121° C.

| (2) Elemental analysis | | | |
| --- | --- | --- | --- |
| | C | H | N |
| Calculated (%) | 75.90 | 8.63 | 5.71 |
| Found (%) | 75.63 | 8.51 | 5.66 |

Figure 31:
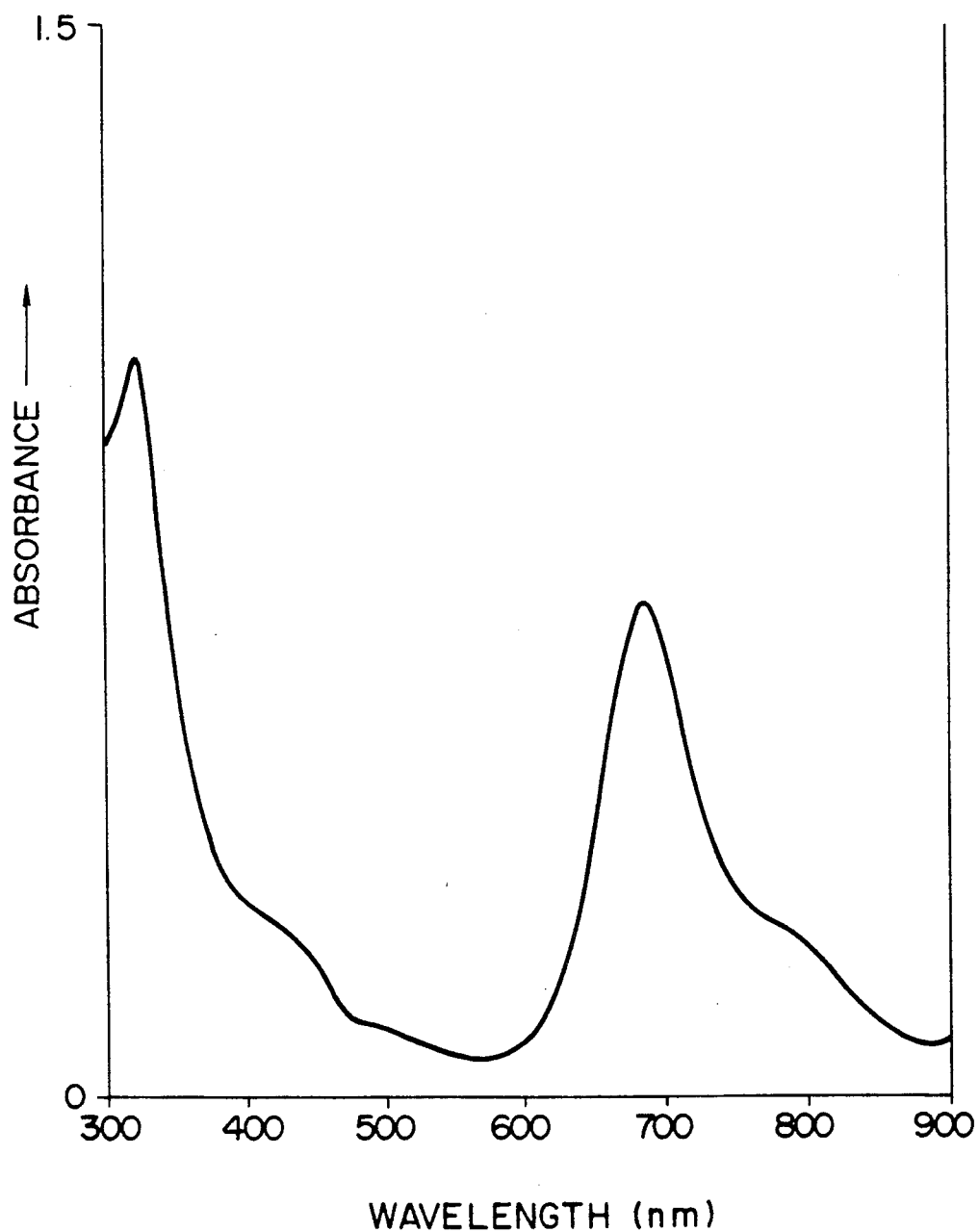
FIG. 31 is an electronic spectrum of tetrakis(n-octadecyloxycarbonyl) copper naphthalocyanine.

(3) Electronic spectrum (CHCl$_3$ solution)
Shown in FIG. 31.

(4) IR spectrum (KBr)
Shown in FIG. 32. There is an absorption attributable to the stretching vibration of C=O of ester, at about 1,720 cm$^{-1}$.

EXAMPLE 11

Synthesis of tetrakis(n-tetradecyloxycarbonyl) vanadyl naphthalocyanine [illustrative compound (3)]

42 mg (0.1 mmol) of 6-(n-tetradecyloxycarbonyl)-2,3-dicyanonaphthalene, 6.4 mg (0.04 mmol) of vanadium trichloride, 0.2 mg of ammonium molybdate and 100 mg of urea were reacted at about 220° C. for about 2.5 hours with thorough stirring. After cooling, the reaction mixture was treated in the same manner as in Example 1 to obtain 21 mg of a black crystal with luster. The folllowing analytical results confirmed that the crystal was tetrakis(n-tetradecyloxycarbonyl) vanadyl naphthalocyanine.

(1) Softening point: 210°–212° C.

| (2) Elemental analysis | | | |
| --- | --- | --- | --- |
| | C | H | N |
| Calculated (%) | 74.50 | 7.87 | 6.44 |
| Found (%) | 74.66 | 7.96 | 6.32 |

Figure 33:
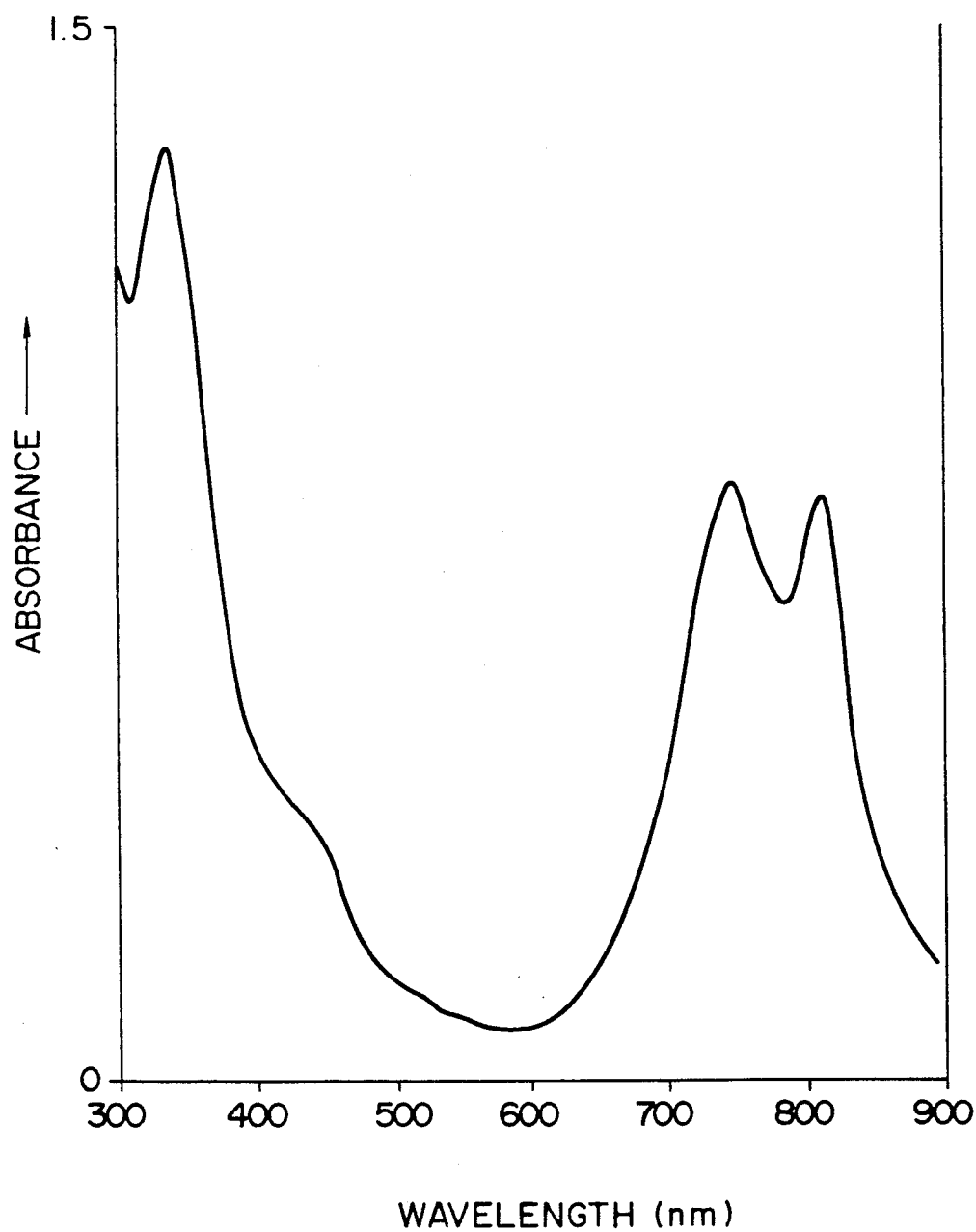
FIG. 33 is an electronic spectrum of tetrakis(n-tetradecyloxycarbonyl) vanadyl naphthalocyanine.

(3) Electronic spectrum (CHCl$_3$ solution)
Shown in FIG. 33.

(4) IR spectrum (KBr)

Figure 34:
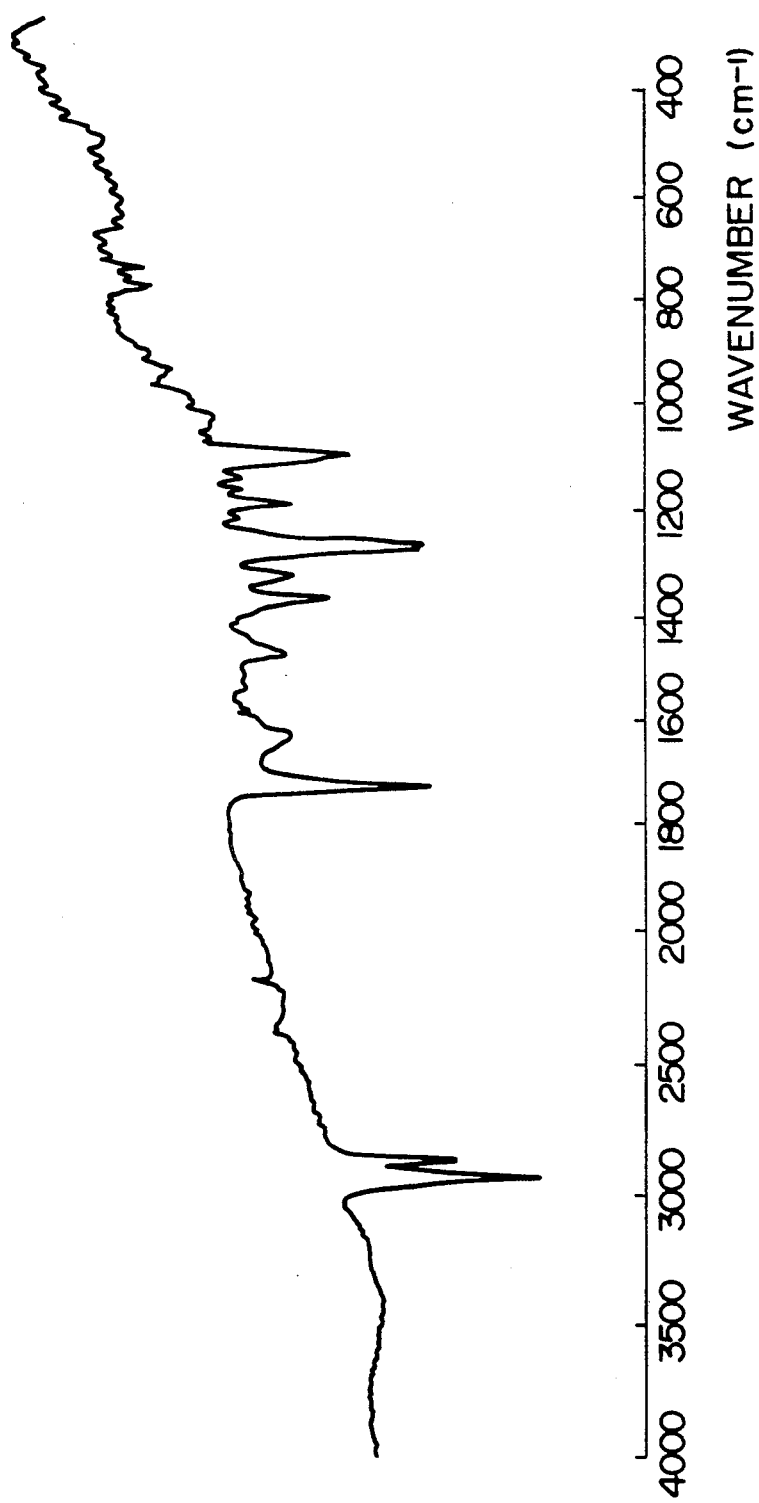
FIG. 34 is an IR spectrum of tetrakis(n-tetradecyloxycarbonyl) vanadyl naphthalocyanine.

Shown in FIG. 34. There is an absorption attributable to the stretching vibration of C=O of ester, at about 1,720 cm$^{-1}$.

EXAMPLE 12

Synthesis of tetrakis(n-tetradecyloxycarbonyl) copper naphthalocyanine [illustrative compound (10)]

42 mg (0.1 mmol) of 6-(n-tetradecyloxycarbonyl)-2,3-dicyanonaphthalene, 5.4 mg (0.03 mmol) of cupric chloride dihydrate, 0.2 mg of ammonium molybdate and 100 mg of urea were reacted at about 220° C. for about 2.5 hours with thorough stirring. After cooling, the reaction mixture was treated in the same manner as in Example 1 to obtain 21 mg of a black crystal with luster. The following analytical result confirmed that the crystal was tetrakis(n-tetradecyloxycarbonyl) copper naphthalocyanine.

(1) Softening point: 168°–171° C.

| (2) Elemental analysis | | | |
|---|---|---|---|
| | C | H | N |
| Calculated (%) | 74.64 | 7.89 | 6.45 |
| Found (%) | 74.82 | 6.76 | 6.37 |

Figure 35:
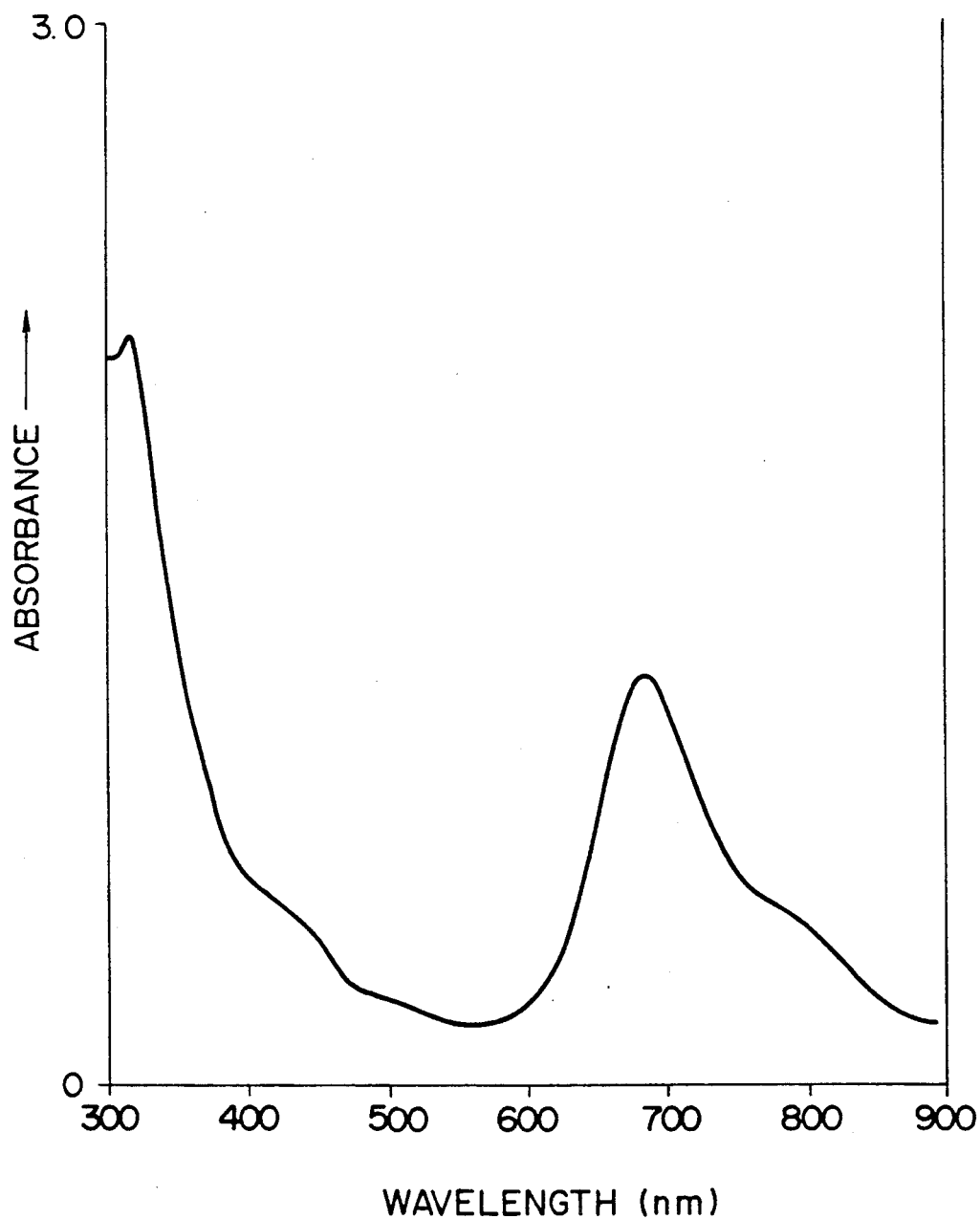
FIG. 35 is an electronic spectrum of tetrakis(n-tetradecyloxycarbonyl) copper naphthalocyanine.

(3) Electronic spectrum (CHCl$_3$ solution)
Shown in FIG. 35.

Figure 36:
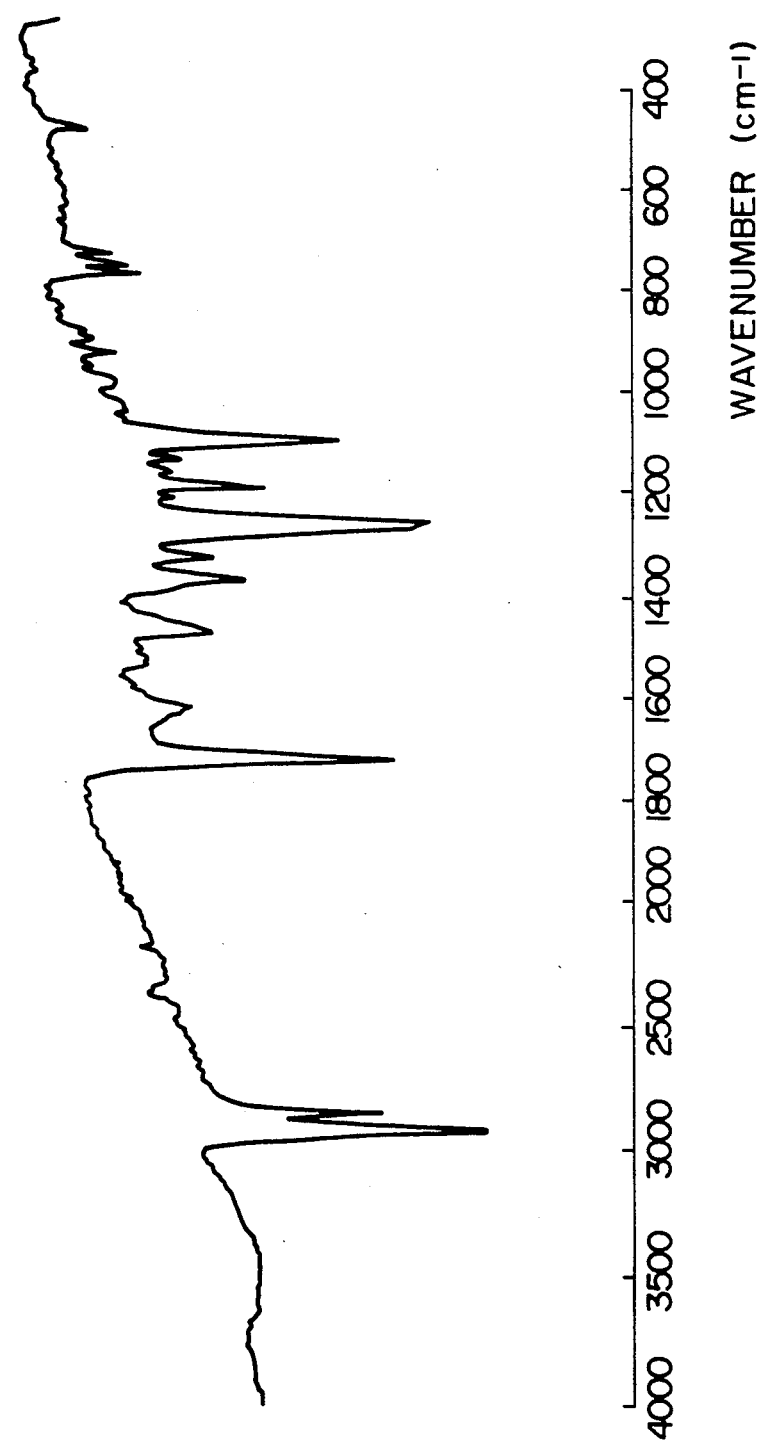
FIG. 36 is an IR spectrum of tetrakis(n-tetradecyloxycarbonyl) copper naphthalocyanine.

(4) IR spectrum (KBr)
Shown in FIG. 36. There is an absorption attributable to the stretching vibration of C=O of ester, at about 1,720 cm$^{-1}$.

EXAMPLE 13

Synthesis of tetrakis(n-hexadecyloxycarbonyl) vanadyl naphthalocyanine [illustrative compound (4)]

45 mg (0.1 mmol) of 6-(n-hexadecyloxycarbonyl)-2,3-dicyanonaphthalene, 6.4 mg (0.04 mmol) of vanadium trichloride, 0.2 mg of ammonium molybdate and 100 mg of urea were reacted at about 220° C. for about 2.5 hours with thorough stirring. After cooling, the reaction mixture was treated in the same manner as in Example 1 to obtain 13 mg of a black crystal with luster. The following analytical results confirmed that the crystal was tetrakis(n-hexadecyloxycarbonyl) vanadyl naphthalocyanine.

(1) Softening point: 151°–154° C.

| (2) Elemental analysis | | | |
|---|---|---|---|
| | C | H | N |
| Calculated (%) | 75.17 | 8.27 | 6.05 |
| Found (%) | 75.26 | 8.19 | 6.13 |

Figure 37:
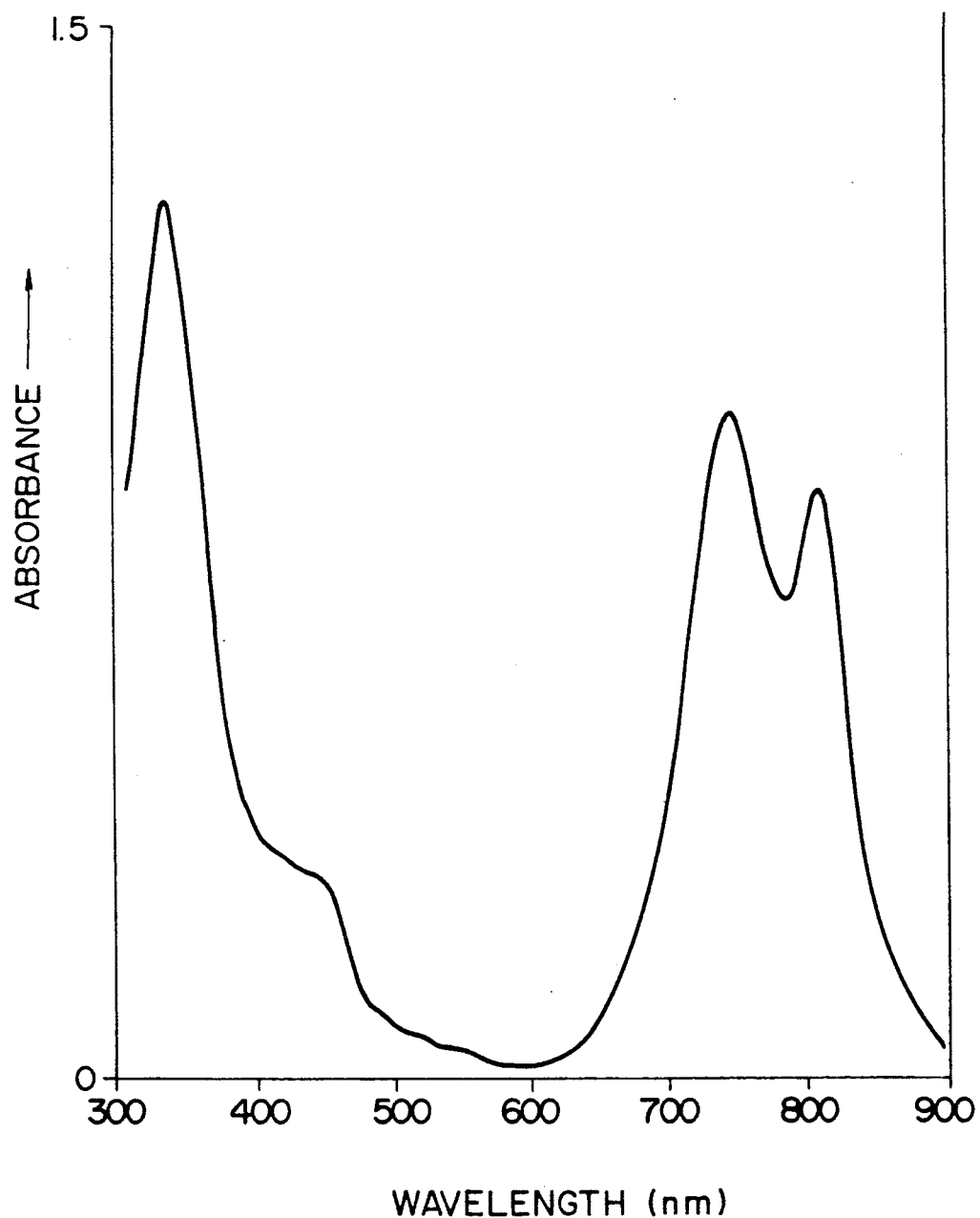
FIG. 37 is an electronic spectrum of tetrakis(n-hexadecyloxycarbonyl) vanadyl naphthalocyanine.

(3) Electronic spectrum (CHCl$_3$ solution)
Shown in FIG. 37.

Figure 38:
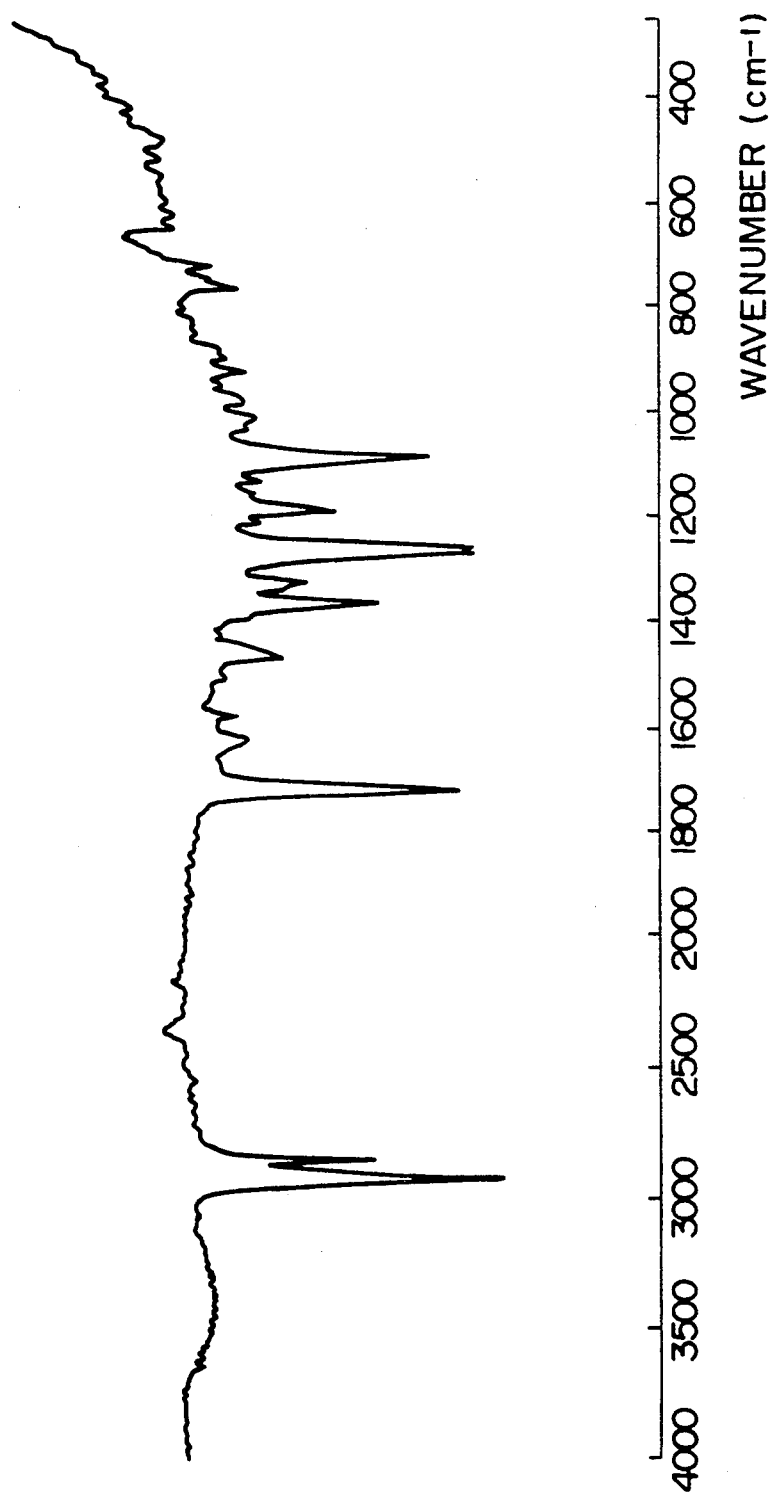
FIG. 38 is an IR spectrum of tetrakis(n-hexadecyloxycarbonyl) vanadyl naphtalocyanine.

(4) IR spectrum (KBr)
Shown in FIG. 38. There is an absorption attributable to the stretching vibration of C=O of ester, at about 1,720 cm$^{-1}$.

EXAMPLE 14

Synthesis of tetrakis(n-eicosyloxycarbonyl) vanadyl naphthalocyanine [illustrative compound (6)]

52 mg (0.1 mmol) of 6-(n-eicosyloxycarbonyl)-2,3-dicyanonaphthalene, 6.4 mg (0.04 mmol) of vanadium trichloride, 0.2 mg of ammonium molybdate and 100 mg of urea were reacted at about 220° C. for about 2.5 hours with thorough stirring. After cooling, the reaction mixture was treated in the same manner as in Example 1 to obtain 26 mg of a black crystal with luster. The following analytical results confirmed that the crystal was tetrakis(n-eicosyloxycarbonyl) vanadyl naphthalocyanine.

(1) Softening point: 83°–85° C.

| (2) Elemental analysis | | | |
|---|---|---|---|
| | C | H | N |
| Calculated (%) | 76.30 | 8.93 | 5.39 |
| Found (%) | 76.92 | 8.87 | 5.28 |

Figure 39:
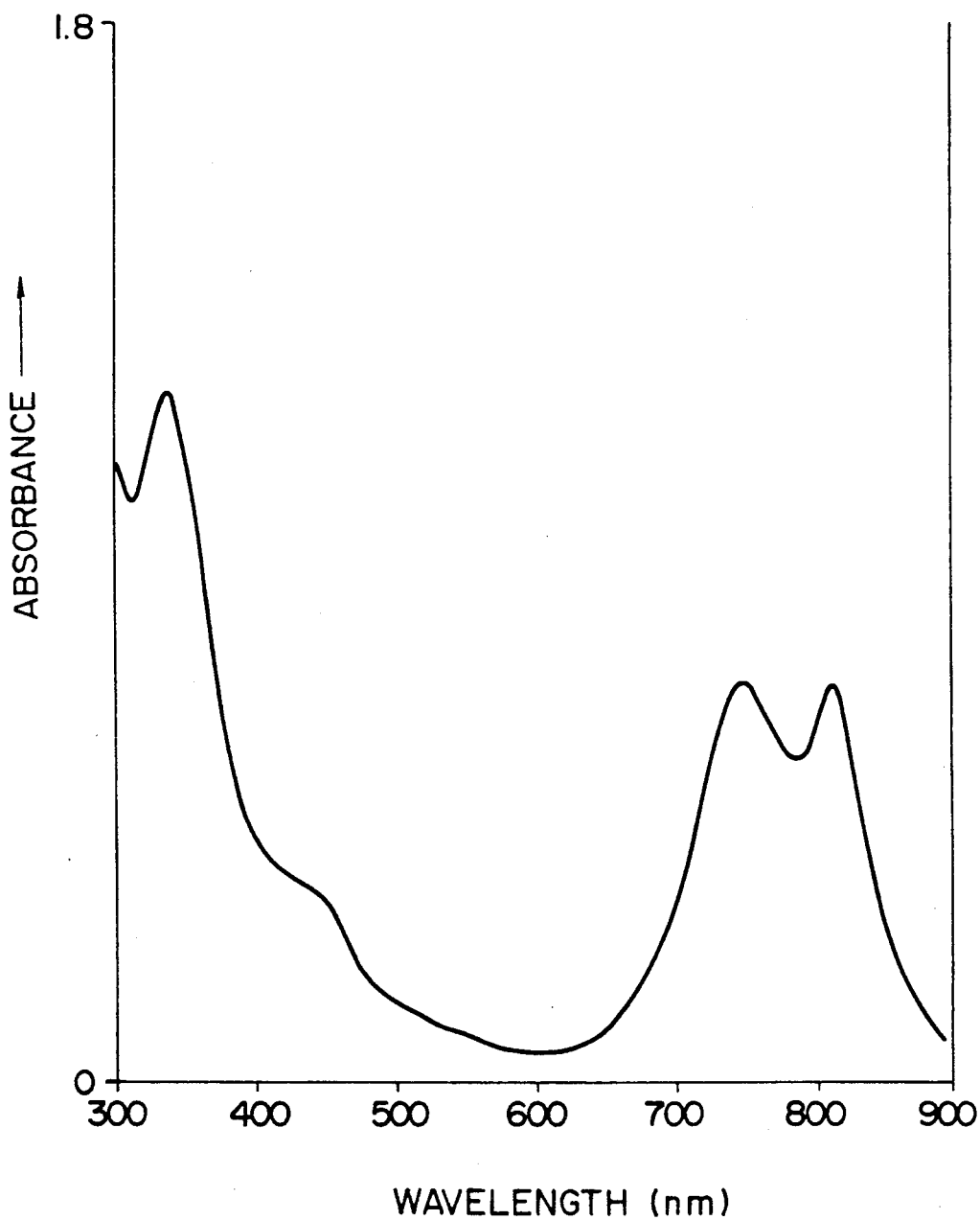
FIG. 39 is an electronic spectrum of tetrakis(n-eicosyloxycarbonyl) vanadyl naphthalocyanine.

(3) Electronic spectrum (CHCl$_3$ solution)
Shown in FIG. 39.

Figure 40:
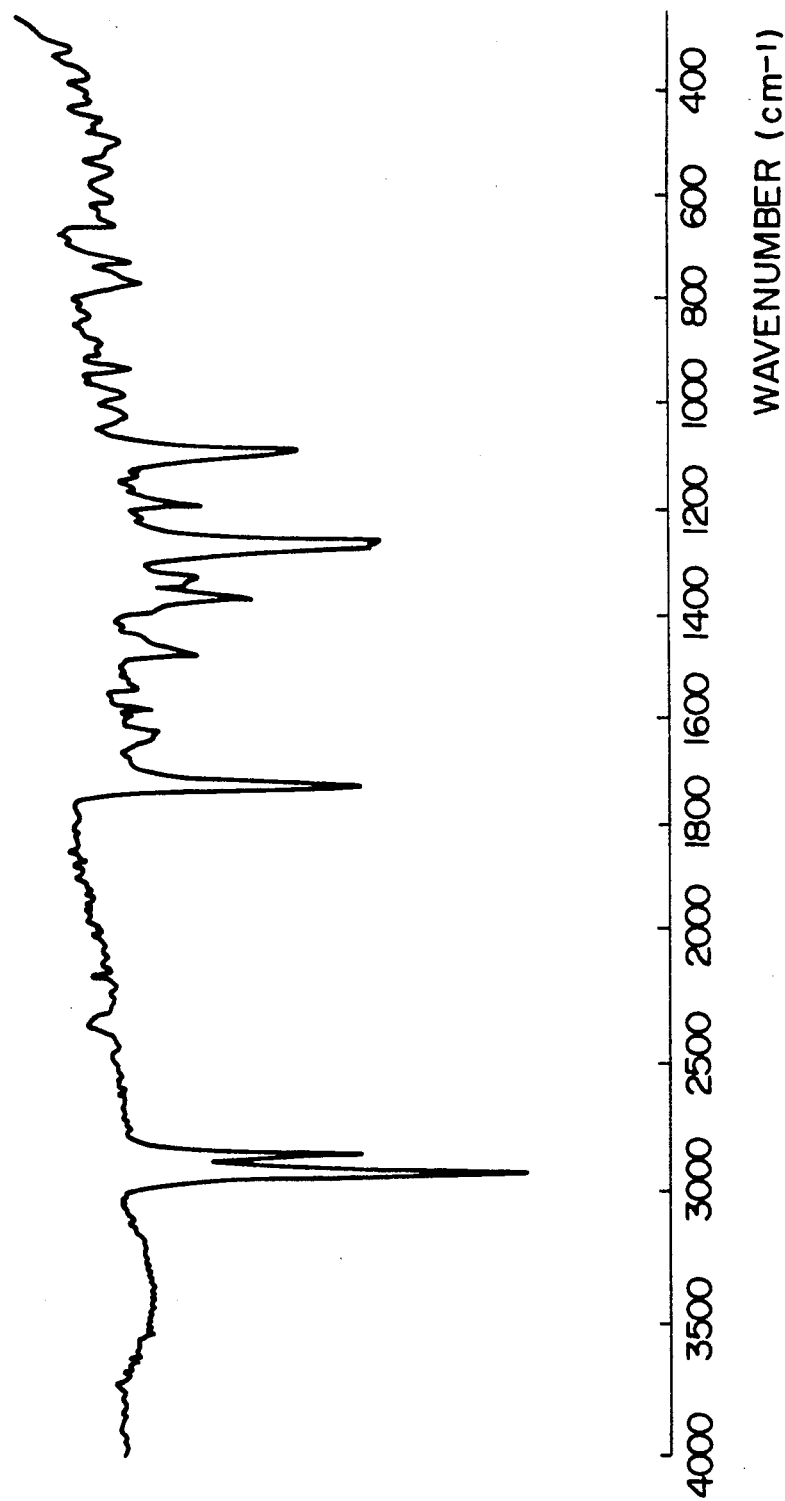
FIG. 40 is an IR spectrum of tetrakis(n-eicosyloxycarbonyl) vanadyl naphthalocyanine.

(4) IR spectrum (KBr)
Shown in FIG. 40. There is an absorption attributable to the stretching vibration of C=O of ester, at about 1,720 cm$^{-1}$.

EXAMPLE 15

Synthesis of tetrakis(n-eicosyloxycarbonyl) copper naphthalocyanine [illustrative compound (11)]

52 mg (0.1 mmol) of 6-(n-eicosyloxycarbonyl)-2,3-dicyanonaphthalene, 5.5 mg (0.03 mmol) of cupric chloride dihydrate, 0.2 mg of ammonium molybdate and 100 mg of urea were reacted at about 220° C. for about 2.5 hours with thorough stirring. After cooling, the reaction mixture was treated in the same manner as in Example 1 to obtain 36 mg of a black crystal with luster. The following analytical results confirmed that the crystal was tetrakis(n-eicosyloxycarbonyl) copper naphthalocyanine.

(1) Softening point: 67°–70° C.

| (2) Elemental analysis | | | |
|---|---|---|---|
| | C | H | N |
| Calculated (%) | 76.43 | 8.94 | 5.40 |
| Found (%) | 76.62 | 8.78 | 5.61 |

Figure 41:
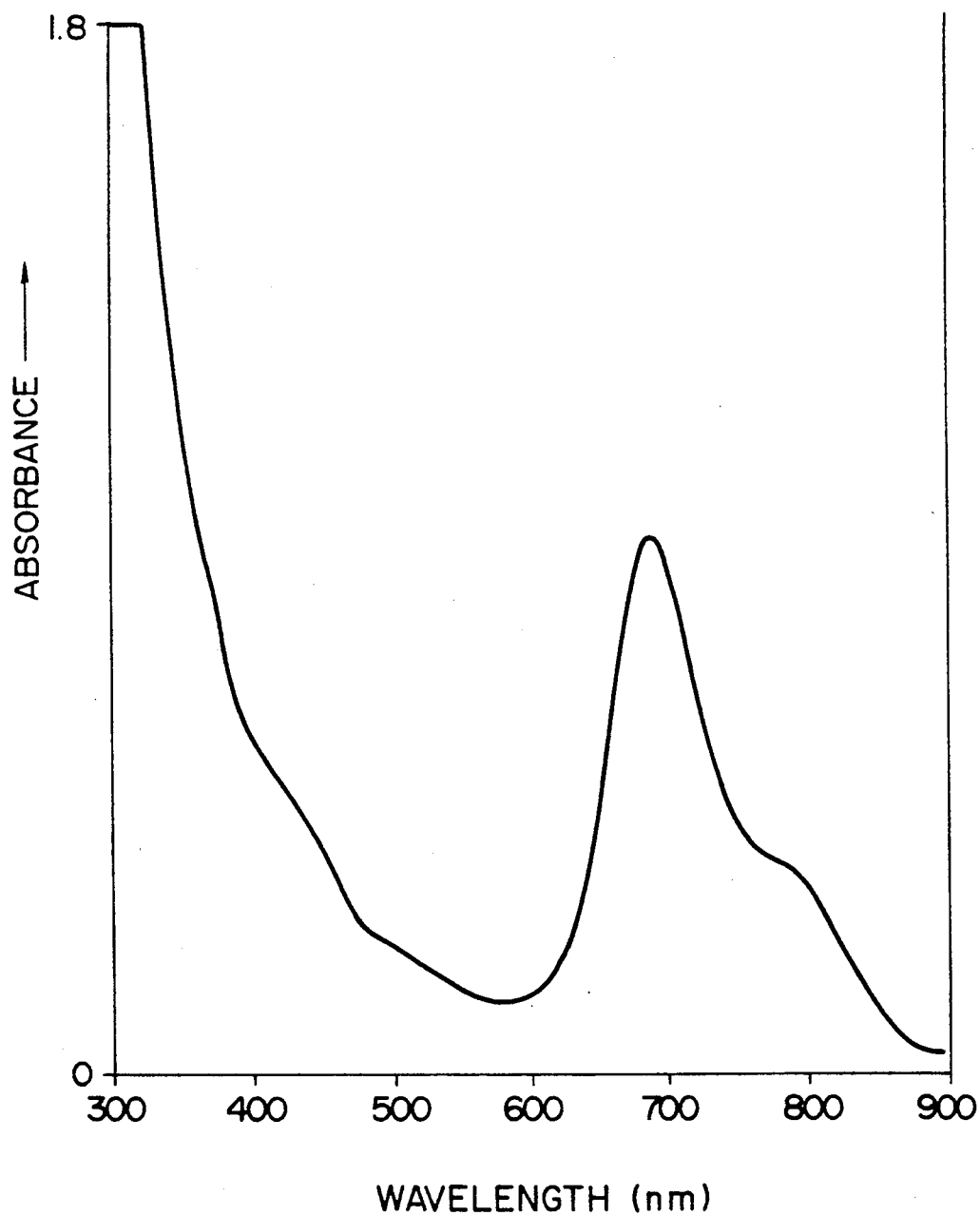
FIG. 41 is an electronic spectrum of tetrakis(n-eicosyloxycarbonyl) copper naphthalocyanine.

(3) Electronic spectrum (CHCl$_3$ solution)
Shown in FIG. 41.

Figure 42:
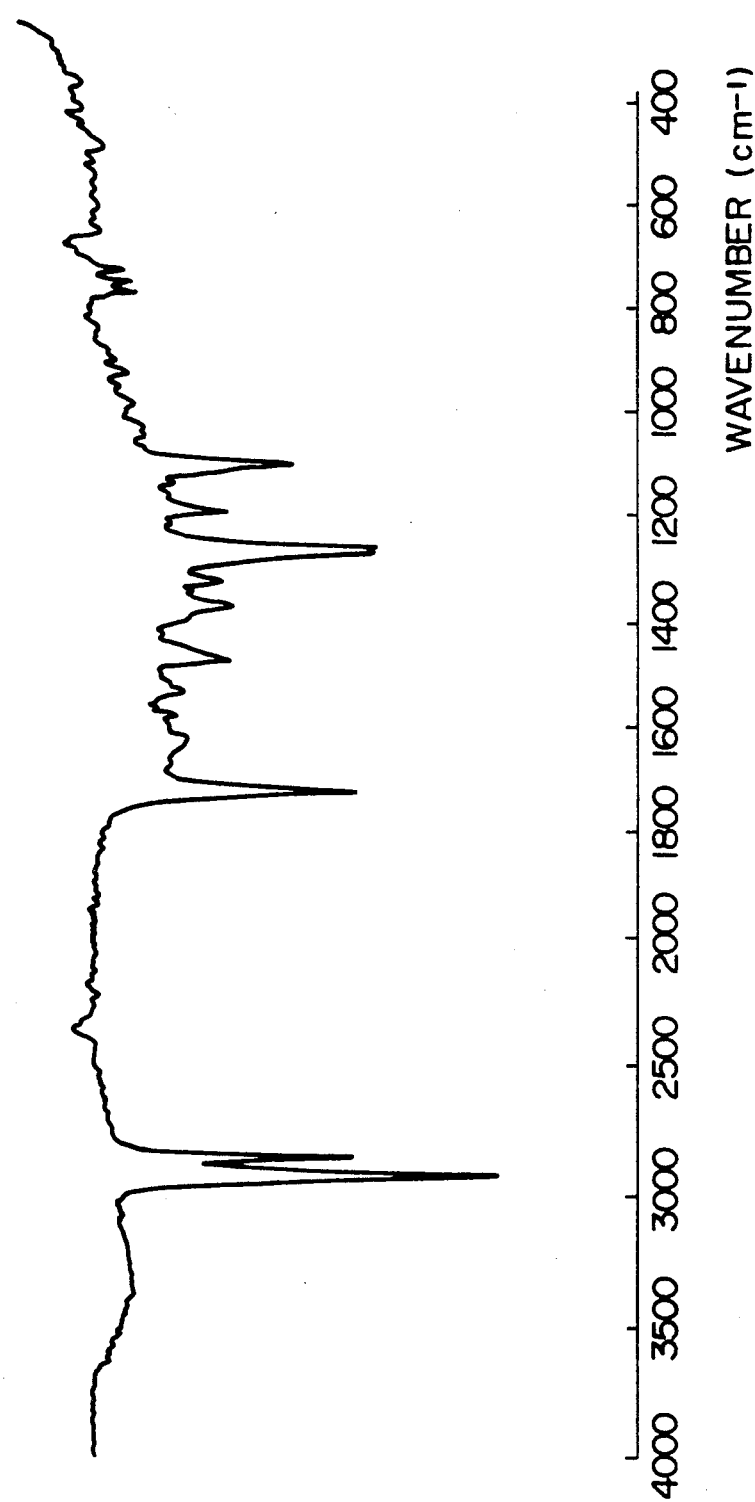
FIG. 42 is an IR spectrum of tetrakis(n-eicosyloxycarbonyl) copper naphthalocyanine.

(4) IR spectrum (KBr)
Shown in FIG. 42. There is an absorption attributable to the stretching vibration of C=O of ester, at about 1,720 cm$^{-1}$.

EXAMPLE 16

Synthesis of tetrakis(n-amyloxycarbonyl) cobalt naphthalocyanine [illustrative compound (20)]

1.46 g (5 mmol) of 6-(n-amyloxycarbonyl)-2,3-dicyanonaphthalene, 0.38 g (1.6 mmol) of cobalt chloride hexahydrate, 10 mg of ammonium molybdate and 5 g of urea were reacted at about 220° C. for about 2.5 hours with thorough stirring. After cooling, the reaction mixture was treated in the same manner as in Example 1 to obtain 823 mg of a black crystal with luster. The following analytical results confirmed that the crystal was tetrakis(n-amyloxycarbonyl) cobalt naphthalocyanine.

(1) Melting point: above 300° C. (stable at least at 300° C. or below)

| (2) Elemental analysis | | | |
|---|---|---|---|
| | C | H | N |
| Calculated (%) | 70.41 | 5.25 | 9.12 |
| Found (%) | 69.54 | 5.02 | 9.36 |

Figure 43:
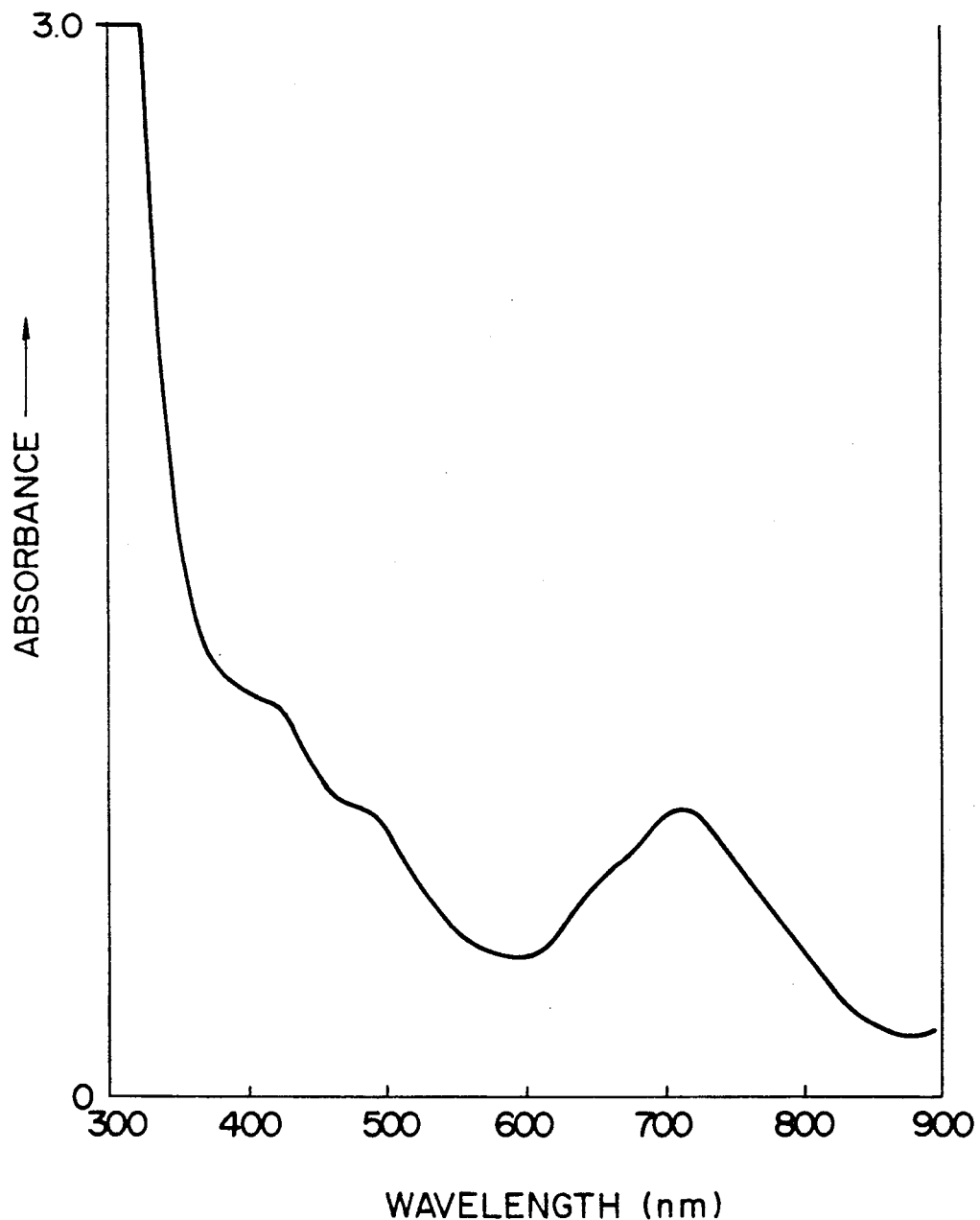
FIG. 43 is an electronic spectrum of tetrakis(n-amyloxycarbonyl) cobalt naphthalocyanine.

(3) Electronic spectrum (CHCl$_3$ solution)
Shown in FIG. 43.

Figure 44:
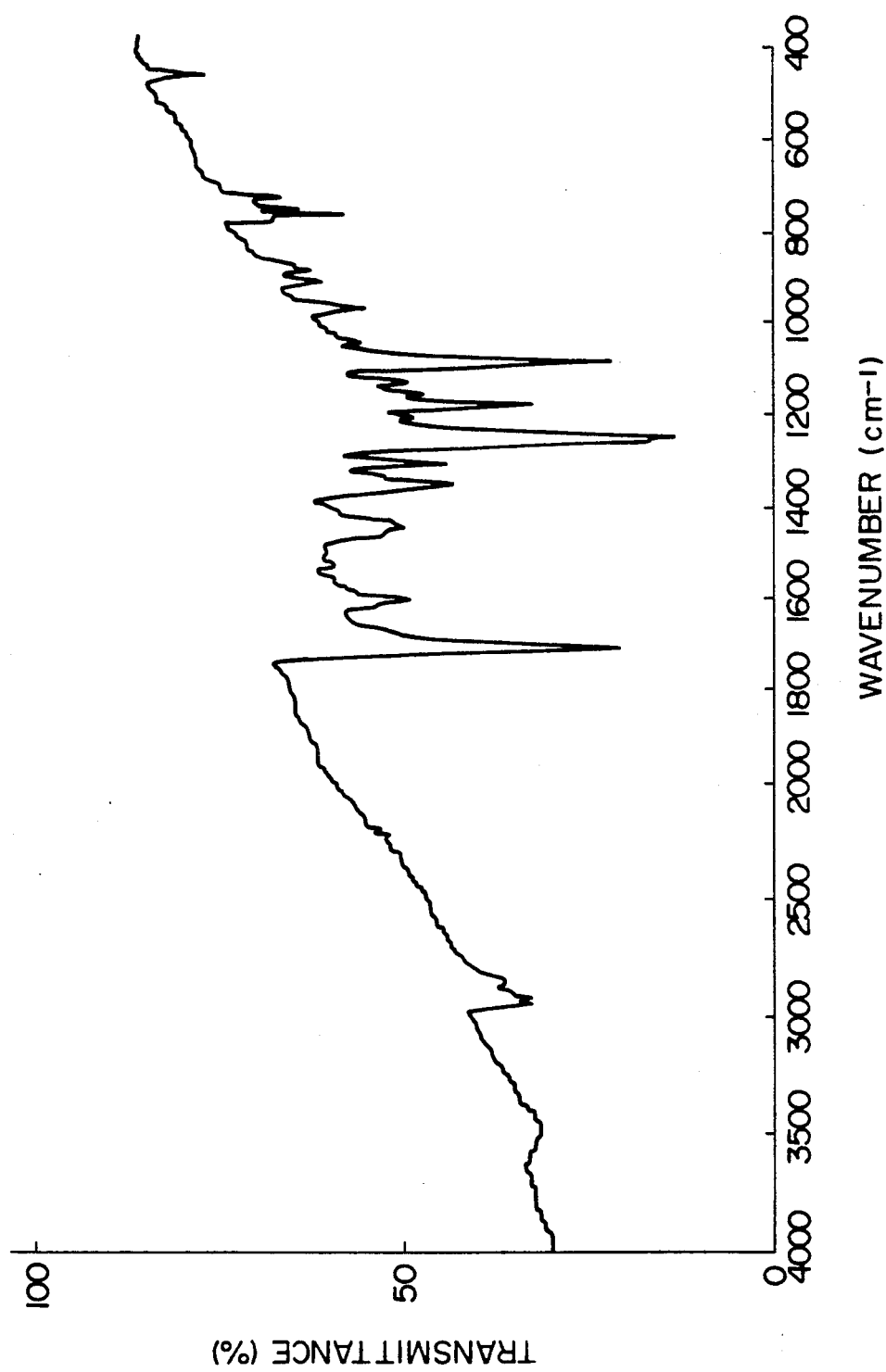
FIG. 44 is an IR spectrum of tetrakis(n-amyloxycarbonyl) cobalt naphthalocyanine.

(4) IR spectrum (KBr)
Shown in FIG. 44. There is an absorption attributable to the stretching vibration of C=O of ester, at about 1,700 cm$^{-1}$.

EXAMPLE 17

Synthesis of tetrakis(n-amyloxycarbonyl) manganese naphthalocyanine [illustrative compound (22)]

1.46 g (5 mmol) of 6-(n-amyloxycarbonyl)-2,3-dicyanonaphthalene, 392 mg (1.6 mmol) of manganese acetate tetrahydrate, 10 mg of ammonium molybdate and 5 g of urea were reacted at about 220° C. for about 2.5 hours with thorough stirring. After cooling, the reaction mixture was treated in the same manner as in Example 1 to obtain 605 mg of a black crystal with luster. The following analytical results confirmed that the crystal was tetrakis(n-amyloxycarbonyl) manganese naphthalocyanine.

(1) Melting point: above 300° C. (stable at least at 300° C. or below)

| (2) Elemental analysis | | | |
|---|---|---|---|
| | C | H | N |
| Calculated (%) | 70.64 | 5.27 | 9.15 |
| Found (%) | 70.79 | 5.19 | 9.66 |

Figure 45:
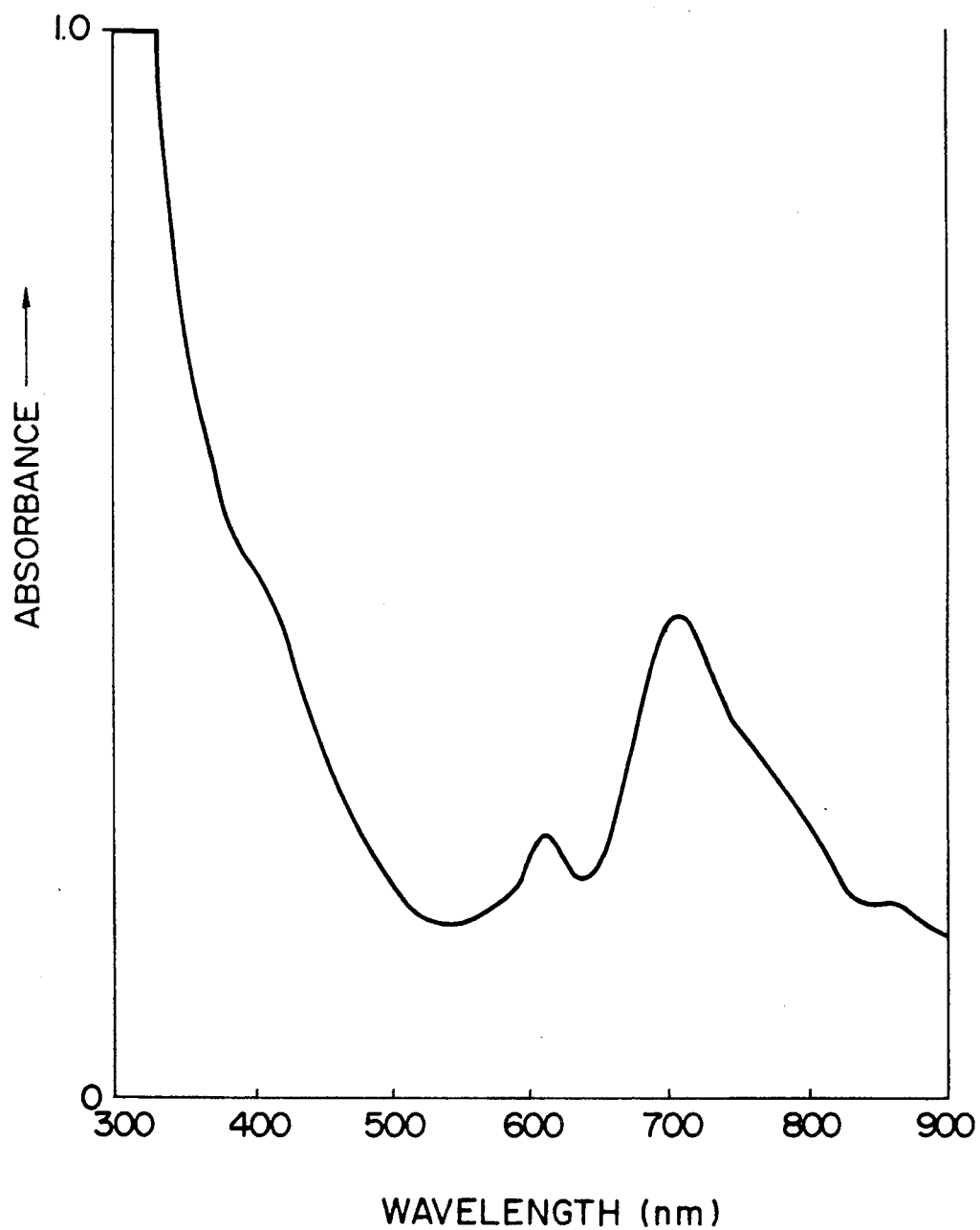
FIG. 45 is an electronic spectrum of tetrakis(n-amyloxycarbonyl) manganese naphthalocyanine.

(3) Electronic spectrum (CHCl$_3$ solution)
Shown in FIG. 45.

Figure 46:
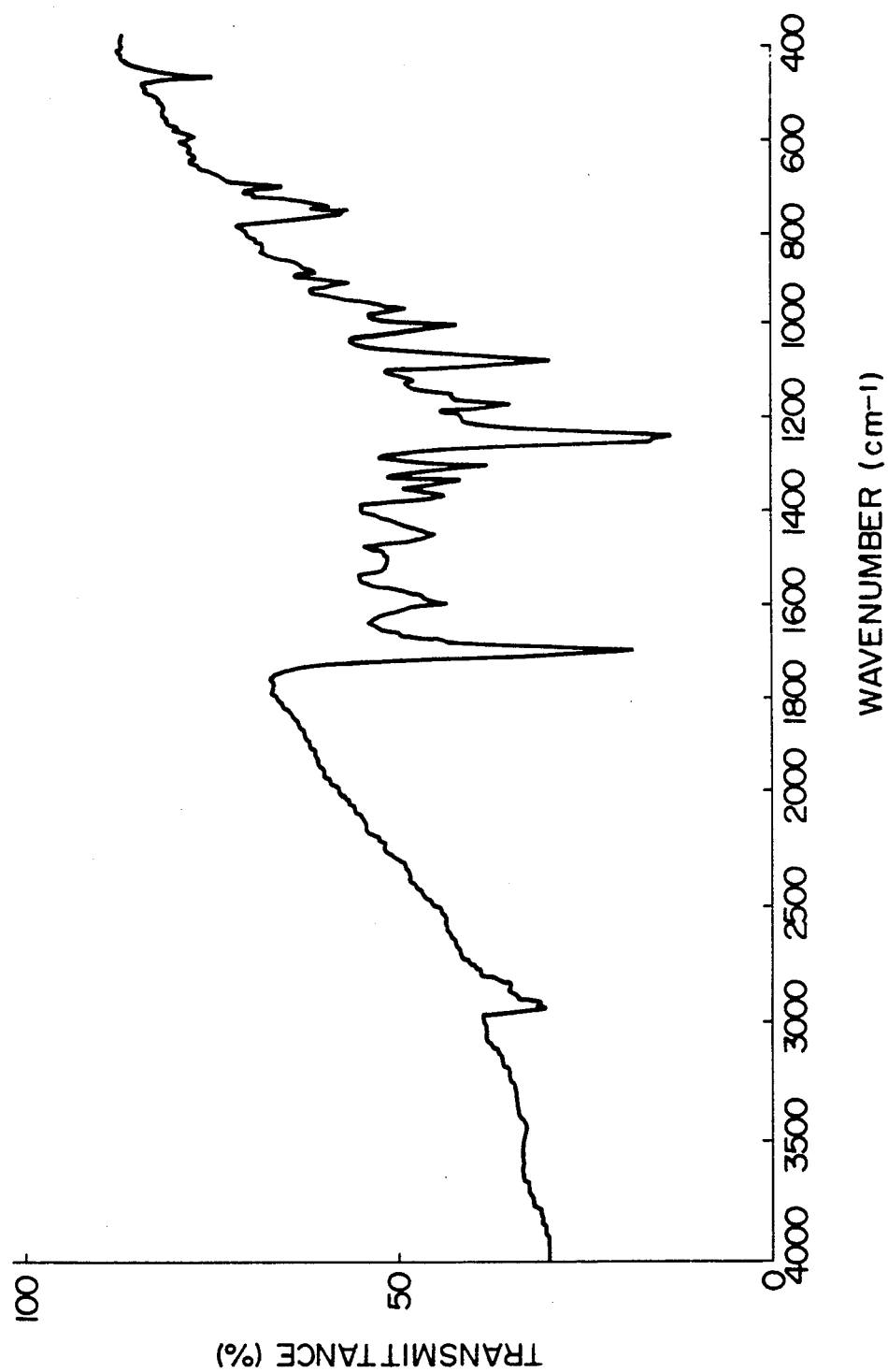
FIG. 46 is an IR spectrum of tetrakis(n-amyloxycarbonyl) manganese naphthalocyanine.

(4) IR spectrum (KBr)
Shown in FIG. 46. There is an absorption attributable to the stretching vibration of C=O of ester, at about 1,700 cm$^{-1}$.

EXAMPLE 18

Synthesis of tetrakis(n-octyloxycarbonyl) chloroindium naphthalocyanine [illustrative compound (27)]

1.67 g (5 mmol) of 6-(n-octyloxycarbonyl)-2,3-dicyanonaphthalene, 470 mg (1.6 mmol) of indium trichloride tetrahydrate, 10 mg of ammonium molybdate and 5 g of urea were reacted at about 220° C. for about 2.5 hours with thorough stirring. The reaction mixture was treated in the same manner as in Example 1 to obtain 1.32 g of a black crystal with luster. The following analytical results confirmed that the crystal was tetrakis(n-octyloxycarbonyl) chloroindium naphthalocyanine.

(1) Melting point: above 300° C. (stable at least at 300° C. or below)

| (2) Elemental analysis | | | | |
|---|---|---|---|---|
| | C | H | N | Cl |
| Calculated (%) | 67.81 | 5.96 | 7.53 | 2.38 |
| Observed (%) | 67.88 | 5.74 | 7.78 | 1.99 |

Figure 47:
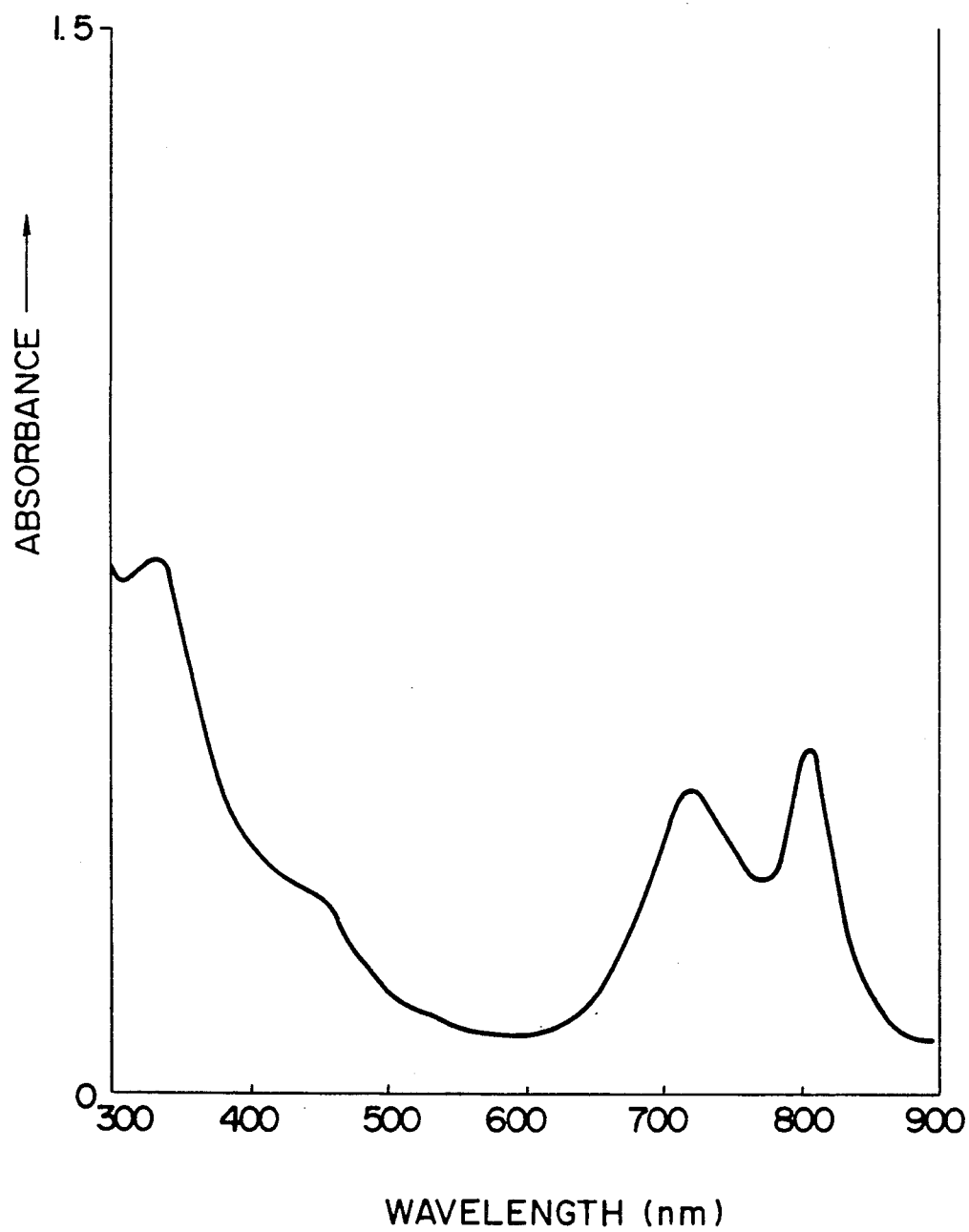
FIG. 47 is an electronic spectrum of tetrakis(n-octyloxycarbonyl) chloroindium naphthalocyanine.

(3) Electronic spectrum (CHCl$_3$ solution)
Shown in FIG. 47.

Figure 48:
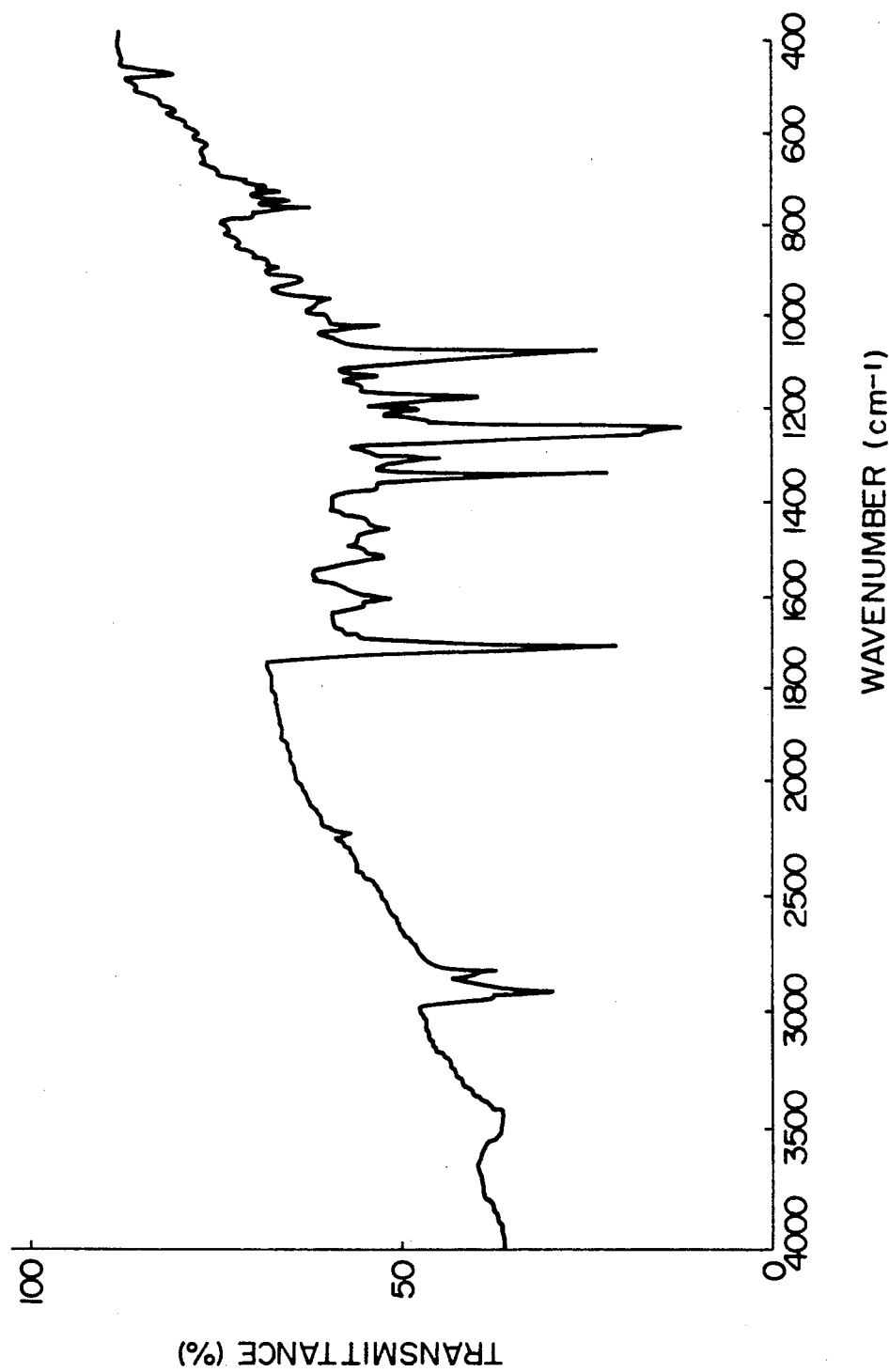
FIG. 48 is an IR spectrum of tetrakis(n-octyloxycarbonyl) chloroindium naphthalocyanine.

(4) IR spectrum (KBr)
Shown in FIG. 48. There is an absorption attributable to the stretching vibration of C=O of ester, at about 1,700 cm$^{-1}$.

EXAMPLE 19

Synthesis of tetrakis(n-octyloxycarbonyl) chloroaluminum naphthalocyanine [illustrative compound (24)]

1.67 g (5 mmol) of 6-(n-octyloxycarbonyl)-2,3-dicyanonaphthalene, 213 mg (1.6 mmol) of aluminum chloride, 10 mg of ammonium molybdate and 5 g of urea were reacted at about 220° C. for about 2.5 hours with thorough stirring. After cooling, to the reaction mixture in solid form was added 40 ml of methanol, and then the whole mixture was stirred thoroughly at about 50° C. for 30 minutes. The insoluble material was collected by filtration and washed thoroughly with methanol and acetone in this order. The resulting solid was freed of impurities by extraction with methanol for about 100 hours and then with acetone for about 50 hours in a Soxhlet's extractor. Then, Soxhlet extraction was conducted with chloroform for about 20 hours. The resulting dark green chloroform solution was subjected to filtration when hot, and the filtrate was concentrated to dryness under reduced pressure to obtain 243 mg of a black crystal with luster. The following analytical results confirmed that the crystal was tetrakis(n-octyloxycarbonyl) chloroaluminum naphthalocyanine.

(1) Melting point: above 300° C. (stable at least at 300° C. or below)

| (2) Elemental analysis | | | | |
|---|---|---|---|---|
| | C | H | N | Cl |
| Calculated (%) | 72.06 | 6.34 | 8.00 | 2.53 |
| Found (%) | 71.81 | 6.27 | 7.74 | 2.07 |

Figure 49:
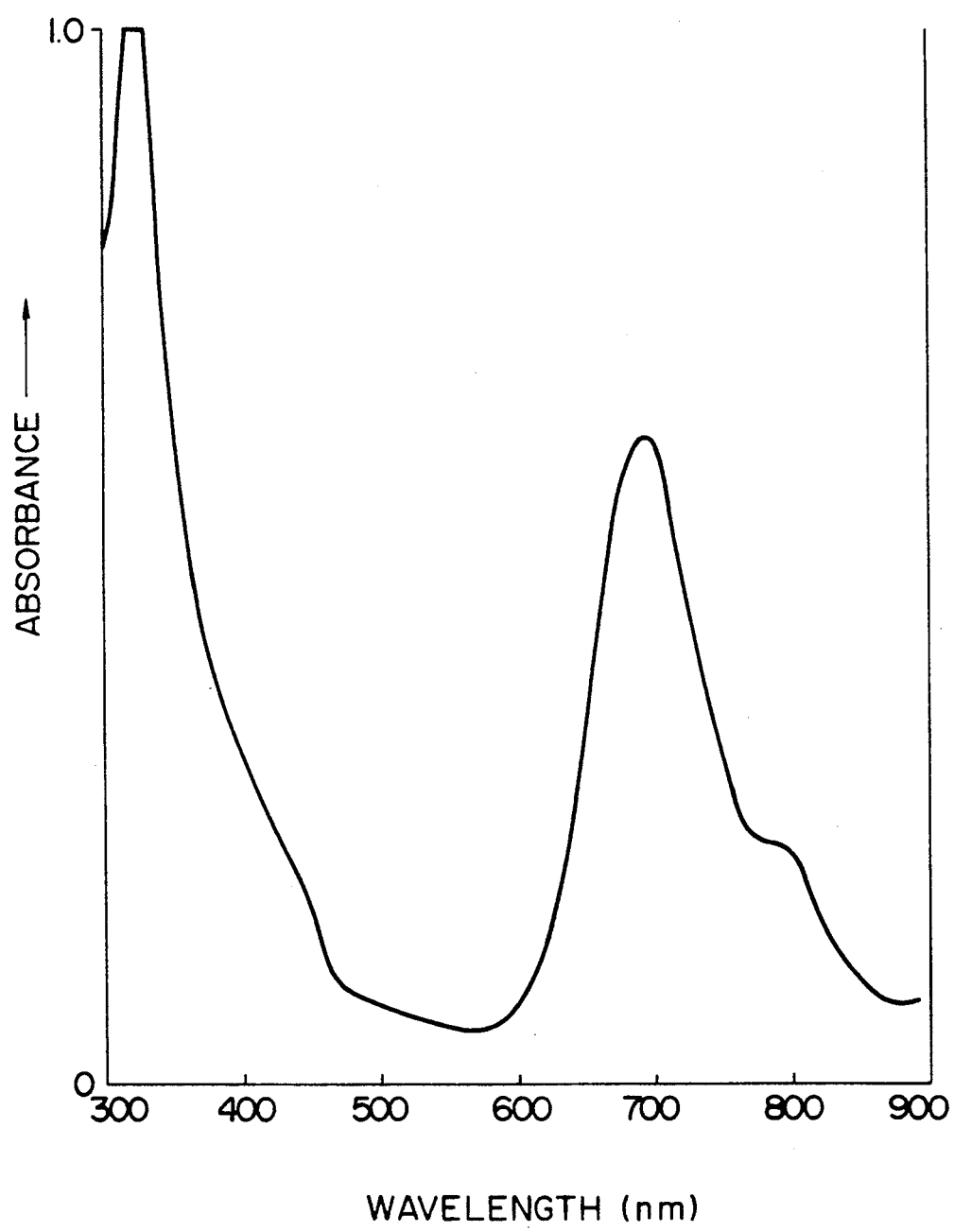
FIG. 49 is an electronic spectrum of tetrakis(n-octyloxycarbonyl) chloroaluminum naphthalocyanine.

(3) Electronic spectrum (CHCl$_3$ solution)
Shown in FIG. 49.

Figure 50:
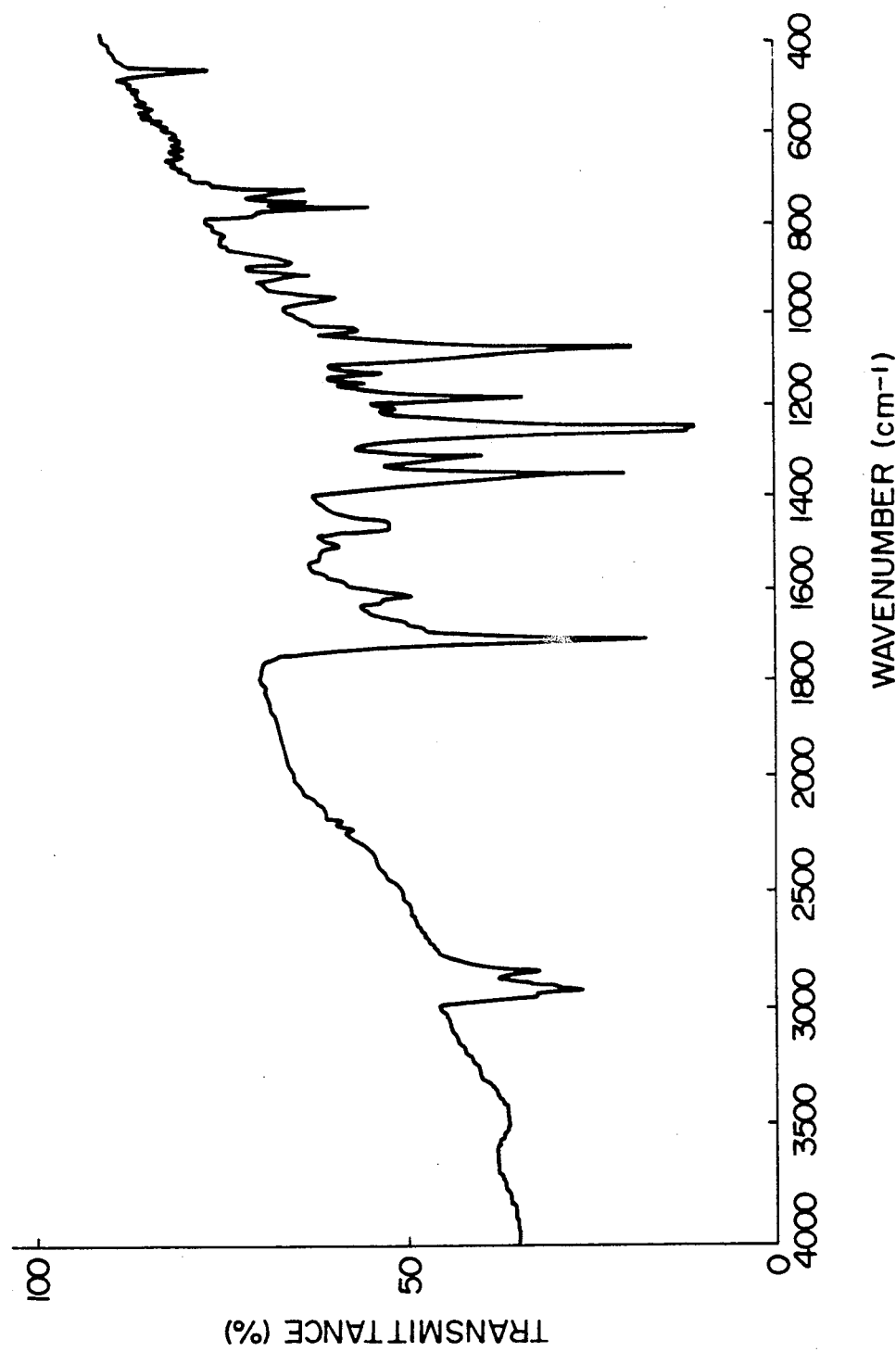
FIG. 50 is an IR spectrum of tetrakis(n-octyloxycarbonyl) chloroaluminum naphthalocyanine.

(4) IR spectrum (KBr)
Shown in FIG. 50. There is an absorption attributable to the stretching vibration of C=O of ester, at about 1,700 cm$^{-1}$.

EXAMPLE 20

Synthesis of tetrakis(n-amyloxycarbonyl) silicon naphthalocyanine [illustrative compound (29)]

1.46 g (5 mmol) of 6-(n-amyloxycarbonyl)-2,3-dicyanonaphthalene, 0.29 ml (2.5 mmol) of silicon tetrachloride, 10 mg of ammonium molybdate and 5 g of urea were reacted at about 220° C. for about 2.5 hours with thorough stirring. After cooling, to the reaction mixture in solid form was added 40 ml of 5% hydrochloric acid, and the whole mixture was stirred thoroughly at about 50° C. for 30 minutes. The resulting insoluble material was collected by filtration and then washed thoroughly with water, methanol and acetone in this order. The resulting solid was freed of impurities by extraction with methanol for about 100 hours and then with acetone for about 100 hours in a Soxhlet's extractor, after which soxhlet extraction was conducted with chloroform for 20 hours. The resulting dark green chloroform solution was subjected to filtration, and the filtrate was concentrated to dryness under reduced pressure to obtain 247 mg of a black crystal with luster.

The following analytical results confirmed that the crystal was tetrakis(n-amyloxycarbonyl) silicon naphthalocyanine.

(1) Melting point: above 300° C. (stable at least at 300° C. or below)

(2) Elemental analysis

|  | C | H | N |
|---|---|---|---|
| Calculated (%) | 72.22 | 5.39 | 9.36 |
| Found (%) | 72.41 | 5.52 | 9.29 |

Figure 51:
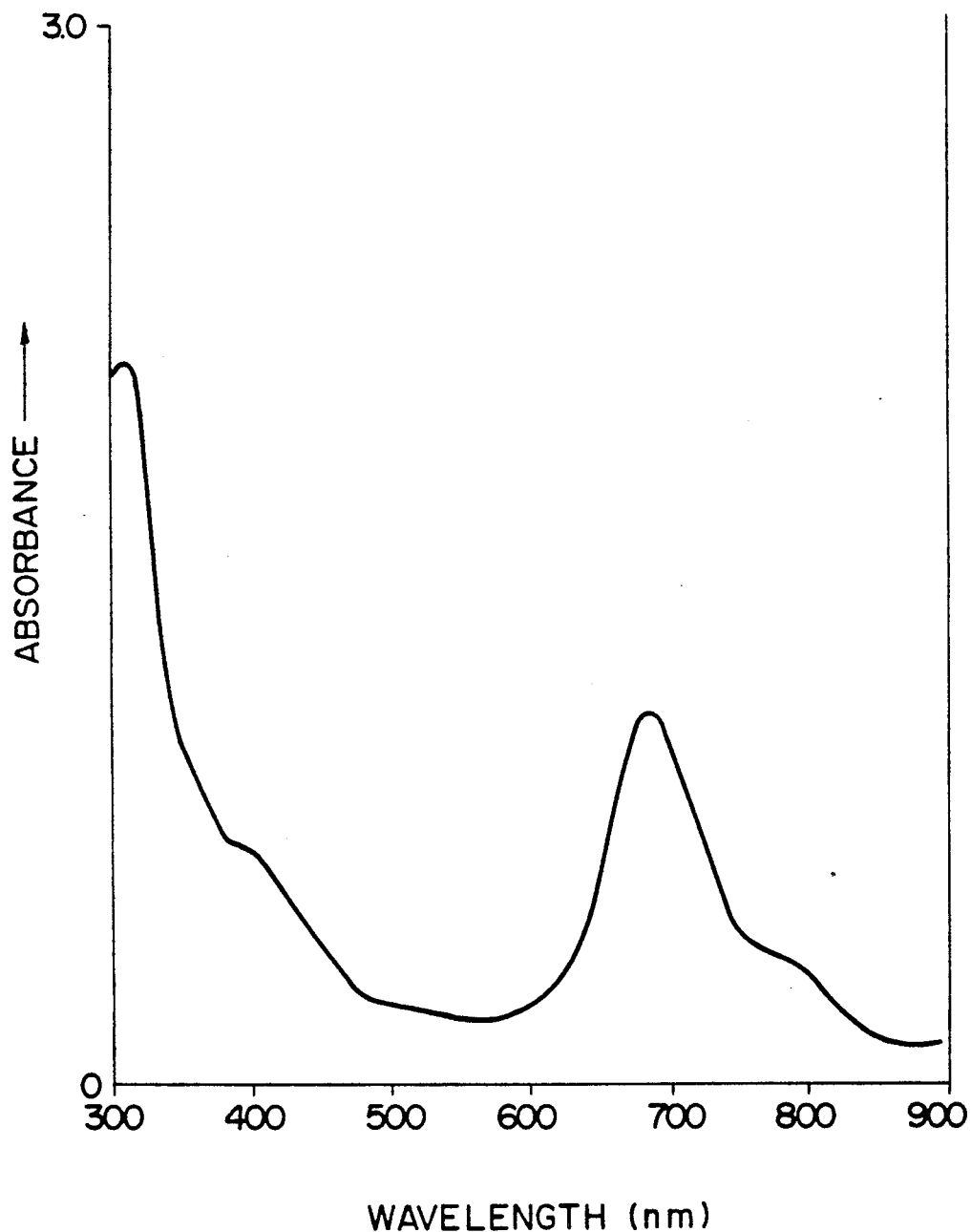
FIG. 51 is an electronic spectrum of tetrakis(n-amyloxycarbonyl) silicon naphthalocyanine.

(3) Electronic spectrum (CHCl$_3$ solution)
Shown in FIG. 51.

Figure 52:
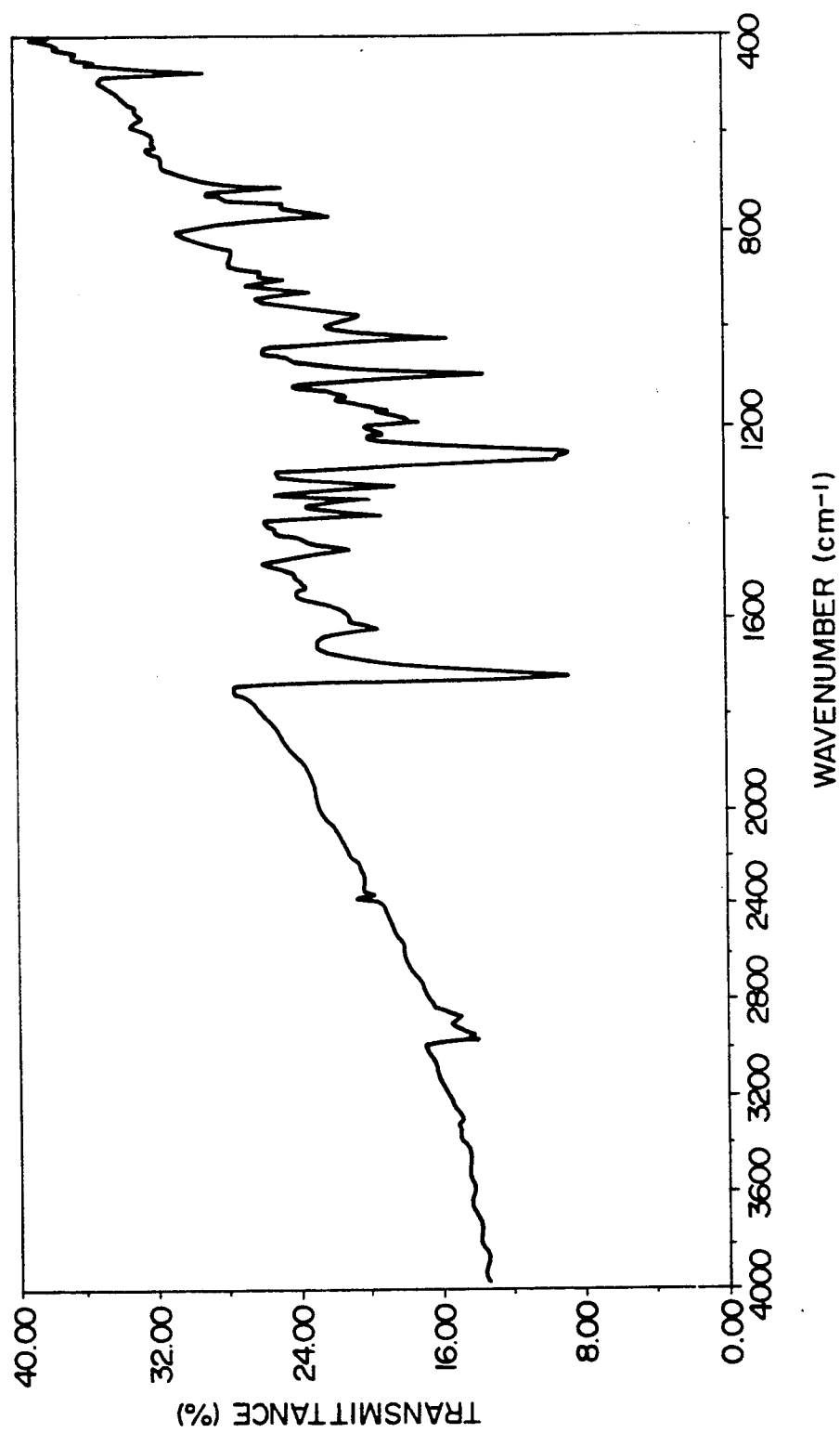
FIG. 52 is an IR spectrum of tetrakis(n-amyloxycarbonyl) silicon naphthalocyanine.

(4) FT-IR spectrum (KBr)
Shown in FIG. 52. There is an absorption attributable to the stretching vibration of C=O of ester, at about 1,716 cm$^{-1}$.

EXAMPLE 21

Synthesis of tetrakis(n-amyloxycarbonyl) germanium naphthalocyanine [illustrative compound (31)]

1.46 g (5 mmol) of 6-(n-amyloxycarbonyl)-2,3-dicyanonaphthalene, 0.28 ml (2.47 mmol) of germanium tetrachloride, 10 mg of ammonium molybdate and 5 g of urea were reacted at about 220° C. for about 2.5 hours with thorough stirring. After cooling, the reaction mixture was treated in the same manner as in Example 20 to obtain 786 mg of a black crystal with luster. The following analytical results confirmed that the crystal was tetrakis(n-amyloxycarbonyl) germanium naphthalocyanine.

(1) Melting point: above 300° C. (stable at least at 300° C. or below)

(2) Elemental analysis

|  | C | H | N |
|---|---|---|---|
| Calculated (%) | 69.63 | 5.19 | 9.02 |
| Found (%) | 69.36 | 5.06 | 9.28 |

Figure 53:
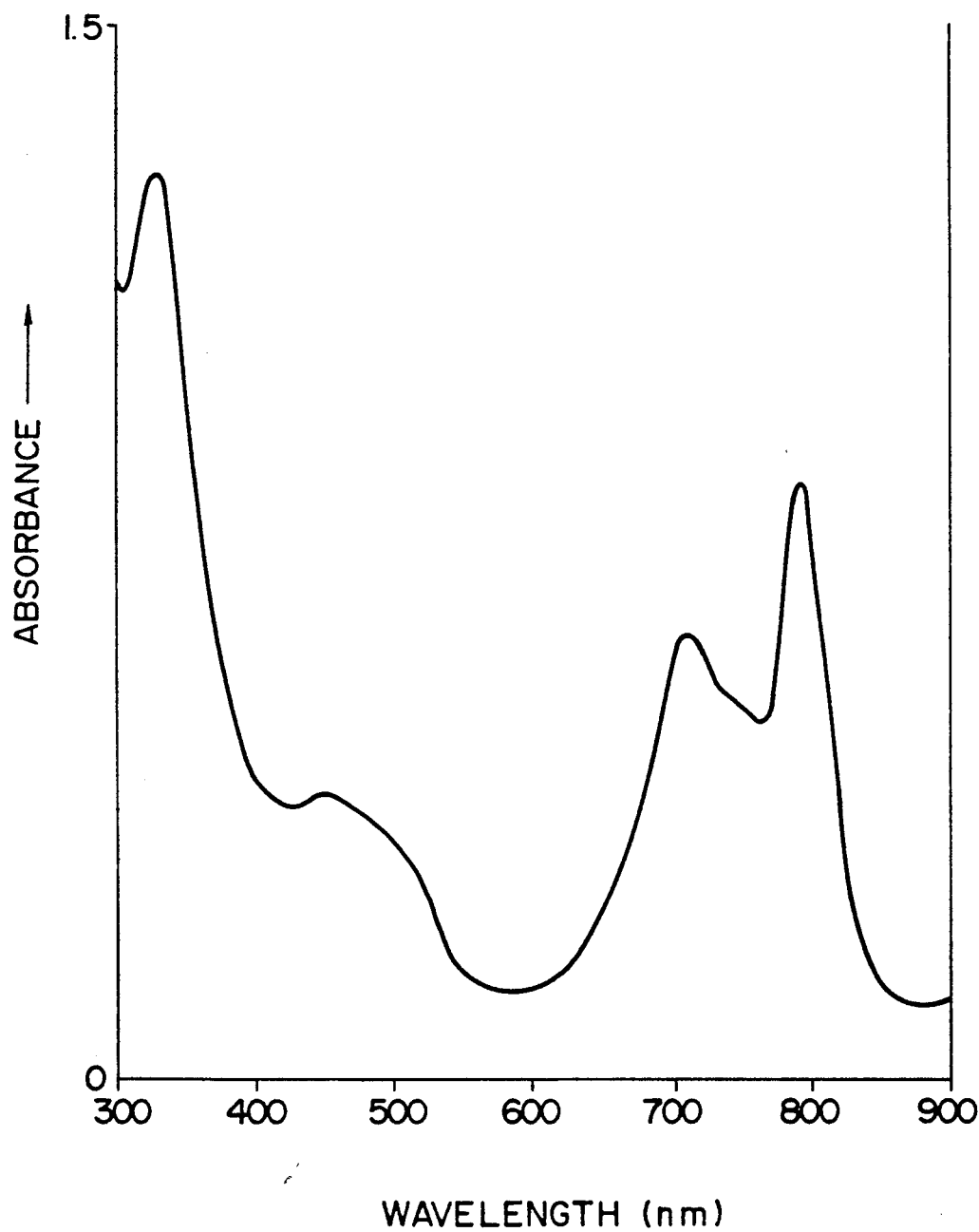
FIG. 53 is an electronic spectrum of tetrakis(n-amyloxycarbonyl) germanium naphthalocyanine.

(3) Electronic spectrum (CHCl$_3$ solution)
Shown in FIG. 53.

Figure 54:
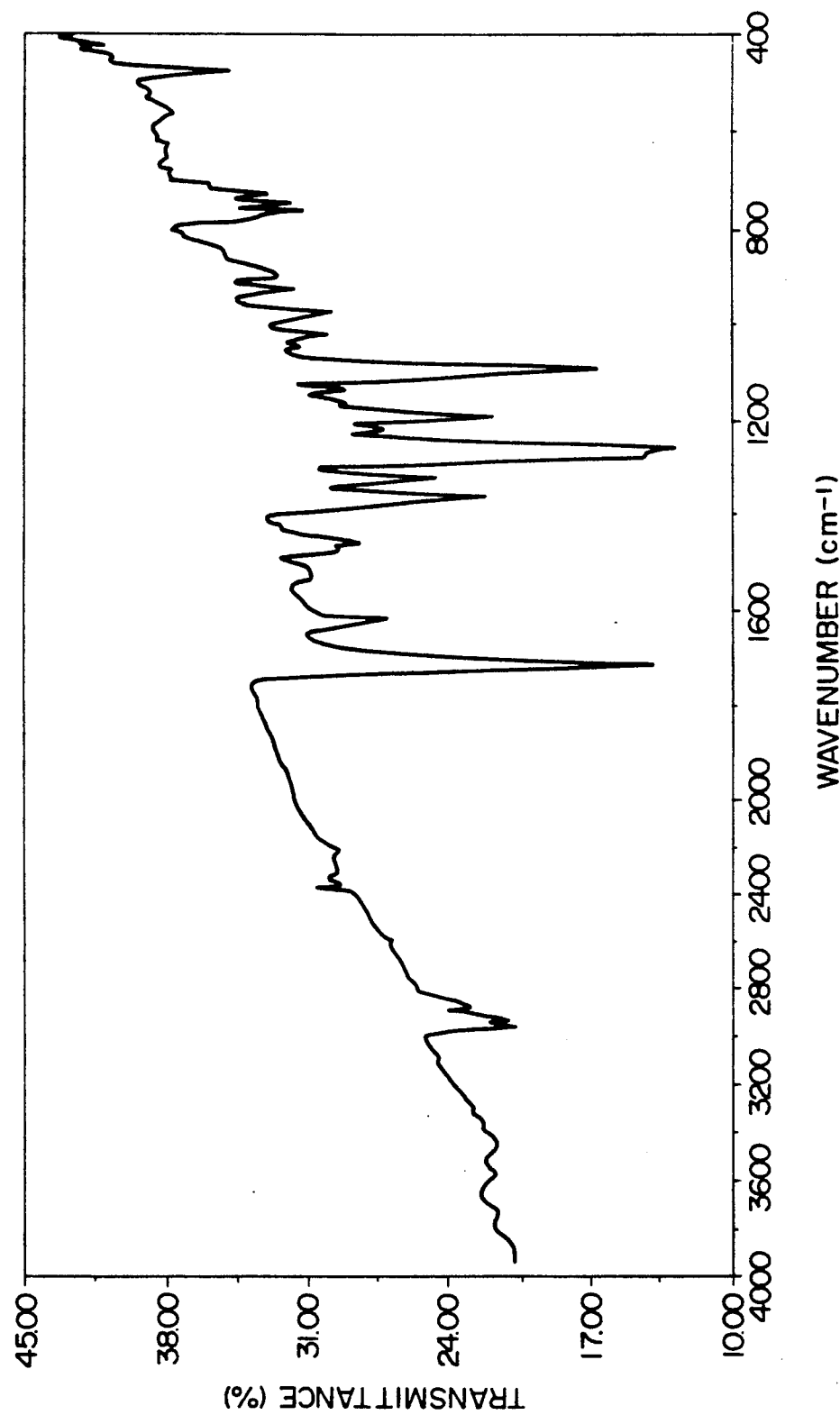
FIG. 54 is an IR spectrum of tetrakis(n-amyloxycarbonyl) germanium naphthalocyanine.

(4) FT-IR spectrum (KBr)
Shown in FIG. 54. There is an absorption attributable to the stretching vibration of C=O of ester, at about 1,716 cm$^{-1}$.

EXAMPLE 22

Synthesis of tetrakis(n-amyloxycarbonyl) tin naphthalocyanine [illustrative compound (33)]

1.46 g (5 mmol) of 6-(n-amyloxycarbonyl)-2,3-dicyanonaphthalene, 474 mg (2.5 mmol) of stannous chloride, 10 mg of ammonium molybdate and 5 g of urea were reacted at about 220° C. for about 2.5 hours with thorough stirring. After cooling, the reaction mixture was treated in the same manner as in Example 1 to obtain 767 mg of a black crystal with luster. The following analytical results confirmed that the crystal was tetrakis(n-amyloxycarbonyl) tin naphthalocyanine.

(1) Melting point: above 300° C. (stable at least at 300° C. or below)

(2) Elemental analysis

|  | C | H | N |
|---|---|---|---|
| Calculated (%) | 67.14 | 5.01 | 8.70 |
| Found (%) | 66.82 | 4.74 | 8.33 |

Figure 55:
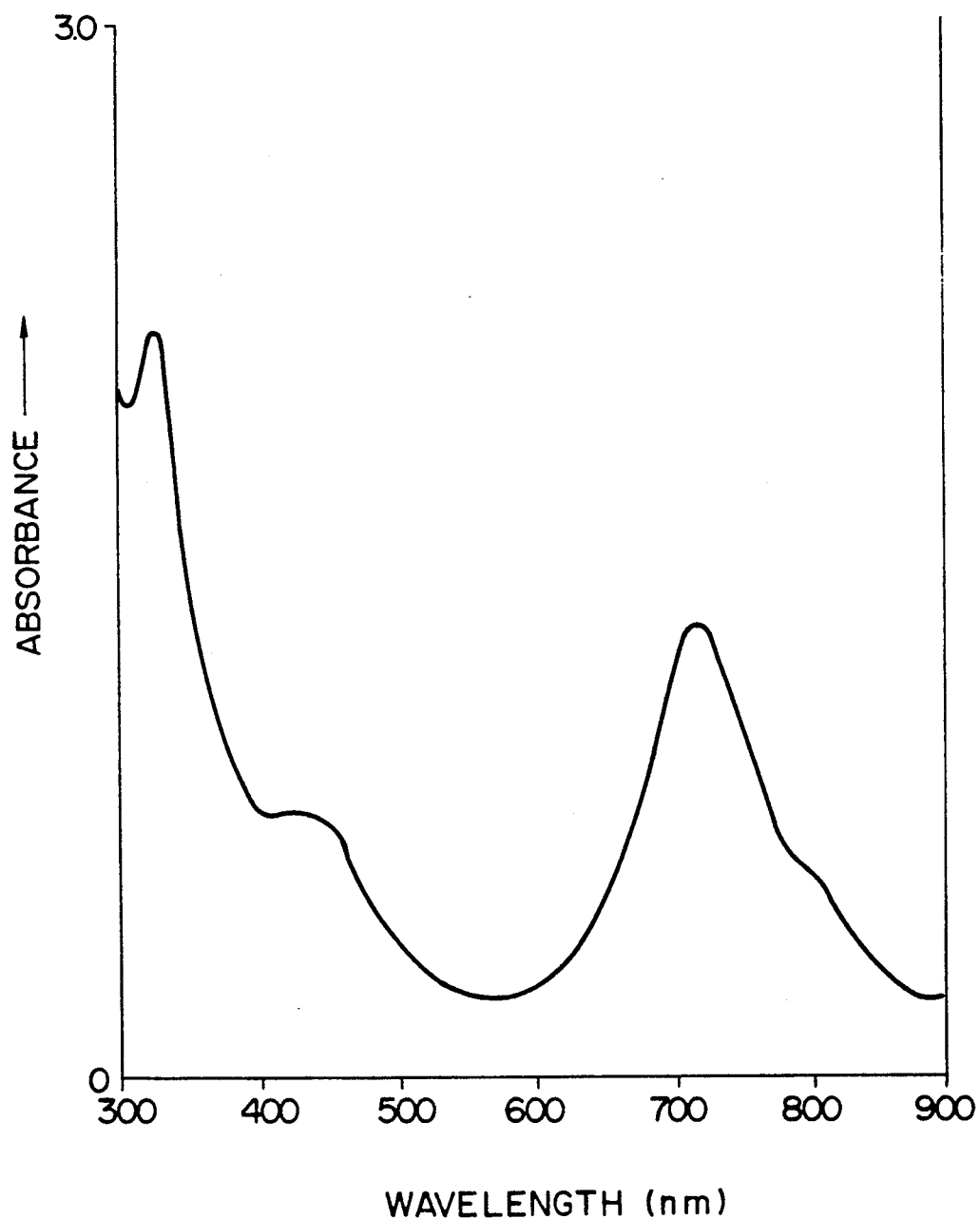
FIG. 55 is an electronic spectrum of tetrakis(n-amyloxycarbonyl) tin naphthalocyanine.

(3) Electronic spectrum (CHCl$_3$ solution)
Shown in FIG. 55.

Figure 56:
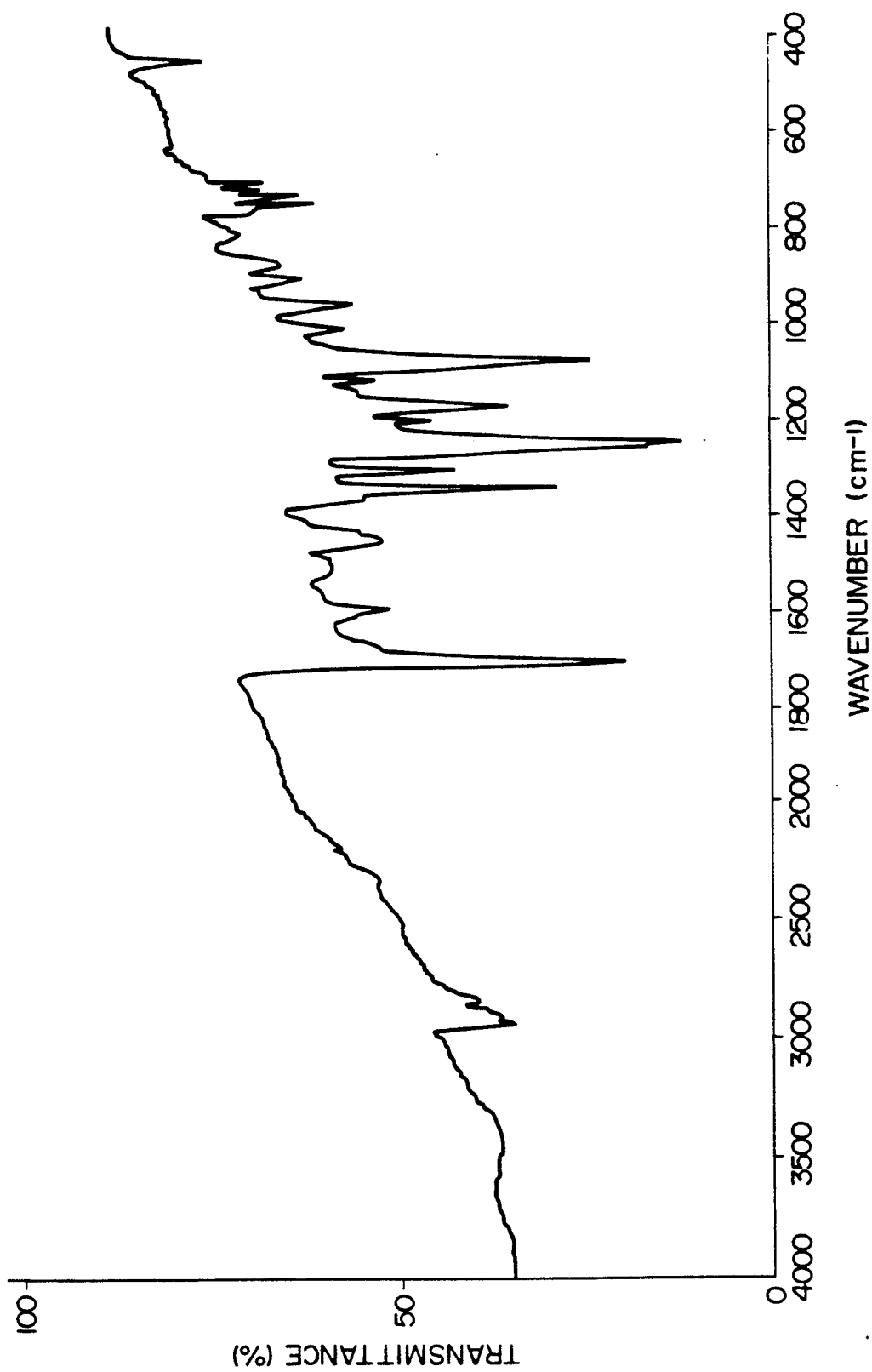
FIG. 56 is an IR spectrum of tetrakis(n-amyloxycarbonyl) tin naphthalocyanine.

(4) IR spectrum (KBr)
Shown in FIG. 56. There is an absorption attributable to the stretching vibration of C=O of ester, at about 1,700 cm$^{-1}$.

EXAMPLE 23

Synthesis of bis(triethylsiloxy)germaniumtetrakis(n-amyloxycarbonyl)naphthalocyanine [illustrative compound (41)]

1.46 g (5 mmol) of 6-(n-amyloxycarbonyl)-2,3-dicyanonaphthalene, 10 mg of ammonium molybdate and 5 g of urea were mixed with 0.28 ml (2.5 mmol) of germanium tetrachloride, and the mixture was heated at about 220° C. for about 2.5 hours with thorough stirring. After cooling, to the reaction mixture in solid form was added water, and the whole mixture was subjected to filtration. The resulting black solid was thoroughly washed with methanol and then dried to obtain 3.06 g of a black solid. From the following analytical results, this black solid is believed to be dichlorogermanium-tetrakis(n-amyloxycarbonyl)naphthalocyanine of the general formula (V) (in the general formula (V), R$^1$ are all an n-amyl group; n is 1; M is Ge; and X is a chlorine atom). This compound was used for the subsequent reaction without further purification.

Figure 57:
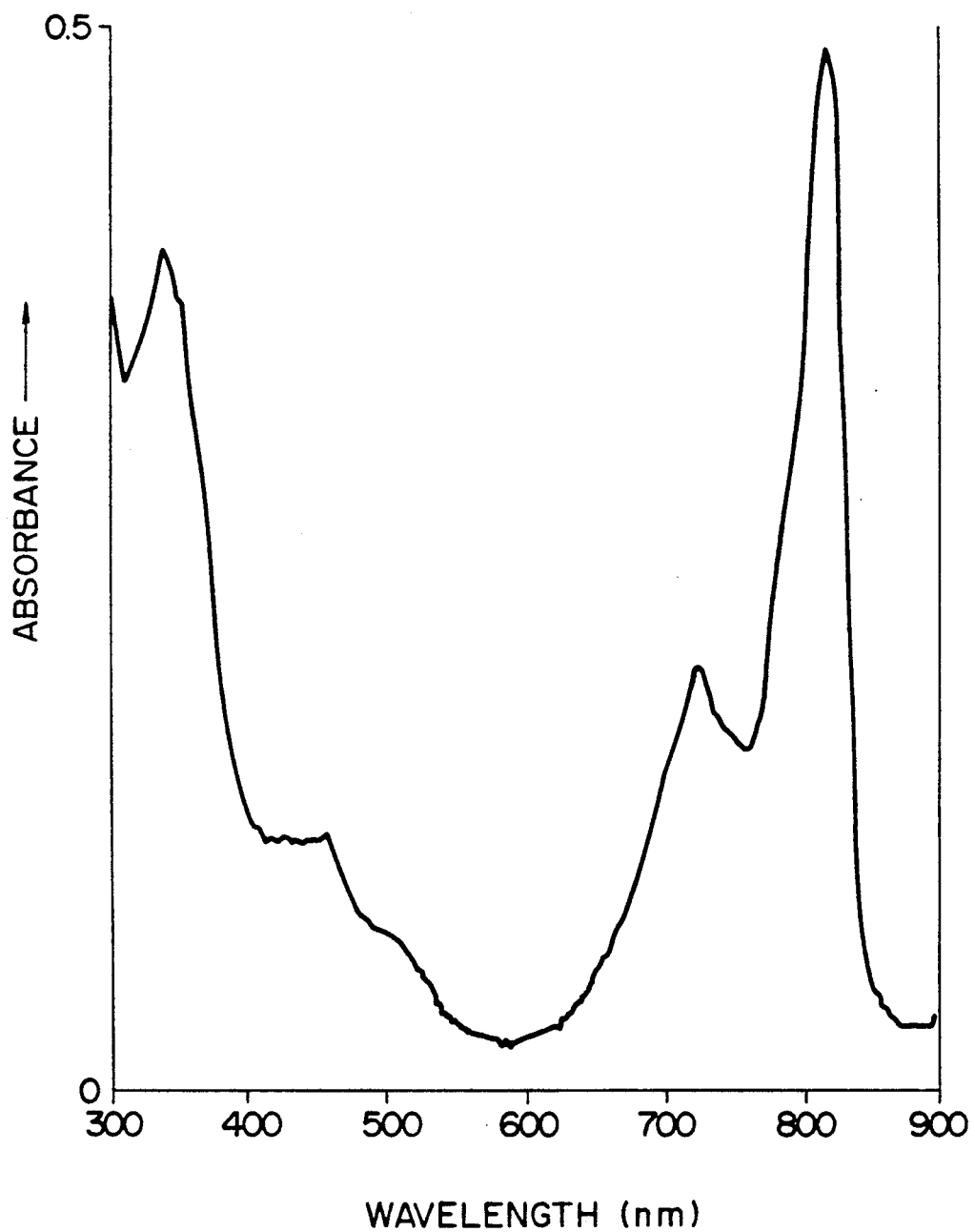
FIG. 57 is an electronic spectrum of dichlorogermanium-tetrakis(n-amyloxycarbonyl)naphthalocyanine in its chloroform solution.

(1) Electronic spectrum (CHCl$_3$ solution)
Shown in FIG. 57.

Figure 58:
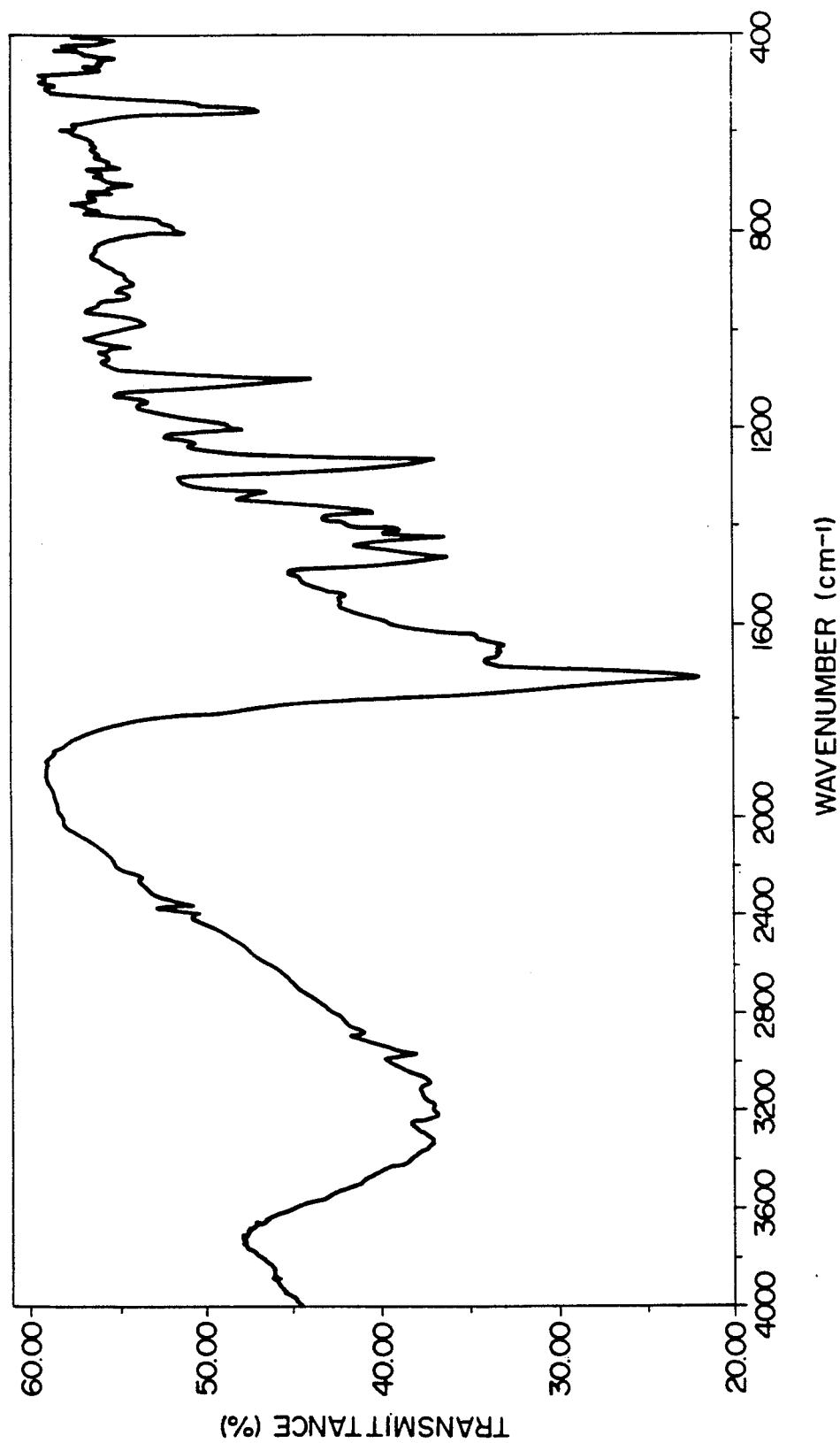
FIG. 58 is an IR spectrum of dichlorogermanium-tetrakis(n-amyloxycarbonyl)naphthalocyanine.

(2) IR spectrum (KBr)
Shown in FIG. 58. There is an absorption attributable to the stretching vibration of C=O of ester, at about 1,710 cm$^{-1}$.

766 mg (0.58 mmol) of the thus obtained dichlorogermanium-tetrakis(n-amyloxycarbonyl)naphthalocyanine was refluxed for about 2 hours in a mixed solvent consisting of 19 ml of an concentrated aqueous ammonia solution, 19 ml of ethanol and 76 ml of water. After cooling, the reaction mixture was filtered, and the resulting solid was thoroughly washed with methanol and dried to obtain 213 mg of a black solid. From the following analytical results, the black solid was believed to be dihydroxygermanium-tetrakis(n-amyloxycarbonyl)-naphthalocyanine of the general formula (VI) (in the general formula (VI), R$^1$ are all an n-amyl group; n is and M is Ge). This compound was used in the subsequent reaction without further purification.

Figure 59:
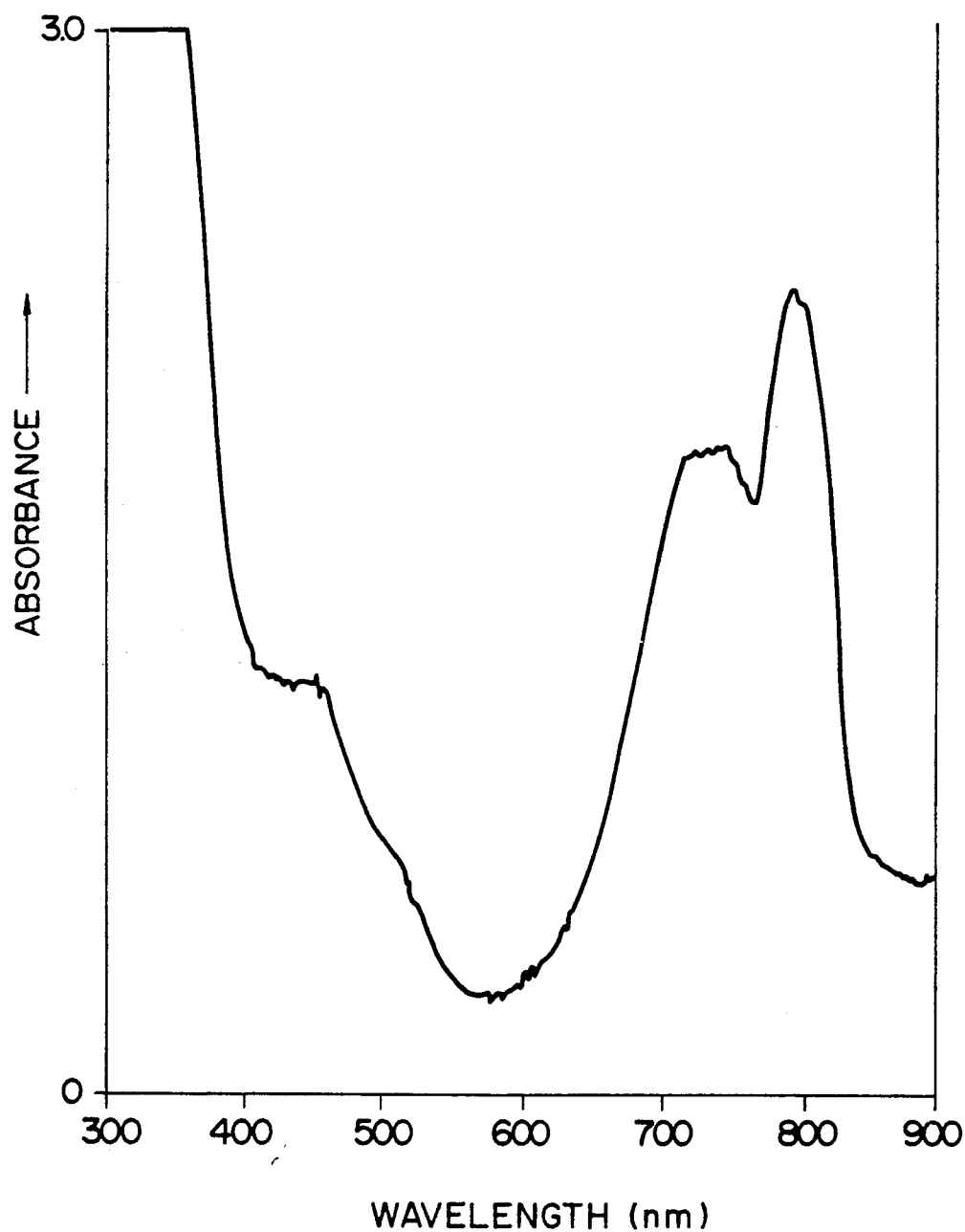
FIG. 59 is an electronic spectrum of dihydroxygermanium-tetrakis(n-amyloxycarbonyl)naphthalocyanine in its chloroform solution.

(1) Electronic spectrum (CHCl$_3$ solution)
Shown in FIG. 59.

Figure 60:
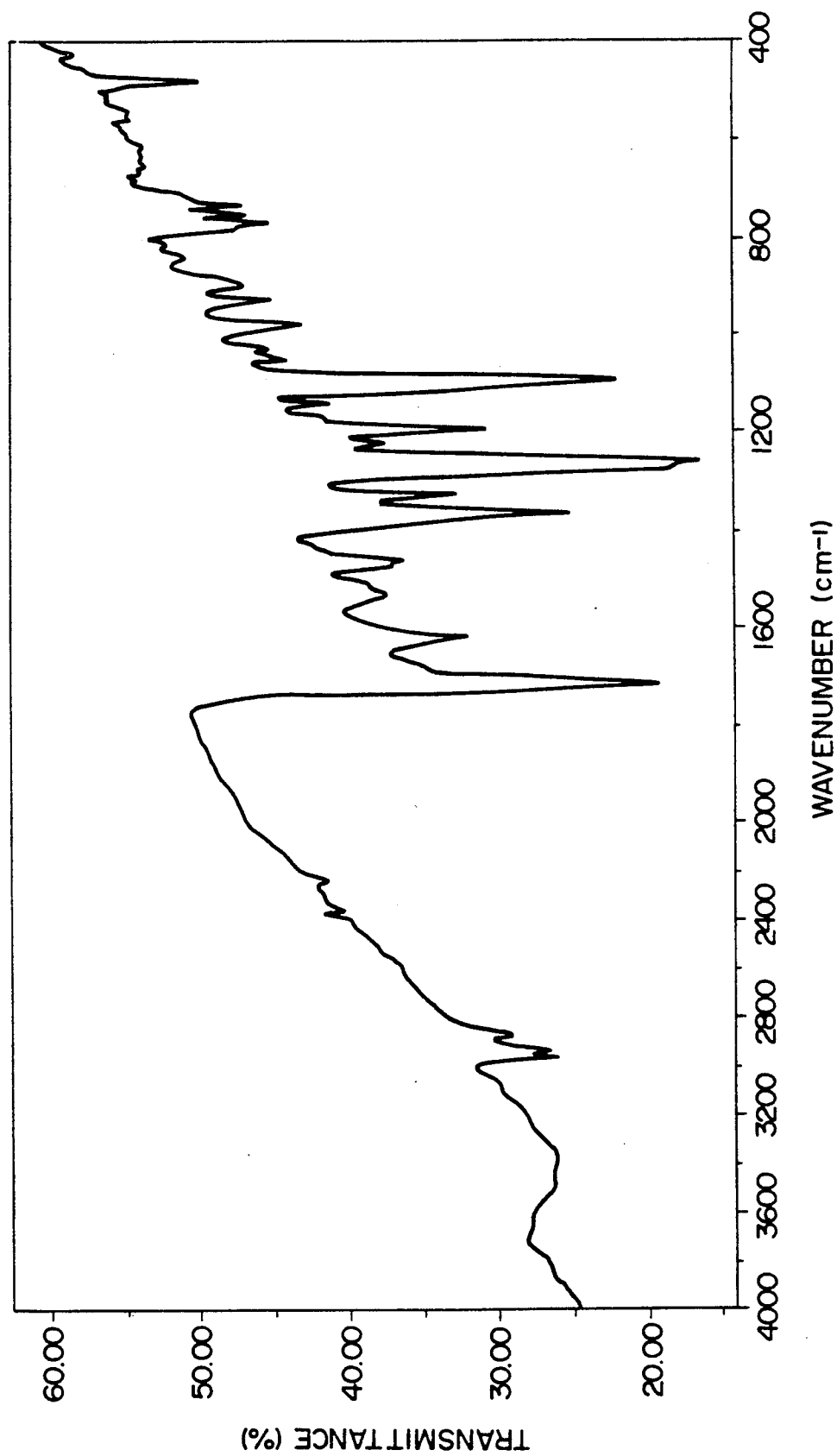
FIG. 60 is an IR spectrum of dihydroxygermanium-tetrakis(n-amyloxycarbonyl)naphthalocyanine.

(2) IR spectrum (KBr)
Shown in FIG. 60. There is an absorption attributable to the stretching vibration of C=O of ester, at about 1,700 cm$^{-1}$.

210 mg (0.16 mmol) of the thus obtained dihydroxygermanium-tetrakis(n-amyloxycarbonyl)naphthalocyanine was refluxed in 15 ml of chlorobenzene in the presence of 0.6 ml of triethylsilanol for about 1 hour. The reaction mixture was concentrated to about 5 ml. After cooling, about 50 ml of methanol was added thereto and the mixture was allowed to stand for a while. The resulting precipitate was collected by filtration, washed thoroughly with methanol and then dried thoroughly. The resulting black solid was purified by alumina thin layer chromatography using benzene as an eluent to obtain 18 mg of a dark green solid. The following analytical results confirmed that the dark green solid was bis(triethylsiloxy)germanium-tetrakis(n-amyloxycarbonyl)naphthalocyanine [illustrative compound (41)].

(1) Melting point: above 300° C. (stable at least at 300° C. or below)

|  | (2) Elemental analysis | | |
| --- | --- | --- | --- |
|  | C | H | N |
| Calculated (%) | 67.06 | 6.30 | 7.45 |
| Found (%) | 66.84 | 6.27 | 7.44 |

Figure 61:
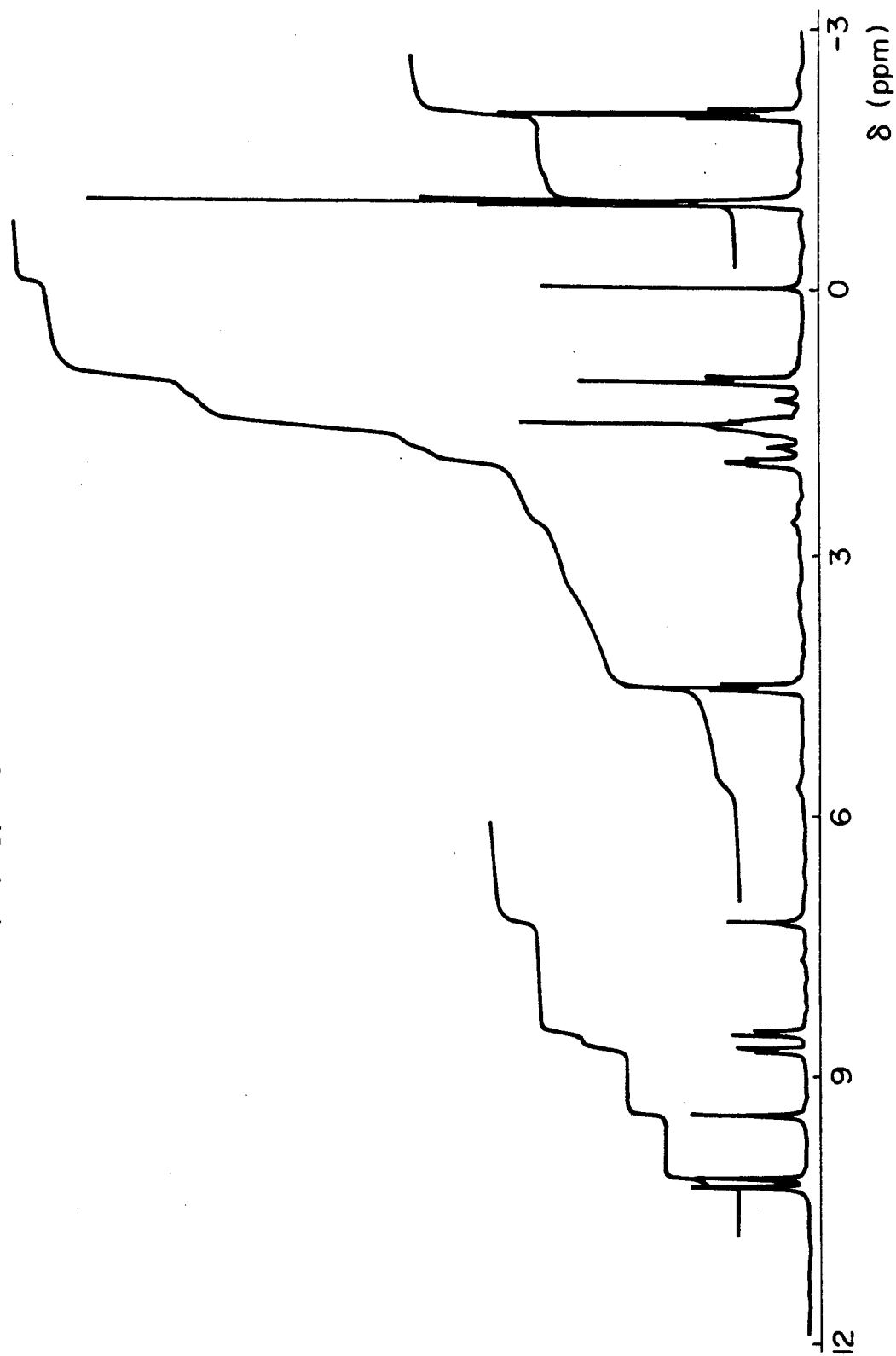
FIG. 61 is an NMR of bis(triethylsiloxy)germanium-tetrakis(n-amyloxycarbonyl)naphthalocyanine.

(3) NMR spectrum (solvent: CDCl$_3$)
Shown in FIG. 61.
δ 10.27 (4H, br-s); 10.17 (4H, br-s); 9.45 (4H, br-s); 8.73 (4H, d, J=8.70 Hz); 8.53 (4H, dd, J=8.70, 1.53 Hz); 4.58 (8H, t, J=6.71 Hz); 2.00 (8H, quintet, J=6.71 Hz); 1.59 (16H, m); 1.07 (12H, t, J=7.02 Hz); −1.00 (18H, t, J=7.94 Hz); −2.01 (12H, q, J=7.94 Hz).

Figure 62:
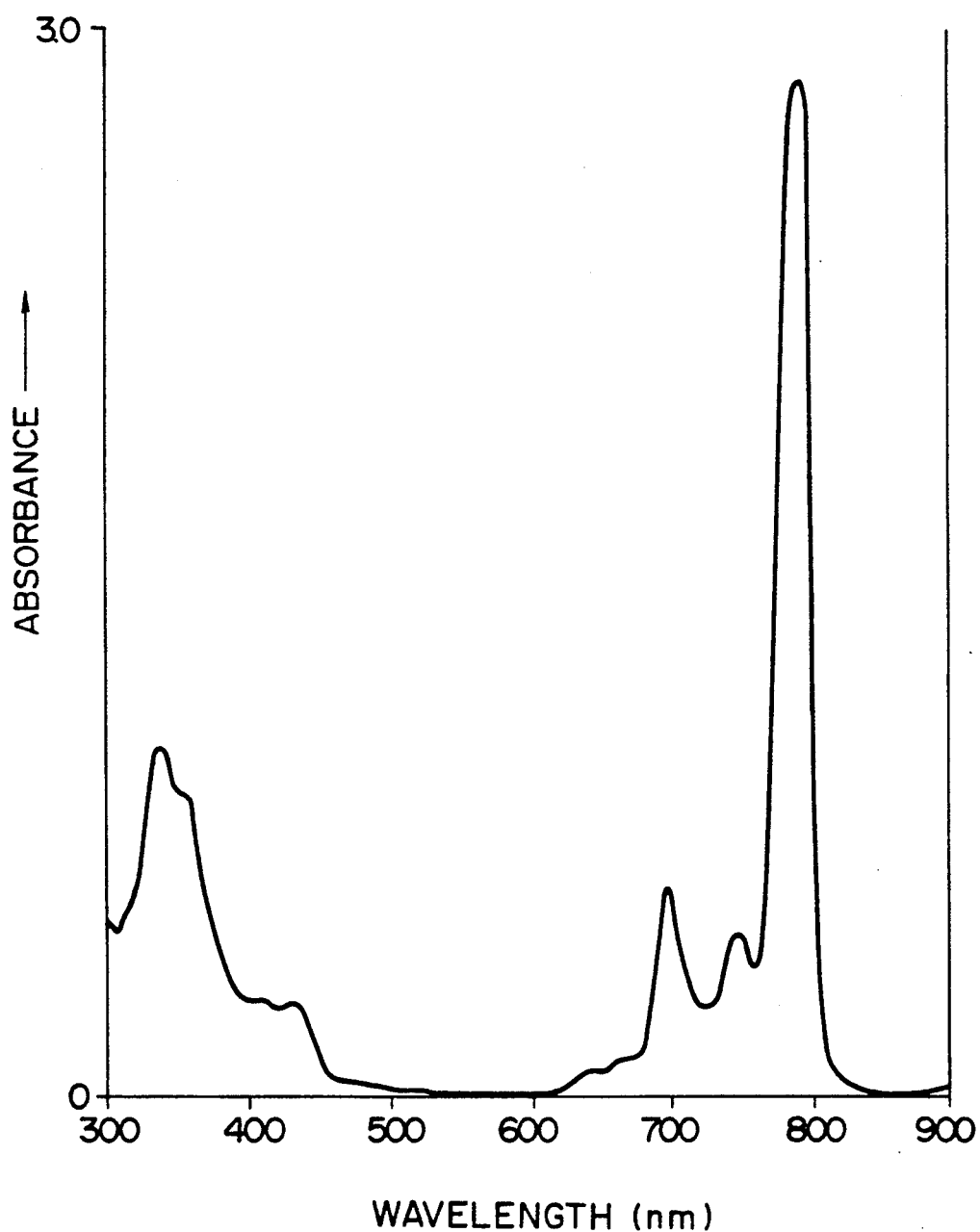
FIG. 62 is an electronic spectrum of bis(triethylsiloxy)germanium-tetrakis(n-amyloxycarbonyl)naphthalocyanine in its chloroform solution.
Figure 63:
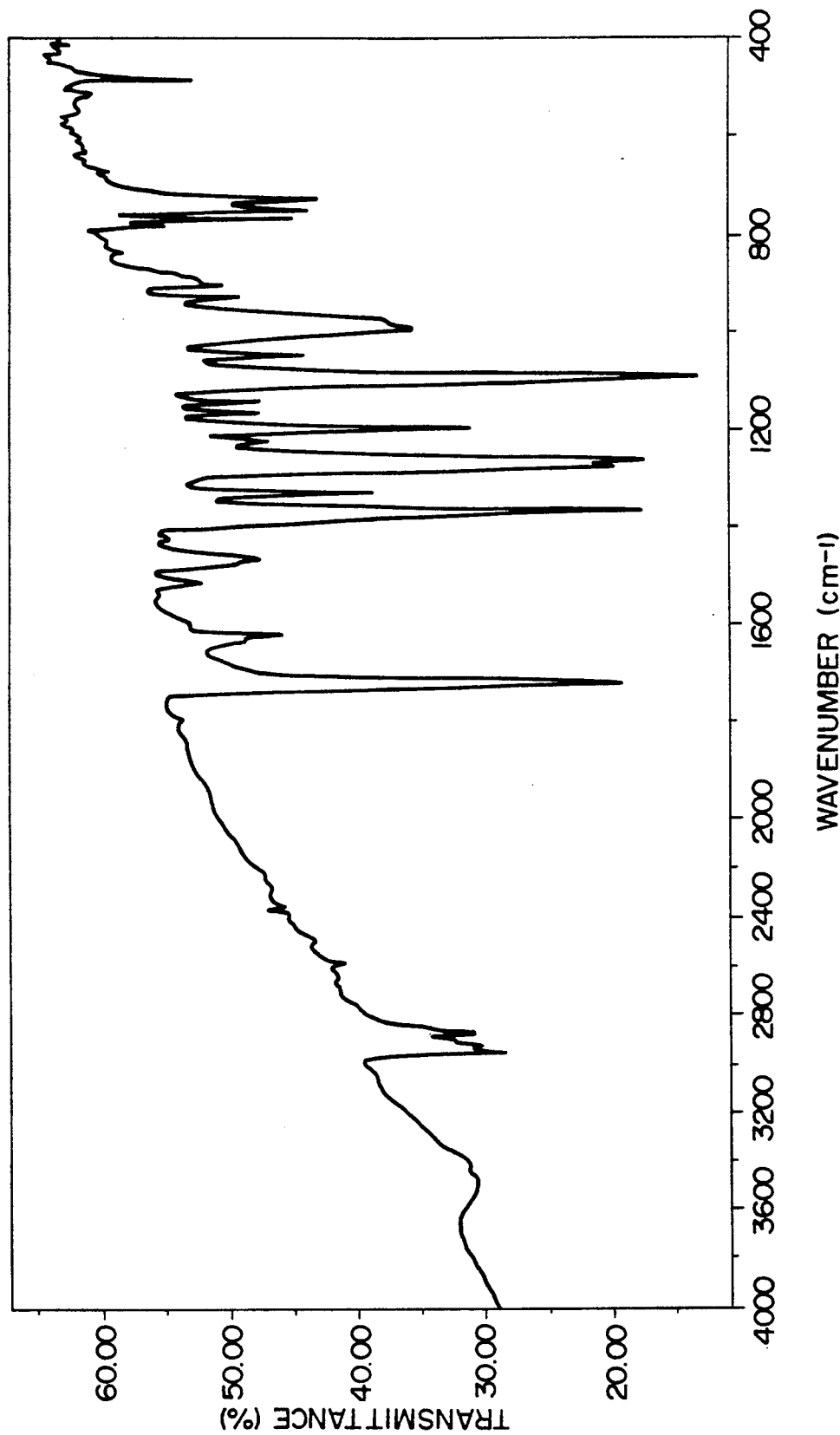
FIG. 63 is an IR spectrum of bis(triethylsiloxy)germanium-tetrakis(n-amyloxycarbonyl)naphthalocyanine.

(4) Electronic spectrum (CHCl$_3$ solution)
Shown in FIG. 62.

(4) IR spectrum (KBr)
Shown in FIG. 62. There is an absorption attributable to the stretching vibration of C=O of ester, at about 1,720 cm$^{-1}$.

EXAMPLE 24

Synthesis of bistributylsiloxy)germaniumtetrakis(n-amyloxycarbonyl)naphthalocyanine [illustrative compound (43)]

255 mg (0.2 mmol) of the dihydroxygermaniumtetrakis(n-amyloxycarbonyl)naphthalocyanine synthesized in the same manner as in Example 23 was refluxed in 19 ml of chlorobenzene in the presence of 1 ml of tributylsilanol for about 1 hour. The reaction mixture was concentrated to about 5 ml. After cooling, about 5 ml of methanol was added thereto, and the whole mixture was allowed to stand for a while. The resulting precipitate was collected by filtration, washed thoroughly with methanol and dried thoroughly. The resulting black solid was purified by alumina thin layer chromatography using benzene as an eluent to obtain 13 mg of a dark green solid. The following analytical results confirmed that the dark green solid was bis(-tributylsiloxy)germaniumtetrakis-(n-amyloxycarbonyl)-naphthalocyanine [illustrative compound (43)].

(1) Melting point: 280°–290° C. (decomposed)

|  | (2) Elemental analysis | | |
| --- | --- | --- | --- |
|  | C | H | N |
| Calculated (%) | 68.93 | 7.11 | 6.70 |
| Found (%) | 69.17 | 7.32 | 6.58 |

Figure 64:
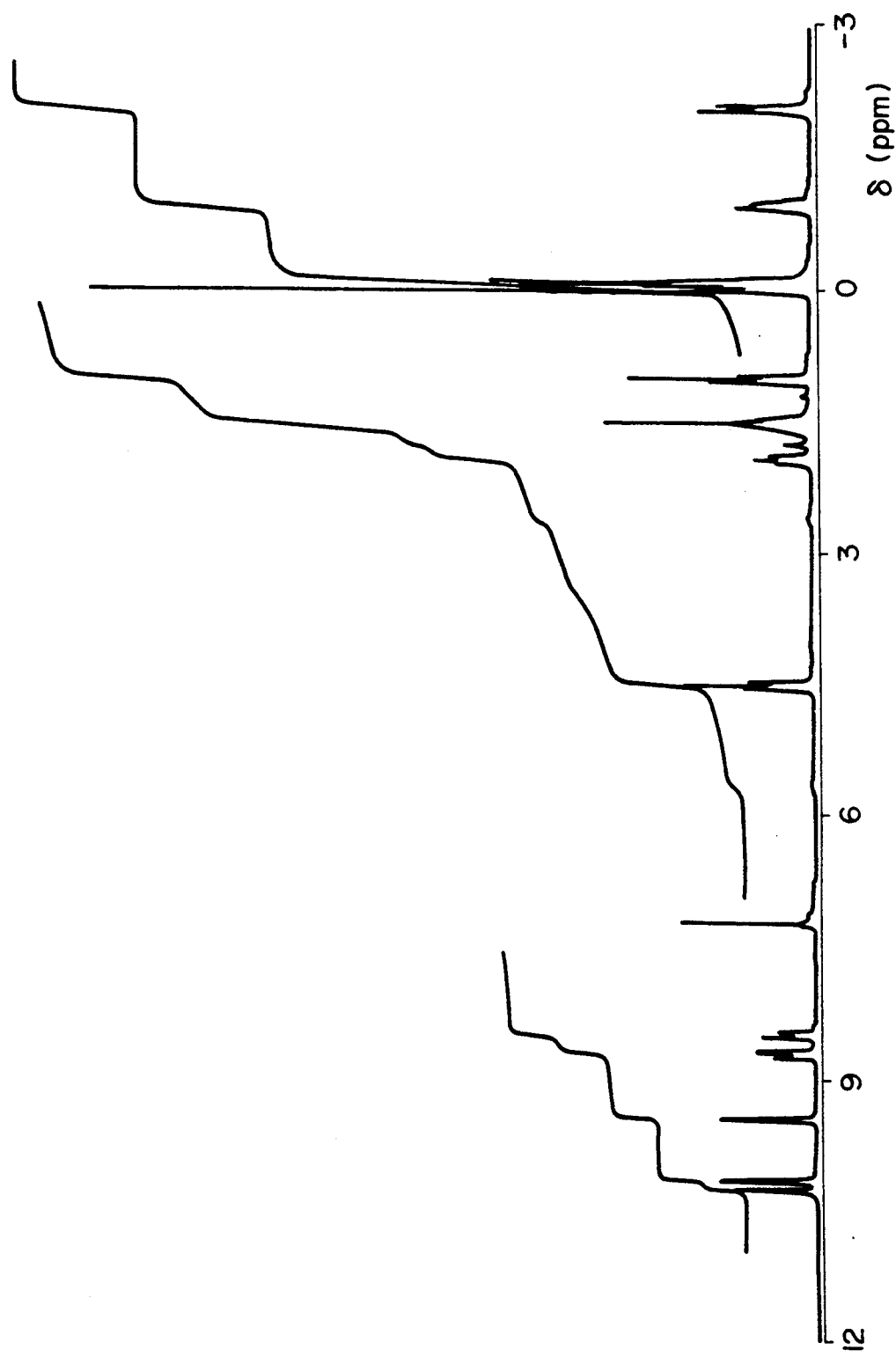
FIG. 64 is an NMR spectrum of bis(tributylsiloxy)-germanium-tetrakis(n-amyloxycarbonyl)naphthalocyanine.

(3) NMR spectrum (solvent: CDCl$_3$)
Shown in FIG. 64.
δ 10.19 (4H, s); 10.08 (4H, s); 9.39 (4H, br-s); 8.66 (4H, d, J=8.70 Hz); 8.46 (4H, dd, J=8.70, 1.53 Hz); 4.51 (8H, t, J=6.72 Hz); 1.93 (8H, quintet, J=6.72 Hz); 1.50 (16H, m); 1.00 (12H, t, J=7.02 Hz); −0.09 (30H, m); −0.99 (12H, quintet-like m); −2.08 (12H, t-like m).

Figure 65:
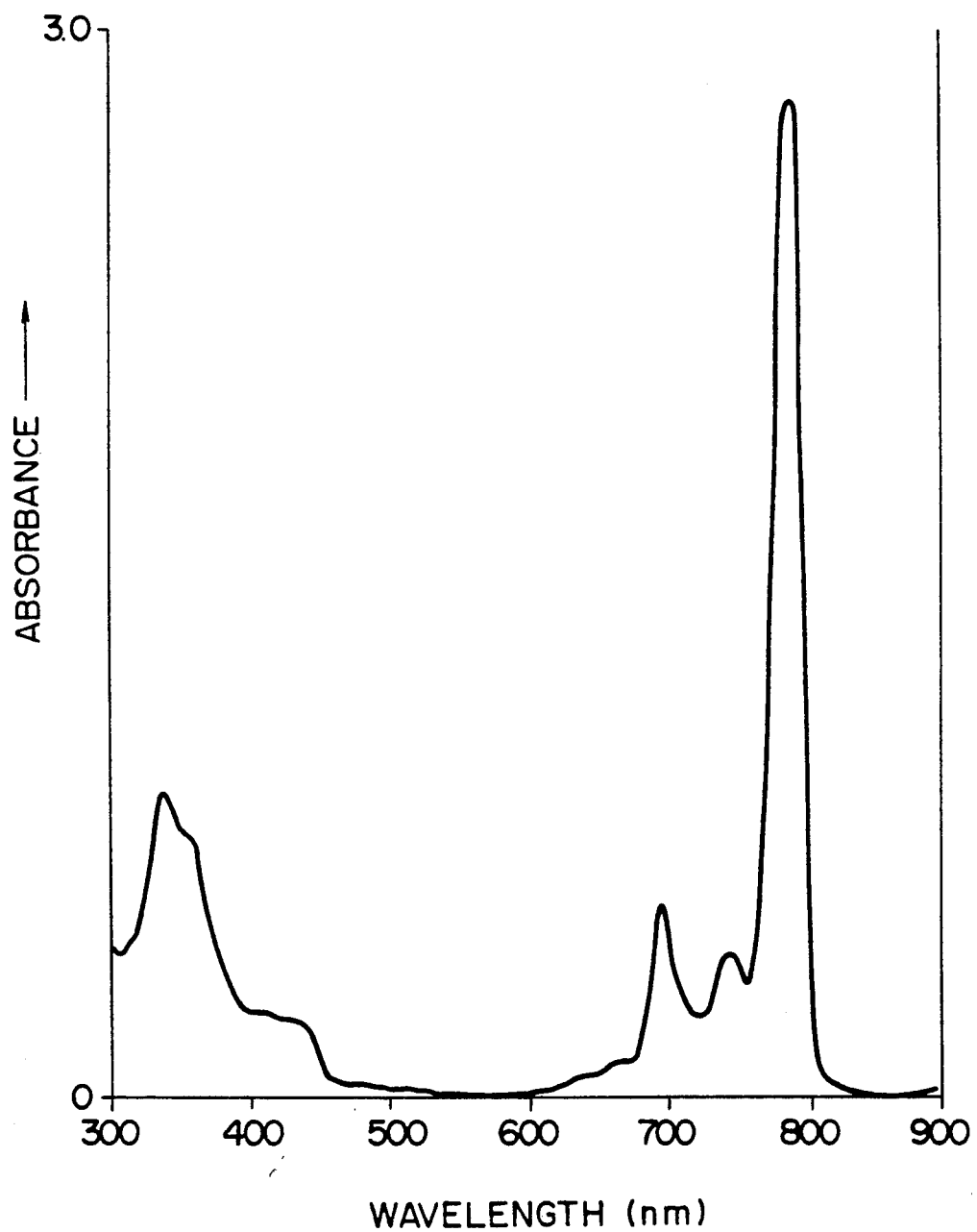
FIG. 65 is an electronic spectrum of bis(tributylsiloxy)germanium-tetrakis(n-amyloxycarbonyl)naphthalocyanine in its tetrahydrofuran solution.

(4) Electronic spectrum (tetrahydrofuran solution)
Shown in FIG. 65.

Figure 66:
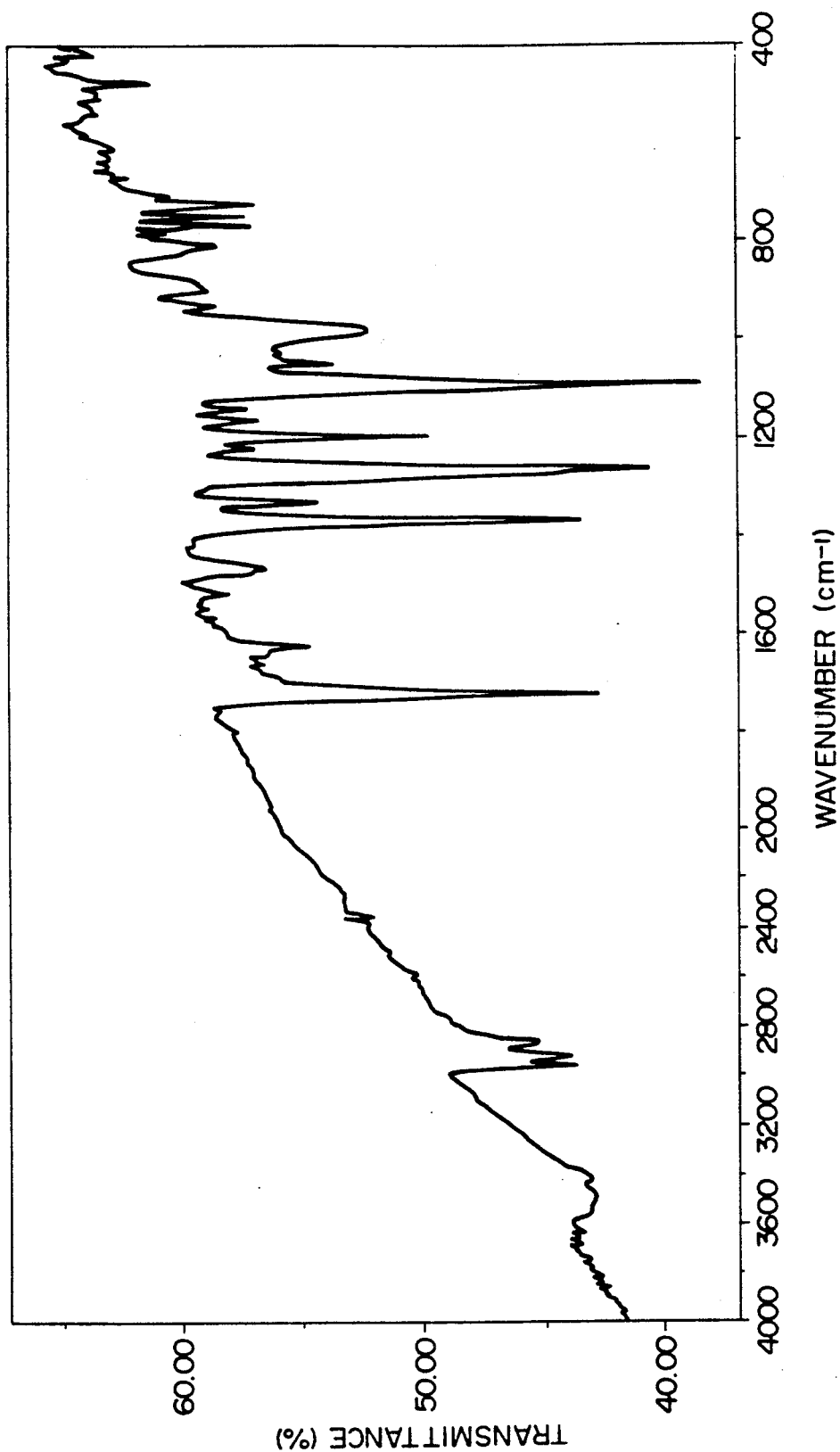
FIG. 66 is an IR spectrum of bis(tributylsiloxy)germanium-tetrakis(n-amyloxycarbonyl)naphthalocyanine.

(5) IR spectrum (KBr)
Shown in FIG. 66. There is an absorption attributable to the stretching vibration of C=O of ester, at about 1,720 cm$^{-1}$.

EXAMPLE 25

Synthesis of bis(triethylsiloxy)germaniumtetrakis(n-octyloxycarbonyl)naphthalocyanine [illustrative compound (44)]

1.67 g (5 mmol) of 6-(n-octyloxycarbonyl)-2,3-dicyanonaphthalene, 10 mg of ammonium molybdate and 5 g of urea were mixed with 0.28 ml (2.5 mmol) of germanium tetrachloride, and the mixture was heated at about 220° C. for about 2.5 hours with thorough stirring. After cooling, the reaction mixture was treated in the same manner as in Example 23 to obtain 3.35 g of a blackkish green solid. From the following analytical results, the solid was believed to be dichlorogermanium-tetrakis(noctyloxycarbonyl)naphthalocyanine of the general formula (V) [in the formula (V), R$^1$ are all an n-octyl group; n is 1; M is Ge; and X is a chlorine atom]. The solid was used in the subsequent reaction without further purification.

Figure 67:
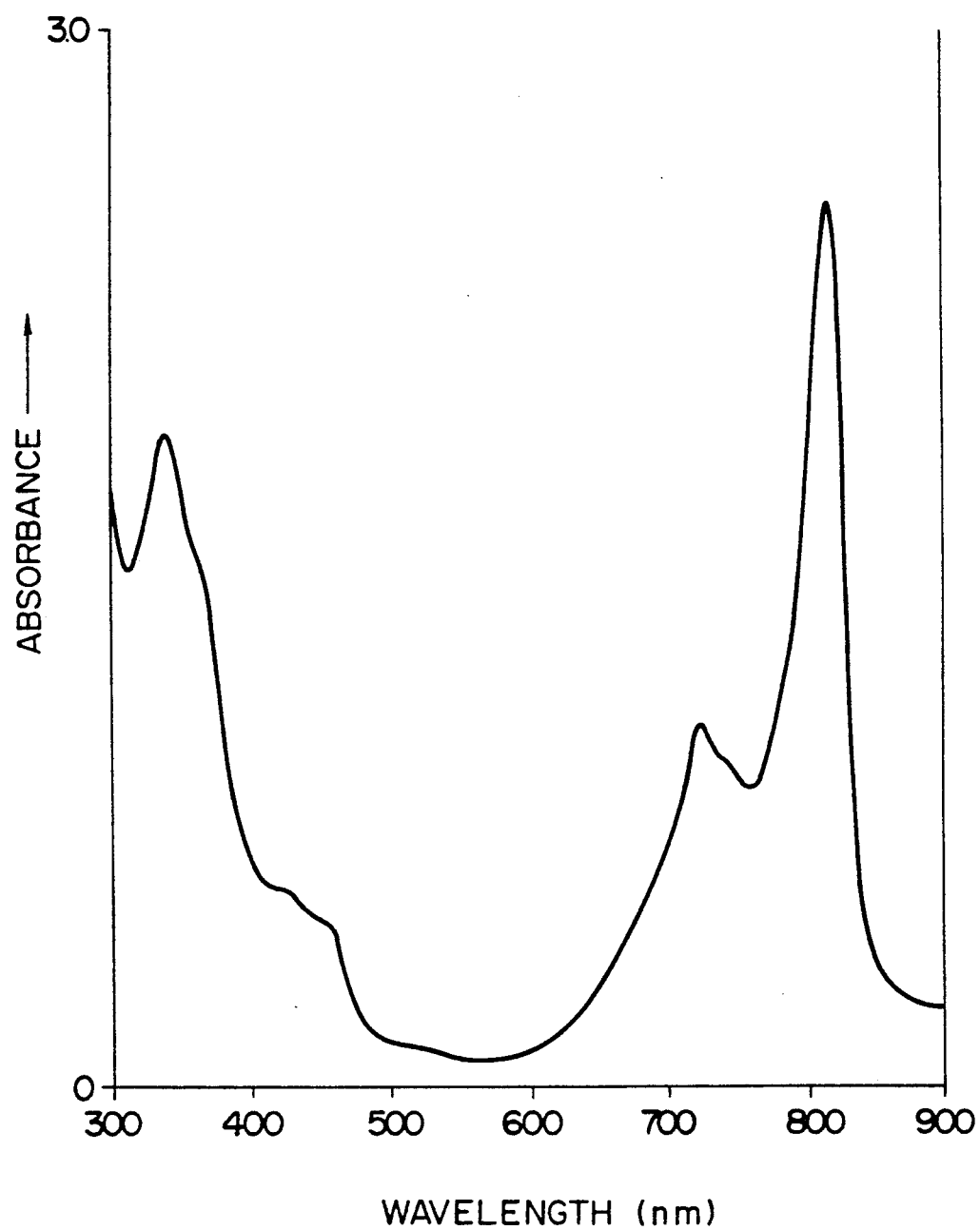
FIG. 67 is an electronic spectrum of dichlorogermanium-tetrakis(n-octyloxycarbonyl)naphthalocyanine in its chloroform solution.

(1) Electronic spectrum (CHCl$_3$ solution)
Shown in FIG. 67.

Figure 68:
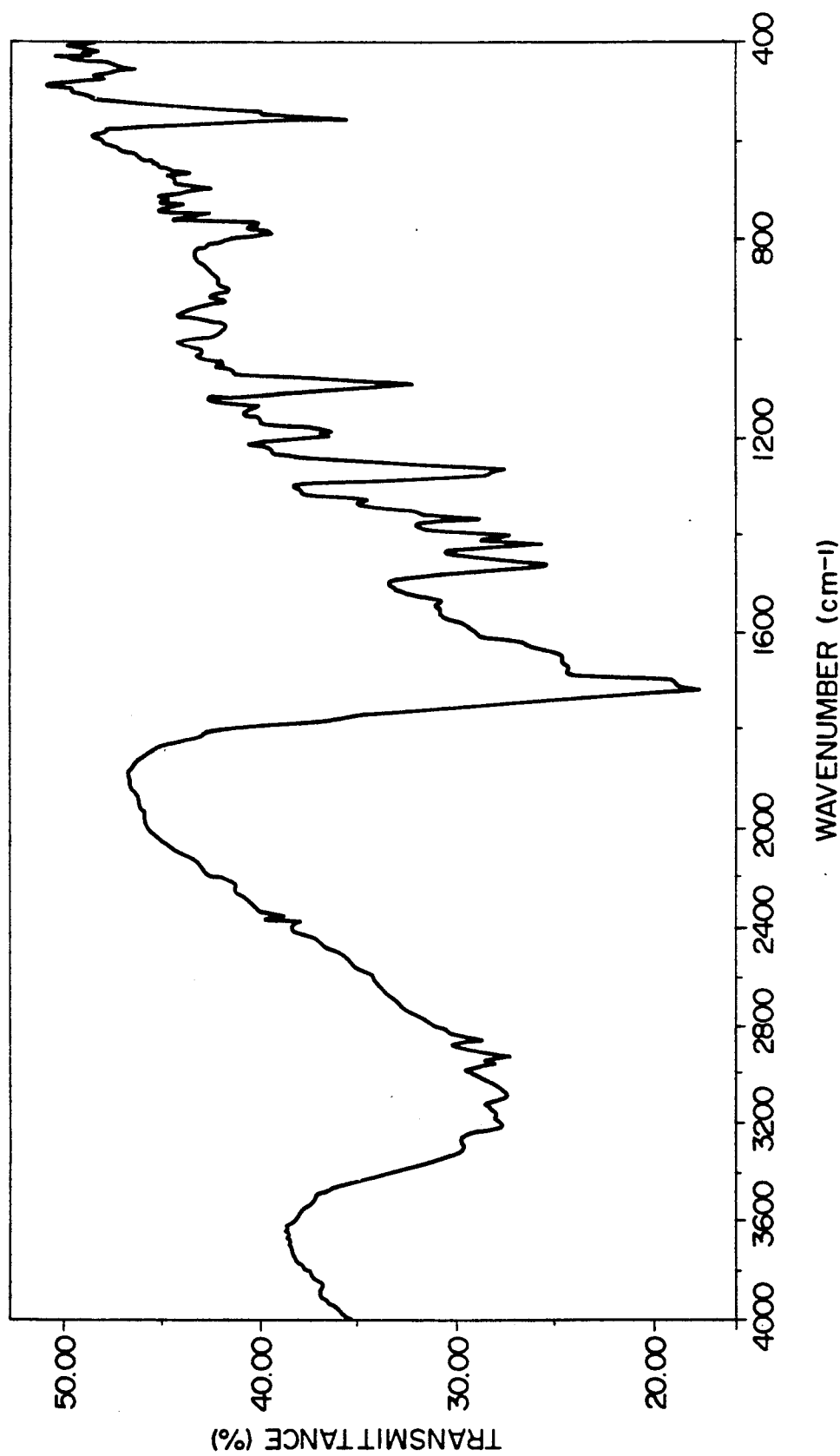
FIG. 68 is an IR spectrum of dichlorogermaniumtetrakis(n-octyloxycarbonyl)naphthalocyanine.

(2) IR spectrum (KBr)
Shown in FIG. 68. There is an absorption attributable to the stretching vibration of C=O of ester, at about 1,710 cm$^{-1}$.

2 g (1.35 mmol) of the above obtained dichlorogermanium-tetrakis(n-octyloxycarbonyl)naphthalocyanine was refluxed in a mixed solvent consisting of 50 ml of a concentrated aqueous ammonia solution, 50 ml of ethanol and 200 ml of water for about 2 hours. After cooling, the reaction mixture was treated in the same manner as in Example 23 to obtain 758 mg of a green solid. From the following analytical results, the green solid was believed to be dihydroxygermanium-tetrakis(n-octyloxycarbonyl)naphthalocyanine of the general formula (VI) [in the general formula (VI), R$^1$ are all an n-octyl group; n is 1; and M is Ge]. The solid was used in the subsequent reaction without further purification.

Figure 69:
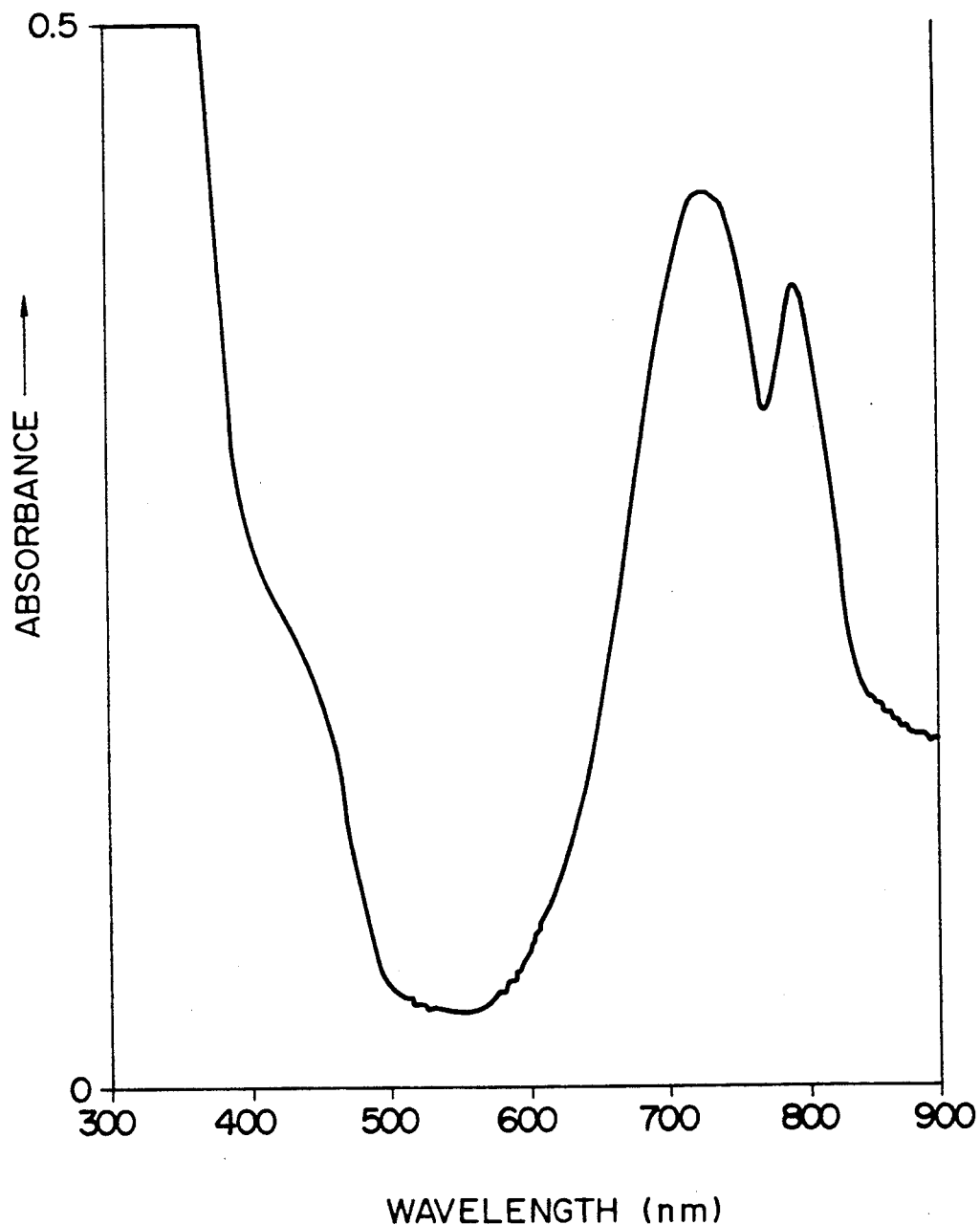
FIG. 69 is an electronic spectrum of dihydroxygermanium-tetrakis(n-octyloxycarbonyl)naphthalocyanine in its chloroform solution.

(1) Electronic spectrum (CHCL$_3$ solution)
Shown in FIG. 69.

Figure 70:
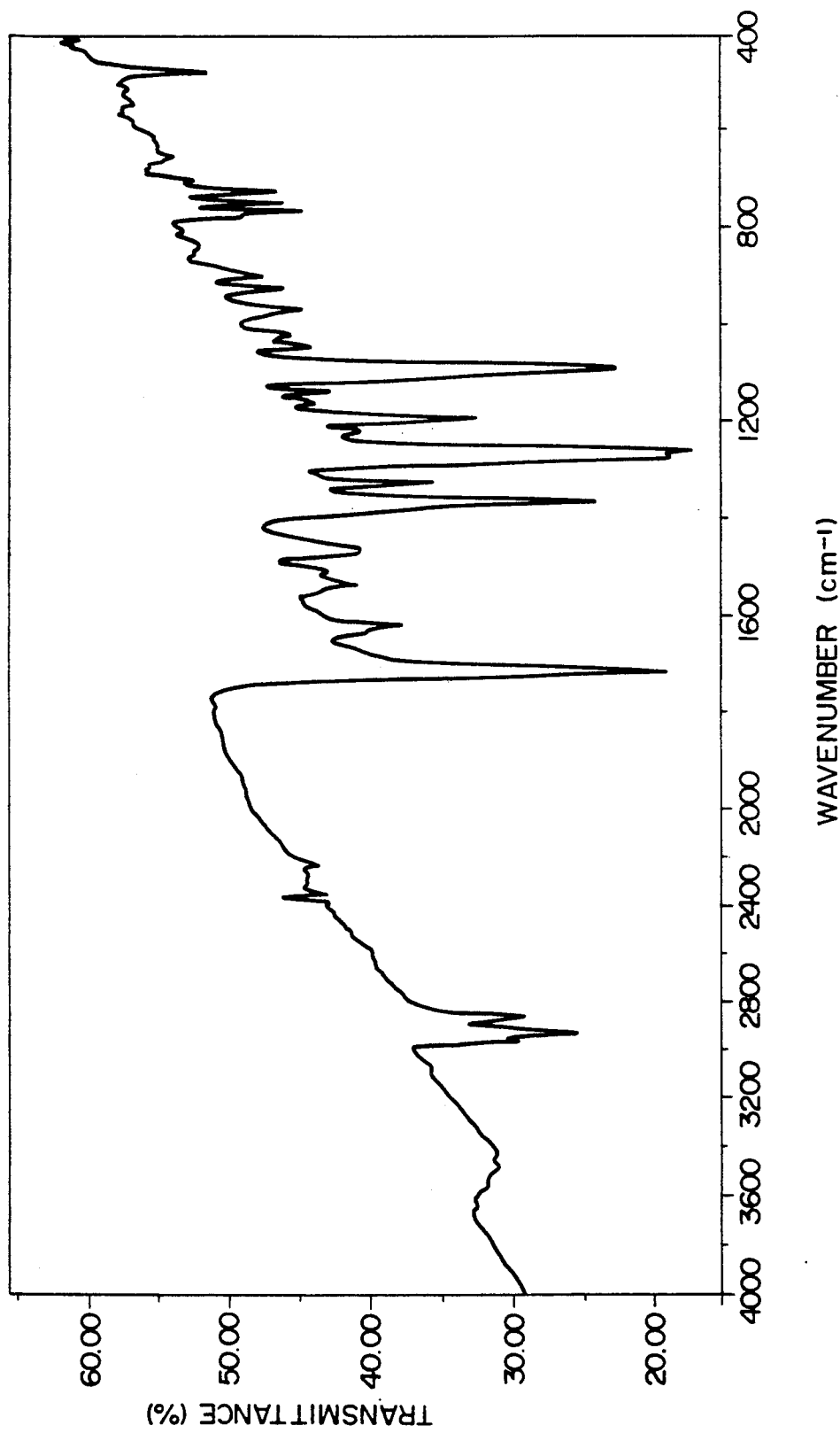
FIG. 70 is an IR spectrum of dihydroxygermanium-tetrakis(n-octyloxycarbonyl)naphthalocyanine.

(2) IR spectrum (KBr)
Shown in FIG. 70. There is an absorption attributable to the stretching vibration of C=O of ester, at about 1,700 cm$^{-1}$.

360 mg (0.25 mmol) of the above obtained dihydroxygermanium-tetrakis(n-octyloxycarbonyl)naphthalocyanine was refluxed in 24 ml of chlorobenzene in the presence of 1.2 ml of triethylsilanol for about 1 hour. The reaction mixture was concentrated to about 5 ml. After cooling, about 50 ml of methanol was added to the concentrate, and the mixture was allowed to stand for a while. The resulting precipitate was collected by filtration, thoroughly washed with methanol and dried thoroughly. The resulting dark green solid was purified by alumina thin layer chromatography using a benzene/hexane (1:1) mixed solvent as an eluent to obtain 47 mg of a dark green solid. The following analytical results confirmed that the dark green solid was bis(triethylsiloxy) germanium-tetrakis(n-octyloxycarbonyl)-naphthalocyanine [illustrative compound (44)].

(1) Melting point: 280° C. (decomposed)

| | (2) Elemental analysis | | |
|---|---|---|---|
| | C | H | N |
| Calculated (%) | 68.93 | 7.11 | 6.70 |
| Found (%) | 68.85 | 7.03 | 6.71 |

Figure 71:
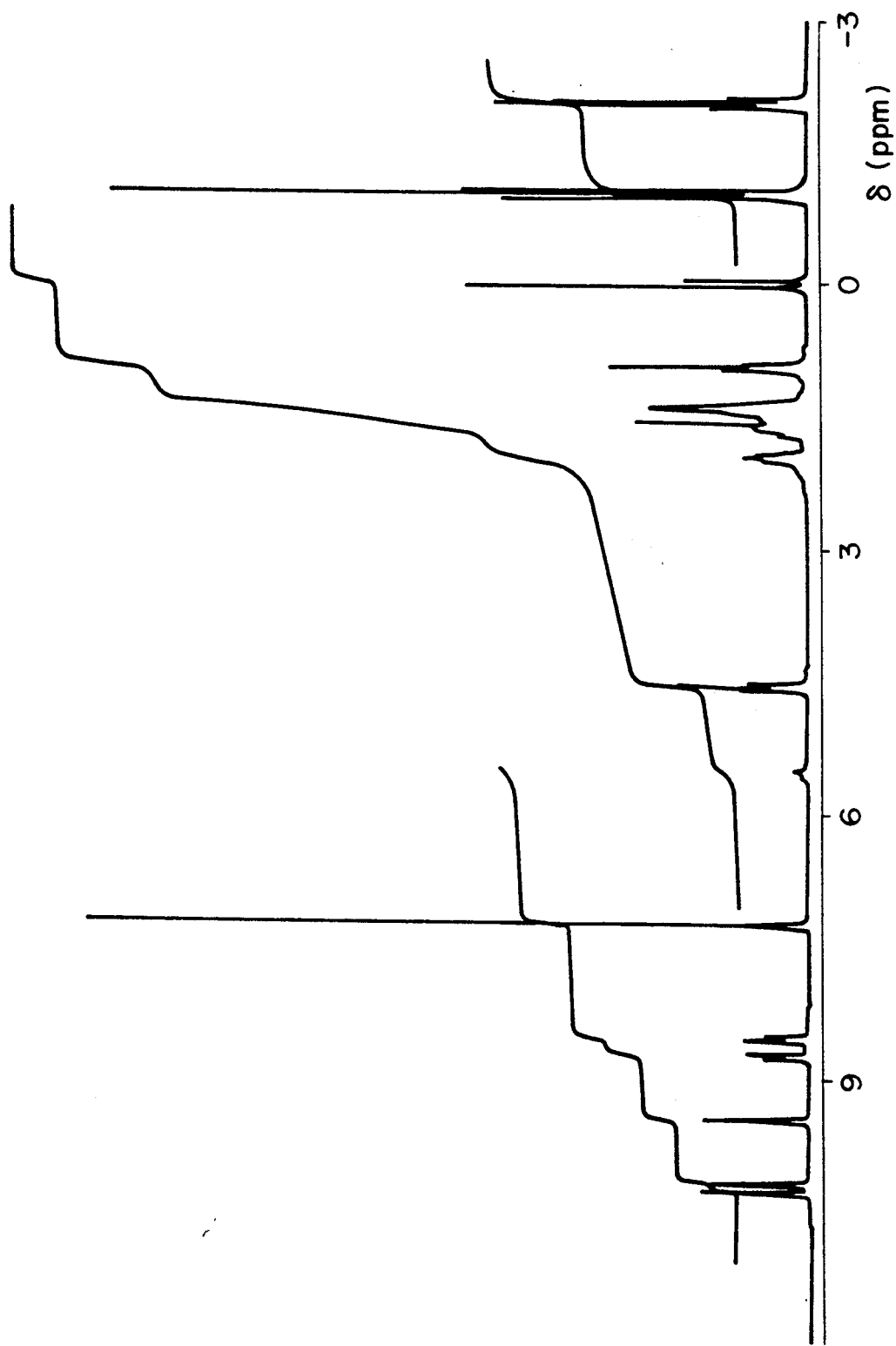
FIG. 71 is an NMR spectrum of bis(triethylsiloxy)-germanium-tetrakis(n-octyloxycarbonyl)naphthalocyanine.

(3) NMR spectrum (solvent: CDCl$_3$)
Shown in FIG. 71.

δ 10.20 (4H, s); 10.09 (4H, s); 9.38 (4H, s); 8.65 (4H, d, J=8.55 Hz); 8.46 (4H, dd, J=8.55, 1.52 Hz); 4.51 (8H, t, J=6.41 Hz); 1.91 (8H, quintet, J=6.41 Hz); 1.51 (40H, m); 0.89 (12H, t, J=6.72 Hz); −1.07 (18H, t, J=7.94 Hz); −2.08 (12H, q, J=7.94 Hz).

Figure 72:
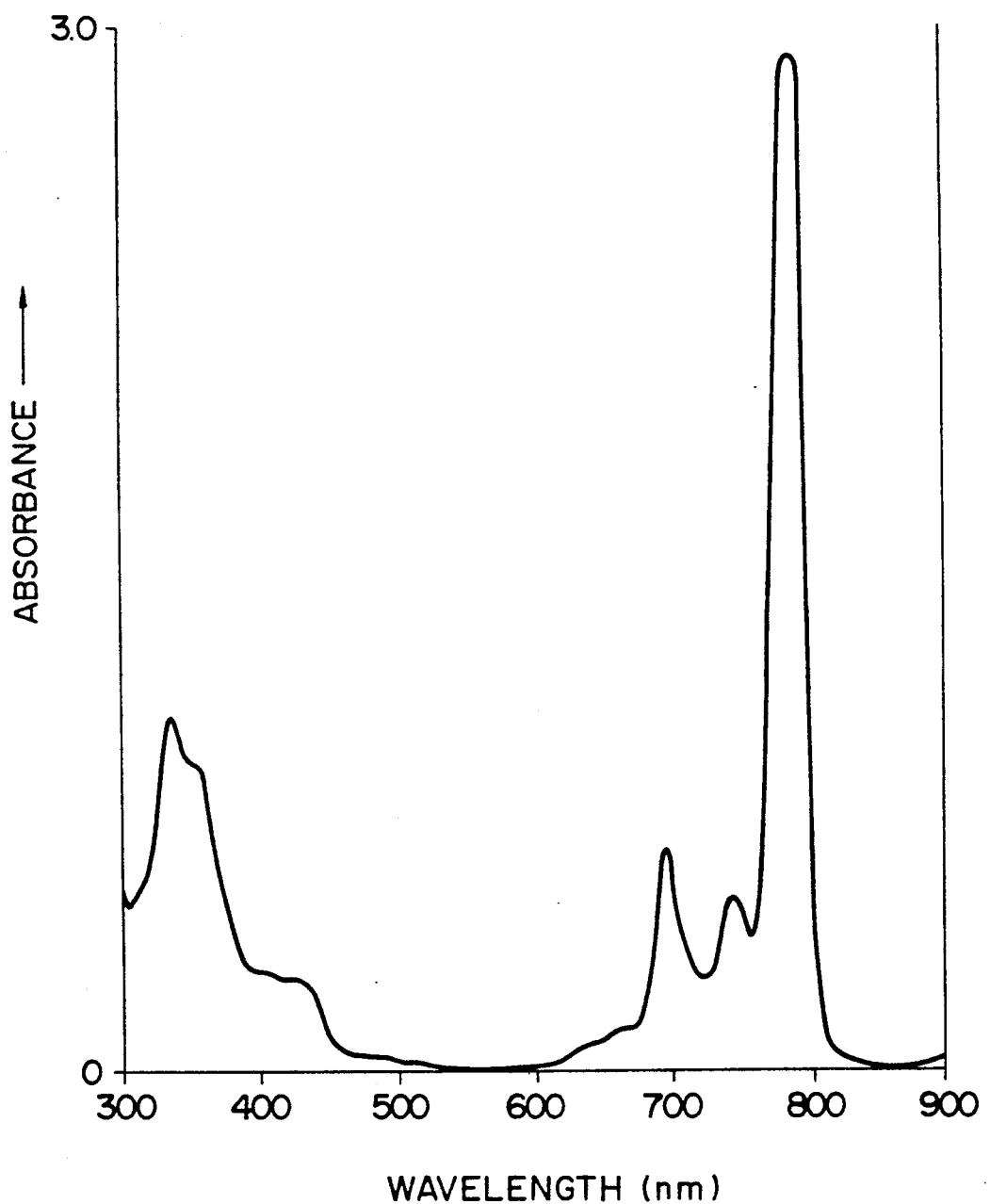
FIG. 72 is an electronic spectrum of bis(triethylsiloxy)germanium-tetrakis(n-octyloxycarbonyl)naphthalocyanine in its tetrahydrofuran solution.

(4) Electronic spectrum (tetrahydrofuran solution)
Shown in FIG. 72.

Figure 73:
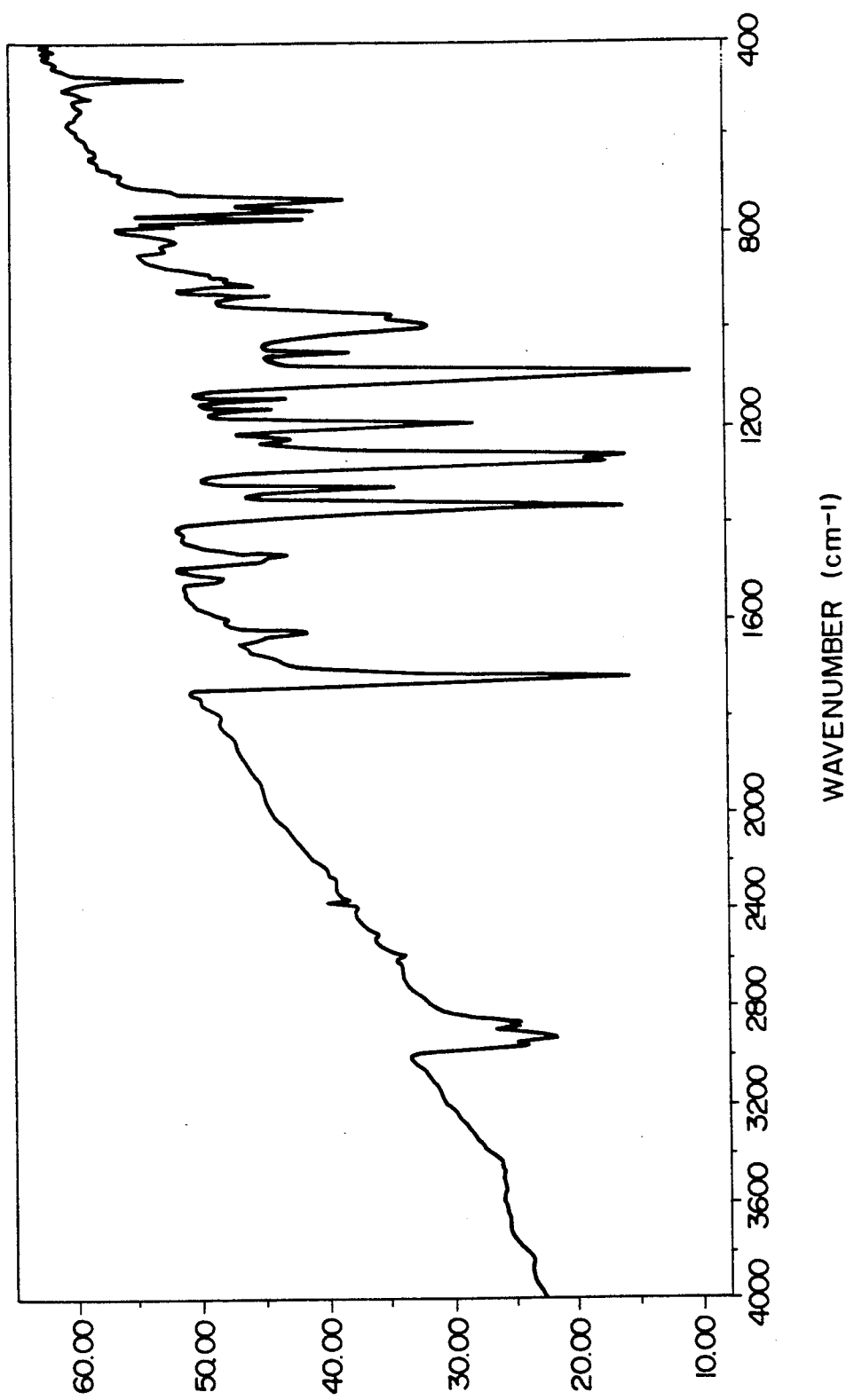
FIG. 73 is an IR spectrum of bis(triethylsiloxy)germanium-tetrakis(n-octyloxycarbonyl)naphthalocyanine.

(5) IR spectrum (KBr)
Shown in FIG. 73. There is an absorption attributable to the stretching vibration of C=O of ester, at about 1,720 cm$^{-1}$.

EXAMPLE 26

Synthesis of bis(tributylsiloxy)germanium-tetrakis(n-octyloxycarbonyl)naphthalocyanine [illustrative compound (45)]

289 mg (0.2 mmol) of the dihydroxygermanium-tetrakis(n-octyloxycarbonyl)naphthalocyanine obtained in Example 25 was refluxed in 19 ml of chlorobenzene in the presence of 1 ml of tributylsilanol for about 1 hour. The reaction mixture was concentrated to about 5 ml. After cooling, about 50 ml of methanol was added to the concentrate and the mixture was allowed to stand for a while. The resulting precipitate was collected by filtration, thoroughly washed with methanol and dried thoroughly. The resulting dark green solid was purified by alumina thin layer chromatography using benzene as an eluent to obtain 41 mg of a dark green solid. The following analytical results confirmed that the dark green solid was bis(tri-butylsiloxy)germanium-tetrakis(n-octyloxycarbonyl)naphthalocyanine [illustrative compound (45)].

(1) Melting point: 195°-200° C.

| | (2) Elemental analysis | | |
|---|---|---|---|
| | C | H | N |
| Calculated (%) | 70.46 | 7.77 | 6.09 |
| Found (%) | 70.12 | 7.73 | 6.18 |

Figure 74:
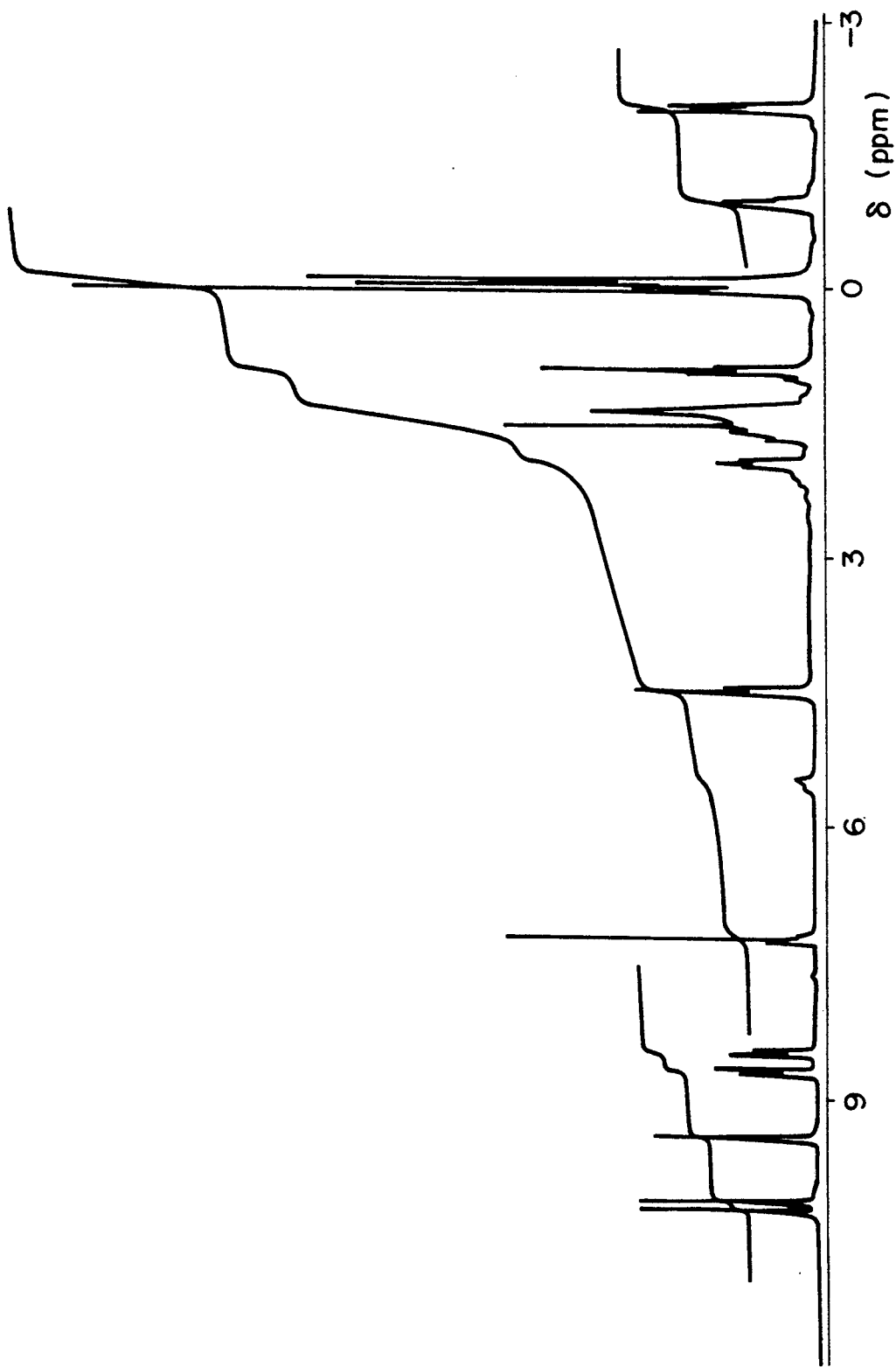
FIG. 74 is an NMR spectrum of bis(tributylsiloxy)-germanium-tetrakis(n-octyloxycarbonyl)naphthalocyanine.

(3) NMR spectrum (solvent: CDCl$_3$)
Shown in FIG. 74.

δ 10.19 (4H, s); 10.08 (4H, s); 9.39 (4H, s); 8.66 (4H, d, J=8.85 Hz); 8.46 (4H, dd, J=8.85, 1.53 Hz); 4.50 (8H, t, J=6.71 Hz); 1.92 (8H, quintet, J=6.71 Hz); 1.50 (40H, m); 0.90 (12H, t, J=6.71 Hz); −0.09 (30H, m); −0.99(12H, quintet-like m); −2.08 (12H, t-like m).

Figure 75:
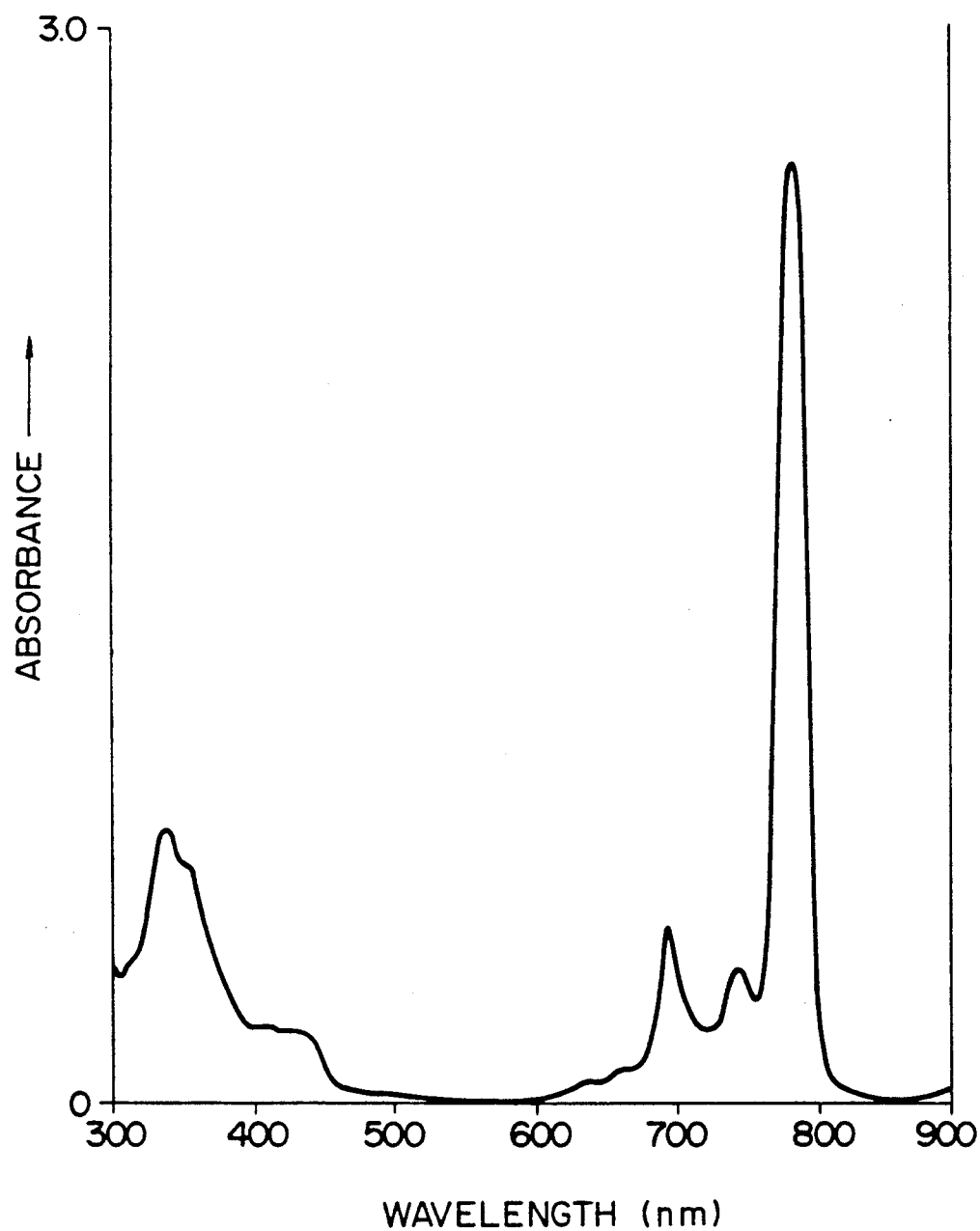
FIG. 75 is an electronic spectrum of bis(tributylsiloxy)germanium-tetrakis(n-octyloxycarbonyl)naphthalocyanine in its tetrahydrofuran solution.

(4) Electronic spectrum (tetrahydrofuran solution)
Shown in FIG. 75.

Figure 76:
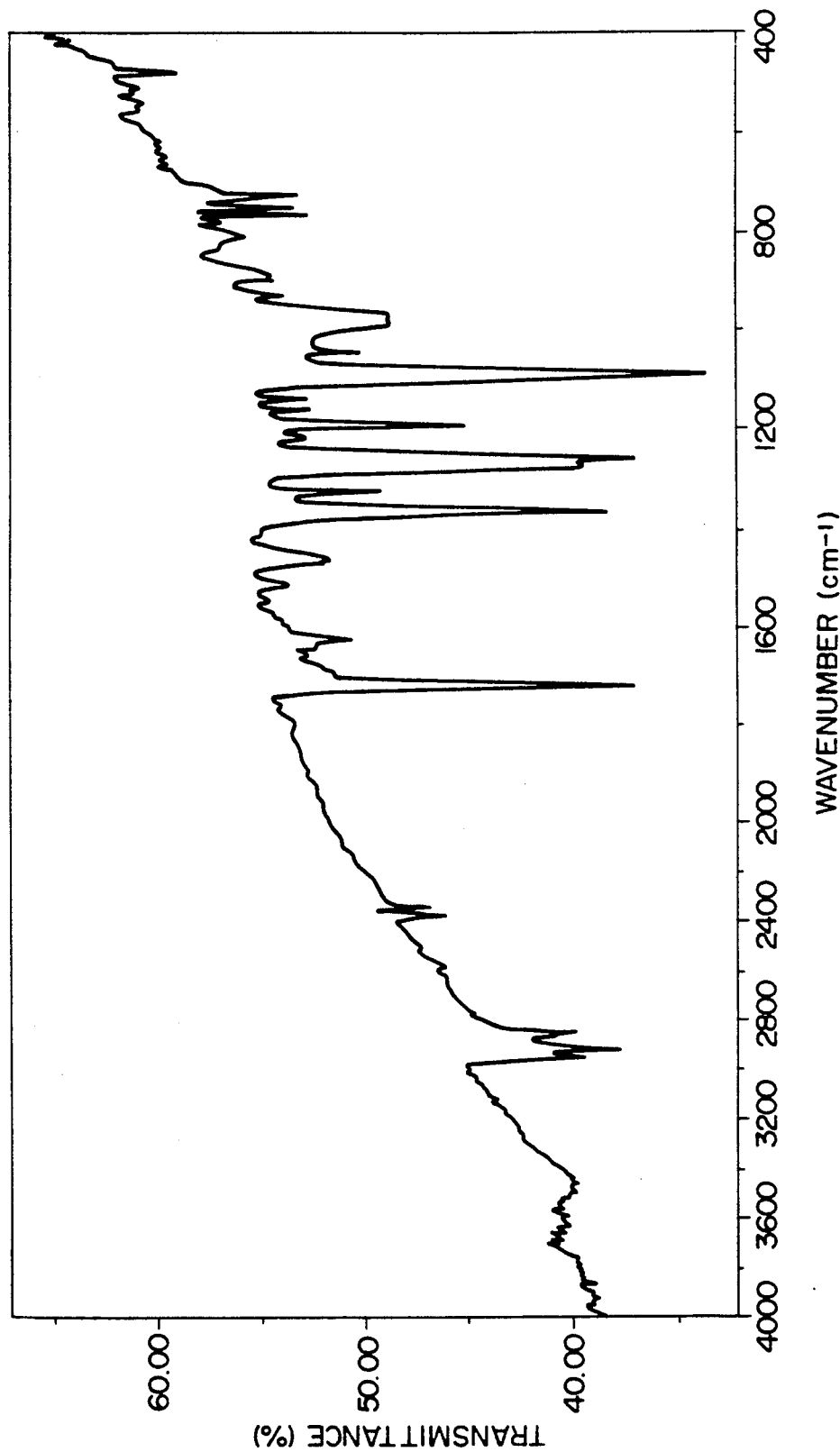
FIG. 76 is an IR spectrum of bis(tributylsiloxy)germanium-tetrakis(n-octyloxycarbonyl)naphthalocyanine.

(5) IR spectrum (KBr)
Shown in FIG. 76. There is an absorption attributable to the stretching vibration of C=O of ester, at about 1,720 cm$^{-1}$.

EXAMPLE 27

Synthesis of bis(n-dodecyloxy)germanium-tetrakis(n-amyloxycarbonyl)naphthalocyanine [illustrative compound (53)]

320 mg (0.25 mmol) of the dihydroxygermanium-tetrakis(n-amyloxycarbonyl)naphthalocyanine obtained in Example 23 was refluxed in 25 ml of chlorobenzene in the presence of 1.4 g (7.5 mmol) of 1-dodecanol for about 1 hour. The reaction mixture was concentrated to about 5 ml. After cooling, about 50 ml of methanol was added thereto and the mixture was allowed to stand for a while. The resulting precipitate was collected by filtration, thoroughly washed with methanol and dried thoroughly. The resulting black solid was purified by alumina thin layer chromatography using benzene as an eluent to obtain 12 mg of a dark green solid. The following analytical results confirmed that the dark green solid was bis(n-dodecyloxy)germanium-tetrakis(n-amyloxycarbonyl)naphthalocyanine [illustrative compound (53)].

(1) Melting point: 230°-240° C.

| | (2) Elemental analysis | | |
|---|---|---|---|
| | C | H | N |
| Calculated (%) | 71.50 | 7.13 | 6.95 |
| Found (%) | 71.73 | 7.18 | 7.09 |

Figure 77:
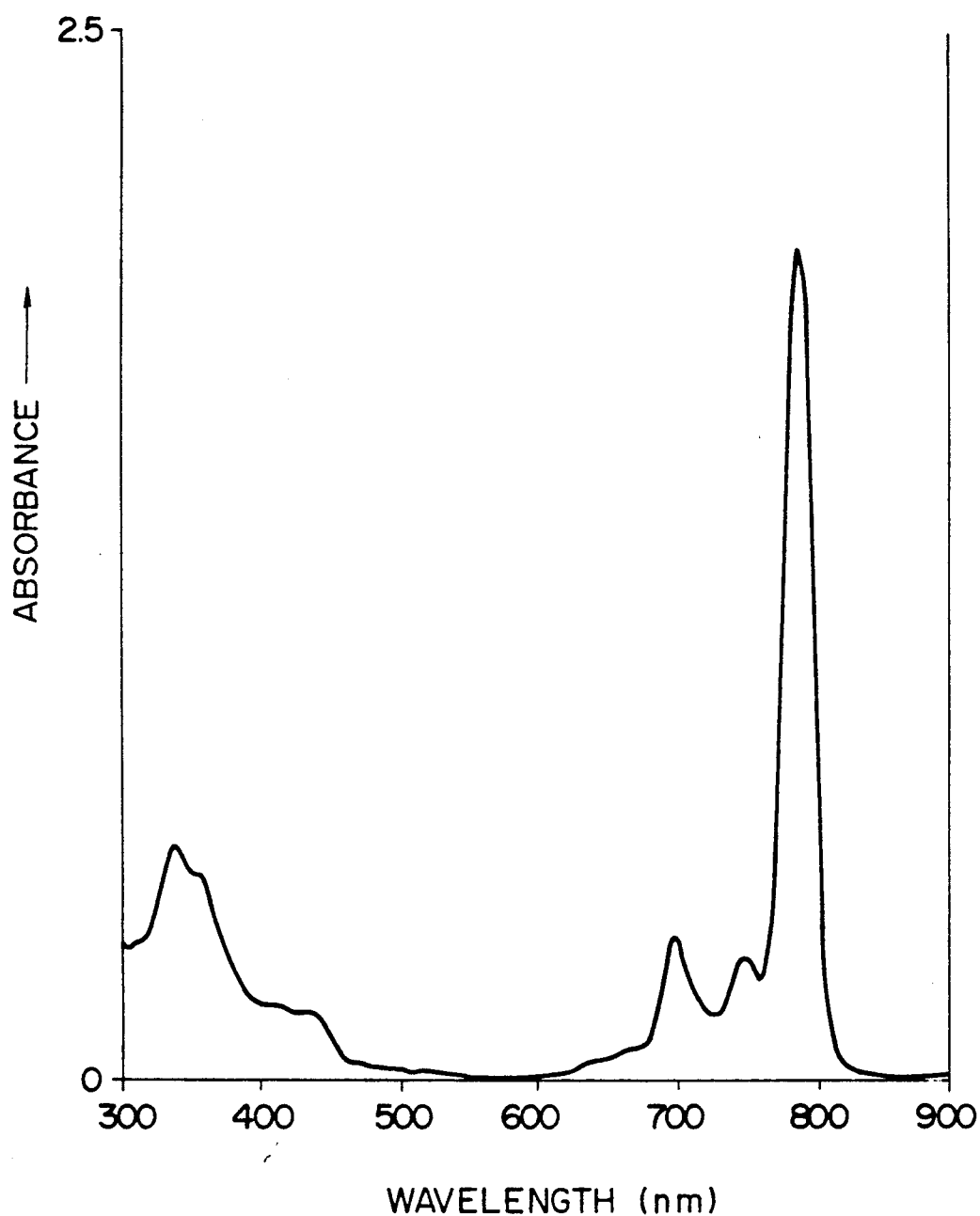
FIG. 77 is an electronic spectrum of bis(n-dodecyloxy)germanium-tetrakis(n-amyloxycarbonyl)naphthalocyanine in its chloroform solution.

(3) Electronic spectrum (CHCl$_3$ solution)
Shown in FIG. 77.

Figure 78:
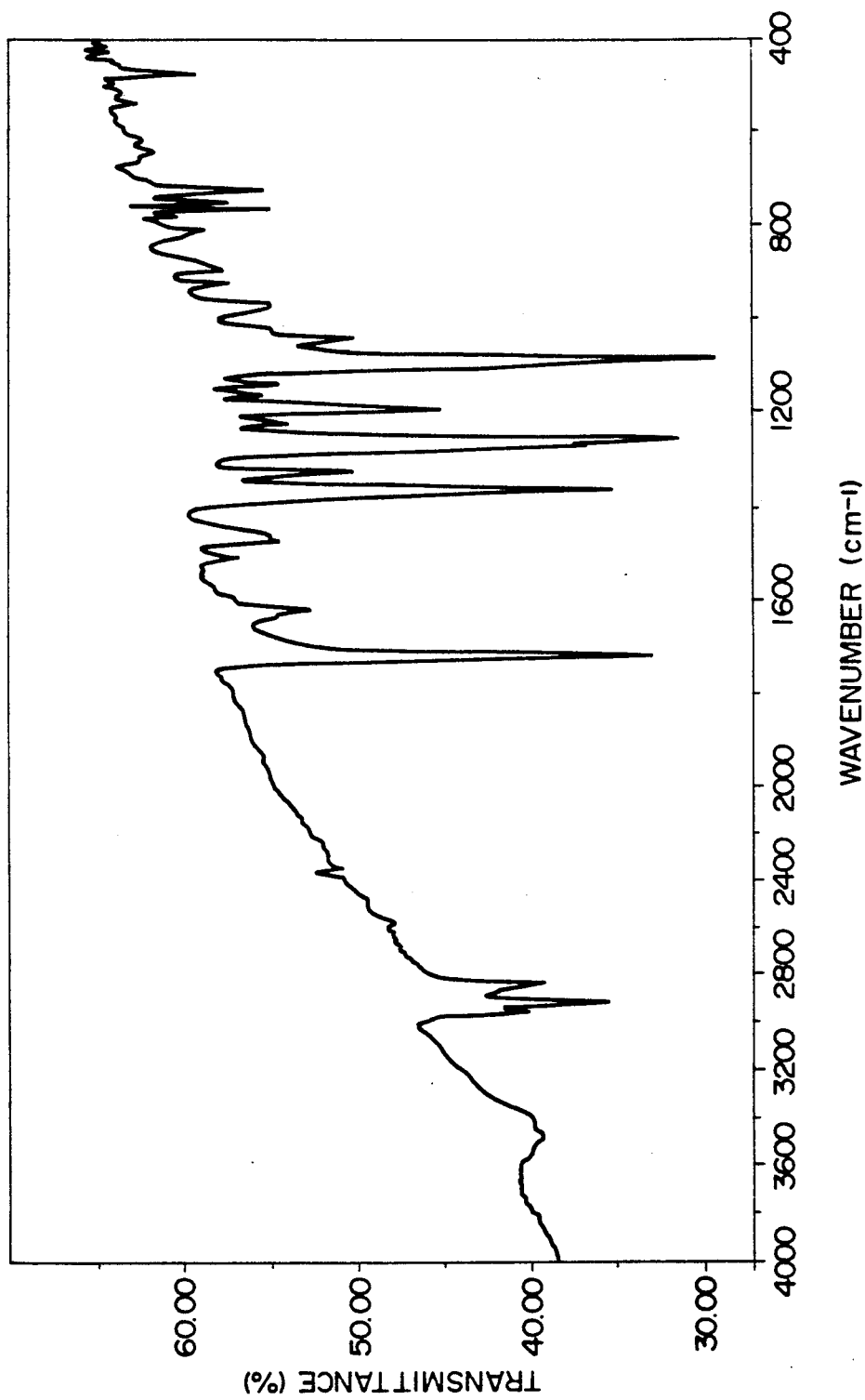
FIG. 78 is an IR spectrum of bis(n-dodecyloxy)germanium-tetrakis(n-amyloxycarbonyl)naphthalocyanine.

(4) IR spectrum (KBr)
Shown in FIG. 78. There is an absorption attributable to the stretching vibration of C=O of ester, at about 1,720 cm$^{-1}$.

EXAMPLE 28

Synthesis of bis(n-octadecyloxy)germanium-tetrakis(n-amyloxycarbonyl)naphthalocyanine [illustrative compound (54)]

320 mg (0.25 mmol) of the dihydroxygermanium-tetrakis(n-amyloxycarbonyl)naphthalocyanine obtained in the same manner as in Example 23 was refluxed in 25 ml of chlorobenzene in the presence of 2.03 g (7.5 mmol) of 1-octadecanol for about 1 hour. The reaction mixture was concentrated to about 5 ml. After cooling, about 50 ml of methanol was added thereto, and the whole mixture was allowed to stand for a while. The resulting precipitate was collected by filtration, thoroughly washed with methanol and dried thoroughly. The resulting black solid was purified by alumina thin layer chromatography using benzene as an eluent to obtain 16 mg of a dark green solid. The following analytical results confirmed that the dark green solid was (n-octadecyloxy)germanium-tetrakis(n-amyloxycarbonyl)-naphthalocyanine [illustrative compound (54)].

(1) Melting point: 220°-230° C. (decomposed)

| | (2) Elemental analysis | | |
|---|---|---|---|
| | C | H | N |
| Calculated (%) | 72.84 | 7.81 | 6.29 |
| Found (%) | 72.56 | 7.64 | 6.38 |

Figure 79:
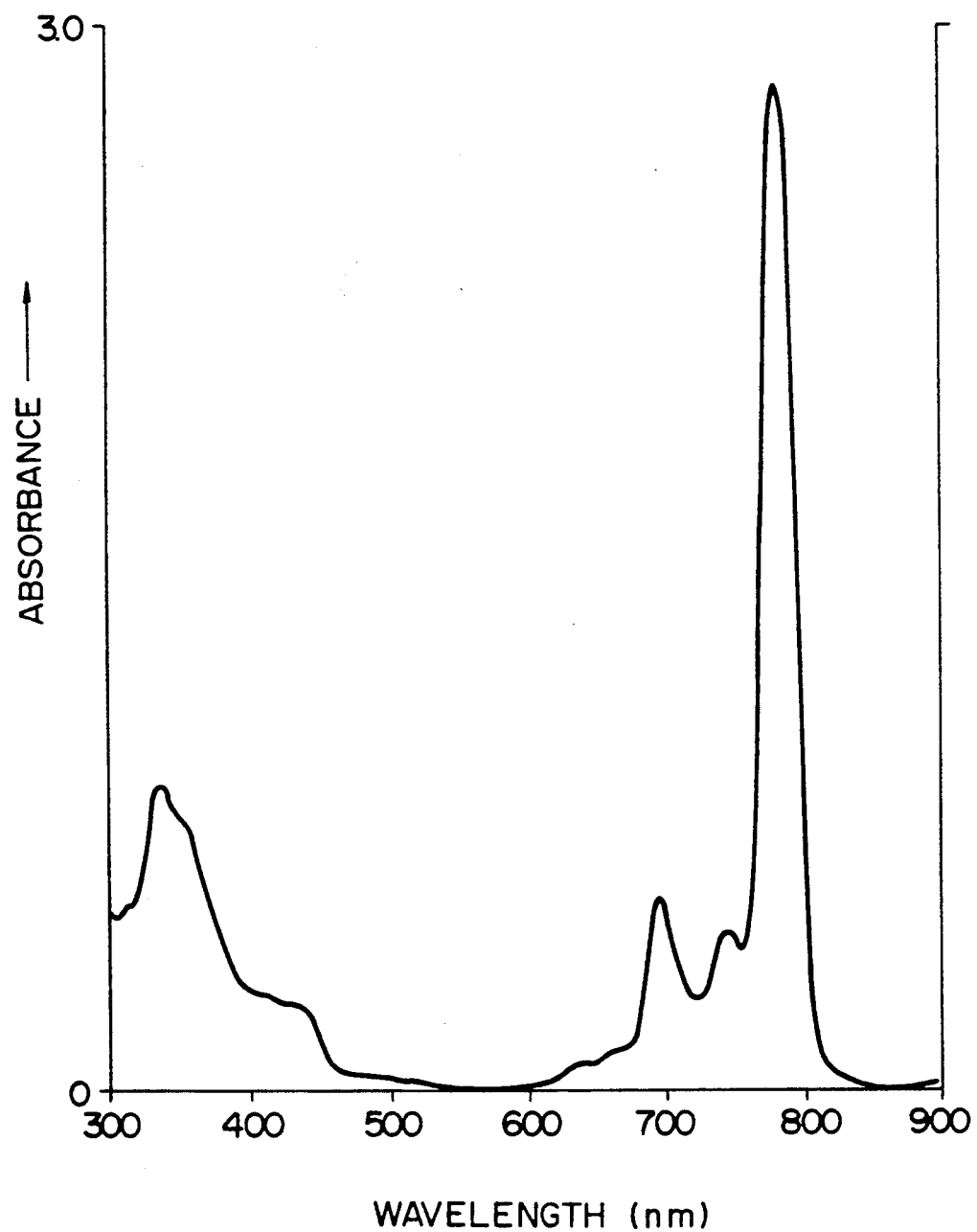
FIG. 79 is an electronic spectrum of bis-(n-octadecyloxy)germanium-tetrakis(n-amyloxycarbonyl)-naphthalocyanine in its tetrahydrofuran solution.

(3) Electronic spectrum (tetrahydrofuran solution)
Shown in FIG. 79.

(4) IR spectrum (KBr)

Figure 80:
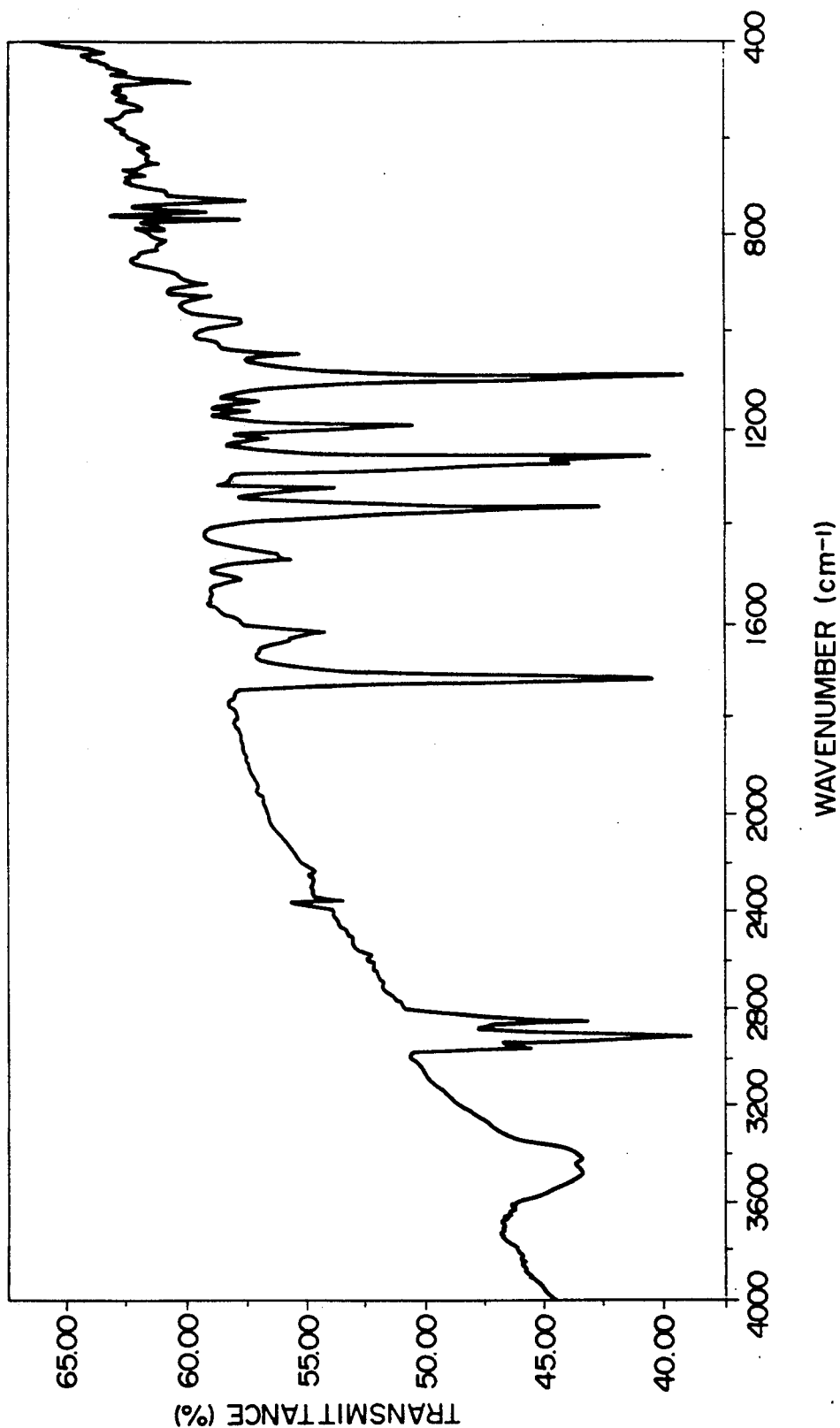
FIG. 80 is an IR spectrum of bis(n-octadecyloxy)germanium-tetrakis(n-amyloxycarbonyl)naphthalocyanine.

Shown in FIG. 80. There is an absorption attributable to the stretching vibration of C=O of ester, at about 1,720 cm$^{-1}$.

EXAMPLE 29

Synthesis of bis(n-decyloxy)germanium-tetrakis(n-octyloxycarbonyl)naphthalocyanine [illustrative compound (55)]

360 mg (0.25 mmol) of the dihydroxygermanium-tetrakis-(n-octyloxycarbonyl)naphthalocyanine obtained in the same manner as in Example 25 was refluxed in 24 ml of chlorobenzene in the presence of 1.4 g (7.5 mmol) of 1-dodecanol for about 1 hour. The reaction mixture was concentrated to about 5 ml. After cooling, about 50 ml of methanol was added thereto, and the whole mixture was allowed to stand for a while. The resulting precipitate was collected by filtration, thoroughly washed with methanol and dried thoroughly. The resulting dark green solid was purified by alumina thin layer chromatography using a benzene/ hexane (1:1) mixed solvent as an eluent to obtain 30 mg of a dark green solid. The following analytical results confirmed that the dark green solid was bis(n-dodecyloxy)germanium-tetrakis-(n-octyloxycarbonyl)naphthalocyanine [illustrative compound (55)].

(1) Melting point: 220°–230° C. (decomposed)

|  | (2) Elemental analysis | | |
|---|---|---|---|
|  | C | H | N |
| Calculated (%) | 72.84 | 7.81 | 6.29 |
| Found (%) | 72.81 | 7.72 | 6.35 |

Figure 81:
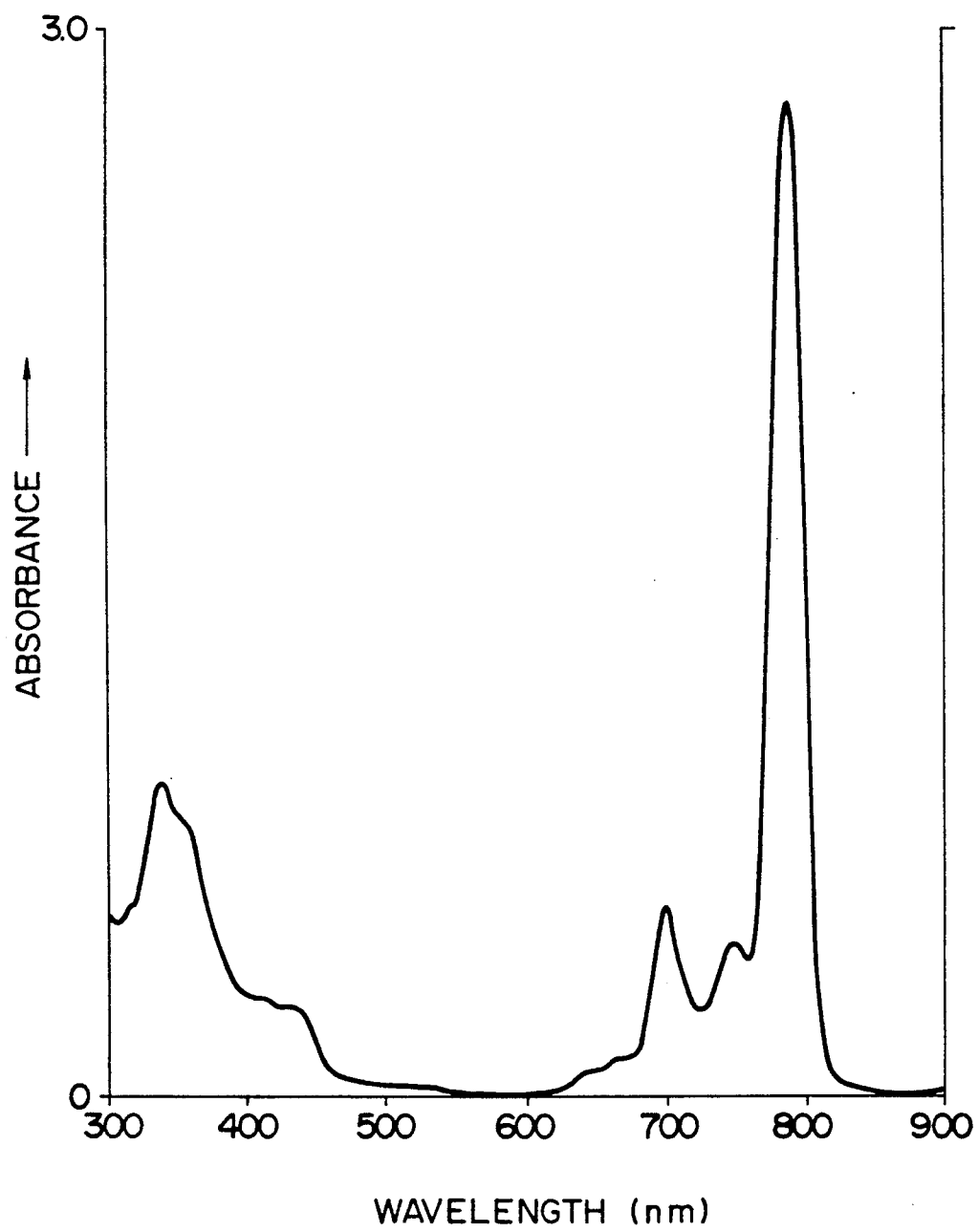
FIG. 81 is an electronic spectrum of bis(n-dodecyloxy)germanium-tetrakis(n-octyloxycarbonyl)naphtahlocyanine in its chloroform solution.

(3) Electronic spectrum (chloroform solution)
Shown in FIG. 81.

Figure 82:
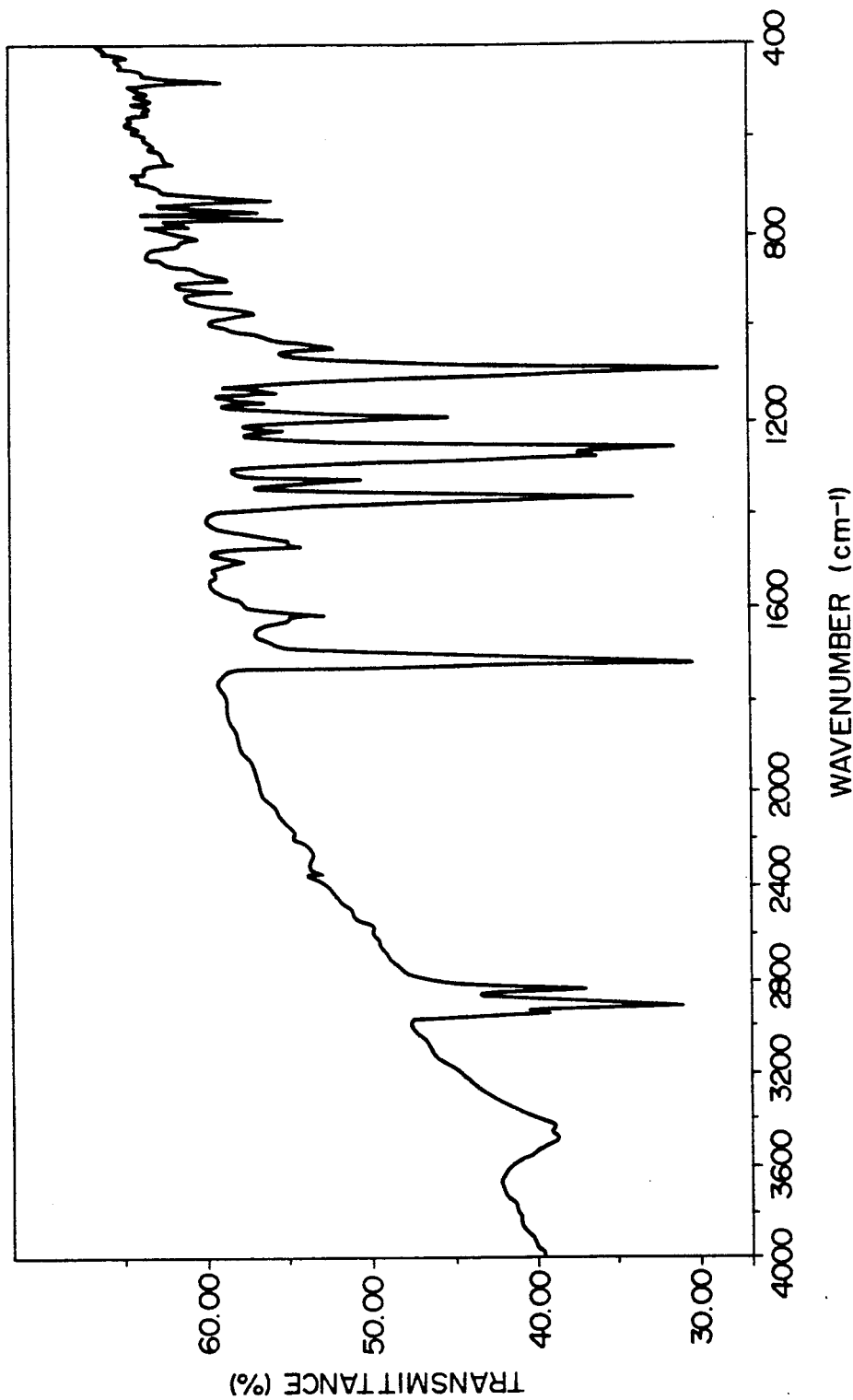
FIG. 82 is an IR spectrum of bis(n-dodecyloxy)germanium-tetrakis(n-octyloxycarbonyl)naphthalocyanine.

(4) IR spectrum (KBr)
Shown in FIG. 82. There is an absorption attributable to the stretching vibration of C=O of ester, at about 1,720 cm$^{-1}$.

EXAMPLE 30

Synthesis of bis(n-octadecyloxy)germanium-tetrakis(n-octyloxycarbonyl)naphthalocyanine [illustrative compound (56)]

360 mg (0.25 mmol) of the dihydroxygermanium-tetrakis(n-octyloxycarbonyl)naphthalocyanine was refluxed in 25 ml of chlorobenzene in the presence of 2.03 g (7.5 mmol) of 1-octadecanol for about 1 hour. The reaction mixture was concentrated to about 5 ml. After cooling, about 50 ml of methanol was added thereto, and the whole mixture was allowed to stand for a while. The resulting precipitate was collected by filtration, thoroughly washed with methanol and dried thoroughly. The resulting dark green solid was purified by alumina thin layer chromatography using benzene as an eluent to obtain 26 mg of a dark green solid. The following analytical results confirmed that the dark green solid was bis(n-octadecyloxy)germanium-tetrakis(n-octyloxycarbonyl)naphthalocyanine [illustrative compound (56)].

(1) Melting point: 200°–210° C. (decomposed)

|  | (2) Elemental analysis | | |
|---|---|---|---|
|  | C | H | N |
| Calculated (%) | 73.94 | 8.38 | 5.75 |
| Found (%) | 73.78 | 8.16 | 5.62 |

Figure 83:
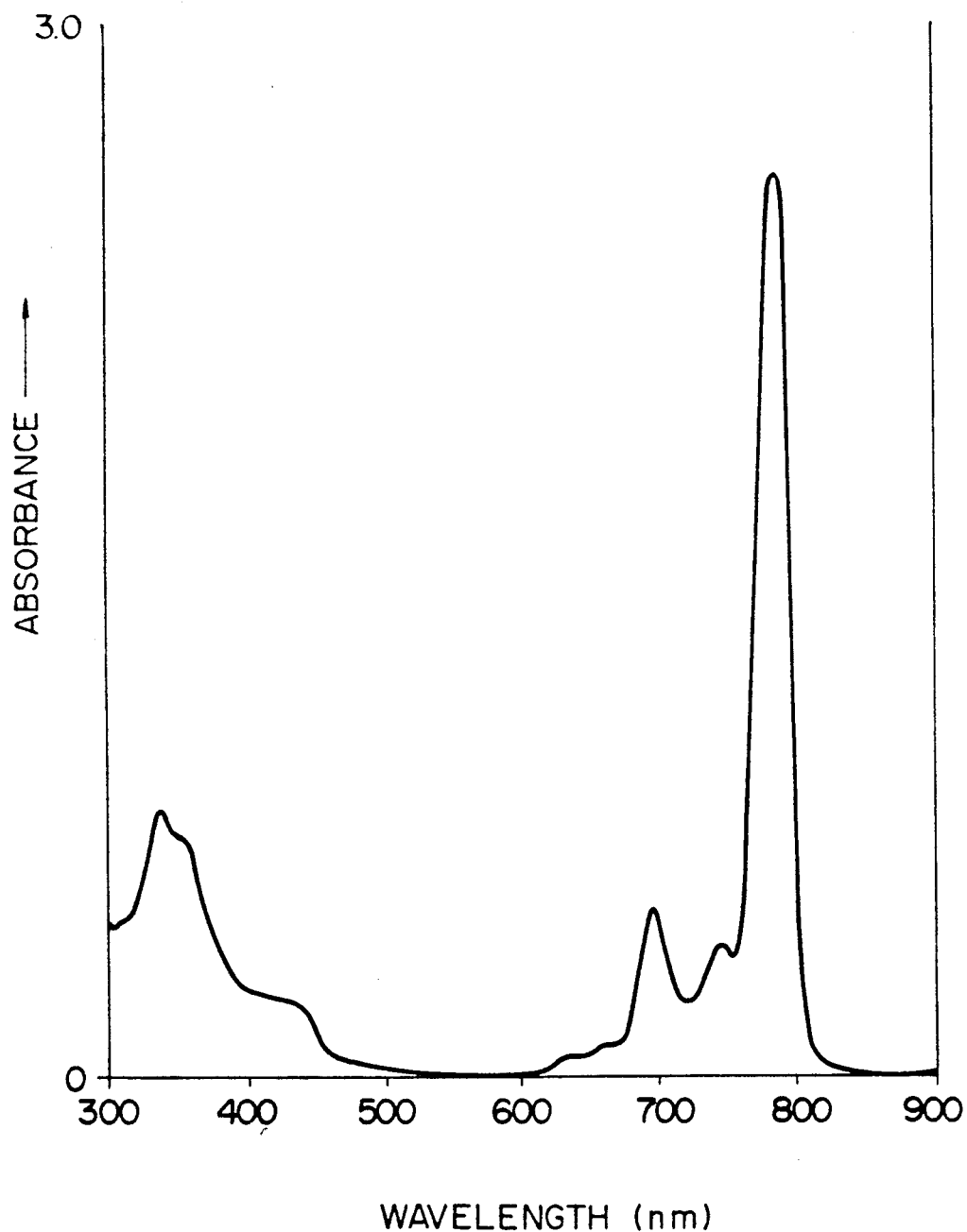
FIG. 83 is an electronic spectrum of bis(n-octadecyloxy)germanium-tetrakis(n-octyloxycarbonyl)naphthalocyanine in its tetrahydrofuran solution.
Figure 85:
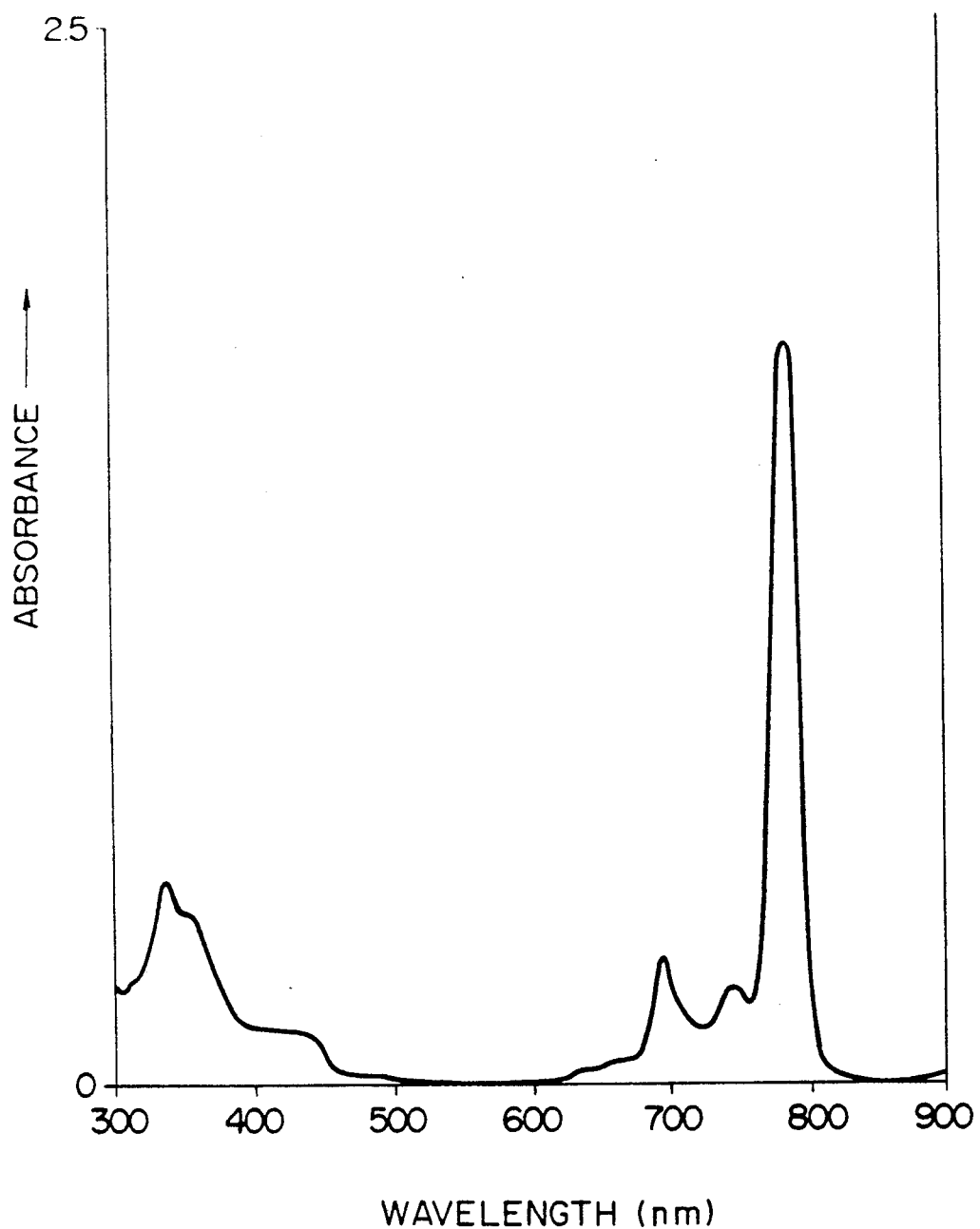
FIG. 85 is an electronic spectrum of bis(triethylsiloxy)germanium-tetrakis(n-amyloxycarbonyl)naphthalocyanine in its tetrahydrofuran solution.
Figure 86:
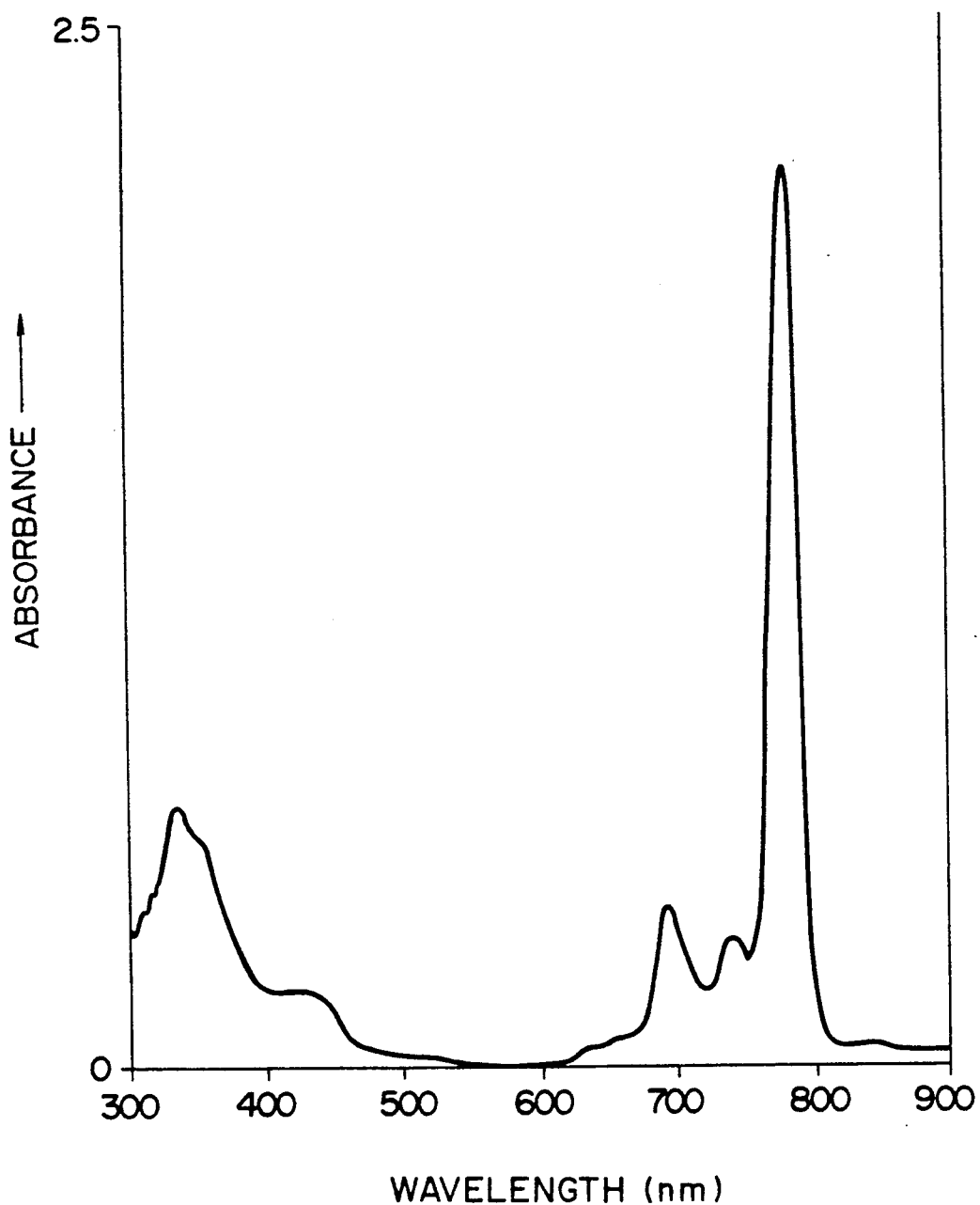
FIG. 86 is an electronic spectrum of bis(triethylsiloxy)germanium-tetrakis(n-amyloxycarbonyl)naphthalocyanine in its acetone solution.
Figure 87:
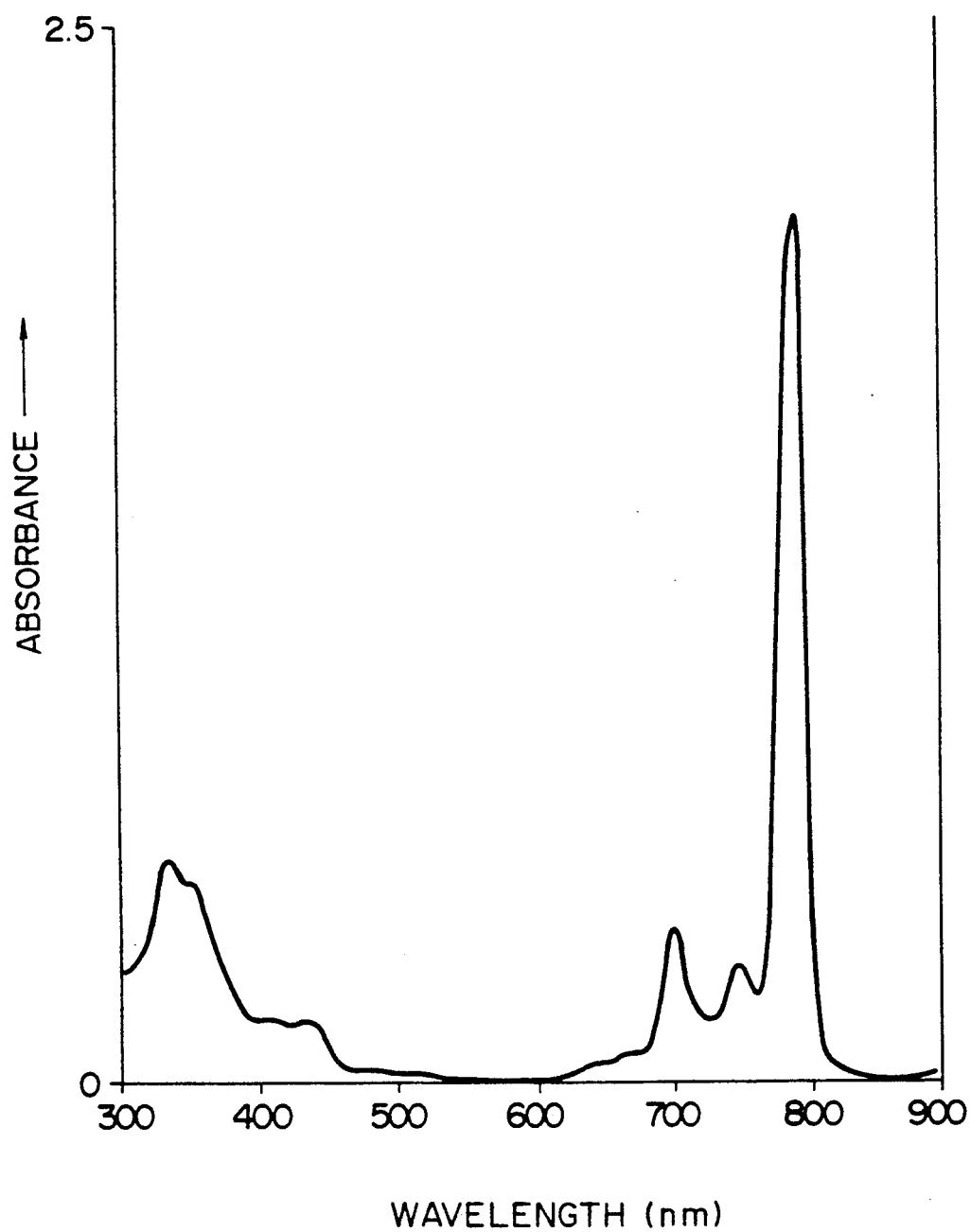
FIG. 87 is an electronic spectrum of bis(triethylsiloxy)germanium-tetrakis(n-amyloxycarbonyl)naphthalocyanine in its benzene solution.

(3) Electronic spectrum (tetrahydrofuran solution)
Shown in FIG. 83.

(4) IR spectrum (KBr)
Shown in FIG. 84. There is an absorption attributable to the stretching vibration of C=O of ester, at about 1,720 cm$^{-1}$.

TEST 1

Bis(triethylsiloxy)germanium-tetrakis(n-amyloxycarbonyl)naphthalocyanine [illustrative compound (41)] was dissolved in various solvents and measured for electronic spectrum in each solution. FIGS. 62, 85, 86 and 87 show the electronic spectra of the illustrative compound in chloroform, tetrahydrofuran, acetone and benzene, respectively. As is clear from these spectra, there was observed no change of absorption spectrum due to the change of type of solvent used or due to the change of concentration of illustrative compound in solution.

TEST 2

Figure 88:
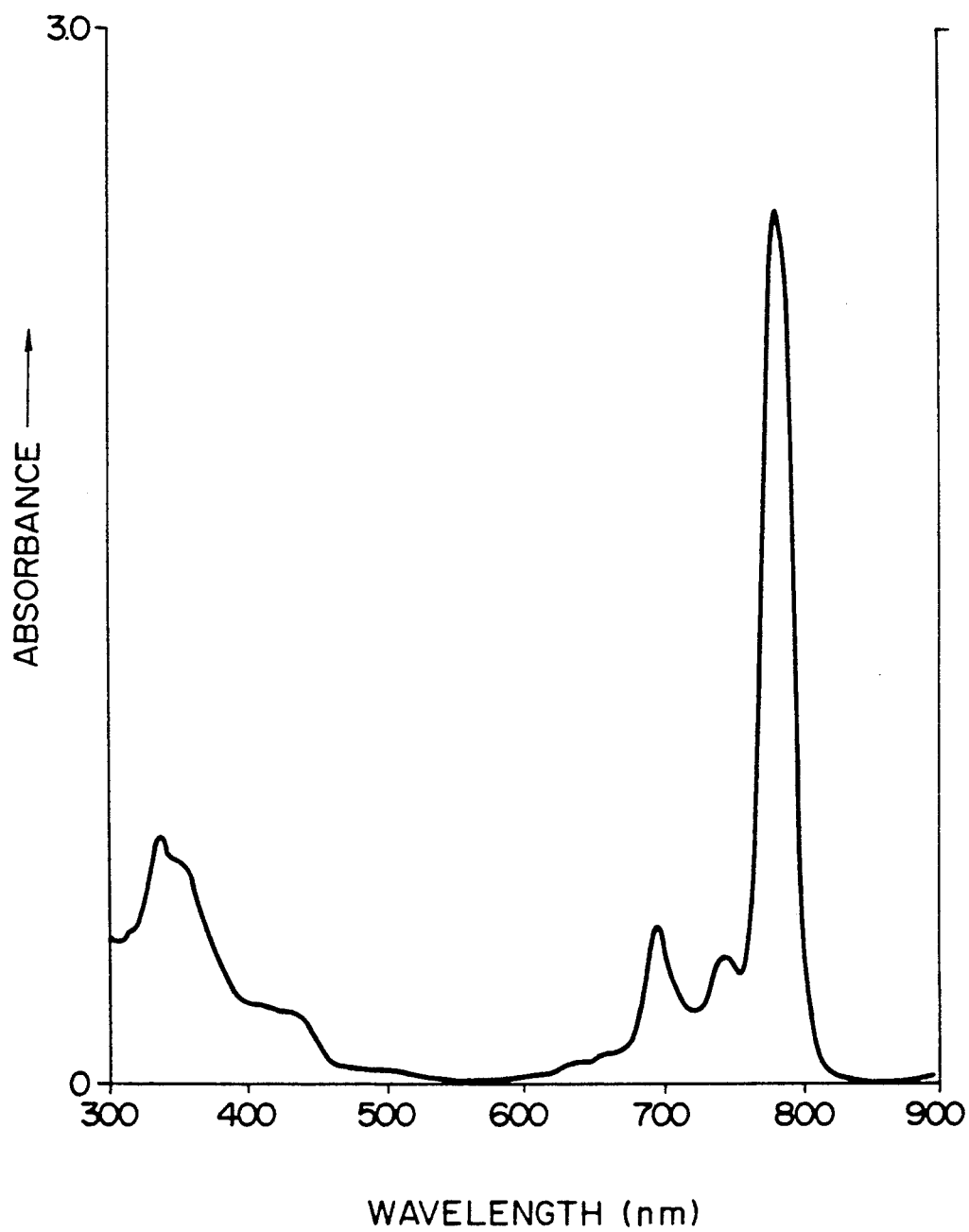
FIG. 88 is an electronic spectrum of bis(n-dodecyloxy)germanium-tetrakis(n-amyloxycarbonyl)naphthalocyanine in its tetrahydrofuran solution.
Figure 89:
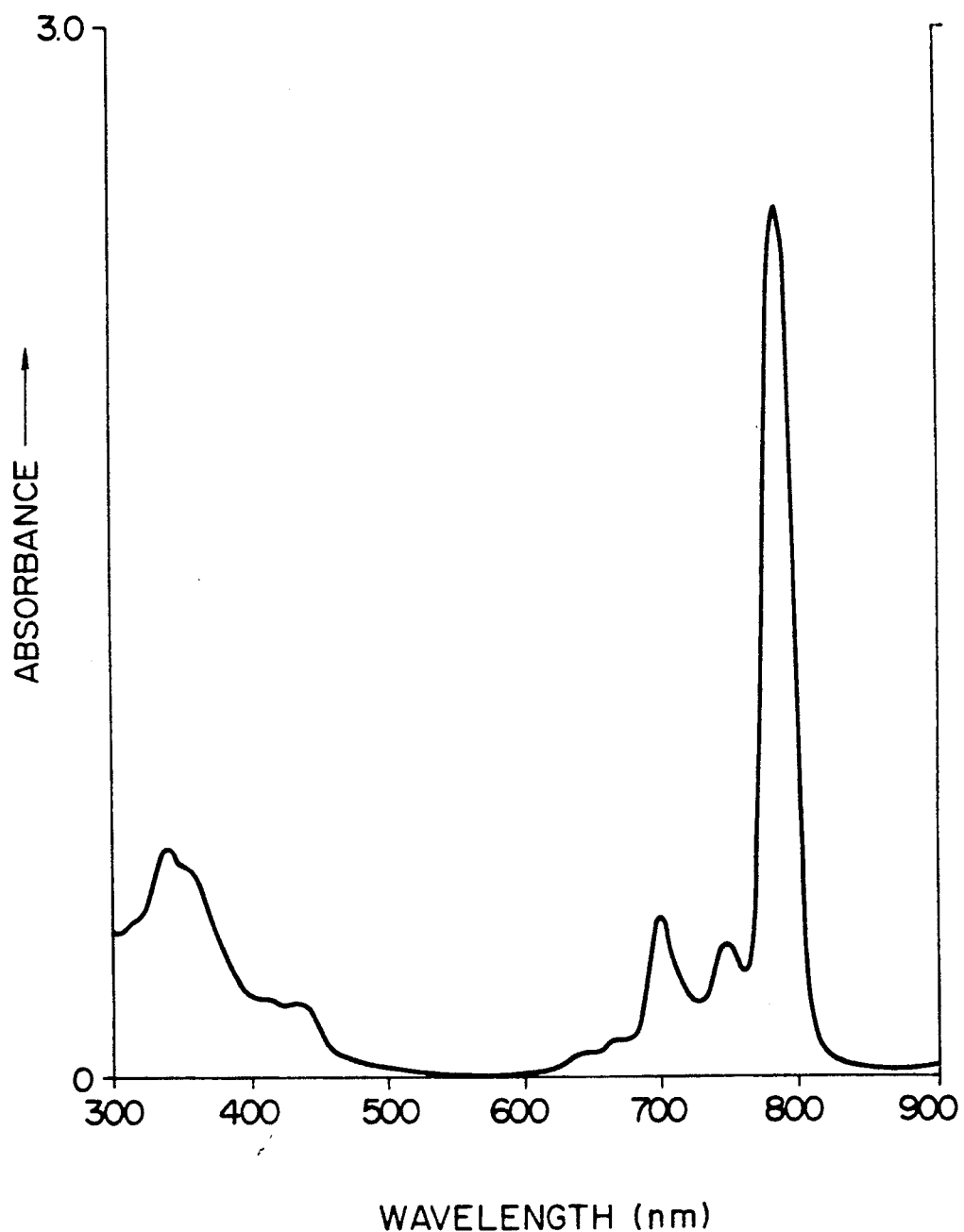
FIG. 89 is an electronic spectrum of bis(n-dodecyloxy)germanium-tetrakis(n-amyloxycarbonyl)naphthalocyanine in its benzene solution.

Bis(n-dodecyloxy)germanium-tetrakis(n-amyloxycarbonyl)naphthalocyanine [illustrative compound (53)] was dissolved in various solvents and measured for electronic spectrum in each solution. FIGS. 77, 88 and 89 show the electronic spectra of the illustrative compound in chloroform, tetrahydrofuran and benzene, respectively. As is clear from these spectra, there was observed no change of absorption spectrum due to the change of type of solvent used or due to the change of concentration of illustrative compound in solution.

COMPARATIVE TEST 1

Figure 90A:
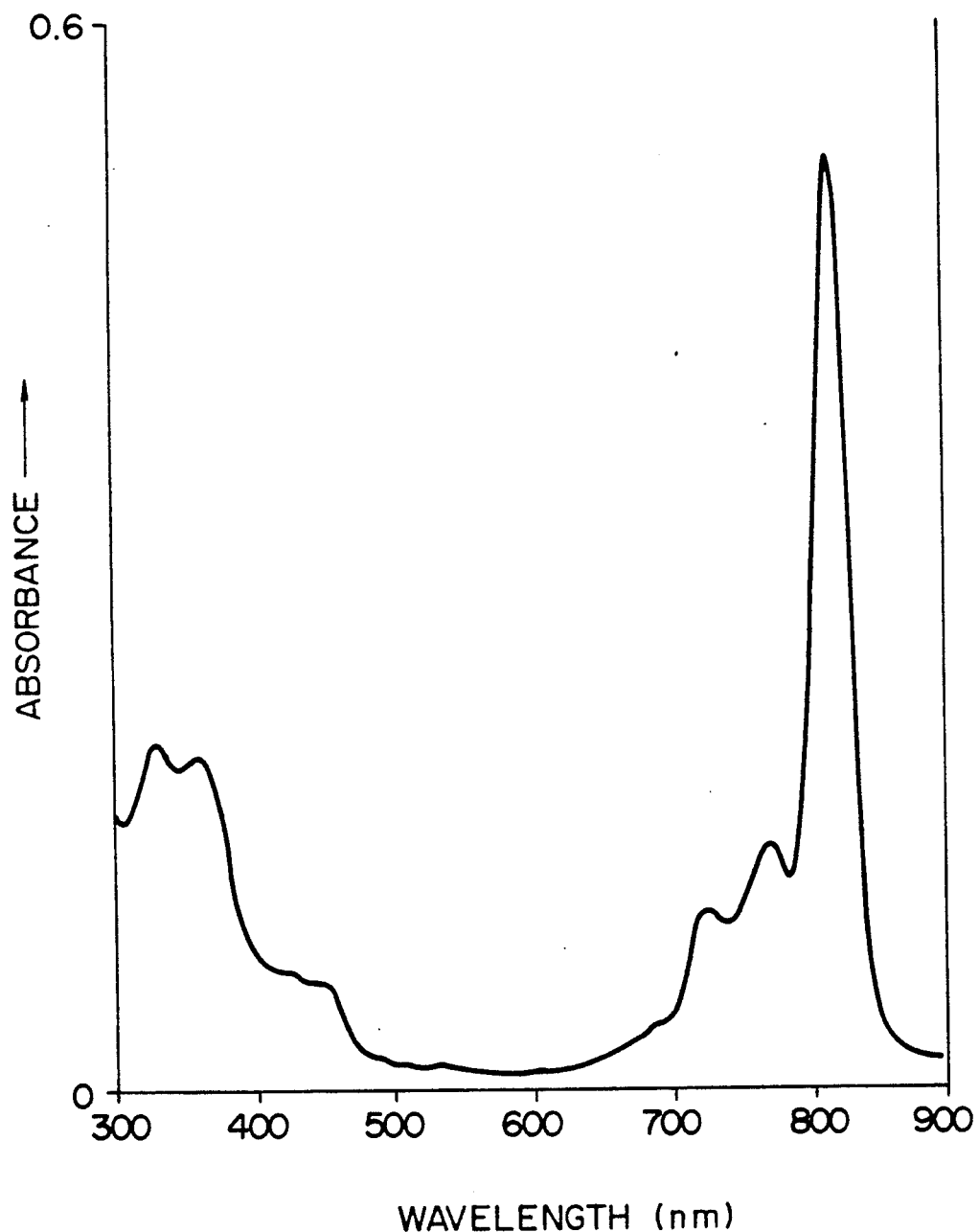
FIG. 90 is an electronic spectrum of tetra(t-butyl) vanadyl naphthalocyanine in its chloroform solution, wherein (a) is $2.37 \times 10^{-5}$M and (b) is $1.89 \times 10^{-5}$M.
Figure 90B:
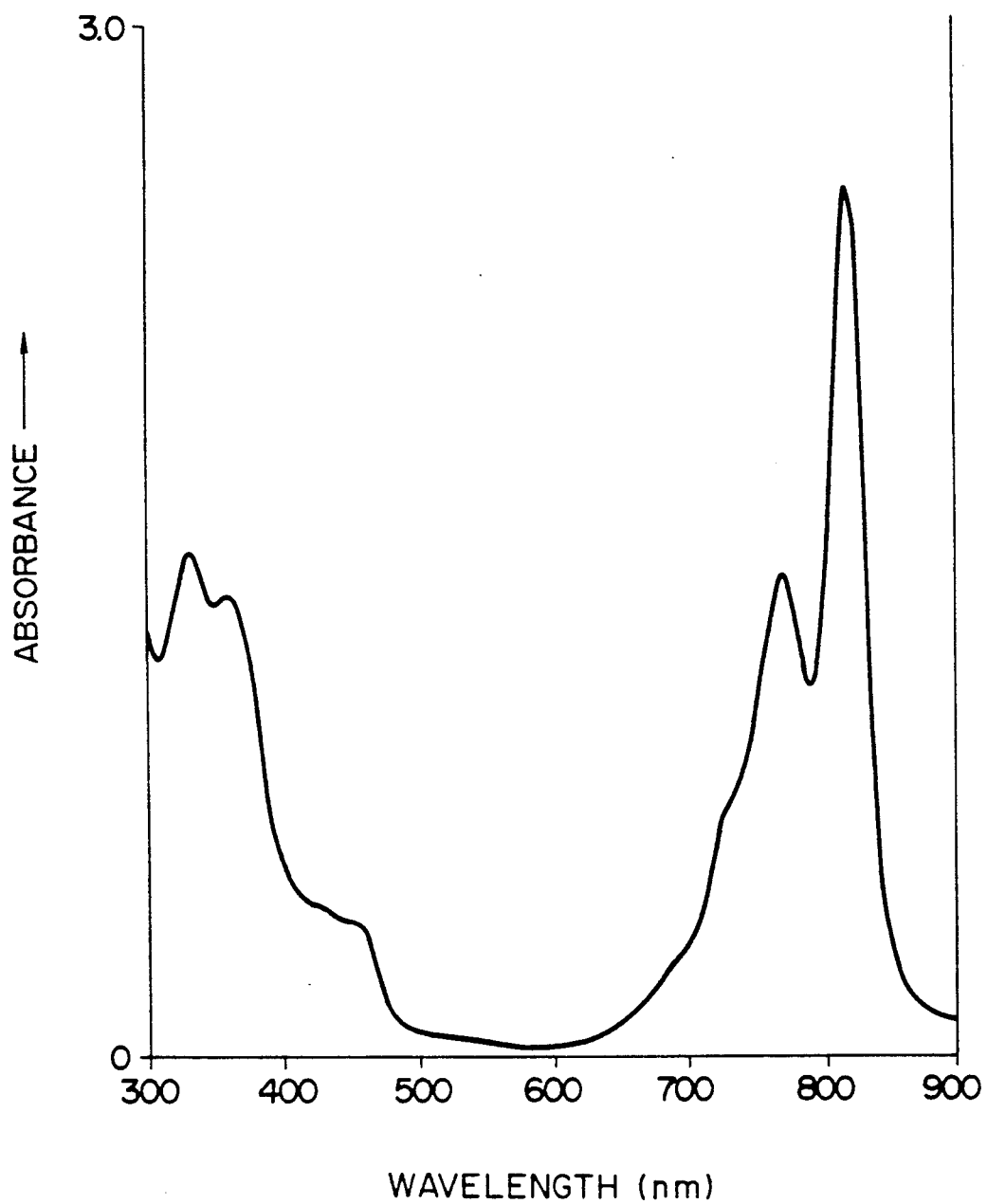
Figure 91:
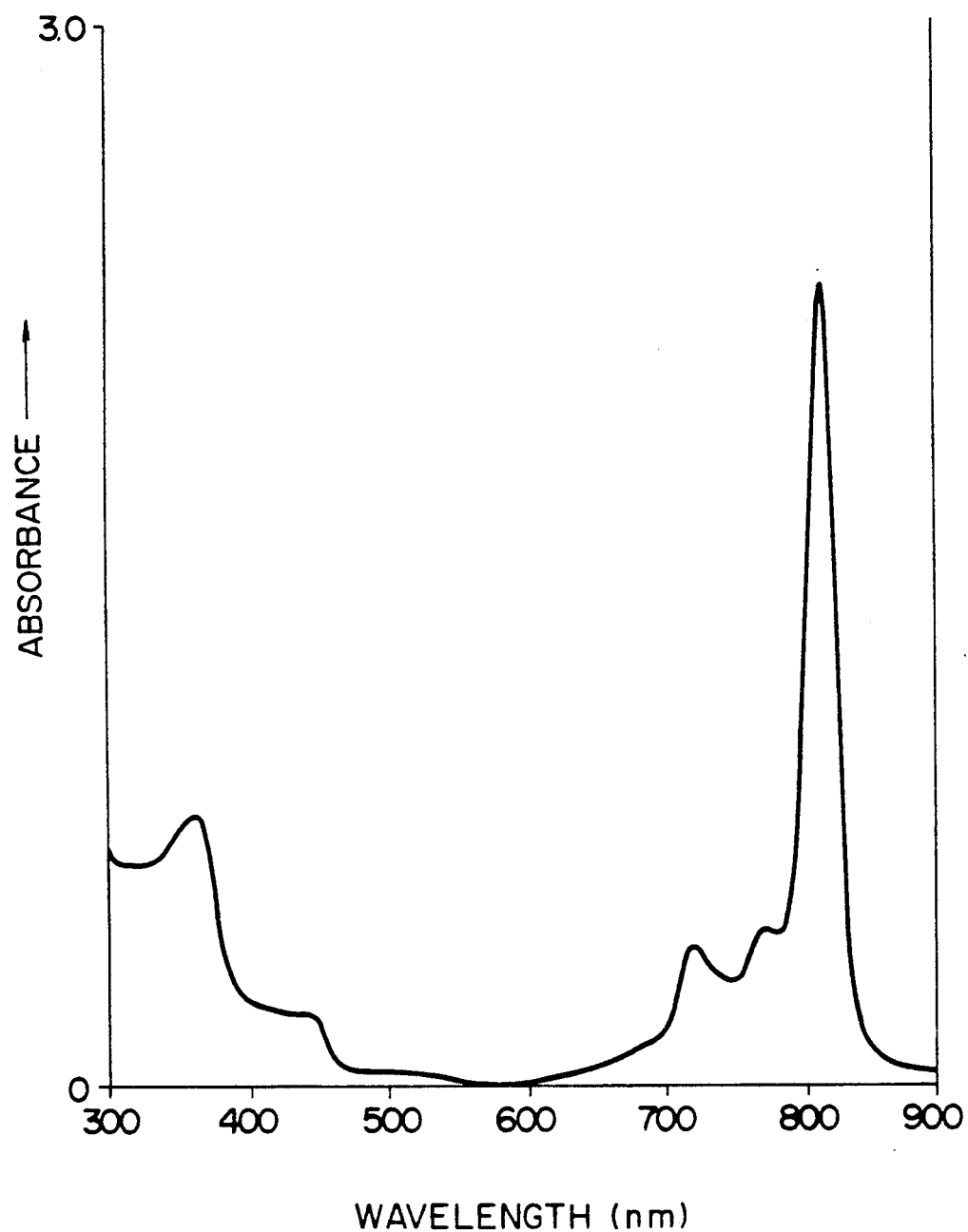
FIG. 91 is an electronic spectrum of tetra(t-butyl) vanadyl naphthalocyanine in its benzene solution ($9.5 \times 10^{-5}$M)

Tetra(t-butyl) vanadyl naphthalocyanine synthesized according to the method described in Zhurnal Obschchei Khimii, Vol. 42, p. 696, 1972 was dissolved in chloroform and measured for electronic spectrum. The result is shown in FIG. 90. The same compound was dissolved in benzene and measured for electronic spectrum. The result is shown in FIG. 91. As is clear from FIG. 90 and FIG. 91, in the above compound, the absorption spectrum changed with the change of type of solvent used and also with the change of concentration of the compound in solution. As the concentration became higher, the absorption at about 800 nm became lower and the absorption at 720–730 nm became higher.

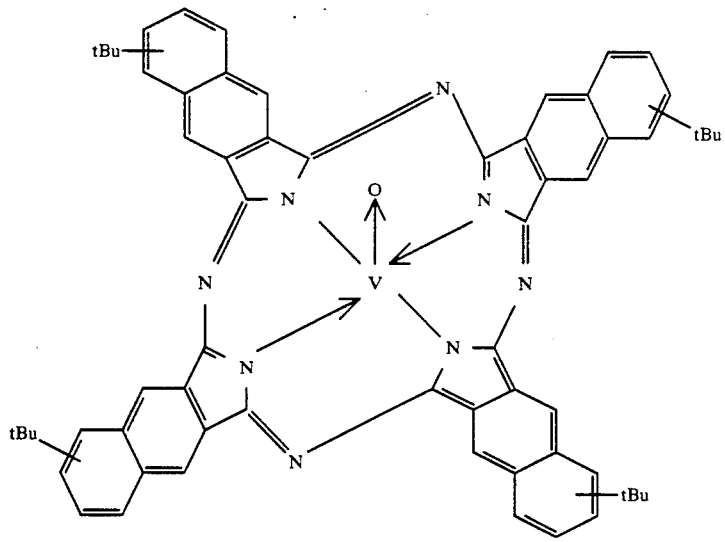

TEST 3

Figure 92:
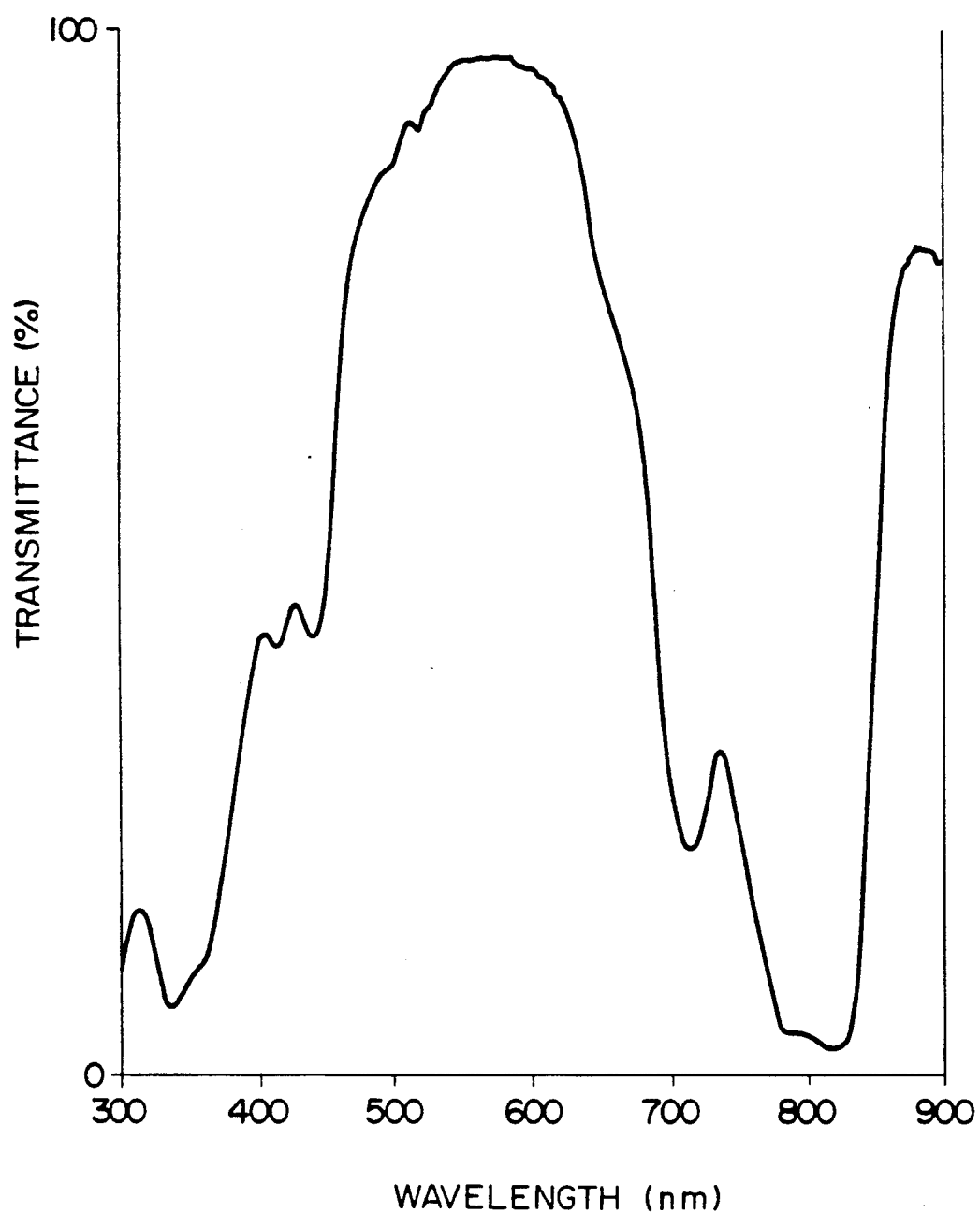
FIG. 92 is a transmission spectrum of a spin coating film of bis(tributylsiloxy)germanium-tetrakis(n-octyloxycarbonyl)naphthalocyanine.
Figure 93:
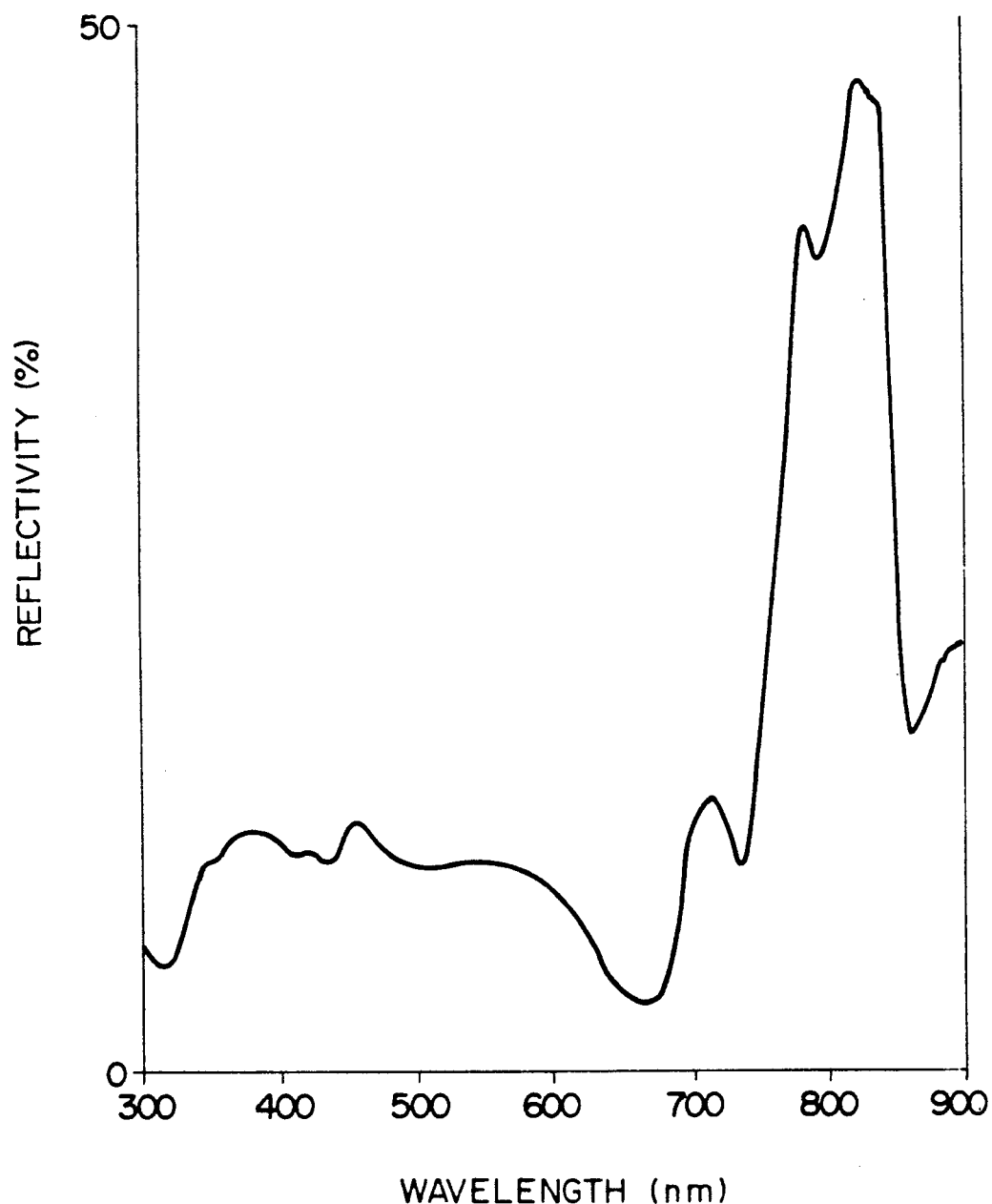
FIG. 93 is a 5° regular reflection spectrum of a spin coating film of bis(tributylsiloxy)germanium-tetrakis(n-octyloxycarbonyl)naphthalocyanine.

A solution consisting of 2 parts by weight of bis(-tributylsiloxy)germanium-tetrakis(n-octyloxycarbonyl)naphthalocyanine [illustrative compound (45)] and 98 parts by weight of 1,1,2-trichloroethane was spin-coated on a glass plate and dried at 80° C. for about 15 minutes to form an organic film. This organic film was measured for transmission spectrum and 5° regular reflection spectrum, and the spectra are shown in FIG. 92 and FIG. 93, respectively. As is clear from these figures, the film shows a high light absorbability and a high reflectivity (up to 47%) at a diode laser beam region (780–830 nm).

COMPARATIVE TEST 2

Figure 94:
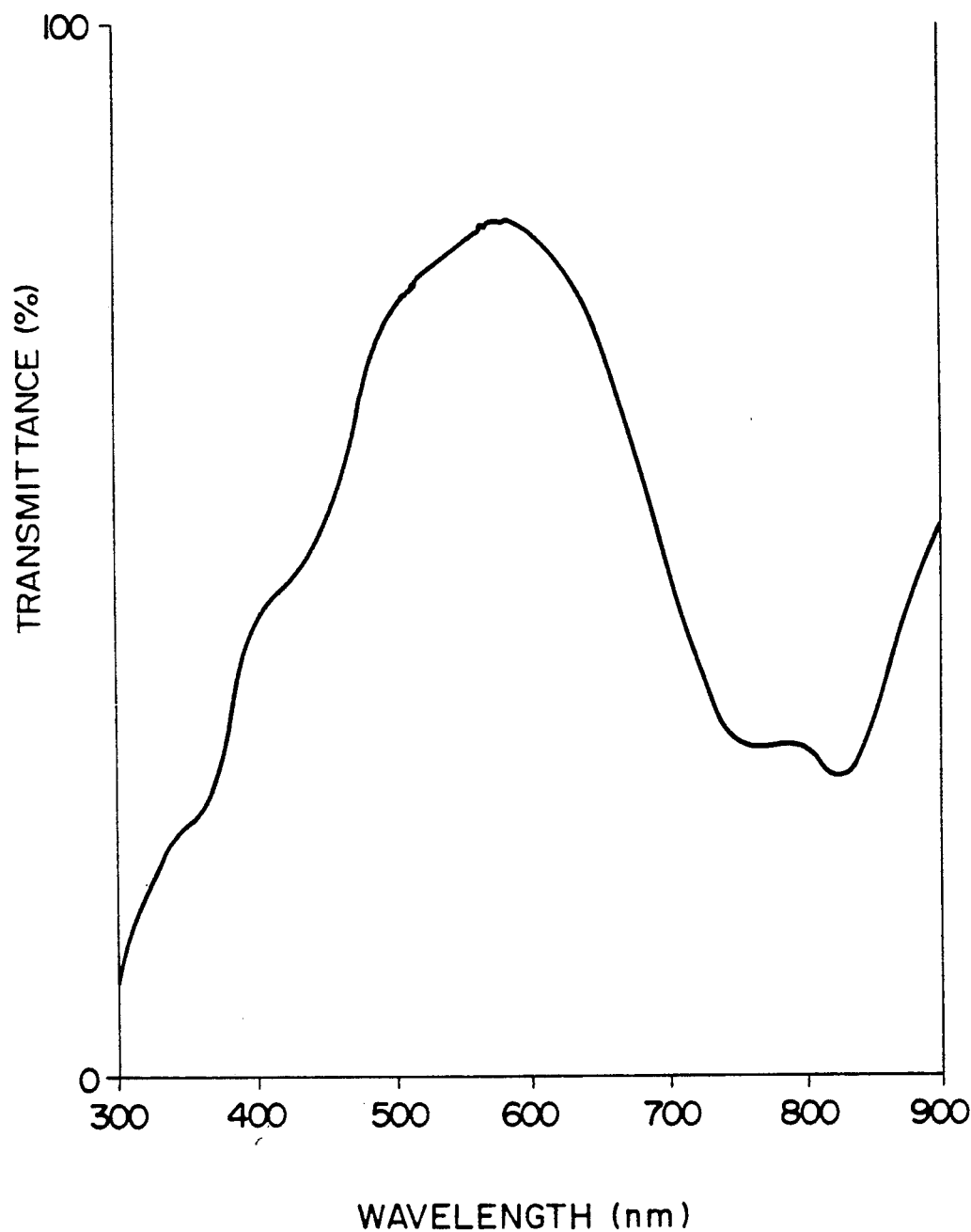
FIG. 94 is a transmission spectrum of a spin coating film of tetra(t-butyl) vanadyl naphthalocyanine.
Figure 95:
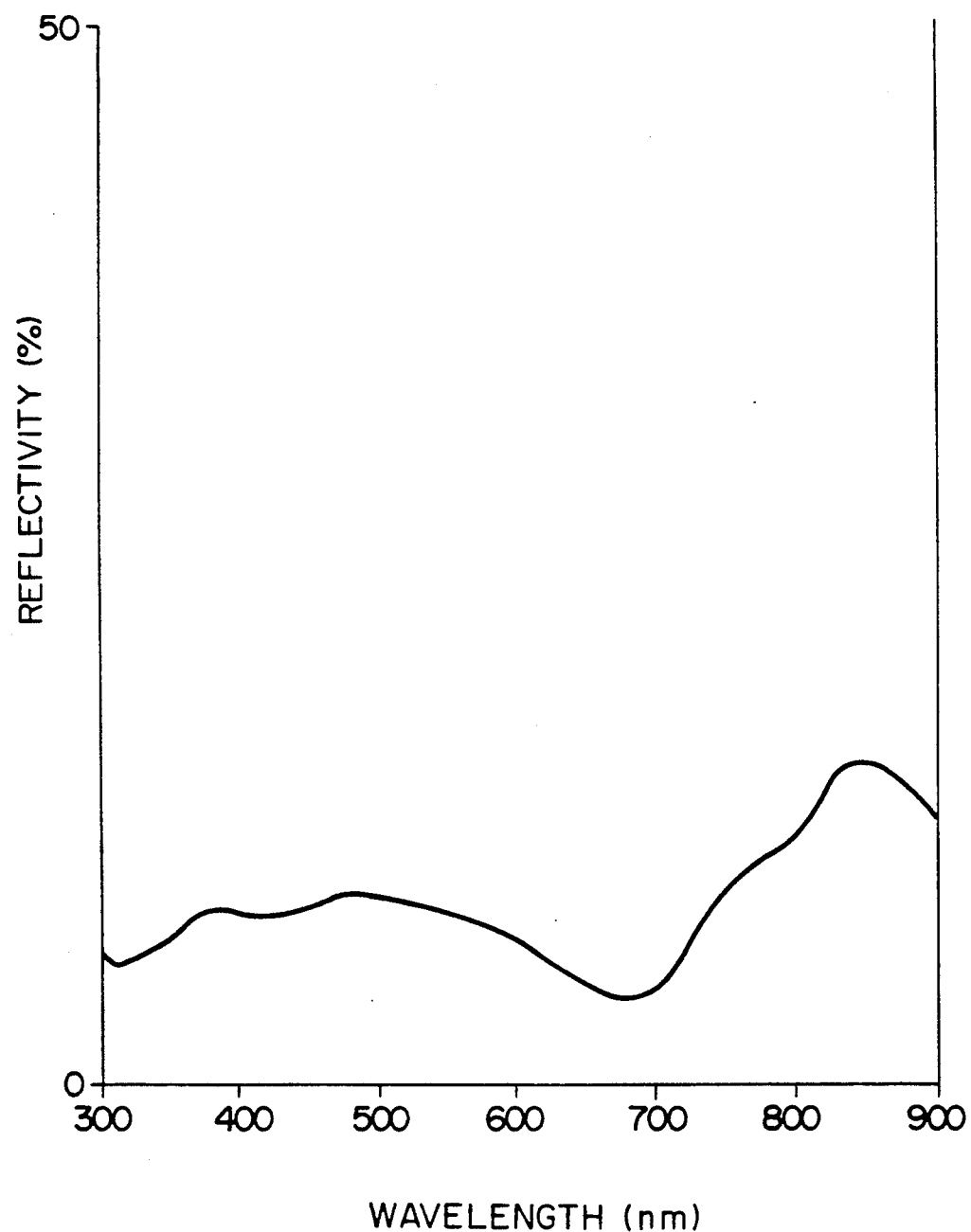
FIG. 95 is a 5° regular reflection spectrum of a spin coating film of tetra(t-butyl) vanadyl naphthalocyanine.
Figure 96:
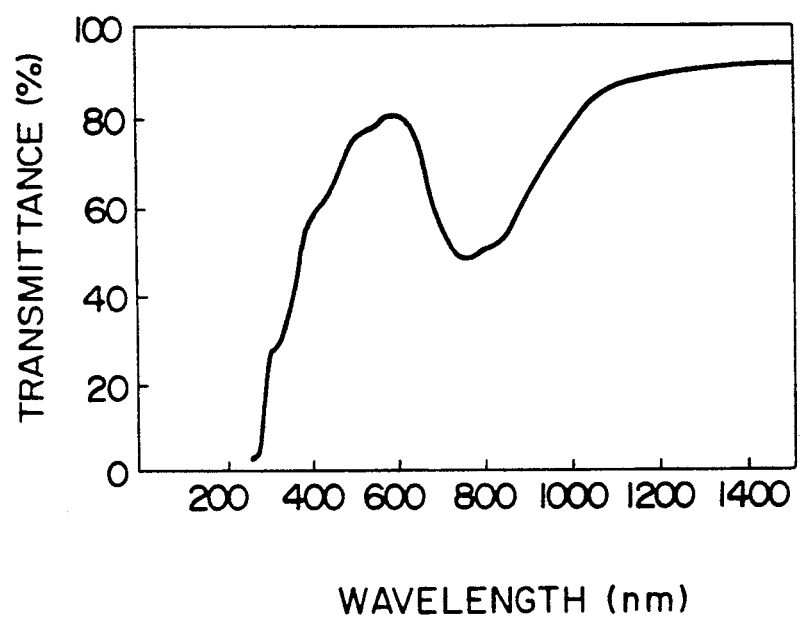
FIG. 96 is an electronic spectrum of a spin coating film of tetrakis(n-amyloxycarbonyl) vanadyl naphthalocyanine.

An organic film of the tetra(t-butyl) vanadyl naphtahlocyanine used in Comparative Test 1 was formed on a glass plate in the same manner as in Test 3. This organic film was measured for transmission spectrum and 5° regular reflection spectrum, and the spectra are shown in FIG. 94 and FIG. 95, respectively. As is clear from these figures, the film did not show a high light absorbability and a high reflectivity (the reflectivity was below 20%) at a diode laser beam region (780–830 nm).

TEST 4

The solubilities of bis(tributylsiloxy)-germanium-tetrakis(n-octyloxycarbonyl)naphthalocyanine [illustrative compound (45)] in various solvents were measured. The results are as follows.

| Solvent | Solubility (%) of illustrative compound (45) |
|---|---|
| Benzene | 14 |
| Toluene | >20 |
| Xylene | >20 |
| Tetrahydrofuran | >20 |
| 1,2-Dichloroethane | 11 |
| 1,1,2-Trichloroethane | >20 |
| Chloroform | >20 |

Each solubility was measured as follows. Into a 2-ml sample tube were charged 100 mg of bis(tributylsiloxy)-germanium-tetrakis(n-octyloxycarbonyl)naphthalocyanine and 0.5 ml of a solvent. The sample tube was then stoppered tightly and subjected to ultrasonic vibration at 40° C. for 15 minutes, after which the tube was allowed to stand overnight at room temperature. The tube contents was filtered through a filter paper. The residue on the filter paper was collected, dried under reduced pressure and weighed. The solubility was calculated using the following formula.

Solubility = [0.1 − weight of residue on filter paper (g)] ÷ 0.5 × 100

EXAMPLE 31

A solution consisting of 4 parts by weight of tetrakis(n-octyloxycarbonyl) vanadyl naphthalocyanine [illustrative compound (2)] and 96 parts by weight of chloroform was spin-coated on a polymethyl methacrylate 2p plate of 1.5 mm in thickness and 150 mm in diameter and then dried at about 80° C. for about 15 minutes to form a recording layer on the plate. The recording layer has a thickness of about 2,000 Å according to a measurement by Talystep. The thus produced optical recording medium was mounted on a turn table so that the substrate (the polymethyl methacrylate plate) contacted with the turn table. While the turn table was being rotated at a speed of 1,000 rpm, a pulse signal of 1 MHz was recorded on the ring-shaped portion of the recording layer between 40 mm and 60 mm from the center of the recording medium, by using an optical head equipped with a diode laser whose beam had a wavelength of 830 nm and whose output was 8 mW at the substrate surface and by applying the laser beam emitted from the optical head from the lower side of the optical recording medium, namely, the substrate side so as to concentrate on the above mentioned portion of the recording layer. Then, using the same apparatus and the same manner as above, the recorded signal were regenerated by keeping the diode laser output at 0.7 mW at the substrate surface. In this case, the S/N ratio (the signal-to-noise ratio) was 56 dB, and accordingly signal writing and reading out were very good.

EXAMPLE 32

A chloroform solution of tetrakis(n-octyloxycarbonyl) copper naphthalocyanine [illustrative compound (9)] was spin-coated on a polymethyl methacrylate 2p plate of 1.5 mm in thickness and 150 mm in diameter in the same manner as in Example 31 to form a recording layer on the plate. The recording layer had a thickness of about 2,500 Å. The thus produced optical recording medium was subjected to recording and reading out in the same manner as in Example 31, in which the S/N ratio was 51 dB. Thus, signal writing and reading out were very good.

EXAMPLE 33

A chloroform solution of tetrakis(n-octyloxycarbonyl) zinc naphthalocyanine [illustrative compound (14)] was spin-coated on a polymethyl methacrylate two-layer plate of 1.5 mm in thickness and 150 mm in diameter in the same manner as in Example 31 to form a recording layer on the plate. The recording layer had a thickness of about 3,000 Å. The thus produced optical recording medium was subjected to signal recording and reading out in the same manner as in Example 31, in which the S/N ratio was 49 dB. Thus, signal writing and reading out were very good.

EXAMPLE 34

A chloroform solution of tetrakis(n-amyloxycarbonyl) vanadyl naphthalocyanine [illustrative compound (1)] was spin-coated on a polymethyl methacrylate 2p plate of 1.5 mm in thickness and 150 mm in diameter in the same manner as in Example 31 to form a recording layer on the plate. The recording layer had a thickness of about 2,600 Å. The thus produced optical recording medium was subjected to signal recording and reading out in the same manner as in Example 31, in which the S/N ratio was 50 dB. Thus, signal writing and reading out were very good.

EXAMPLE 35

A chloroform solution of tetrakis(n-amyloxycarbonyl) copper naphthalocyanine [illustrative compound (8)] was spin-coated on a polymethyl methacrylate 2p plate of 1.5 mm in thickness and 150 mm in diameter in the same manner as in Example 31 to form a recording layer on the plate. The recording layer had a thickness of about 2,300 Å. The thus produced optical recording medium was subjected to signal recording and reading out in the same manner as in Example 31, in which the S/N ratio was 51 dB. Thus, signal writing and reading out were very good.

EXAMPLE 36

A chloroform solution of tetrakis(n-amyloxycarbonyl) zinc naphthalocyanine [illustrative compound (13)] was spin-coated on a polymethyl methacrylate 2p plate of 1.5 mm in thickness and 150 mm in diameter in the same manner as in Example 31 to form a recording layer on the plate. The recording layer had a thickness of about 2,500 Å. The thus produced optical recording medium was subjected to signal recording and reading out in the same manner as in Example 31, in which the S/N ratio was 52 dB. Thus, signal writing and reading out were very good.

EXAMPLE 37

A chloroform solution of tetrakis(n-amyloxycarbonyl) nickel naphthalocyanine [illustrative compound (16)] was spin-coated on a polymethyl methacrylate 2p plate of 1.5 mm in thickness and 150 mm in diameter in the same manner as in Example 31 to form a recording layer on the plate. The recording layer had a thickness of about 2,100 Å. The thus produced optical recording medium was subjected to signal recording and reading out in the same manner as in Example 31, in which the S/N ratio was 54 dB. Thus, signal writing and reading out were very good.

EXAMPLE 38

A chloroform solution of tetrakis(n-amyloxycarbonyl) palladium naphthalocyanine [illustrative compound (18)] was spin-coated on a polymethyl methacrylate 2p plate of 1.5 mm in thickness and 150 mm in diameter in the same manner as in Example 31 to form a recording layer on the plate. The recording layer had a thickness of about 2,300 Å. The thus produced recording medium was subjected to signal recording and reading out in the same manner as in Example 31, in which the S/N ratio was 51 dB. Thus, signal writing and reading out were very good.

EXAMPLE 39

A solution consisting of 2 parts by weight of tetrakis(n-octyloxycarbonyl) chloroindium naphthalocyanine [illustrative compound (27)] and 98 parts by weight of chloroform was spin-coated on a polymethyl methacrylate 2p plate of 1.5 mm in thickness and 150 mm in diameter and then dried at about 80° C. for about 15 minutes to form a recording layer on the plate. The recording layer had a thickness of about 1,000 Å. The thus produced optical recording medium was subjected to signal recording and reading out in the same manner as in Example 31, in which the S/N ratio was 54 dB. Thus, signal writing and reading out were very good.

EXAMPLE 40

A chloroform solution of tetrakis(n-octyloxycarbonyl)chloroaluminumnaphthalocyanine [illustrative compound (24)] was spin-coated on a polymethyl methacrylate 2p plate of 1.5 mm in thickness and 150 mm in diameter in the same manner as in Example 39 to form a recording layer on the plate. The recording layer had a thickness of about 1,500 Å. The thus produced optical recording medium was subjected to signal recording and reading out in the same manner as in Example 39, in which the S/N ratio was 51 dB. Thus, signal writing and reading out were very good.

EXAMPLE 41

A chloroform solution of tetrakis(n-amyloxycarbonyl) cobalt naphthalocyanine [illustrative compound (20)] was spin-coated on a polymethyl methacrylate 2p plate of 1.5 mm in thickness and 150 mm in diameter in the same manner as in Example 39 and then dried at about 80° C. for about 15 minutes to form a recording layer on the plate. The recording layer had a thickness of about 1,100 Å. The thus produced optical recording medium was subjected to signal recording and reading out in the same manner as in Example 39, in which the S/N ratio was 49 dB. Thus, signal writing and reading out were very good.

EXAMPLE 42

A chloroform solution of tetrakis(n-amyloxycarbonyl) manganese naphthalocyanine [illustrative compound (22)] was spin-coated on a polymethyl methacrylate 2p plate of 1.5 mm in thickness and 150 mm in diameter in the same manner as in Example 39 to form a recording layer on the plate. The recording layer had a thickness of about 1,300 Å. The thus produced optical recording medium was subjected to signal recording and reading out in the same manner as in Example 39, in which the S/N ratio was 51 dB. Thus, signal writing and reading out were very good.

EXAMPLE 43

A chloroform solution of tetrakis(n-amyloxycarbonyl) silicon naphthalocyanine [illustrative compound (29)] was spin-coated on a polymethyl methacrylate 2p plate of 1.5 mm in thickness and 150 mm in diameter in the same manner as in Example 39 and then dried at about 80° C. for about 15 minutes to form a recording layer on the plate. The recording layer had a thickness of about 1,000 Å. The thus produced recording medium was subjected to signal recording and reading out in the same manner as in Example 39, in which the S/N ratio was 52 dB. Thus, signal writing and reading out were very good.

EXAMPLE 44

A chloroform solution of tetrakis(n-amyloxycarbonyl) germanium naphthalocyanine [illustrative compound (31)] was spin-coated on a polymethyl methacrylate 2p plate of 1.5 mm in thickness and 150 mm in diameter in the same manner as in Example 39 to form a recording layer on the plate. The recording layer had a thickness of about 900 Å. The thus produced optical recording medium was subjected to signal recording and reading out in the same manner as in Example 39, in which the S/N ratio was 51 dB. Thus, signal writing and reading out were very good.

EXAMPLE 45

A chloroform solution of tetrakis(n-amyloxycarbonyl) tin naphthalocyanine [illustrative compound (33)] was spin-coated on a polymethyl methacrylate 2p plate of 1.5 mm in thickness and 150 mm in diameter in the same manner as in Example 39 to form a recording layer on the plate. The recording layer had a thickness of about 1,100 Å. The thus produced optical recording medium was subjected to signal recording and reading out in the same manner as in Example 39, in which the S/N ratio was 49 dB. Thus, signal writting and reading out were very good.

EXAMPLE 46

A solution consisting of 2 parts by weight of bis(triethylsiloxy)germanium-tetrakis(n-amyloxycarbonyl)-naphthalocyanine [illustrative compound (41)] and 98 parts by weight of toluene was spin-coated on a polymethyl methacrylate 2p plate of 1.2 mm in thickness and 130 mm in diameter and then dried at about 80° C. for about 15 minutes to form a recording layer on the plate. The recording layer had a thickness of about 1,000 Å according to a measurement by Talystep. The thus produced optical recording medium was mounted on a turn table so that the substrate (the polymethyl methacrylate plate) contacted with the turn table. While the turn table was being rotated at a speed of 900 rpm, a pulse signal of 2 MHz was recorded on the ring-shaped portion of the recording layer between 40 mm and 60 mm from the center of the recording medium, by using an optical head equipped with a diode laser whose beam had a wavelength of 830 nm and whose output was 6 mW at the substrate surface and by applying the laser beam emitted from the optical head from the lower side of the optical recording medium, namely, the substrate side so as to focus on the above mentioned portion of the recording layer. Then, using the same apparatus and the same manner as above, the recorded signal were read out by keeping the diode laser output at 0.7 mW at the substrate surface. In this case, the C/N ratio (the carrier-to-noise ratio) was 57 dB, and accordingly signal writing and reading out were very good.

EXAMPLE 47

A solution consisting of 2 parts by weight of bis(tributylsiloxy)germanium-tetrakis(n-amyloxycarbonyl)-naphthalocyanine [illustrative compound (43)] and 98 parts by weight of toluene was spin-coated on a polymethyl methacrylate 2p plate of 1.2 mm in thickness and 130 mm in diameter in the same manner as in Example 46 to form a recording layer on the plate. The recording layer had a thickness of about 700 Å. The thus produced optical recording medium was subjected to signal recording and reading out in the same manner as in Example 46, in which the C/N ratio was 55 dB. Thus, signal writing and reading out were very good.

EXAMPLE 48

A solution consisting of 2 parts by weight of bis(triethylsiloxy)germanium-tetrakis(n-octyloxycarbonyl)-naphthalocyanine [illustrative compound (44)] and 98 parts by weight of toluene was spin-coated on a polymethyl methacrylate 2p plate of 1.2 mm in thickness and 130 mm in diameter in the same manner as in Example 46 to form a recording layer on the plate. The recording layer had a thickness of about 800 Å. The thus produced optical recording medium was subjected to signal recording and reading out in the same manner as in Example 46, in which the C/N ratio was 56 dB. Thus, signal writing and reading out were very good.

EXAMPLE 49

A solution consisting of 2 parts by weight of bis(tributylsiloxy)germanium-tetrakis(n-octyloxycarbonyl)naphthalocyanine [illustrative compound (45)] and 98 parts by weight of toluene was spin-coated on a polymethyl methacrylate 2p plate of 1.2 mm in thickness and 130 mm in diameter in the same manner as in Example 46 to form a recording layer on the plate. The recording layer had a thickness of about 600 Å. The thus produced optical recording medium was subjected to signal recording and reading out in the same manner as in Example 46, in which the C/N ratio was 57 dB. Thus, signal writing and reading out were very good.

EXAMPLE 50

A solution consisting of 2 parts by weight of bis(n-dodecyloxy)germanium-tetrakis(n-amyloxycarbonyl)-naphthalocyanine [illustrative compound (53)] and 98 parts by weight of toluene was spin-coated on a polymethyl methacrylate 2p plate of 1.2 mm in thickness and 130 mm in diameter in the same manner as in Example 46 to form a recording layer on the plate. The recording layer had a thickness of about 1,000 Å. The thus produced optical recording medium was subjected to signal recording and reading out in the same manner as in Example 46, in which the C/N ratio was 52 dB. Thus, signal writing and reading out were very good.

EXAMPLE 51

A solution consisting of 2 parts by weight of bis(n-octadecyloxy)germanium-tetrakis(n-amyloxycarbonyl)-naphthalocyanine [illustrative compound (54)] and 98 parts by weight of toluene was spin-coated on a polymethyl methacrylate two-layer plate of 1.2 mm in thickness and 130 mm in diameter in the same manner as in Example 46 to form a recording layer on the plate. The recording layer had a thickness of about 700 Å. The thus produced optical recording medium was subjected to signal recording and reading out in the same manner as in Example 46, in which the C/N ratio was 54 dB. Thus, signal writing and reading out were very good.

EXAMPLE 52

A solution consisting of 2 parts by weight of bis(n-dodecyloxy)germanium-tetrakis(n-octyloxycarbonyl)-naphthalocyanine [illustrative compound (55)] and 98 parts by weight of toluene was spin-coated on a polymethyl methacrylate 2p plate of 1.2 mm in thickness and 130 mm in diameter in the same manner as in Example 46 to form a recording layer on the plate. The recording layer had a thickness of about 800 Å. The thus produced optical recording medium was subjected to signal recording and reading out in the same manner as in Example 46, in which the C/N ratio was 55 dB. Thus, signal writing and reading out were very good.

EXAMPLE 53

A solution consisting of 2 parts by weight of bis(n-octadecyloxy)germanium-tetrakis(n-octyloxycarbonyl)naphthalocyanine [illustrative compound (56)] and 98 parts by weight of toluene was spin-coated on a polymethyl methacrylate 2p plate of 1.2 mm in thickness and 130 mm in diameter in the same manner as in Example 46 to form a recording layer on the plate. The recording layer had a thickness of about 600 Å. The thus produced optical recording medium was subjected to signal recording and reading out in the same manner as in Example 46, in which the C/N ratio was 53 dB. Thus, signal writing and reading out were very good.

EXAMPLE 54

There was prepared a chloroform solution containing 1% of tetrakis(n-amyloxycarbonyl) vanadyl naphthalocyanine [illustrative compound (1)]. The solution was spin-coated on a glass substrate of 1.2 mm in thickness to form a recording layer of 70 nm in thickness on the glass substrate. The thus produced recording medium was irradiated with a diode laser beam having a wavelength of 830 nm from the glass substrate side to evaluate its recording characteristic. Recording was possible under conditions of 1.6 $\mu$m (beam diameter), 0.5 m/sec (line speed) and 6.4 mW. To evaluate the stability against reading out light, a reading out light of 1 mW was applied repeatedly. Repeated application of $10^6$ times gave on change in reflectivity.

COMPARATIVE TEST 3

A dichloroethane solution of a cyanine type dye NK-2905 (a product of Nihon Kankoshikiso Kenkyusho) was spin-coated on a glass substrate to form a recording layer of 50 nm in thickness on the glass substrate. The thus produced recording medium was irradiated with a laser beam in the same manner as in Example 54 to evaluate its recording characteristic. Recording was possible at 4.8 mW. The recording medium was also evaluated for its stability against reading out light. The reflectivity began to decrease from around $4 \times 10^4$ times (the times of repeated light application) and dropped to 70% of the initial value after light application of $10^6$ times.

EXAMPLE 55

A chloroform solution of tetrakis(n-octyloxycarbonyl) zinc naphtahlocyanine [illustrative compound (14)] was spin-coated on a glass substrate to form a recording layer of 70 nm in thickness on the glass substrate. The thus produced recording medium was irradiated with a diode laser beam having a wavelength of 780 nm from the glass substrate side to evaluate its recording characteristic. Recording was possible under conditions of 1.6 $\mu$m (beam diameter), 0.5 m/sec (line speed) and 6.9 mW. To evaluate the stability against reading out light, a reading out light of 1 mW was repeatedly applied to the recording medium. Repeated application of $10^6$ times gave no change in reflectivity.

EXAMPLE 56

A chloroform solution of tetrakis(n-octyloxycarbonyl) chloroaluminum naphthalocyanine [illustrative compound (24)] was spin-coated on a glass substrate to form a recording layer of 90 nm in thickness on the glass substrate. The thus produced recording medium was irradiated with a laser beam in the same manner as in Example 54 to evaluate its recording characteristic. Recording was possible at 6.6 mW. The stability against reading out light was also evaluated in the same manner as in Example 54. Repeated light application of $10^6$ times gave no change in reflectivity.

EXAMPLE 57

A chloroform solution containing tetrakis(n-amyloxycarbonyl) nickel naphthalocyanine [illustrative compound (16)] and a polystyrene at 1:1 proportions was spin-coated on a glass substrate having an aluminum reflection film to form a recording layer of 150 nm in thickness. The thus produced recording medium was irradiated with a laser beam in the same manner as in Example 54 to evaluate its recording characteristic. Recording was possible at 9.6 mW. The stability against reading out light was also evaluated in the same manner as in Example 54. Repeated light application $10^6$ times gave on change in reflectivity.

EXAMPLE 58

A chloroform solution of the bis(trihexylsiloxy)tin-tetrakis(n-amyloxycarbonyl)naphthalocyanine [illustrative compound (64)] synthesized in the same manner as in Example 23 was spin-coated on a glass substrate of 1.2 mm in thickness to form a recording layer of 70 nm in thickness on the glass substrate. The thus produced recording medium was irradiated with a diode laser beam having a wavelength of 780 nm from the glass substrate side to evaluate its recording characteristic. Recording was possible under conditions of 1.6 $\mu$m (beam diameter), 0.5 m/sec (line speed) and 4.6 mW. To evaluate the stability against reading out light, a reading out light of 1 mW was applied repeatedly. Repeated application of $10^6$ times gave no change in reflectivity.

COMPARATIVE TEST 4

A dichloroethane solution of a cyanine dye NK-2873 (a product of Nihon Kankoshikiso Kenkyusho) was spin-coated on a glass substrate to form a recording layer of 50 nm in thickness on the glass substrate. The thus produced recording medium was irradiated with a laser beam in the same manner as in Example 54 to evaluate its recording characteristic. Recording was possible at 5.2 mW. The recording medium was also evaluated for its stability against reading out light. The reflectivity began to decrease from around $5 \times 10^4$ times (times of repeated light application) and dropped to 70% of the initial value after application of $10^6$ times.

EXAMPLE 59

A dichloroethane solution of the bis(tributylsiloxy)-tin-tetrakis(n-octyloxycarbonyl)naphthalocyanine [illustrative compound (65)] synthesized in the same manner as in Example 23 was spin-coated on a glass substrate to form a recording layer of 50 nm on the glass substrate. The thus produced recording medium was irradiated with a laser beam in the same manner as in Example 54 to evaluate its recording characteristic. Recording was possible at 4.4 mW. The stability against reading out light was also evaluated in the same manner as in Example 54. Repeated light application of $10^6$ times gave no change in reflectivity.

EXAMPLE 60

A chloroform solution of the bis(triethylsiloxy)germanium-tetrakis(n-octyloxycarbonyl)naphthalocyanine [illustrative compound (44)] synthesized in Example 25 was spin-coated on a glass substrate to form a recording layer of 50 nm on the glass substrate. The thus produced recording medium was irradiated with a laser beam in the same manner as in Example 54 to evaluated its recording characteristic. Recording was possible at 4.9 mW. The stability against reading out light was also evaluated in the same manner as in Example 54. Repeated light application of $10^6$ times gave no change in reflectivity.

EXAMPLE 61

A chloroform solution of the bis(tributylsiloxy)titanium-tetrakis(methoxycarbonyl)naphtahlocyanine [illustrative compound (68)] synthesized in the same manner as in Example 23 was spin-coated on a glass substrate to form a recording layer of 40 nm on the glass substrate. The thus produced recording medium was irradiated with a laser beam in the same manner as in Example 54 to evaluate its recording characteristic. Recording was possible at 4.2 mW. The stability against reading out light was also evaluated in the same manner as in Example 54. Repeated light application of $10^6$ times gave no change in reflectivity.

EXAMPLE 62

A toluene solution of the trihexylsiloxyaluminum-tetrakis(n-amyloxycarbonyl)naphthalocyanine [illustrative compound (69)] synthesized in the same manner as in Example 23 was spin-coated on a polycarbonate substrate of 1.2 mm in thickness having a surface protective layer of Ti chelate of 10 nm to form a recording layer of 60 nm in thickness. The thus produced recording medium was evaluated for its recording characteristic in the same manner as in Example 54, at a line speed of 5 m/sec. Recording was possible at 7.4 mW. The stability against reading out light was also evaluated. Repeated light application of $10^6$ times gave no change in reflectivity.

EXAMPLE 63

A methyl ethyl ketone solution containing the bis(n-octoxy)tin-tetrakis(n-amyloxycarbonyl)naphtahlocyanine [illustrative compound (74)] synthesized in the same manner as in Example 23 and a polystyrene at 2:1 proportions was spin-coated on a glass substrate to form a recording layer of 60 nm in thickness on the glass substrate. The thus produced recording medium was evaluated in the same manner as in Example 54. The recording sensitivity was 4.8 mW and the stability against reading out light was at least $10^6$ times.

EXAMPLE 64

A 1,1,2-trichloroethane solution containing 0.8% by weight of bis(tributylsiloxy)germanium-tetrakis(n-octyloxycarbonyl)naphthalocyanine [illustrative compound (45)] was spin-coated on a glass substrate of 1.2 mm in thickness to form a recording layer of 40 nm on the glass substrate. The thus produced recording medium was irradiated with a diode laser beam having a wavelength of 830 nm from the glass substrate side to evaluate its recording characteristic. Recording was possible under conditions of 1.6 μm (beam diameter), 2.4 m/sec (line speed) and 7.8 mW. To evaluate the stability against reading out light, a reading out light of 0.8 mW was applied repeatedly. Repeated application of $10^6$ times gave no change in reflectivity.

EXAMPLE 65

A 1,2-dichloroethane solution containing 1.5% by weight of bis(n-dodecyloxy)germanium-tetrakis(n-amyloxycarbonyl)naphthalocyanine [illustrative compound (53)] was spin-coated on a glass substrate of 1.2 mm in thickness to form a recording layer of 60 nm on the glass substrate. The thus produced recording medium was irradiated with a diode laser beam having a wavelength of 830 nm from the substrate side to evaluate its recording characteristic. Recording was possible under conditions of 1.6 μm (beam diameter), 2.5 m/sec (line speed) and 8.6 mW. To evaluate the stability against reading out light, a reading out light of 0.8 mW was applied repeatedly. Repeated application of $10^6$ times gave no change in reflectivity.

EXAMPLE 66

A 1,1,2-trichloroethane solution containing bis(-tributylsiloxy)germanium-tetrakis(n-octyloxycarbonyl)naphthalocyanine [illustrative compound (45)] and a polystyrene at 2:1 proportions was spin-coated on a glass substrate of 1.2 mm in thickness to form a recording layer of 80 nm in thickness on the glass substrate. The thus produced recording medium was irradiated with a diode laser beam having a wavelength of 830 nm from the substrate side to evaluate the recording characteristic. Recording was possible under conditions of 2 m/sec (line speed) and 6 mW. To evaluate the stability against reading out light, a reading out light of 1 mW was applied repeatedly. Repeated application of $10^6$ times gave no change in reflectivity.

The naphthalocyanine derivatives according to the first or second aspect of the present invention or obtained according to the third or fourth aspect of the present invention are novel compounds and are useful, for example, as a material for the recording layer of the optical recording medium according to the fifth aspect of the present invention or obtained according to the sixth aspect of the present invention.

What is claimed is:

1. A naphthalocyanine derivative represented by the general formula (II)

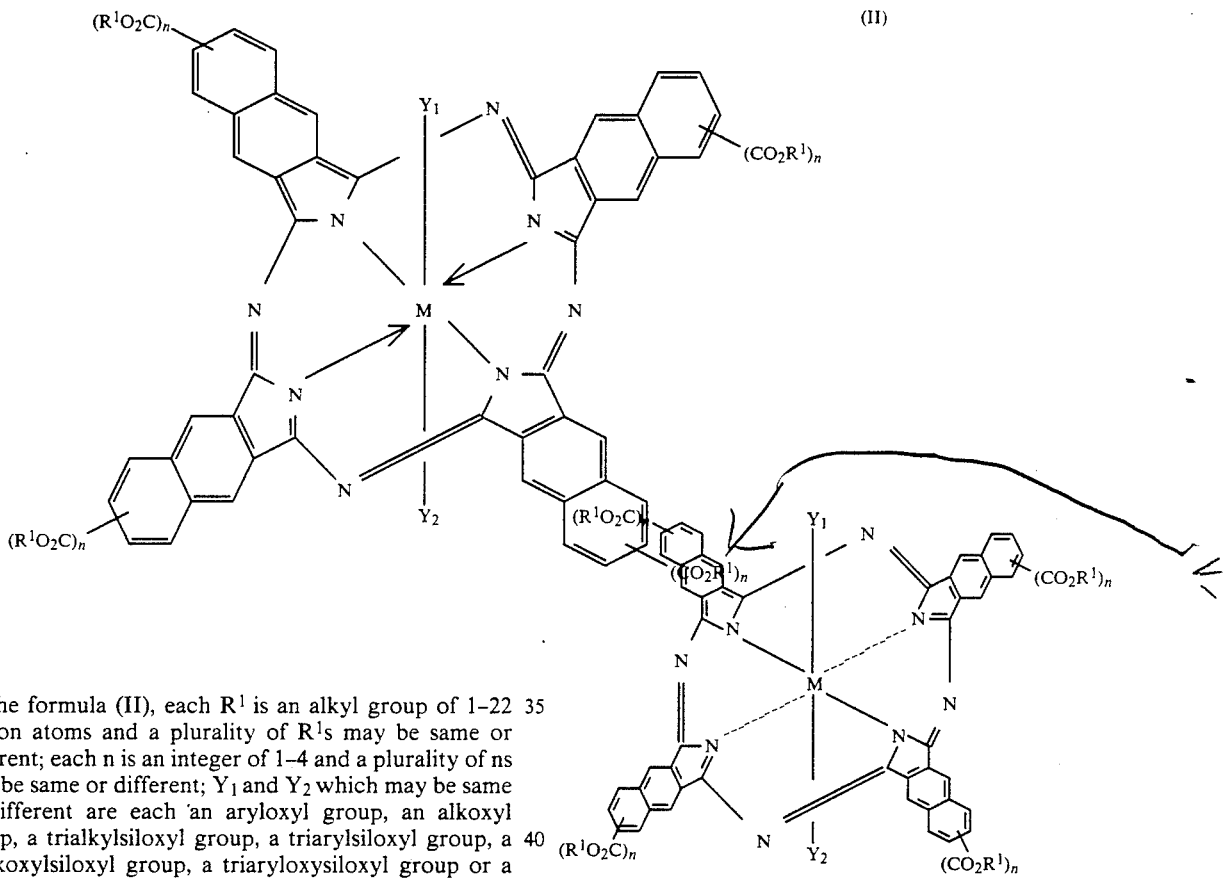

[in the formula (II), each $R^1$ is an alkyl group of 1-22 carbon atoms and a plurality of $R^1$s may be same or different; each n is an integer of 1-4 and a plurality of ns may be same or different; $Y_1$ and $Y_2$ which may be same or different are each an aryloxyl group, an alkoxyl group, a trialkylsiloxyl group, a triarylsiloxyl group, a trialkoxylsiloxyl group, a triaryloxysiloxyl group or a trityloxyl group; M is Al, Ti, Si, Ge or Sn; and only $Y_1$ covalently binds with M when M is Al, and $Y_1$ and $Y_2$ covalently bind with M when M is Ti, Si, Ge or Sn].

2. A naphthalocyanine derivative according to claim 1, wherein in the general formula (II), M is Ge.

3. A naphthalocyanine derivative according to claim 1 or 2, wherein in the general formula (II), n is 1.

4. A naphthalocyanine derivative according to claim 1 or 2, wherein in the general formula (II), $Y_1$ and $Y_2$ are each a trialkysiloxyl group.

5. A naphthalocyanine derivative according to claim 1 or 2, wherein in the general formula (II), $Y_1$ and $Y_2$ are each an alkoxyl group.

6. A naphthalocyanine derivative according to claim 3, wherein in the general formula [II] $Y_1$ and $Y_2$ are each a trialkylsiloxyl group.

7. A naphthalocyanine derivative according to claim 3, wherein in the general formula [II] $Y_1$ and $Y_2$ are each an alkoxyl group.

8. An optical information recording medium comprising a film layer capable of being thermally deformed upon laser irradiation to record information thereon, said information being read from said deformation by a difference in reflection between deformed and non-deformed areas and said layer consisting essentially of a naphthalocyanine derivative represented by the general formula (II)

in the formula (II), each $R^1$ is an alkyl group of 1-22 carbon atoms and a plurality of $R^1$s may be same or different; each n is an integer of 1-4 and a plurality of ns may be same or different; $Y_1$ and $Y_2$ which may be same or different are each an aryloxyl group, an alkoxyl group, a trialkylsiloxyl group, a triarylsiloxyl group, a trialkoxylsiloxyl group, a triaryloxysiloxyl group or a trityloxyl group; M is Al, Ti, Si, Ge or Sn; and only $Y_1$ covalently binds with M when M is Al, and $Y_1$ and $Y_2$ covalently bind with M when M is Ti, Si, Ge or Sn.

9. An optical information recording medium according to claim 8, wherein in the formula (II), M is Ge.

10. An optical information recording medium according to claim 8 or 9, wherein in the formula (II), n is 1.

11. An optical information recording medium according to any of claims 8, 9 and 10, wherein in the formula (II), $Y_1$ and $Y_2$ are each a trialkylsiloxyl group.

12. An optical information recording medium according to any of claims 8, 9 and 10, wherein in the formula (II), $Y_1$ and $Y_2$ are each an alkoxyl group.

13. A process for producing an optical information recording medium, which comprises forming a recording film layer on a substrate by coating on the substrate an organic solvent solution mainly containing a naphthalocyanine derivative represented by the general formula (II)

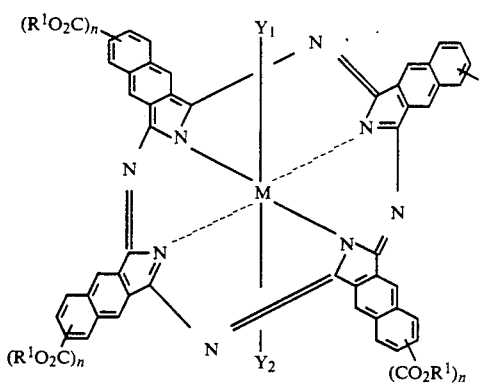

[in the formula (II), each $R^1$ is an alkyl group of 1-22 carbon atoms and a plurality of $R^1$s may be same or different; each n is an integer of 1-4 and a plurality of ns may be same or different; $Y_1$ and $Y_2$ which may be same or different are each an aryloxyl group, an alkoxyl group, a trialkylsiloxyl group, a triarylsiloxyl group, a trialkoxylsiloxyl group, a triaryloxysiloxyl group or a trityloxyl group; M is Al, Ti, Si, Ge or Sn; and only $Y_1$ covalently binds with M when M is Al, and $Y_1$ and $Y_2$ covalently bind with M when M is Ti, Si, Ge or Sn].

14. A process for producing an optical information recording medium according to claim 13, wherein in the general formula (II), M is Ge.

15. A process for producing an optical information recording medium according to claim 13 or 14, wherein in the formula (II), n is 1.

16. A process for producing an optical information recording medium according to any of claims 13, 14 and 15, wherein in the formula (II), $Y_1$ and $Y_2$ are each a trialkylsiloxyl group.

17. A process for producing an optical information recording medium according to any of claims 13, 14 and 15, wherein in the formula (II), $Y_1$ and $Y_2$ are each an alkoxyl group.

* * * * *

UNITED STATES PATENT AND TRADEMARK OFFICE
CERTIFICATE OF CORRECTION

PATENT NO. : 5,219,706
DATED : June 15, 1993
INVENTOR(S) : TAI, et al

It is certified that error appears in the above-indentified patent and that said Letters Patent is hereby corrected as shown below:

On the title page, left-hand column:

"[73] Assignee: Hitachi, Ltd., Tokyo, Japan"

should read:

--[73] Assignees: Hitachi Chemical Company; Hitachi, Ltd., both of Tokyo, Japan

Signed and Sealed this

Twelfth Day of January, 1999

Attest:

*Attesting Officer*    *Acting Commissioner of Patents and Trademarks*